US008901094B2

(12) United States Patent
Kokaia et al.

(10) Patent No.: US 8,901,094 B2
(45) Date of Patent: Dec. 2, 2014

(54) USE OF NUCLEIC ACID SEQUENCES FOR THE TREATMENT OF EPILEPSY

(75) Inventors: Merab Kokaia, Lund (SE); David Woldbye, Kopenhagen (DK)

(73) Assignee: Combigene AB (SE)

(*) Notice: Subject to any disclaimer, the term of this patent is extended or adjusted under 35 U.S.C. 154(b) by 576 days.

(21) Appl. No.: 12/308,959

(22) PCT Filed: Jul. 4, 2007

(86) PCT No.: PCT/SE2007/050494
§ 371 (c)(1), (2), (4) Date: Mar. 13, 2009

(87) PCT Pub. No.: WO2008/004972
PCT Pub. Date: Jan. 10, 2008

(65) Prior Publication Data
US 2010/0010070 A1 Jan. 14, 2010

(30) Foreign Application Priority Data
Jul. 4, 2006 (SE) ....................................... 0601456

(51) Int. Cl.
*A61K 48/00* (2006.01)
*A61K 31/7088* (2006.01)
*C12N 15/86* (2006.01)
*C12N 15/861* (2006.01)
*C12N 15/867* (2006.01)
*C12N 15/869* (2006.01)

(52) U.S. Cl.
CPC ......... *A61K 48/005* (2013.01); *C12N 2799/025* (2013.01); *C12N 2799/027* (2013.01)
USPC ............................................................ 514/44

(58) Field of Classification Search
USPC ............................................................ 514/44
See application file for complete search history.

(56) References Cited

U.S. PATENT DOCUMENTS 5,194,596 A * 3/1993 Tischer et al. ................ 530/399
5,350,836 A * 9/1994 Kopchick et al. ............. 530/399
7,723,288 B2 5/2010 During et al.
2002/0048791 A1* 4/2002 Zhelnin et al. ............... 435/69.1
2003/0228284 A1 12/2003 McCown et al.

FOREIGN PATENT DOCUMENTS

WO WO-2005/037211 A2 4/2005

OTHER PUBLICATIONS

Guo et al, Proc Natl Acad Sci 101(25):9205-9210, 2004.*
Hult and Berglund, Curr Opin Biotechnol 14:395-400, 2003.*
Rasmusson et al, Biol. Psychiatry 47(6):526-539, 2000.*
Minth et al, GenBank Accession P01303; GI:128117, 1992.*
Gerald et al, GenBank Accession P49146; GI:1352610, 1996.*
Koulu et al, GenBank Accession BD103561; GI:22649135, 2002.*
Gehlert et al, GenBank Accession U42766; GI:1174045, 1996.*
Woldbye and Kokaia, Neuropeptides 38:253-260, 2004.*
"International Application Serial No. PCT/SE2007/050494, International Search Report mailed Dec. 19, 2007", 8 pgs.
"International Application Serial No. PCT/SE2007/050494, Written Opinion mailed Dec. 19, 2007", 8 pgs.
El Bahh, B., et al., "The anti-epileptic actions of neuropeptide Y in the hippocampus are mediated by $Y_2$ and not $Y_5$ receptors", *European Journal of Neuroscience*, 22, (2005), 1417-1430.
Ishikura, N., et al., "Neuropeptide Y and somatostatin participate differently in the seizure-generating mechanisms following trimethyltin-induced hippocampal damage", *Neuroscience Research*, 44, (2002), 237-248.
Lin, E. D., et al., "Differential Actions of NPY on Seizure Modulation via Y1 and Y2 Receptors: Evidence from Receptor Knockout Mice", *Epilepsia*, 47(4), (2006), 773-780.
Lin, E. D., et al., "Effects of rAAV-Mediated NPY and Galanin Overexpression in Rat Hippocampus on Rat Behaviour and Seizure Modulation", *31st Annual Meeting, Society for Neuroscience*, Nov. 10-15, 2001, (Abstract Only). [online]. [retrieved on Oct. 23, 2007]. Retrieved from the Internet: <URL: http://sfn.scholarone.com/itin2001/main.html?new__page__id=126&abstract__id=12421>, (2001), 1 pg.
Mazarati, A. M., "Galinin and galanin receptors in epilepsy", *Neuropeptides*, 38, (2004), 331-343.
Richichi, C., et al., "Anticonvulsant and Antiepileptogenic Effects Mediated by Adeno-Associated Virus Vector Neuropeptide Y Expression in the Rat Hippocampus", *The Journal of Neuroscience*, 24(12), (2004), 3051-3059.
Warrington, JR., K. H., "Treatment of human disease by adeno-associated viral gene transfer", *Hum Genet.*, 119, (2006), 571-603.
Woldbye, D. P., et al., "Differential suppression of seizures via Y2 and Y5 neuropeptide Y receptors", *Neurobiology of Disease*, 20, (2005), 760-772.
"European Application Serial No. 07769040.2, Supplementary European Search Report dated Jul. 14, 2010", 8 pgs.
McCown, T. J., "Adeno-associaterd Virus-Mediated Expression and Constitutive Secretion of Galanin Suppresses Limbic Seizure Activity in Vivo", Molecular Therapy, 14(1), (2006), 63-68.
Meurs, A., et al., "Clinical Potential of Neiropeptide Y Receptor Ligands in the Treatment of Epilepsy", Current Topics in Medicinal Chemistry, 7, (2007), 1660-1674.

(Continued)

*Primary Examiner* — Kevin Hill
(74) *Attorney, Agent, or Firm* — Schwegman Lundberg & Woessner, P.A.

(57) ABSTRACT

The present invention relates to the use of one or more expression vectors comprising certain nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), in the preparation of a medicament for treatment of a disorder of the nervous system, such as a neurological or a psychiatric disease chosen from epilepsy, depression, and anxiety. The invention further relates to vectors that comprise nucleic acid sequences encoding the above combination, to compositions comprising such vectors and to a method of delivery and expression of the above combination of nucleic acid sequences into cells of the nervous system to treat neurological or psychiatric diseases in humans or animals.

12 Claims, 8 Drawing Sheets

(56) References Cited

OTHER PUBLICATIONS

Vezzani, A., et al., "Gene Therapy in Epilepsy", Epilepsy Currents, 4(3), (2004), 87-90.
Vezzani, A., et al., "Overexpression of NPY and Y2 receptors in epileptic brain tissue: an endogenous neuroprotective mechanism in temporal lobe epilepsy?", Neuropeptides, 38, (2004), 245-252.
Haberman, R. P., et al., "Attenuation of seizures and neuronal death by adeno-associated virus vector galanin expression and secretion", *Nature Medicine*, 9(8), (Aug. 2003), 1076-1080.
Lin, E. D., et al., "Modulation of seizure activities by raav-mediated neuropeptide Y overexpression in the hippocampus of NPY receptor knockout mice", *Program No. 212.22. Abstract Viewer/Itinerary Planner*, Society for Neuroscience,(2003), 1 pg.
Lin, E. D., et al., "Recombinant AAV-mediated expression of galanin in rat hippocampus suppressses seizure development", *European Journal of Neuroscience*, 18, (2003), 2087-2092.
Benmaamar, R., et al., "Induced down-regulation of neuropeptide Y-Y1 receptors delays initiation of kindling", *European Journal of Neuroscience*, 18, (2003), 768-774.
Bijak, M., et al., "Neuropeptide Y supresses epileptiform activity in rat frontal cortex and hippocampus in vitro via different NPY receptor subtypes", *Neuroscience Letters*, 268, (1999), 115-118.
Foti, S., et al., "Adeno-associated virus-mediated expression and constitutive secretion of NPY or NPY 13-36 suppresses seizure activity in vivo", *Gene Therapy*, 14, (2007), 1534-1536.
Gerald, C., et al., "A receptor subtype involved in neuropeptide-Y-induced food intake", *Nature*, 382, (1996), 168-171.
Gøtzsche, C. R., "Combined gene overexpression of neuropeptide Y and its receptor Y5 in the hippocampus suppresses seizures", *Neurobiology of Disease*, (2011), 9 pgs.
Guo, H., et al., "Y5 Receptors Mediate Neuropeptide Y Actions at Excitatory Synapses in Area CA3 of the Mouse Hippocampus", *J Neurophysiol*, 87, (2002), 558-566.
Marsh, D. J., et al., "Role of the Y5 neuropeptide Y receptor in limbic seizures", *Proc. Natl. Acad. Sci. USA*, 96(23), (1999), 13518-13523.
Woldbye, D. P. D., et al., "Adeno-associated viral vector-induced overexpression of neuropeptide Y Y2 receptors in the hippocampus suppresses seizures", *Brain*, 133, (2010), 2278-2788.
Woldbye, D. P. D., et al., "Powerful inhibition of kainic acid seizures by neuropeptide Y via Y5-like receptors", *Nature Medicine*, 3(7), (Jul. 1997), 761-761.
"European Application Serial No. 07769040.2, Office Action mailed Jul. 3, 2013", 4 pgs.
"European Application Serial No. 07769040.2, Office Action mailed Dec. 18, 2013", 4 pgs.
"European Application Serial No. 07769040,2, Response filed Jan. 25, 2011 in reference to European Search Report mailed Jul. 14, 2010", 16 pgs.
"European Application Serial No. 07769040.2, Response filed Oct. 29, 2013 to Office Action mailed Jul. 3, 2013", 171 pgs.

* cited by examiner

SEQUENCE LISTING

```
<160> NUMBER OF SEQ ID NOS: 172

<210> SEQ ID NO 1
<211> LENGTH: 551
<212> TYPE: DNA
<213> ORGANISM: Homo sapiens

<400> SEQUENCE: 1

accccatccg ctggctctca cccctcggag acgctcgccc gacagcatag tacttgccgc      60

ccagccacgc ccgcgcgcca gccaccatgc taggtaacaa gcgactgggg ctgtccggac     120

tgaccctcgc cctgtccctg ctcgtgtgcc tgggtgcgct ggccgaggcg taccccctcca    180

agccggacaa cccgggcgag gacgcaccag cggaggacat ggccagatac tactcggcgc     240

tgcgacacta catcaacctc atcaccaggc agagatatgg aaaacgatcc agcccagaga     300

cactgatttc agacctcttg atgagagaaa gcacagaaaa tgttcccaga actcggcttg     360

aagaccctgc aatgtggtga tgggaaatga gacttgctct ctggcctttt cctattttca     420

gcccatattt catcgtgtaa aacgagaatc cacccatcct accaatgcat gcagccactg     480

tgctgaattc tgcaatgttt tcctttgtca tcattgtata tatgtgtgtt taaataaagt     540

atcatgcatt c                                                          551


<210> SEQ ID NO 2
<211> LENGTH: 294
<212> TYPE: DNA
<213> ORGANISM: Homo sapiens

<400> SEQUENCE: 2

atgctaggta acaagcgact ggggctgtcc ggactgaccc tcgccctgtc cctgctcgtg      60

tgcctgggtg cgctggccga ggcgtacccc tccaagccgg acaacccggg cgaggacgca     120

ccagcggagg acatggccag atactactcg gcgctgcgac actacatcaa cctcatcacc     180

aggcagagat atggaaaacg atccagccca gagacactga tttcagacct cttgatgaga     240

gaaagcacag aaaatgttcc cagaactcgg cttgaagacc ctgcaatgtg gtga           294


<210> SEQ ID NO 3
<211> LENGTH: 97
<212> TYPE: PRT
<213> ORGANISM: Homo sapiens

<400> SEQUENCE: 3

Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
            20                  25                  30
```

```
Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
    50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp


<210> SEQ ID NO 4
<211> LENGTH: 411
<212> TYPE: DNA
<213> ORGANISM: MKacaca mulatta

<400> SEQUENCE: 4

gccagccacc atgctaggta gcaagcgact ggggctgtcc ggactgaccc tcgccctgtc     60

cctgctcgtg tgcctgggtg cgctggccga ggcgtaccct tccaaaccgg acaacccggg    120

cgaggacgcg ccagcggagg acatggccag atactactcg gcgctgcgac actacatcaa    180

cctcatcacc aggcagaggt atggcaaacg atctagccca gagacactga tttcagacct    240

cttgatgaga gaaagcacag aaaatgttcc cagaactcgg cttgaagacc cttcaatgtg    300

gtgatgggaa atgaaacttg ctctctgatc ttttcctatt ttcagcccat atttcatcgt    360

gtaaaatgag agtccaccca tcctaccaat gcatgcagcc actgtgctga a             411


<210> SEQ ID NO 5
<211> LENGTH: 294
<212> TYPE: DNA
<213> ORGANISM: Macaca mulatta

<400> SEQUENCE: 5

atgctaggta gcaagcgact ggggctgtcc ggactgaccc tcgccctgtc cctgctcgtg     60

tgcctgggtg cgctggccga ggcgtaccct tccaaaccgg acaacccggg cgaggacgcg    120

ccagcggagg acatggccag atactactcg gcgctgcgac actacatcaa cctcatcacc    180

aggcagaggt atggcaaacg atctagccca gagacactga tttcagacct cttgatgaga    240

gaaagcacag aaaatgttcc cagaactcgg cttgaagacc cttcaatgtg gtga          294


<210> SEQ ID NO 6
<211> LENGTH: 97
<212> TYPE: PRT
<213> ORGANISM: Macaca mulatta

<400> SEQUENCE: 6

Met Leu Gly Ser Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
            20                  25                  30

Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
    50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ser Met
                85                  90                  95
```

Trp

<210> SEQ ID NO 7
<211> LENGTH: 561
<212> TYPE: DNA
<213> ORGANISM: Mus musculus

<400> SEQUENCE: 7
gtggatctct tctctcacag aggcacccag agcagagcac ccgccgctca gcgacgactg 60
cccgcccgcc acgatgctag gtaacaagcg aatggggctg tgtggactga ccctcgctct 120
atctctgctc gtgtgtttgg gcattctggc tgaggggtac ccctccaagc cggacaatcc 180
gggcgaggac gcgccagcag aggacatggc cagatactac tccgctctgc gacactacat 240
caatctcatc accagacaga gatatggcaa gagatccagc cctgagacac tgatttcaga 300
cctcttaatg aaggaaagca cagaaaacgc ccccagaaca aggcttgaag acccttccat 360
gtggtgatgg gaaatgaaac ttgttctccc gacttttcca agtttccacc ctcatctcat 420
ctcatcccct gaaaccagtc tgcctgtccc accaatgcat gccaccacta ggctggactc 480
cgccccattt cccttgttgt tgttgttgta tatatgtgtg tttaaataaa gtaccatgca 540
ttcaaaaaaa aaaaaaaaaa a 561

<210> SEQ ID NO 8
<211> LENGTH: 294
<212> TYPE: DNA
<213> ORGANISM: Mus musculus

<400> SEQUENCE: 8
atgctaggta acaagcgaat ggggctgtgt ggactgaccc tcgctctatc tctgctcgtg 60
tgtttgggca ttctggctga ggggtacccc tccaagccgg acaatccggg cgaggacgcg 120
ccagcagagg acatggccag atactactcc gctctgcgac actacatcaa tctcatcacc 180
agacagagat atggcaagag atccagccct gagacactga tttcagacct cttaatgaag 240
gaaagcacag aaaacgcccc cagaacaagg cttgaagacc cttccatgtg gtga 294

<210> SEQ ID NO 9
<211> LENGTH: 97
<212> TYPE: PRT
<213> ORGANISM: Mus musculus

<400> SEQUENCE: 9

Met Leu Gly Asn Lys Arg Met Gly Leu Cys Gly Leu Thr Leu Ala Leu
1 5 10 15

Ser Leu Leu Val Cys Leu Gly Ile Leu Ala Glu Gly Tyr Pro Ser Lys
20 25 30

Pro Asp Asn Pro Gly Glu Asp Ala Pro Ala Glu Asp Met Ala Arg Tyr
35 40 45

Tyr Ser Ala Leu Arg His Tyr Ile Asn Leu Ile Thr Arg Gln Arg Tyr
50 55 60

Gly Lys Arg Ser Ser Pro Glu Thr Leu Ile Ser Asp Leu Leu Met Lys
65 70 75 80

Glu Ser Thr Glu Asn Ala Pro Arg Thr Arg Leu Glu Asp Pro Ser Met
85 90 95

Trp

<210> SEQ ID NO 10

<211> LENGTH: 539
<212> TYPE: DNA
<213> ORGANISM: Rattus norvegicus

<400> SEQUENCE: 10

```
caagctcatt cctcgcagag gcgcccagag cagagcaccc gctgcgcaga gaccacagcc     60

cgcccgccat gatgctaggt aacaaacgaa tggggctgtg tggactgacc ctcgctctat    120

ccctgctcgt gtgtttgggc attctggctg aggggtaccc ctccaagccg gacaatccgg    180

gcgaggacgc gccagcagag gacatggcca gatactactc cgctctgcga cactacatca    240

atctcatcac cagacagaga tatggcaaga gatccagccc tgagacactg atttcagatc    300

tcttaatgag agaaagcaca gaaaatgccc ccagaacaag gcttgaagac ccttccatgt    360

ggtgatggga aatgaaactt gctctcctga cttttcctag tttcccccca catctcatct    420

catcctgtga aaccagtctg cctgtcccac ccaatgcatg ccaccaccag gctggattcc    480

gacccatttc ccttgttgtc gttgtatata tgtgtgttta aataaagtat catgcattc     539
```

<210> SEQ ID NO 11
<211> LENGTH: 297
<212> TYPE: DNA
<213> ORGANISM: Rattus norvegicus

<400> SEQUENCE: 11

```
atgatgctag gtaacaaacg aatggggctg tgtggactga ccctcgctct atccctgctc     60

gtgtgtttgg gcattctggc tgaggggtac ccctccaagc cggacaatcc gggcgaggac    120

gcgccagcag aggacatggc cagatactac tccgctctgc gacactacat caatctcatc    180

accagacaga gatatggcaa gagatccagc cctgagacac tgatttcaga tctcttaatg    240

agagaaagca cagaaaatgc ccccagaaca aggcttgaag acccttccat gtggtga       297
```

<210> SEQ ID NO 12
<211> LENGTH: 98
<212> TYPE: PRT
<213> ORGANISM: Rattus norvegicus

<400> SEQUENCE: 12

```
Met Met Leu Gly Asn Lys Arg Met Gly Leu Cys Gly Leu Thr Leu Ala
1               5                   10                  15

Leu Ser Leu Leu Val Cys Leu Gly Ile Leu Ala Glu Gly Tyr Pro Ser
            20                  25                  30

Lys Pro Asp Asn Pro Gly Glu Asp Ala Pro Ala Glu Asp Met Ala Arg
        35                  40                  45

Tyr Tyr Ser Ala Leu Arg His Tyr Ile Asn Leu Ile Thr Arg Gln Arg
    50                  55                  60

Tyr Gly Lys Arg Ser Ser Pro Glu Thr Leu Ile Ser Asp Leu Leu Met
65                  70                  75                  80

Arg Glu Ser Thr Glu Asn Ala Pro Arg Thr Arg Leu Glu Asp Pro Ser
                85                  90                  95

Met Trp
```

<210> SEQ ID NO 13
<211> LENGTH: 2773
<212> TYPE: DNA
<213> ORGANISM: Homo sapiens

<400> SEQUENCE: 13

```
aatctttagg atctgagcag gagaaatacc agcggatctt ccccactctg ctcccttcca     60
```

```
ttcccaccct tccttcttta ataagcagga gcgaaaaaga caaattccaa agaggattgt    120

tcagttcaag ggaatgaaga attcagaata attttggtaa atggattcca atatggggaa    180

taagaataag ctgaacagtt gacctgcttt gaagaaacat actgtccatt tgtctaaaat    240

aatctataac aaccaaacca atcaaaatga attcaacatt attttcccag gttgaaaatc    300

attcagtcca ctctaatttc tcagagaaga atgcccagct tctggctttt gaaaatgatg    360

attgtcatct gcccttggcc atgatattta ccttagctct tgcttatgga gctgtgatca    420

ttcttggtgt ctctggaaac ctggccttga tcataatcat cttgaaacaa aaggagatga    480

gaaatgttac caacatcctg attgtgaacc tttccttctc agacttgctt gttgccatca    540

tgtgtctccc ctttacattt gtctacacat taatggacca ctgggtcttt ggtgaggcga    600

tgtgtaagtt gaatcctttt gtgcaatgtg tttcaatcac tgtgtccatt ttctctctgg    660

ttctcattgc tgtggaacga catcagctga taatcaaccc tcgagggtgg agaccaaata    720

atagacatgc ttatgtaggt attgctgtga tttgggtcct tgctgtggct tcttctttgc    780

ctttcctgat ctaccaagta atgactgatg agccgttcca aaatgtaaca cttgatgcgt    840

acaaagacaa atacgtgtgc tttgatcaat ttccatcgga ctctcatagg ttgtcttata    900

ccactctcct cttggtgctg cagtattttg gtccactttg ttttatattt atttgctact    960

tcaagatata tatacgccta aaaaggagaa acaacatgat ggacaagatg agagacaata   1020

agtacaggtc cagtgaaacc aaaagaatca atatcatgct gctctccatt gtggtagcat   1080

ttgcagtctg ctggctccct cttaccatct ttaacactgt gtttgattgg aatcatcaga   1140

tcattgctac ctgcaaccac aatctgttat tcctgctctg ccacctcaca gcaatgatat   1200

ccacttgtgt caaccccata ttttatgggt tcctgaacaa aaacttccag agagacttgc   1260

agttcttctt caacttttgt gatttccggt ctcgggatga tgattatgaa acaatagcca   1320

tgtccacgat gcacacagat gtttccaaaa cttctttgaa gcaagcaagc ccagtcgcat   1380

ttaaaaaaat caacaacaat gatgataatg aaaaaatctg aaactactta tagcctatgg   1440

tcccggatga catctgttta aaaacaagca caacctgcaa catactttga ttacctgttc   1500

tcccaaggaa tggggttgaa atcatttgaa aatgactaag attttcttgt cttgcttttt   1560

actgcttttg ttgtagttgt cataattaca tttggaacaa aaggtgtggg ctttggggtc   1620

ttctggaaat agttttgacc agacatcttt gaagtgcttt ttgtgaattt atgcatataa   1680

tataaagact tttatactgt acttattgga atgaaatttc tttaaagtat tactattaac   1740

tgacttcaga agtacctgcc atccaatacg gtcattagat tgggtcatct tgattagatt   1800

agattagatt agattgtcaa cagattgggc catccttact ttatgatagg catcatttta   1860

gtgtgttaca atagtaacag tatgcaaaag cagcattcag gagccgaaag atagtctgaa   1920

gtcattcaga agtggtttga ggtttctgtt ttttggtggt ttttgtttgt tttttttttt   1980

tcaccttaag ggaggattta atttgctccc aactgattgt cacttaaatg aaaatttaaa   2040

aatgaataaa aagacatact tctcagctgc aaatattatg gagaattggg gcacccacag   2100

gaatgaagag agaaagcagc tccctaactt caaaaccatt ttggtacctg acaacaagag   2160

cattttagag taattaattt aataaagtaa attagtattg ctgcaaatag ctaaattata   2220

tttatttgaa ttgatggtca agagattttc cattttttttt acagactgtt cagtgtttgt   2280

caagctttct ggcataaata tgtactcaaa aggcatttcc gcttacaatt tgtagaaaca   2340

caaaatgcgt tttccataca gcagtgccta tatagtgact gatttttaac tttcaatgtc   2400
```

```
catctttcaa aggaagtaac accaaggtac aatgttaaag gaatattcac tttacctagc   2460

agggaaaaat acacaaaaac tgcagatact tcatatagcc cattttaact tgtataaact   2520

gtgtgacttg tggcgtctta taaataatgc actgtaaaga ttactgaata gttgtgtcat   2580

gttaatgtgc ctaatttcat gtatcttgta atcatgattg agcctcagaa tcatttggag   2640

aaactatatt ttaaagaaca agacatactt caatgtatta tacagataaa gtattacatg   2700

tgtttgattt taaaagggcg gacattttat taaaatcaat attgtttttg ctttttcaaa   2760

aaaaaaaaaa aaa                                                      2773
```

<210> SEQ ID NO 14
<211> LENGTH: 1155
<212> TYPE: DNA
<213> ORGANISM: Homo sapiens

<400> SEQUENCE: 14

```
atgaattcaa cattattttc ccaggttgaa aatcattcag tccactctaa tttctcagag     60

aagaatgccc agcttctggc ttttgaaaat gatgattgtc atctgccctt ggccatgata    120

tttaccttag ctcttgctta tggagctgtg atcattcttg gtgtctctgg aaacctggcc    180

ttgatcataa tcatcttgaa acaaaaggag atgagaaatg ttaccaacat cctgattgtg    240

aacctttcct tctcagactt gcttgttgcc atcatgtgtc tcccctttac atttgtctac    300

acattaatgg accactgggt ctttggtgag gcgatgtgta agttgaatcc ttttgtgcaa    360

tgtgtttcaa tcactgtgtc cattttctct ctggttctca ttgctgtgga acgacatcag    420

ctgataatca accctcgagg gtggagacca aataatagac atgcttatgt aggtattgct    480

gtgatttggg tccttgctgt ggcttcttct ttgcctttcc tgatctacca agtaatgact    540

gatgagccgt tccaaaatgt aacacttgat gcgtacaaag acaaatacgt gtgctttgat    600

caatttccat cggactctca taggttgtct tataccactc tcctcttggt gctgcagtat    660

tttggtccac tttgttttat atttatttgc tacttcaaga tatatatacg cctaaaaagg    720

agaaacaaca tgatggacaa gatgagagac aataagtaca ggtccagtga aaccaaaaga    780

atcaatatca tgctgctctc cattgtggta gcatttgcag tctgctggct ccctcttacc    840

atctttaaca ctgtgtttga ttggaatcat cagatcattg ctacctgcaa ccacaatctg    900

ttattcctgc tctgccacct cacagcaatg atatccactt gtgtcaaccc catattttat    960

gggttcctga acaaaaactt ccagagagac ttgcagttct tcttcaactt ttgtgatttc   1020

cggtctcggg atgatgatta tgaaacaata gccatgtcca cgatgcacac agatgtttcc   1080

aaaacttctt tgaagcaagc aagcccagtc gcatttaaaa aaatcaacaa caatgatgat   1140

aatgaaaaaa tctga                                                    1155
```

<210> SEQ ID NO 15
<211> LENGTH: 384
<212> TYPE: PRT
<213> ORGANISM: Homo sapiens

<400> SEQUENCE: 15

```
Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45
```

```
Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
    290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Phe Asn
                325                 330                 335

Phe Cys Asp Phe Arg Ser Arg Asp Asp Asp Tyr Glu Thr Ile Ala Met
            340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asn Asp Asp Asn Glu Lys Ile
    370                 375                 380
```

<210> SEQ ID NO 16
<211> LENGTH: 1152
<212> TYPE: DNA
<213> ORGANISM: Macaca mulatta

<400> SEQUENCE: 16

```
atgaattcaa cattattttc ccaggttgaa aaccactcag tccactctaa tttctcagag      60

aagaatgccc agcttttggc ttttgaaaat gatgattgtc atctgccctt ggccatgata     120

tttaccttag ctcttgctta tggagctgtg atcattcttg gtgtctctgg aaacctggcc     180

ttgatcataa tcatcctgaa acaaaaggag atgagaaatg ttaccaacat cctgattgtg     240
```

```
aacctttcct tctcagactt gcttgtcgcc atcatgtgtc tcccctttac atttgtctac    300

acattaatgg accactgggt ctttggtgag gcaatgtgta agttgaatcc ttttgtgcaa    360

tgtgtttcaa tcactgtgtc cattttctct ctggttctca ttgctgtgga acgacatcag    420

ctgataatca accctcgagg gtggagacca aataatagac atgcttatgt aggtattgct    480

gtgatttggg tccttgctgt ggcttcttct ctgcctttcc tgatctacca agtaatgact    540

gatgagccgt tccaaaatgt aacacttgat gcgtacaaag acaaatacgt gtgctttgat    600

caatttccat cggactctca taggttgtct tataccactc tcctcttggt gctgcagtat    660

tttggtccac tttgttttat atttatttgc tacttcaaga tatatatacg cttaaaaagg    720

agaaacaaca tgatggacaa gatgagagac aataagtaca ggtccagtga aaccaaaaga    780

atcaatatca tgctgctctc cattgtggta gcatttgcag tctgctggct acctcttacc    840

atctttaaca ctgtgtttga ttggaatcat cagatcattg ctacctgcaa ccacaatctg    900

ttattcctgc tctgccacct cacagcaatg atatccactt gtgtcaaccc catattttat    960

ggattcctga acaaaaactt ccagagagac ttgcagttct tctttaactt ttgtgatttc   1020

cggtctcggg atgatgatta tgaaacaata gccatgtcca ccatgcacac ggatgtttcc   1080

aagacttctt tgaagcaagc aagcccagtc gcatttaaaa aaatcaacaa tgatgataat   1140

gaaagaatct ga                                                        1152
```

<210> SEQ ID NO 17
<211> LENGTH: 383
<212> TYPE: PRT
<213> ORGANISM: Macaca mulatta

<400> SEQUENCE: 17

```
Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205
```

```
Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
    290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Phe Asn
                325                 330                 335

Phe Cys Asp Phe Arg Ser Arg Asp Asp Asp Tyr Glu Thr Ile Ala Met
            340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asp Asp Asn Glu Arg Ile
    370                 375                 380
```

<210> SEQ ID NO 18
<211> LENGTH: 2157
<212> TYPE: DNA
<213> ORGANISM: Mus musculus

<400> SEQUENCE: 18

```
gtaagagtat gctgaagatt tgatccgttt tgaagaacta taactgtcca tttatctaat      60

cggtaacaac aaaacataaa aaaatgaact caactctgtt ctccaaggtt gaaaatcact     120

caattcacta taatgcctca gagaattctc cacttctggc ttttgaaaat gatgactgcc     180

acctgccctt ggctgtgata ttcaccttgg ctctcgctta tggggcggtg attattcttg     240

gcgtctctgg aaacctggca ttgatcataa tcattctgaa acagaaggag atgagaaatg     300

tcaccaacat tctgatcgtg aacctctcct tctcagactt gctcgttgcg gtcatgtgtc     360

tcccgttcac ttttgtatat acactgatgg accactgggt cttcggggag accatgtgca     420

aactgaatcc ctttgtacag tgtgtctcca tcacagtatc cattttctcg ctggttctca     480

tcgctgtgga acggcatcag ctaatcatca acccaagagg gtggagacca aacaatagac     540

atgcttacat aggcattact gtcatttggg tccttgcagt ggcttcttct ctgccctttg     600

tgatctatca aattctgacc gacgagccct tccaaaatgt gtcacttgcg gcgttcaagg     660

acaagtatgt gtgctttgac aaattcccat ctgactctca caggctgtct tacacgactc     720

tcctcctggt gctgcagtat ttcggcccac tctgctttat attcatatgc tacttcaaga     780

tatacattcg cttgaaaagg agaaacaaca tgatggacaa gatccgggac agtaagtaca     840

ggtccagtga gaccaagcga atcaacatca tgctgctctc cattgtggtc gccttcgccg     900

tctgctggct gccccttacc atcttcaaca ctgtgttcga ctggaaccac cagatcattg     960

ccacctgcaa ccacaatctg ctgtttctgc tctgtcacct caccgccatg atctccacct    1020

gcgtcaaccc catcttttat ggattcctga acaaaaattt ccagagagac ttgcagttct    1080

tcttcaactt ttgtgacttc cggtctcgag acgatgacta cgagaccata gccatgtcta    1140
```

```
ccatgcatac ggatgtgtcc aagacgtctc tgaagcaggc tagcccagtc gcatttaaaa   1200

aaatcagtat gaatgacaat gaaaaagtct gaagctgctc agagcatatg gtcccaggcc   1260

atatctgtgg aaaaacaagc acagcctgcc gcatgctttc tttacctatg ctctgggga    1320

acggaatgag gcgcgcttgg aaagcccagg acatctgtgt taaatttgac tgcttttgat   1380

ggttgccctg attacttaga aatctagatt actttgtaat ctatctctgg caacagtttt   1440

gactagatgt cctgtgtgtg tgtgtgtgtg tgtgtgtgtg tgtgtgtgtg tgtgtgtgtg   1500

tatgtgtgtg cgcgcgcgcg cgcgcgcacg tgcaaaagag aaagagagag agagaaggag   1560

agagacagac agactgcctg tctgtctgtc tgtctgtctt tctttatgta tgtgtttgaa   1620

ttatgcatat gacaaagagt tttacattgt gtttgttgga gtgaatttct ctgaagtaat   1680

gtcatgagct catttcaaaa gcagtcacca cctgatattc tcgagaggct gaattttcaa   1740

gatcagatga gatttccgag accccggact accttcgttc cctgctaggc atcatcttag   1800

tctgtcacaa gggtgacagt atacaaagtc accttttga atgtgcctga gtcaaaagag    1860

tgtctgaagt catttggcag catcttttcc ttttcctctc tatttctgta aggactcaat   1920

ttcttatact cctaattgag tcttgcctaa gataaagata agtaaagaac accttttcag   1980

ctgtggatat caccaggagt taggccaccc acaagaatga agtggcagct gggcgtggtg   2040

gcacacacct ttaatcccag cacttgggag gcagagacag gtggatttct gagtttgagg   2100

ccagcctggt ctacaaagtg agttccagaa cagccagggc tatacagagc tcgtgcc      2157
```

<210> SEQ ID NO 19
<211> LENGTH: 1149
<212> TYPE: DNA
<213> ORGANISM: Mus musculus

<400> SEQUENCE: 19

```
atgaactcaa ctctgttctc caaggttgaa aatcactcaa ttcactataa tgcctcagag     60

aattctccac ttctggcttt tgaaaatgat gactgccacc tgcccttggc tgtgatattc    120

accttggctc tcgcttatgg ggcggtgatt attcttggcg tctctggaaa cctggcattg    180

atcataatca ttctgaaaca gaaggagatg agaaatgtca ccaacattct gatcgtgaac    240

ctctccttct cagacttgct cgttgcggtc atgtgtctcc cgttcacttt tgtatataca    300

ctgatggacc actgggtctt cggggagacc atgtgcaaac tgaatccctt tgtacagtgt    360

gtctccatca cagtatccat tttctcgctg gttctcatcg ctgtggaacg gcatcagcta    420

atcatcaacc caagagggtg gagaccaaac aatagacatg cttacatagg cattactgtc    480

atttgggtcc ttgcagtggc ttcttctctg ccctttgtga tctatcaaat tctgaccgac    540

gagcccttcc aaaatgtgtc acttgcggcg ttcaaggaca agtatgtgtg ctttgacaaa    600

ttcccatctg actctcacag gctgtcttac acgactctcc tcctggtgct gcagtatttc    660

ggcccactct gctttatatt catatgctac ttcaagatat acattcgctt gaaaaggaga    720

aacaacatga tggacaagat ccgggacagt aagtacaggt ccagtgagac caagcgaatc    780

aacatcatgc tgctctccat tgtggtcgcc ttcgccgtct gctggctgcc ccttaccatc    840

ttcaacactg tgttcgactg gaaccaccag atcattgcca cctgcaacca caatctgctg    900

tttctgctct gtcacctcac cgccatgatc tccacctgcg tcaaccccat cttttatgga    960

ttcctgaaca aaaatttcca gagagacttg cagttcttct tcaacttttg tgacttccgg   1020

tctcgagacg atgactacga gaccatagcc atgtctacca tgcatacgga tgtgtccaag   1080

acgtctctga agcaggctag cccagtcgca tttaaaaaaa tcagtatgaa tgacaatgaa   1140
```

aaagtctga 1149

<210> SEQ ID NO 20
<211> LENGTH: 382
<212> TYPE: PRT
<213> ORGANISM: Mus musculus

<400> SEQUENCE: 20

Met Asn Ser Thr Leu Phe Ser Lys Val Glu Asn His Ser Ile His Tyr
1 5 10 15

Asn Ala Ser Glu Asn Ser Pro Leu Leu Ala Phe Glu Asn Asp Asp Cys
20 25 30

His Leu Pro Leu Ala Val Ile Phe Thr Leu Ala Leu Ala Tyr Gly Ala
35 40 45

Val Ile Ile Leu Gly Val Ser Gly Asn Leu Ala Leu Ile Ile Ile Ile
50 55 60

Leu Lys Gln Lys Glu Met Arg Asn Val Thr Asn Ile Leu Ile Val Asn
65 70 75 80

Leu Ser Phe Ser Asp Leu Leu Val Ala Val Met Cys Leu Pro Phe Thr
85 90 95

Phe Val Tyr Thr Leu Met Asp His Trp Val Phe Gly Glu Thr Met Cys
100 105 110

Lys Leu Asn Pro Phe Val Gln Cys Val Ser Ile Thr Val Ser Ile Phe
115 120 125

Ser Leu Val Leu Ile Ala Val Glu Arg His Gln Leu Ile Ile Asn Pro
130 135 140

Arg Gly Trp Arg Pro Asn Asn Arg His Ala Tyr Ile Gly Ile Thr Val
145 150 155 160

Ile Trp Val Leu Ala Val Ala Ser Ser Leu Pro Phe Val Ile Tyr Gln
165 170 175

Ile Leu Thr Asp Glu Pro Phe Gln Asn Val Ser Leu Ala Ala Phe Lys
180 185 190

Asp Lys Tyr Val Cys Phe Asp Lys Phe Pro Ser Asp Ser His Arg Leu
195 200 205

Ser Tyr Thr Thr Leu Leu Leu Val Leu Gln Tyr Phe Gly Pro Leu Cys
210 215 220

Phe Ile Phe Ile Cys Tyr Phe Lys Ile Tyr Ile Arg Leu Lys Arg Arg
225 230 235 240

Asn Asn Met Met Asp Lys Ile Arg Asp Ser Lys Tyr Arg Ser Ser Glu
245 250 255

Thr Lys Arg Ile Asn Ile Met Leu Leu Ser Ile Val Val Ala Phe Ala
260 265 270

Val Cys Trp Leu Pro Leu Thr Ile Phe Asn Thr Val Phe Asp Trp Asn
275 280 285

His Gln Ile Ile Ala Thr Cys Asn His Asn Leu Leu Phe Leu Leu Cys
290 295 300

His Leu Thr Ala Met Ile Ser Thr Cys Val Asn Pro Ile Phe Tyr Gly
305 310 315 320

Phe Leu Asn Lys Asn Phe Gln Arg Asp Leu Gln Phe Phe Phe Asn Phe
325 330 335

Cys Asp Phe Arg Ser Arg Asp Asp Asp Tyr Glu Thr Ile Ala Met Ser
340 345 350

Thr Met His Thr Asp Val Ser Lys Thr Ser Leu Lys Gln Ala Ser Pro
355 360 365

```
Val Ala Phe Lys Lys Ile Ser Met Asn Asp Asn Glu Lys Val
    370                 375                 380
```

<210> SEQ ID NO 21
<211> LENGTH: 1801
<212> TYPE: DNA
<213> ORGANISM: Rattus norvegicus

<400> SEQUENCE: 21

```
ggcgaacaga cggattcttt aaaagatata cgttcgcttg aaaaggagaa acaacatgat     60

ggacaaaatc agggacagta agtacaggtc cagtgagacc aaacgaatca acgtcatgct    120

gctctccatc gtggtcgcct tcgcggtctg ctggctgccc cttaccatct tcaacactgt    180

gttcgactgg aatcaccaga tcattgccac ctgcaaccac aatctgctgt tcctgctctg    240

ccacctcacg gccatgatct ccacctgcgt caaccccatc ttttatggat tcctgaacaa    300

aaatttccag agagacttgc agttcttctt caacttttgt gacttccggt ctcgagacga    360

cgactacgag actatagcca tgtctaccat gcatacggac gtgtccaaga cttctttgaa    420

gcaggcaagc ccggttgcat ttaaaaaaat cagtatgaat gacaatgaaa aaatctgaag    480

ctgctgagaa catacggtcc caggctacat ctgtggaaaa acaagcacag cctgtcacat    540

gctttcatta cctgtgctcc cagggaatgg attgaggcag gtttggaaag tccaggacat    600

cctgtgttgg gttttactgc ttttgtgatg gttgccgtga ttacttggca atctagatta    660

ctttgtaatc tatctggcaa cagttttgac cagactctgt gtgtgtgtgt gtgtgtgtgt    720

gtgtgtctgt ctgtctgtct gtctgtgggt atgtgtgtga aattatccat aacaaggagt    780

cttatatcgt atttattgga gtgaatttgt ctgaagtaat gtcatgagct cacttcaaaa    840

gcagtaccta cctgatattc tcaagataat tagattttca agatcagatg agatttccaa    900

gaccttggac taccttcatt ccatgctagg cattatgtta gtctgttaca agggtgacag    960

tatacaaaag tcacctttta ggatgtgccg gagccaaaag agagtctgaa gtcatttggc   1020

agtatctttt ttctctctct ctttttgaga ggtctagatt tgttattcag ctacaattga   1080

gtcttgctta agataaataa gaaggcggct ttcagctgtg tatatatccg ggcgttaggc   1140

cattcacaag aatgaagtgg caaagcaggt cgctgatttc aaaattcctc tgacaaccaa   1200

agcattaatt agtcatttaa tatgtaaact agtcttgcta cagatagata aattgcatcc   1260

aaaggacttg atcatcaaga ggtttttgca tcgctcatca gagcattcag caccatcaag   1320

ctttcttgcg caagcacgtg actctgagag catttctaac tcatactgca tagaaacata   1380

agatgcgttt tccatacaac agtgcctgca tagtaactag tgtttaactc tcaccattta   1440

tccttcatgg cagatgacac atggacaatg tttatgtagg taccctcatc gaactggtaa   1500

ctgttcctaa aaatgtcatg tggccagccc atcctaattt gtataaactg tataacgtgt   1560

ggagttttat aatcatatac tattatatca tagaatactg agtagccctg taatattaat   1620

atatttactt tcacatatct tgtaatcatg atttagactc agaaaagata ctttgaagaa   1680

caagagagtt tcaatgtatt atataaaaat gttgcctgta tgtgatttta gaagggcaaa   1740

cactttctgt attaaaactg ggctttttca gaggaaaaaa aaaaaaaaaa aaaaaaaaaa   1800

a                                                                   1801
```

<210> SEQ ID NO 22
<211> LENGTH: 423
<212> TYPE: DNA
<213> ORGANISM: Rattus norvegicus

<400> SEQUENCE: 22

```
atgatggaca aaatcaggga cagtaagtac aggtccagtg agaccaaacg aatcaacgtc      60

atgctgctct ccatcgtggt cgccttcgcg gtctgctggc tgccccttac catcttcaac     120

actgtgttcg actggaatca ccagatcatt gccacctgca accacaatct gctgttcctg     180

ctctgccacc tcacggccat gatctccacc tgcgtcaacc ccatctttta tggattcctg     240

aacaaaaatt tccagagaga cttgcagttc ttcttcaact tttgtgactt ccggtctcga     300

gacgacgact acgagactat agccatgtct accatgcata cggacgtgtc caagacttct     360

ttgaagcagg caagcccggt tgcatttaaa aaaatcagta tgaatgacaa tgaaaaaatc     420

tga                                                                   423
```

<210> SEQ ID NO 23
<211> LENGTH: 140
<212> TYPE: PRT
<213> ORGANISM: Rattus norvegicus

<400> SEQUENCE: 23

```
Met Met Asp Lys Ile Arg Asp Ser Lys Tyr Arg Ser Ser Glu Thr Lys
1               5                   10                  15

Arg Ile Asn Val Met Leu Leu Ser Ile Val Val Ala Phe Ala Val Cys
            20                  25                  30

Trp Leu Pro Leu Thr Ile Phe Asn Thr Val Phe Asp Trp Asn His Gln
        35                  40                  45

Ile Ile Ala Thr Cys Asn His Asn Leu Leu Phe Leu Leu Cys His Leu
    50                  55                  60

Thr Ala Met Ile Ser Thr Cys Val Asn Pro Ile Phe Tyr Gly Phe Leu
65                  70                  75                  80

Asn Lys Asn Phe Gln Arg Asp Leu Gln Phe Phe Phe Asn Phe Cys Asp
                85                  90                  95

Phe Arg Ser Arg Asp Asp Asp Tyr Glu Thr Ile Ala Met Ser Thr Met
            100                 105                 110

His Thr Asp Val Ser Lys Thr Ser Leu Lys Gln Ala Ser Pro Val Ala
        115                 120                 125

Phe Lys Lys Ile Ser Met Asn Asp Asn Glu Lys Ile
    130                 135                 140
```

<210> SEQ ID NO 24
<211> LENGTH: 3747
<212> TYPE: DNA
<213> ORGANISM: Homo sapiens

<400> SEQUENCE: 24

```
gaattcggcc gctgagagac cctggacact gttcctgctc cctcgccacc aaaacttctc      60

ctccagtccc ctcccctgca ggaccatcgc ccgcagcctc tgcacctgtt ttcttgtgtt     120

taagggtggg gtttgccccc ctccccacgc tcccatctct gatcctccca ccttcacccg     180

cccaccccgc gagtgagtgc ggtgcccagg cgcgcttggc ctgagaggtc ggcagcagac     240

ccggcagcgc caaccgccca gccgctctga ctgctccggc tgcccgcccg cgcggcgcgg     300

gctgtcctgg accctaggag gggacggaac cggacttgcc tttgggcacc ttccagggcc     360

ctctccaggt cggctggcta atcatcggac agacggactg cacacatctt gtttccgcgt     420

ctccgcaaaa acgcgaggtc caggtcagtt gtagactctt gtgctggttg caggccaagt     480

ggacctgtac tgaaaatggg tccaataggt gcagaggctg atgagaacca gacagtggaa     540
```

```
gaaatgaagg tggaacaata cgggccacaa acaactccta gaggtgaact ggtccctgac    600
cctgagccag agcttataga tagtaccaag ctgattgagg tacaagttgt tctcatattg    660
gcctactgct ccatcatctt gcttggggta attggcaact ccttggtgat ccatgtggtg    720
atcaaattca agagcatgcg cacagtaacc aactttttca ttgccaatct ggctgtggca    780
gatcttttgg tgaacactct gtgtctaccg ttcactctta cctatacctt aatgggggag    840
tggaaaatgg gtcctgtcct gtgccacctg gtgccctatg cccagggcct ggcagtacaa    900
gtatccacaa tcaccttgac agtaattgcc ctggaccggc acaggtgcat cgtctaccac    960
ctagagagca agatctccaa gcgaatcagc ttcctgatta ttggcttggc ctggggcatc   1020
agtgccctgc tggcaagtcc cctggccatc ttccgggagt attcgctgat tgagatcatt   1080
ccggactttg agattgtggc ctgtactgaa aagtggcctg gcgaggagaa gagcatctat   1140
ggcactgtct atagtctttc ttccttgttg atcttgtatg ttttgcctct gggcattata   1200
tcattttcct acactcgcat ttggagtaaa ttgaagaacc atgtcagtcc tggagctgca   1260
aatgaccact accatcagcg aaggcaaaaa accaccaaaa tgctggtgtg tgtggtggtg   1320
gtgtttgcgg tcagctggct gcctctccat gccttccagc ttgccgttga cattgacagc   1380
caggtcctgg acctgaagga gtacaaactc atcttcacag tgttccacat tatcgccatg   1440
tgctccactt ttgccaatcc ccttctctat ggctggatga acagcaacta cagaaaggct   1500
ttcctctcgg ccttccgctg tgagcagcgg ttggatgcca ttcactctga ggtgtccgtg   1560
acattcaagg ctaaaaagaa cctggaggtc agaaagaaca gtggccccaa tgactctttc   1620
acagaggcta ccaatgtcta aggaagctgt ggtgtgaaaa tgtatggatg aattctgacc   1680
agagctatga atctggttga tggcggctca caagtgaaaa ctgatttccc attttaaaga   1740
agaagtggat ctaaatggaa gcatctgctg tttaattcct ggaaaactgg ctgggcagag   1800
cctgtgtgaa aatactggaa ttcaaagata aggcaacaaa atggtttact taacagttgg   1860
ttgggtagta ggttgcatta tgagtaaaag cagagagaag tacttttgat tattttcctg   1920
gagtgaagaa aacttgaaca agaaattggt attatcaaag cattgctgag agacggtggg   1980
aaaataagtt gactttcaaa tcacgttagg acctggattg aggaggtgtg cagttcgctg   2040
ctccctgctt ggcttatgaa aacaccactg aacagaaatt tctccaggga gccacaggct   2100
ctccttcatc gcattttgat ttttttgttc attctctaga caaaatccat cagggaatgc   2160
tgcaggaaac gattgccaac tatacgaatg gcttcgagga gataaactga aatttgctat   2220
ataattaata ttttggcaga tgatagggga actcctcaac actcagtggg ccaattgttc   2280
ttaaaaccaa ttgcacgttt ggtgaaagtt tcttcaactc tgaatcaaaa gctgaaattc   2340
tcagaattac aggaaatgca aaccatcatt taatttctaa tttcaagtta catccgcttt   2400
atggagatac tatttagata acaagaatac aacttgatac ttttattgtt ataccttttt   2460
gaacatgtat gatttctgtt gttattccta ttggagctaa gtttgtctac actaaaattt   2520
aaatcagact agagaataat ttttgtggca tgttgtaaca tttcacagta tttacaagct   2580
atttttgcac aggtacatag ctctcatgta tttaaagaac actgcagtgt tattttcttt   2640
gaaattcatc ctccacggac ccattcatac taaataaaac aatgtaatta cattaaaatg   2700
gacctatctg taagaggtac taaaaacact ggattcattt catcttgcaa atgttgtatt   2760
tcaaaccagt ttcacataag ttatttgtct tcttttcaaa ataattagct atatttttat   2820
ataatatgaa tatatacata aaaattgttt ctataaattg tagaacatag atgctacagt   2880
```

```
atttttttatt taattatatt atgaataaaa ttgttatttc aatagtaccc aaccaaagat   2940

gcttaaaaac cttctatgtt cataaaaaat aacaactgag atgttaaaat agtcatacgt   3000

ctttagatgc tattaaagtt tcattagtca tatttttgta aatatgacag aatttgtgaa   3060

tatattttta aagcaaaaaa cttcaacatg catatgatat atagttacaa cattaatttt   3120

atgaactgga gagctttact ttgtggatat atttaaaatt catattatag ctcctattaa   3180

attccttcca tgatagatat aaaggactgg tttttaagtg cactgcactt ctggaatact   3240

gaaaaagaat gaaaacaata tgttagatta ggtgtaagac tttaagaagc gaacaaaaag   3300

taatgtatat ctgtaatata taatcaaatg attcattttt ctgttagact aggcaaattg   3360

ttcaaaaata accttttttgt cttttaagta gcagtcactt tgcttaagat gctaatagaa   3420

aactgtggtt aaagatttac cctccctctt ggtgaattat tacactgtaa gaaatgtata   3480

tgctactgtg ttacatgttg tattagtaaa ttattagaat ccaattaatg attcaattaa   3540

catatatctt atccaattca ttatgtcaat tcattaataa aataccttttt atgtagaggc   3600

tttatgttgc aattaaaaag ttgggaaaat gaaaaaaaaa aaaaaaaaaa aaaaaaaaaa   3660

aaaaaaaaaa aaaaaaaaaa aaaaaaaaaa aaaaaaaaaa aaaaaaaaaa aaaaaaaaaa   3720

aaaaaaaaaa aaaaaaaaaa aaaaaaa                                       3747
```

<210> SEQ ID NO 25
<211> LENGTH: 1146
<212> TYPE: DNA
<213> ORGANISM: Homo sapiens

<400> SEQUENCE: 25

```
atgggtccaa taggtgcaga ggctgatgag aaccagacag tggaagaaat gaaggtggaa     60

caatacgggc cacaaacaac tcctagaggt gaactggtcc ctgaccctga gccagagctt    120

atagatagta ccaagctgat tgaggtacaa gttgttctca tattggccta ctgctccatc    180

atcttgcttg ggggtaattgg caactccttg gtgatccatg tggtgatcaa attcaagagc    240

atgcgcacag taaccaactt tttcattgcc aatctggctg tggcagatct tttggtgaac    300

actctgtgtc taccgttcac tcttacctat accttaatgg gggagtggaa aatgggtcct    360

gtcctgtgcc acctggtgcc ctatgcccag ggcctggcag tacaagtatc cacaatcacc    420

ttgacagtaa ttgccctgga ccggcacagg tgcatcgtct accacctaga gagcaagatc    480

tccaagcgaa tcagcttcct gattattggc ttggcctggg gcatcagtgc cctgctggca    540

agtcccctgg ccatcttccg ggagtattcg ctgattgaga tcattccgga ctttgagatt    600

gtggcctgta ctgaaaagtg gcctggcgag gagaagagca tctatggcac tgtctatagt    660

ctttcttcct tgttgatctt gtatgttttg cctctgggca ttatatcatt ttcctacact    720

cgcatttgga gtaaattgaa gaaccatgtc agtcctggag ctgcaaatga ccactaccat    780

cagcgaaggc aaaaaaccac caaaatgctg gtgtgtgtgg tggtggtgtt tgcggtcagc    840

tggctgcctc tccatgcctt ccagcttgcc gttgacattg acagccaggt cctggacctg    900

aaggagtaca aactcatctt cacagtgttc cacattatcg ccatgtgctc cacttttgcc    960

aatccccttc tctatggctg gatgaacagc aactacagaa aggctttcct ctcggccttc   1020

cgctgtgagc agcggttgga tgccattcac tctgaggtgt ccgtgacatt caaggctaaa   1080

aagaacctgg aggtcagaaa gaacagtggc cccaatgact ctttcacaga ggctaccaat   1140

gtctaa                                                              1146
```

<210> SEQ ID NO 26
<211> LENGTH: 381
<212> TYPE: PRT
<213> ORGANISM: Homo sapiens

<400> SEQUENCE: 26

```
Met Gly Pro Ile Gly Ala Glu Ala Asp Glu Asn Gln Thr Val Glu Glu
1               5                   10                  15

Met Lys Val Glu Gln Tyr Gly Pro Gln Thr Thr Pro Arg Gly Glu Leu
            20                  25                  30

Val Pro Asp Pro Glu Pro Glu Leu Ile Asp Ser Thr Lys Leu Ile Glu
        35                  40                  45

Val Gln Val Val Leu Ile Leu Ala Tyr Cys Ser Ile Ile Leu Leu Gly
    50                  55                  60

Val Ile Gly Asn Ser Leu Val Ile His Val Val Ile Lys Phe Lys Ser
65                  70                  75                  80

Met Arg Thr Val Thr Asn Phe Phe Ile Ala Asn Leu Ala Val Ala Asp
                85                  90                  95

Leu Leu Val Asn Thr Leu Cys Leu Pro Phe Thr Leu Thr Tyr Thr Leu
            100                 105                 110

Met Gly Glu Trp Lys Met Gly Pro Val Leu Cys His Leu Val Pro Tyr
        115                 120                 125

Ala Gln Gly Leu Ala Val Gln Val Ser Thr Ile Thr Leu Thr Val Ile
    130                 135                 140

Ala Leu Asp Arg His Arg Cys Ile Val Tyr His Leu Glu Ser Lys Ile
145                 150                 155                 160

Ser Lys Arg Ile Ser Phe Leu Ile Ile Gly Leu Ala Trp Gly Ile Ser
                165                 170                 175

Ala Leu Leu Ala Ser Pro Leu Ala Ile Phe Arg Glu Tyr Ser Leu Ile
            180                 185                 190

Glu Ile Ile Pro Asp Phe Glu Ile Val Ala Cys Thr Glu Lys Trp Pro
        195                 200                 205

Gly Glu Glu Lys Ser Ile Tyr Gly Thr Val Tyr Ser Leu Ser Ser Leu
    210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Asn His Val Ser Pro Gly Ala Ala Asn
                245                 250                 255

Asp His Tyr His Gln Arg Arg Gln Lys Thr Thr Lys Met Leu Val Cys
            260                 265                 270

Val Val Val Val Phe Ala Val Ser Trp Leu Pro Leu His Ala Phe Gln
        275                 280                 285

Leu Ala Val Asp Ile Asp Ser Gln Val Leu Asp Leu Lys Glu Tyr Lys
    290                 295                 300

Leu Ile Phe Thr Val Phe His Ile Ile Ala Met Cys Ser Thr Phe Ala
305                 310                 315                 320

Asn Pro Leu Leu Tyr Gly Trp Met Asn Ser Asn Tyr Arg Lys Ala Phe
                325                 330                 335

Leu Ser Ala Phe Arg Cys Glu Gln Arg Leu Asp Ala Ile His Ser Glu
            340                 345                 350

Val Ser Val Thr Phe Lys Ala Lys Lys Asn Leu Glu Val Arg Lys Asn
        355                 360                 365

Ser Gly Pro Asn Asp Ser Phe Thr Glu Ala Thr Asn Val
    370                 375                 380
```

<210> SEQ ID NO 27
<211> LENGTH: 1146
<212> TYPE: DNA
<213> ORGANISM: Macaca mulatta

<400> SEQUENCE: 27

```
atgggtccaa taggtacaga ggctgatgag aaccagacag tggaagaaat gaaggtggaa     60
caatatgggc cacaaaccac tcctagaggt gaactggtcc ctgatcctga gccagagctt    120
atagatagta ccaagctgat tgaggtacaa gttgtcctca tattggccta ttgctccatc    180
atcttgcttg ggtaattgg caactccttg gtgatccacg tggtgatcaa attcaagagc     240
atgcgcacag taaccaactt tttcatcgcc aatctggctg tggcagatct tgtggtgaat    300
actctgtgtc taccattcac tcttacctac accttaatgg gggagtggaa aatgggtcct    360
gtcctgtgcc acctggtgcc ctatgcacag ggcctggcag tacaagtatc cacaatcacc    420
ttgacagtaa ttgccctgga ccggcacagg tgcatcgtct accacctgga gagcaagatc    480
tccaagcgta tcagcttcct gattattggc ttggcctggg gcatcagtgc cctgctagca    540
agtcccctgg ccatcttccg ggagtattca ctgattgaga tcattccgga ttttgagatt    600
gtggcctgta ctgaaaaatg gcctggcgag gaaaagagca tctatggcac tgtctacagt    660
ctttcttcct tgttgatcct gtacgttttg cctctgggca taatatcatt ttcctacact    720
cgcatttgga gtaaattgaa gagccatgtc agtcctggag ctgcaaatga ccactaccat    780
cagcgaaggc aaaaaaccac caaaatgctg gtgtgcgtgg tggtggtgtt tgcggtcagc    840
tggctgcctc tccatgcctt ccagcttgcc gttgacattg acagccatgt cctggacctg    900
aaggagtaca aactcatctt cacagtgttc cacatcatcg ccatgtgctc cacttttgcc    960
aatccccttc tctatggctg gatgaacagc aactatagaa aggctttcct ctctgccttc   1020
cgctgtgagc agcggttgga tgccattcac tctgaggtgt ccgtgacatt caaggctaaa   1080
aagaacctgg aggtcagaaa aaatagtggc cccaatgact ctttcacaga agctaccaat   1140
gtctaa                                                              1146
```

<210> SEQ ID NO 28
<211> LENGTH: 381
<212> TYPE: PRT
<213> ORGANISM: Macaca mulatta

<400> SEQUENCE: 28

```
Met Gly Pro Ile Gly Thr Glu Ala Asp Glu Asn Gln Thr Val Glu Glu
1               5                   10                  15

Met Lys Val Glu Gln Tyr Gly Pro Gln Thr Thr Pro Arg Gly Glu Leu
            20                  25                  30

Val Pro Asp Pro Glu Pro Glu Leu Ile Asp Ser Thr Lys Leu Ile Glu
        35                  40                  45

Val Gln Val Val Leu Ile Leu Ala Tyr Cys Ser Ile Ile Leu Leu Gly
    50                  55                  60

Val Ile Gly Asn Ser Leu Val Ile His Val Val Ile Lys Phe Lys Ser
65                  70                  75                  80

Met Arg Thr Val Thr Asn Phe Phe Ile Ala Asn Leu Ala Val Ala Asp
                85                  90                  95

Leu Val Val Asn Thr Leu Cys Leu Pro Phe Thr Leu Thr Tyr Thr Leu
            100                 105                 110

Met Gly Glu Trp Lys Met Gly Pro Val Leu Cys His Leu Val Pro Tyr
        115                 120                 125
```

```
Ala Gln Gly Leu Ala Val Gln Val Ser Thr Ile Thr Leu Thr Val Ile
    130                 135                 140

Ala Leu Asp Arg His Arg Cys Ile Val Tyr His Leu Glu Ser Lys Ile
145                 150                 155                 160

Ser Lys Arg Ile Ser Phe Leu Ile Ile Gly Leu Ala Trp Gly Ile Ser
                165                 170                 175

Ala Leu Leu Ala Ser Pro Leu Ala Ile Phe Arg Glu Tyr Ser Leu Ile
            180                 185                 190

Glu Ile Ile Pro Asp Phe Glu Ile Val Ala Cys Thr Glu Lys Trp Pro
        195                 200                 205

Gly Glu Glu Lys Ser Ile Tyr Gly Thr Val Tyr Ser Leu Ser Ser Leu
    210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Ser His Val Ser Pro Gly Ala Ala Asn
                245                 250                 255

Asp His Tyr His Gln Arg Arg Gln Lys Thr Thr Lys Met Leu Val Cys
            260                 265                 270

Val Val Val Val Phe Ala Val Ser Trp Leu Pro Leu His Ala Phe Gln
        275                 280                 285

Leu Ala Val Asp Ile Asp Ser His Val Leu Asp Leu Lys Glu Tyr Lys
    290                 295                 300

Leu Ile Phe Thr Val Phe His Ile Ile Ala Met Cys Ser Thr Phe Ala
305                 310                 315                 320

Asn Pro Leu Leu Tyr Gly Trp Met Asn Ser Asn Tyr Arg Lys Ala Phe
                325                 330                 335

Leu Ser Ala Phe Arg Cys Glu Gln Arg Leu Asp Ala Ile His Ser Glu
            340                 345                 350

Val Ser Val Thr Phe Lys Ala Lys Lys Asn Leu Glu Val Arg Lys Asn
        355                 360                 365

Ser Gly Pro Asn Asp Ser Phe Thr Glu Ala Thr Asn Val
    370                 375                 380
```

<210> SEQ ID NO 29
<211> LENGTH: 3379
<212> TYPE: DNA
<213> ORGANISM: Mus musculus

<400> SEQUENCE: 29

```
ggcacgagct ctgagctgtg cagtgcgggg tccctgatcg agtggcttta gaggtccacc      60

gagaagccga gcaggcacag cattgcagct gttccgcttt gccgctcctg cttctgatct     120

cacttgctgg ctcacaccaa atcggacctg ctttgggtgc ctcccaggta ctgtctccag     180

actggctgtt tagataatcc cttgcttgaa attcctggat tcctcatctg agaaggaaac     240

gcgcaagagt caatacagta agccaagtga gagtgaatgg ttctgaagat gggcccggta     300

ggtgcagagg cagatgagaa tcaaactgta gaagtgaaag tggagcccta tgggccaggg     360

cacactactc ctagaggtga gttgcccccct gatccggagc cggagctcat agacagcacc     420

aaactggtcg aggtgcaggt gatcctcata ttggcctact gctccatcat cttgctaggg     480

gtagttggca actccctggt aatccatgtg gtaatcaaat tcaagagcat gcgcacagta     540

accaactttt ttattgccaa cctggctgtg gcggatcttt tggtgaacac cctgtgcctg     600

ccattcactc ttacctatac cttgatggga gagtggaaaa tgggtccggt cttgtgccat     660
```

-continued

```
ttggtgccct atgcccaggg tctggcggta caagtgtcca caataacttt gacagtcatt    720
gctctggacc gccatcgttg cattgtctac cacctggaga gcaagatctc caagcgaatc    780
agcttcctga tcattggcct ggcctggggc atcagcgctc tgctggcaag tccactggcc    840
atcttccggg aatactccct gattgagatc attcctgact ttgagattgt ggcctgtacc    900
gagaagtggc ctggggaaga gaagagtgtg tatggtacag tctacagcct ttccaccctg    960
ctcatcctgt acgttttgcc tctgggcatc atatctttct cctacacccg tatctggagt   1020
aagctgagga accacgtcag tcctggagct gcaagtgacc attaccatca gcgaaggcac   1080
aaaatgacca aaatgctggt gtgcgtggta gtggtgtttg cagtcagctg gctacccctc   1140
cacgccttcc aactcgctgt ggacatcgac agccacgtcc tggacctgaa ggagtacaaa   1200
ctcatcttca ccgtgttcca cattatcgcc atgtgctcca cctttgccaa ccccccttctc   1260
tatggttgga tgaatagcaa ctacagaaaa gctttcctct cggccttccg ctgtgagcag   1320
aggttggatg ccattcactc ggaggtgtct atgaccttca aggctaaaaa gaacctggaa   1380
gtcaaaaaga acaatggccc cactgactct ttttcggagg ctaccaatgt gtaaggacac   1440
aggtgtgaaa gcacatgggt gaattgtaac cagcgctgcc aatctggtta gggaaggttt   1500
tctggccagt gcatgcagac ctcccattgt attgactcaa aaagcaacag aaccgaagcc   1560
cccgcagttt tatttctgga aaactggctg gcagaaggag gttaaaataa acagattgcc   1620
atggcacaac gttctgatta ccgatgcttg gattgtaggt tgaattctga gtagagaagg   1680
gaaggaaaac agaaacaagg agttggcacc agcatggtta aaagggagaa gtaagtgtta   1740
tctcctgaga gccacagtag gatctgcatc caggcacact gtggactcca tgggctcccc   1800
tcatcacttg atgaaaagct gctaaacaac tcagatttcc ctagggagct acaggctctc   1860
tgttagggtg ttttggtttt attgtgttta cctaagatga aacccaaatg agaatgctat   1920
aggtaaacat ggcttgctac ctaaggcggt gacttcaaga taacgtcaag agaataaaca   1980
cattgctata cgagtaatgt ttcggcaatg atgggagaga ttctaatata atcagtgagc   2040
aattagttgt tgttcagatc aaatgcacta ctgttgaaag tttgtttttt agttcagaat   2100
caaaatctga aattatcata ctgaaaagga atgaaaacaa ttgctttatt tctgtaatag   2160
ccattcctgc ttaggtagat actgtttgga tgacaagcga gcaactcagc tcttctgttt   2220
cttgctaact gctaaagcct tttggaacca cacaactttt gttaccattc ctgcatgaga   2280
gcaaacaaag ttcacactaa aagttaaatc agactaaaac ataattttgt aacaatttga   2340
gtttagttgt aaaaaattga ccccctccac cacagctcta acatgtttac agacactgta   2400
gaactatctt ctttggagtt catccacaat agaccaattt aagttaagta aaaatataat   2460
ttcactaaag tgaacccatt tggtaagaaa tctccaaaac tgagtttatt ccactttgaa   2520
aattttgttt ttatccacaa atttcacata aatgttctct tttttaaatg actatatttt   2580
tggtaacata aatacatata caaaacaaaa gcatattcta taaataggga agcattagaa   2640
aattttattt aatagtttta tgaatatagc ttttatttca aaggtaccca gcccaaagat   2700
aattaaaact ctattttgtt cacacagaaa agtacgaaaa atgagatgtt aaaatagttg   2760
cacttctctg gatgctgacg tttcagtgta ggcatatttt ttgtaaatat ggcagaatct   2820
gtgtgtatat tcctcacaat ttagaaatat ttgatgtagt ctaatattta gttatgatat   2880
taattttgta tatatattta aatctcagac tctggctgtt attaaattcc tttcagtgtg   2940
gaaataaaag attggtctca aagtgaattg ttcttctaga gtactgaaaa ggaataaaac   3000
accagaagaa aaaaatgaat ctaaggtgga acgggaagtc caccttatac actgctgtct   3060
```

gaagtgaatc gttgaactat aaaagacatc tttcctgttg gactctgcac agtcattctg 3120
aaggagcttt ttacttttct atgtgtaaga tacttgctta agatcttagt agaaggttgt 3180
tgtgaagtct ttatgcccct tgcagatttc ctatcctgta caaaacctgt ctgttactgt 3240
gactccggct gtgatggtaa attattggaa tccaattagt gattcaatta acatatttgt 3300
gattgagttc atatgtcaac tcagtattaa agcatctttt atgtgctggt tttaatgtca 3360
aaataaaaag gatttgagg 3379

<210> SEQ ID NO 30
<211> LENGTH: 1158
<212> TYPE: DNA
<213> ORGANISM: Mus musculus

<400> SEQUENCE: 30
atggttctga agatgggccc ggtaggtgca gaggcagatg agaatcaaac tgtagaagtg 60
aaagtggagc cctatgggcc agggcacact actcctagag gtgagttgcc ccctgatccg 120
gagccggagc tcatagacag caccaaactg gtcgaggtgc aggtgatcct catattggcc 180
tactgctcca tcatcttgct aggggtagtt ggcaactccc tggtaatcca tgtggtaatc 240
aaattcaaga gcatgcgcac agtaaccaac tttttttattg ccaacctggc tgtggcggat 300
cttttggtga acaccctgtg cctgccattc actcttacct ataccttgat gggagagtgg 360
aaaatgggtc cggtcttgtg ccatttggtg ccctatgccc agggtctggc ggtacaagtg 420
tccacaataa ctttgacagt cattgctctg gaccgccatc gttgcattgt ctaccacctg 480
gagagcaaga tctccaagcg aatcagcttc ctgatcattg gcctggcctg gggcatcagc 540
gctctgctgg caagtccact ggccatcttc cgggaatact ccctgattga gatcattcct 600
gactttgaga ttgtggcctg taccgagaag tggcctgggg aagagaagag tgtgtatggt 660
acagtctaca gcctttccac cctgctcatc ctgtacgttt tgcctctggg catcatatct 720
ttctcctaca cccgtatctg gagtaagctg aggaaccacg tcagtcctgg agctgcaagt 780
gaccattacc atcagcgaag gcacaaaatg accaaaatgc tggtgtgcgt ggtagtggtg 840
tttgcagtca gctggctacc cctccacgcc ttccaactcg ctgtggacat cgacagccac 900
gtcctggacc tgaaggagta caaactcatc ttcaccgtgt tccacattat cgccatgtgc 960
tccacctttg ccaacccccct tctctatggt tggatgaata gcaactacag aaaagctttc 1020
ctctcggcct tccgctgtga gcagaggttg gatgccattc actcggaggt gtctatgacc 1080
ttcaaggcta aaaagaacct ggaagtcaaa aagaacaatg gccccactga ctctttttcg 1140
gaggctacca atgtgtaa 1158

<210> SEQ ID NO 31
<211> LENGTH: 385
<212> TYPE: PRT
<213> ORGANISM: Mus musculus

<400> SEQUENCE: 31

Met Val Leu Lys Met Gly Pro Val Gly Ala Glu Ala Asp Glu Asn Gln
1 5 10 15

Thr Val Glu Val Lys Val Glu Pro Tyr Gly Pro Gly His Thr Thr Pro
20 25 30

Arg Gly Glu Leu Pro Pro Asp Pro Glu Pro Glu Leu Ile Asp Ser Thr
35 40 45

Lys Leu Val Glu Val Gln Val Ile Leu Ile Leu Ala Tyr Cys Ser Ile

```
    50                  55                  60

Ile Leu Leu Gly Val Val Gly Asn Ser Leu Val Ile His Val Val Ile
65                  70                  75                  80

Lys Phe Lys Ser Met Arg Thr Val Thr Asn Phe Phe Ile Ala Asn Leu
                85                  90                  95

Ala Val Ala Asp Leu Leu Val Asn Thr Leu Cys Leu Pro Phe Thr Leu
            100                 105                 110

Thr Tyr Thr Leu Met Gly Glu Trp Lys Met Gly Pro Val Leu Cys His
        115                 120                 125

Leu Val Pro Tyr Ala Gln Gly Leu Ala Val Gln Val Ser Thr Ile Thr
    130                 135                 140

Leu Thr Val Ile Ala Leu Asp Arg His Arg Cys Ile Val Tyr His Leu
145                 150                 155                 160

Glu Ser Lys Ile Ser Lys Arg Ile Ser Phe Leu Ile Ile Gly Leu Ala
                165                 170                 175

Trp Gly Ile Ser Ala Leu Leu Ala Ser Pro Leu Ala Ile Phe Arg Glu
            180                 185                 190

Tyr Ser Leu Ile Glu Ile Ile Pro Asp Phe Glu Ile Val Ala Cys Thr
        195                 200                 205

Glu Lys Trp Pro Gly Glu Glu Lys Ser Val Tyr Gly Thr Val Tyr Ser
    210                 215                 220

Leu Ser Thr Leu Leu Ile Leu Tyr Val Leu Pro Leu Gly Ile Ile Ser
225                 230                 235                 240

Phe Ser Tyr Thr Arg Ile Trp Ser Lys Leu Arg Asn His Val Ser Pro
                245                 250                 255

Gly Ala Ala Ser Asp His Tyr His Gln Arg Arg His Lys Met Thr Lys
            260                 265                 270

Met Leu Val Cys Val Val Val Val Phe Ala Val Ser Trp Leu Pro Leu
        275                 280                 285

His Ala Phe Gln Leu Ala Val Asp Ile Asp Ser His Val Leu Asp Leu
    290                 295                 300

Lys Glu Tyr Lys Leu Ile Phe Thr Val Phe His Ile Ile Ala Met Cys
305                 310                 315                 320

Ser Thr Phe Ala Asn Pro Leu Leu Tyr Gly Trp Met Asn Ser Asn Tyr
                325                 330                 335

Arg Lys Ala Phe Leu Ser Ala Phe Arg Cys Glu Gln Arg Leu Asp Ala
            340                 345                 350

Ile His Ser Glu Val Ser Met Thr Phe Lys Ala Lys Lys Asn Leu Glu
        355                 360                 365

Val Lys Lys Asn Asn Gly Pro Thr Asp Ser Phe Ser Glu Ala Thr Asn
    370                 375                 380

Val
385


<210> SEQ ID NO 32
<211> LENGTH: 1147
<212> TYPE: DNA
<213> ORGANISM: Rattus norvegicus

<400> SEQUENCE: 32

atgggcccat taggtgcaga ggcagatgag aatcaaactg tagaagtgaa agtggaactc      60

tatgggtcgg ggcccaccac tcctagaggt gagttgcccc ctgatccaga gccggagctc     120

atagacagca ccaaactggt tgaggtgcag gtggtcctta tactggccta ttgttccatc     180
```

```
atcttgctgg gcgtagttgg caactctctg gtaatccatg tggtgatcaa attcaagagc    240

atgcgcacag taaccaactt ttttattgcc aacctggctg tggcggatct tttggtgaac    300

accctgtgcc tgccattcac tcttacctat accttgatgg gggagtggaa aatgggtcca    360

gttttgtgcc atttggtgcc ctatgcccag ggtctggcag tacaagtgtc cacaataact    420

ttgacagtca ttgctttgga ccgacatcgt tgcattgtct accacctgga gagcaagatc    480

tccaagcaaa tcagcttcct gattattggc ctggcgtggg gtgtcagcgc tctgctggca    540

agtccccttg ccatcttccg ggagtactca ctgattgaga ttattcctga ctttgagatt    600

gtagcctgta ctgagaaatg gcccggggag gagaagagtg tgtacggtac agtctacagc    660

ctttccaccc tgctaatcct ctacgttttg cctctgggca tcatatcttt ctcctacacc    720

cggatctgga gtaagctaaa gaaccacgtt agtcctggag ctgcaagtga ccattaccat    780

cagcgaaggc acaaaacgac caaaatgctc gtgtgcgtgg tagtggtgtt tgcagtcagc    840

tggctgcccc tccatgcctt ccaacttgct gtggacatcg acagccatgt cctggacctg    900

aaggagtaca aactcatctt caccgtgttc cacattattg cgatgtgctc caccttcgcc    960

aaccccctte tctatggctg gatgaacagc aactacagaa aagctttcct ctcagccttc   1020

cgctgtgagc agaggttgga tgccattcac tcggaggtgt ccatgacctt caaggctaaa   1080

aagaacctgg aagtcaaaaa gaacaatggc ctcactgact ctttttcaga ggccaccaac   1140

gtgtaag                                                             1147
```

<210> SEQ ID NO 33
<211> LENGTH: 1146
<212> TYPE: DNA
<213> ORGANISM: Rattus norvegicus

<400> SEQUENCE: 33

```
atgggcccat taggtgcaga ggcagatgag aatcaaactg tagaagtgaa agtggaactc     60

tatgggtcgg ggcccaccac tcctagaggt gagttgcccc ctgatccaga gccggagctc    120

atagacagca ccaaactggt tgaggtgcag gtggtcctta tactggccta ttgttccatc    180

atcttgctgg gcgtagttgg caactctctg gtaatccatg tggtgatcaa attcaagagc    240

atgcgcacag taaccaactt ttttattgcc aacctggctg tggcggatct tttggtgaac    300

accctgtgcc tgccattcac tcttacctat accttgatgg gggagtggaa aatgggtcca    360

gttttgtgcc atttggtgcc ctatgcccag ggtctggcag tacaagtgtc cacaataact    420

ttgacagtca ttgctttgga ccgacatcgt tgcattgtct accacctgga gagcaagatc    480

tccaagcaaa tcagcttcct gattattggc ctggcgtggg gtgtcagcgc tctgctggca    540

agtccccttg ccatcttccg ggagtactca ctgattgaga ttattcctga ctttgagatt    600

gtagcctgta ctgagaaatg gcccggggag gagaagagtg tgtacggtac agtctacagc    660

ctttccaccc tgctaatcct ctacgttttg cctctgggca tcatatcttt ctcctacacc    720

cggatctgga gtaagctaaa gaaccacgtt agtcctggag ctgcaagtga ccattaccat    780

cagcgaaggc acaaaacgac caaaatgctc gtgtgcgtgg tagtggtgtt tgcagtcagc    840

tggctgcccc tccatgcctt ccaacttgct gtggacatcg acagccatgt cctggacctg    900

aaggagtaca aactcatctt caccgtgttc cacattattg cgatgtgctc caccttcgcc    960

aacccccttc tctatggctg gatgaacagc aactacagaa aagctttcct ctcagccttc   1020

cgctgtgagc agaggttgga tgccattcac tcggaggtgt ccatgacctt caaggctaaa   1080

aagaacctgg aagtcaaaaa gaacaatggc ctcactgact ctttttcaga ggccaccaac   1140
```

```
gtgtaa                                                              1146


<210> SEQ ID NO 34
<211> LENGTH: 381
<212> TYPE: PRT
<213> ORGANISM: Rattus norvegicus

<400> SEQUENCE: 34

Met Gly Pro Leu Gly Ala Glu Ala Asp Glu Asn Gln Thr Val Glu Val
1               5                   10                  15

Lys Val Glu Leu Tyr Gly Ser Gly Pro Thr Thr Pro Arg Gly Glu Leu
            20                  25                  30

Pro Pro Asp Pro Glu Pro Glu Leu Ile Asp Ser Thr Lys Leu Val Glu
        35                  40                  45

Val Gln Val Val Leu Ile Leu Ala Tyr Cys Ser Ile Ile Leu Leu Gly
    50                  55                  60

Val Val Gly Asn Ser Leu Val Ile His Val Val Ile Lys Phe Lys Ser
65                  70                  75                  80

Met Arg Thr Val Thr Asn Phe Phe Ile Ala Asn Leu Ala Val Ala Asp
                85                  90                  95

Leu Leu Val Asn Thr Leu Cys Leu Pro Phe Thr Leu Thr Tyr Thr Leu
            100                 105                 110

Met Gly Glu Trp Lys Met Gly Pro Val Leu Cys His Leu Val Pro Tyr
        115                 120                 125

Ala Gln Gly Leu Ala Val Gln Val Ser Thr Ile Thr Leu Thr Val Ile
    130                 135                 140

Ala Leu Asp Arg His Arg Cys Ile Val Tyr His Leu Glu Ser Lys Ile
145                 150                 155                 160

Ser Lys Gln Ile Ser Phe Leu Ile Ile Gly Leu Ala Trp Gly Val Ser
                165                 170                 175

Ala Leu Leu Ala Ser Pro Leu Ala Ile Phe Arg Glu Tyr Ser Leu Ile
            180                 185                 190

Glu Ile Ile Pro Asp Phe Glu Ile Val Ala Cys Thr Glu Lys Trp Pro
        195                 200                 205

Gly Glu Glu Lys Ser Val Tyr Gly Thr Val Tyr Ser Leu Ser Thr Leu
    210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Asn His Val Ser Pro Gly Ala Ala Ser
                245                 250                 255

Asp His Tyr His Gln Arg Arg His Lys Thr Thr Lys Met Leu Val Cys
            260                 265                 270

Val Val Val Val Phe Ala Val Ser Trp Leu Pro Leu His Ala Phe Gln
        275                 280                 285

Leu Ala Val Asp Ile Asp Ser His Val Leu Asp Leu Lys Glu Tyr Lys
    290                 295                 300

Leu Ile Phe Thr Val Phe His Ile Ile Ala Met Cys Ser Thr Phe Ala
305                 310                 315                 320

Asn Pro Leu Leu Tyr Gly Trp Met Asn Ser Asn Tyr Arg Lys Ala Phe
                325                 330                 335

Leu Ser Ala Phe Arg Cys Glu Gln Arg Leu Asp Ala Ile His Ser Glu
            340                 345                 350

Val Ser Met Thr Phe Lys Ala Lys Lys Asn Leu Glu Val Lys Lys Asn
        355                 360                 365
```

```
Asn Gly Leu Thr Asp Ser Phe Ser Glu Ala Thr Asn Val
    370                 375                 380
```

<210> SEQ ID NO 35
<211> LENGTH: 1956
<212> TYPE: DNA
<213> ORGANISM: Homo sapiens

<400> SEQUENCE: 35

```
gggcacagga gtgcggccgg gggcggggcc gagtgggccc cggtacgaac cctccgggaa     60
gccgggcgcg ctgcctgccc ttggcccggg gcgcagagcg tcacactgga tctggggagc    120
atcctacccc cactgtggac ctcagtctcc tcacctgaga catgggcggc cccatccgca    180
ccctgtaagc cgcaagccaa ggagattcct ggccccccatc ctggattcac ttaactacat    240
ctcctggtgg aagggccctg ggatctgcac tttcaacatg cttctagaat gattctgatg    300
tttactgaag gttgagaact gcaaccctgt gggattaata atgactagag aatctgagag    360
gcgtcatccc tcaagtgtat cacttagttc aagagtcctg gaatcttttc acatccacta    420
tgaacacctc tcacctcctg gccttgctgc tcccaaaatc tccacaaggt gaaaacagaa    480
gcaaacccct gggcacccca tacaacttct ctgaacattg ccaggattcc gtggacgtga    540
tggtcttcat cgtcacttcc tacagcattg agactgtcgt gggggtcctg ggtaacctct    600
gcctgatgtg tgtgactgtg aggcagaagg agaaagccaa cgtgaccaac ctgcttatcg    660
ccaacctggc cttctctgac ttcctcatgt gcctcctctg ccagccgctg acctccgtct    720
acaccatcat ggactactgg atctttggag agaccctctg caagatgtcg gccttcatcc    780
agtgcatgtc ggtgacggtc tccatcctct cgctcgtcct cgtggccctg gagaggcatc    840
agctcatcat caacccaaca ggctggaagc ccagcatctc acaggcctac ctggggattg    900
tgctcatctg ggtcattgcc tgtgtcctct ccctgccctt cctggccaac agcatcctgg    960
agaatgtctt ccacaagaac cactccaagg ctctggagtt cctggcggat aaggtggtct   1020
gtaccgagtc ctggccactg gctcaccacc gcaccatcta caccaccttc ctgctcctct   1080
tccagtactg cctcccactg ggcttcatct tggtctgtta tgcacgcatc taccggcgcc   1140
tgcagaggca ggggcgcgtg tttcacaagg gcacctacag cttgcgagct gggcacatga   1200
agcaggtcaa tgtggtgctg gtggtgatgg tggtggcctt tgccgtgctc tggctgcctc   1260
tgcatgtgtt caacagcctg gaagactggc accatgaggc catccccatc tgccatggga   1320
acctcatctt cttagtgtgc cacttgcttg ccatggcctc cacctgtgtc aacccattca   1380
tctatggctt tctcaacacc aacttcaaga aggagatcaa ggccctggtg ctgacttgcc   1440
agcagagcgc ccccctggag gagtcagagc atctgcccct gtccacagta catacggaag   1500
tctccaaagg gtccctgagg ctaagtggca ggtccaatcc catttaacca ggtctaggtc   1560
ttctccctgc catgtccctt gccaggctct tccacttagc taagtgggca cactgcaagc   1620
tggggtggca ccccagcatt cctggctttc tggggtccag ataggctggc aagagctgtt   1680
tttgcatcca tttgcatcgt gaagactggc attttgatac ttcagctgtt tgttcctggg   1740
agaattctga gcacagattc cagaggtcac agtaagcctt gcagcttgag ctgaaagatg   1800
ccagagccgg agatgtctgc tggcagcagg cagggttcat tctggtgaca cagcaacaga   1860
tgcctggcct gggaacccag ggatttcacc tccaccagtg agaccacggg gccactgtgg   1920
ggtgagggaa ggagcgcttg gagtcagagc tctaga                             1956
```

<210> SEQ ID NO 36
<211> LENGTH: 1128
<212> TYPE: DNA
<213> ORGANISM: Homo sapiens

<400> SEQUENCE: 36

```
atgaacacct ctcacctcct ggccttgctg ctcccaaaat ctccacaagg tgaaaacaga     60

agcaaacccc tgggcacccc atacaacttc tctgaacatt gccaggattc cgtggacgtg    120

atggtcttca tcgtcacttc ctacagcatt gagactgtcg tgggggtcct gggtaacctc    180

tgcctgatgt gtgtgactgt gaggcagaag gagaaagcca acgtgaccaa cctgcttatc    240

gccaacctgg ccttctctga cttcctcatg tgcctcctct gccagccgct gacctccgtc    300

tacaccatca tggactactg gatctttgga gagaccctct gcaagatgtc ggccttcatc    360

cagtgcatgt cggtgacggt ctccatcctc tcgctcgtcc tcgtggccct ggagaggcat    420

cagctcatca tcaacccaac aggctggaag cccagcatct cacaggccta cctggggatt    480

gtgctcatct gggtcattgc ctgtgtcctc tccctgccct tcctggccaa cagcatcctg    540

gagaatgtct tccacaagaa ccactccaag gctctggagt tcctggcgga taaggtggtc    600

tgtaccgagt cctggccact ggctcaccac cgcaccatct acaccacctt cctgctcctc    660

ttccagtact gcctcccact gggcttcatc ttggtctgtt atgcacgcat ctaccggcgc    720

ctgcagaggc aggggcgcgt gtttcacaag ggcacctaca gcttgcgagc tgggcacatg    780

aagcaggtca atgtggtgct ggtggtgatg gtggtggcct ttgccgtgct ctggctgcct    840

ctgcatgtgt tcaacagcct ggaagactgg caccatgagg ccatccccat ctgccatggg    900

aacctcatct tcttagtgtg ccacttgctt gccatggcct ccacctgtgt caacccattc    960

atctatggct ttctcaacac caacttcaag aaggagatca aggccctggt gctgacttgc   1020

cagcagagcg ccccccctgga ggagtcagag catctgcccc tgtccacagt acatacggaa   1080

gtctccaaag ggtccctgag gctaagtggc aggtccaatc ccatttaa                1128
```

<210> SEQ ID NO 37
<211> LENGTH: 375
<212> TYPE: PRT
<213> ORGANISM: Homo sapiens

<400> SEQUENCE: 37

```
Met Asn Thr Ser His Leu Leu Ala Leu Leu Leu Pro Lys Ser Pro Gln
1               5                   10                  15

Gly Glu Asn Arg Ser Lys Pro Leu Gly Thr Pro Tyr Asn Phe Ser Glu
            20                  25                  30

His Cys Gln Asp Ser Val Asp Val Met Val Phe Ile Val Thr Ser Tyr
        35                  40                  45

Ser Ile Glu Thr Val Val Gly Val Leu Gly Asn Leu Cys Leu Met Cys
    50                  55                  60

Val Thr Val Arg Gln Lys Glu Lys Ala Asn Val Thr Asn Leu Leu Ile
65                  70                  75                  80

Ala Asn Leu Ala Phe Ser Asp Phe Leu Met Cys Leu Leu Cys Gln Pro
                85                  90                  95

Leu Thr Ser Val Tyr Thr Ile Met Asp Tyr Trp Ile Phe Gly Glu Thr
            100                 105                 110

Leu Cys Lys Met Ser Ala Phe Ile Gln Cys Met Ser Val Thr Val Ser
        115                 120                 125

Ile Leu Ser Leu Val Leu Val Ala Leu Glu Arg His Gln Leu Ile Ile
    130                 135                 140
```

```
Asn Pro Thr Gly Trp Lys Pro Ser Ile Ser Gln Ala Tyr Leu Gly Ile
145                 150                 155                 160

Val Leu Ile Trp Val Ile Ala Cys Val Leu Ser Leu Pro Phe Leu Ala
                165                 170                 175

Asn Ser Ile Leu Glu Asn Val Phe His Lys Asn His Ser Lys Ala Leu
            180                 185                 190

Glu Phe Leu Ala Asp Lys Val Val Cys Thr Glu Ser Trp Pro Leu Ala
        195                 200                 205

His His Arg Thr Ile Tyr Thr Thr Phe Leu Leu Leu Phe Gln Tyr Cys
    210                 215                 220

Leu Pro Leu Gly Phe Ile Leu Val Cys Tyr Ala Arg Ile Tyr Arg Arg
225                 230                 235                 240

Leu Gln Arg Gln Gly Arg Val Phe His Lys Gly Thr Tyr Ser Leu Arg
                245                 250                 255

Ala Gly His Met Lys Gln Val Asn Val Val Leu Val Val Met Val Val
            260                 265                 270

Ala Phe Ala Val Leu Trp Leu Pro Leu His Val Phe Asn Ser Leu Glu
        275                 280                 285

Asp Trp His His Glu Ala Ile Pro Ile Cys His Gly Asn Leu Ile Phe
    290                 295                 300

Leu Val Cys His Leu Leu Ala Met Ala Ser Thr Cys Val Asn Pro Phe
305                 310                 315                 320

Ile Tyr Gly Phe Leu Asn Thr Asn Phe Lys Lys Glu Ile Lys Ala Leu
                325                 330                 335

Val Leu Thr Cys Gln Gln Ser Ala Pro Leu Glu Glu Ser Glu His Leu
            340                 345                 350

Pro Leu Ser Thr Val His Thr Glu Val Ser Lys Gly Ser Leu Arg Leu
        355                 360                 365

Ser Gly Arg Ser Asn Pro Ile
    370                 375


<210> SEQ ID NO 38
<211> LENGTH: 1128
<212> TYPE: DNA
<213> ORGANISM: Macaca mulatta

<400> SEQUENCE: 38

atgaacacct ctcacctcct ggccttgcag ctgccaaaat ccctacaggg tgaaaacaga     60

agcaagcccc tgggcatccc atacaacttc tctgatcctt gccaggattc tgtggacatg    120

atggtcttca tcgtcacttc ctacagcatt gagactgtcg tgggggtcct gggtaacctc    180

tgcctgatgt gtgtaactgt gaggcagaag gagaaaacca atgtgaccaa cctgcttatc    240

accaacctgg ccttctctga cttcctcatg tgcctcctct gccagccgct gaccgccatc    300

tataccatca tggattactg gatcttcgga gagaccctct gcaagatgtc ggccttcatc    360

cagtgtgtgt cggtgacggt ctctatcctc tcgctcgtcc ttgtggccct ggagaggcat    420

cagctcatca tcaacccaac aggctggaag cccagcatct ctcaggctta cctggggatt    480

gtgctcatct gggtcattgc ctgtgtcctc tccctgccct tcctggccaa tagcatcctg    540

gagaatgtct tccacaagaa ccactccaag gctctggagt tcctggcgga taaggtggtc    600

tgtactgagt cctggccact ggctcaccac cgcaccatct ataccacctt cctcctcctc    660

ttccagtact gcctcccact gggcttcatc ctggtctgtt atgcacgcat ctaccggcgc    720

ctgcagaggc aggggcgtgt gttccacaag ggcacctaca gcttgcgagc tgggcagatg    780
```

```
aagcaggtca atgtggtgct ggtggcgatg gtggtggcct tcgctgtgct ctggctgcct    840

ctgcatgtgt tcaacagcct ggaggactgg caccatgagg ccatccccat ctgccatggg    900

aacctcatct tcttggtgtg ccacttgctt gccatggcct ccacctgtgt caacccattc    960

atctacggct ttctcaacac caacttcaag aaggagatca aggccctggt gctgacttgc   1020

cagcagagtc ccccctgga ggagttggag catctacccc tgtccacagt acacacggaa   1080

gtctccaaag tgtccctgag gctaaatggc aggtccaatc ccatttaa                1128
```

<210> SEQ ID NO 39
<211> LENGTH: 375
<212> TYPE: PRT
<213> ORGANISM: Macaca mulatta

<400> SEQUENCE: 39

```
Met Asn Thr Ser His Leu Leu Ala Leu Gln Leu Pro Lys Ser Leu Gln
1               5                   10                  15

Gly Glu Asn Arg Ser Lys Pro Leu Gly Ile Pro Tyr Asn Phe Ser Asp
            20                  25                  30

Pro Cys Gln Asp Ser Val Asp Met Met Val Phe Ile Val Thr Ser Tyr
        35                  40                  45

Ser Ile Glu Thr Val Val Gly Val Leu Gly Asn Leu Cys Leu Met Cys
    50                  55                  60

Val Thr Val Arg Gln Lys Glu Lys Thr Asn Val Thr Asn Leu Leu Ile
65                  70                  75                  80

Thr Asn Leu Ala Phe Ser Asp Phe Leu Met Cys Leu Leu Cys Gln Pro
                85                  90                  95

Leu Thr Ala Ile Tyr Thr Ile Met Asp Tyr Trp Ile Phe Gly Glu Thr
            100                 105                 110

Leu Cys Lys Met Ser Ala Phe Ile Gln Cys Val Ser Val Thr Val Ser
        115                 120                 125

Ile Leu Ser Leu Val Leu Val Ala Leu Glu Arg His Gln Leu Ile Ile
    130                 135                 140

Asn Pro Thr Gly Trp Lys Pro Ser Ile Ser Gln Ala Tyr Leu Gly Ile
145                 150                 155                 160

Val Leu Ile Trp Val Ile Ala Cys Val Leu Ser Leu Pro Phe Leu Ala
                165                 170                 175

Asn Ser Ile Leu Glu Asn Val Phe His Lys Asn His Ser Lys Ala Leu
            180                 185                 190

Glu Phe Leu Ala Asp Lys Val Val Cys Thr Glu Ser Trp Pro Leu Ala
        195                 200                 205

His His Arg Thr Ile Tyr Thr Thr Phe Leu Leu Leu Phe Gln Tyr Cys
    210                 215                 220

Leu Pro Leu Gly Phe Ile Leu Val Cys Tyr Ala Arg Ile Tyr Arg Arg
225                 230                 235                 240

Leu Gln Arg Gln Gly Arg Val Phe His Lys Gly Thr Tyr Ser Leu Arg
                245                 250                 255

Ala Gly Gln Met Lys Gln Val Asn Val Val Leu Val Ala Met Val Val
            260                 265                 270

Ala Phe Ala Val Leu Trp Leu Pro Leu His Val Phe Asn Ser Leu Glu
        275                 280                 285

Asp Trp His His Glu Ala Ile Pro Ile Cys His Gly Asn Leu Ile Phe
    290                 295                 300

Leu Val Cys His Leu Leu Ala Met Ala Ser Thr Cys Val Asn Pro Phe
```

-continued

```
305                 310                 315                 320

Ile Tyr Gly Phe Leu Asn Thr Asn Phe Lys Lys Glu Ile Lys Ala Leu
                325                 330                 335

Val Leu Thr Cys Gln Gln Ser Pro Pro Leu Glu Glu Leu Glu His Leu
            340                 345                 350

Pro Leu Ser Thr Val His Thr Glu Val Ser Lys Val Ser Leu Arg Leu
        355                 360                 365

Asn Gly Arg Ser Asn Pro Ile
    370                 375


<210> SEQ ID NO 40
<211> LENGTH: 3628
<212> TYPE: DNA
<213> ORGANISM: Mus musculus

<400> SEQUENCE: 40

tggctgagga acagatctag tgcagagtca gtattcgccc cagcgggatt cagcaagagg     60

tcaaggtacc catcttccag gacgctgagg gcgctgcttg gctgaggccc ctgcagcagg    120

gcgcccggag ggcttcctag ccaggacttg gtgtcacatc tacagacagt agaccagggc    180

ttggtgctcc agtctcctca cctgggacgt ggtggtctgg tacctcgcca ggctgcatct    240

ctgaagtagg ccctttactc ctggagttcc tggatcttct cacacctacc atgaatacct    300

ctcatttctt ggcccctctc ttcccaggat ccctacaggg taagaatggg accaatccat    360

tggattcccc ctataatttc tctgatggct gccaggattc ggcagagctg ttggccttca    420

tcatcaccac ctacagcatt gagaccatct tgggggtcct gggaaacctc tgcttgatat    480

ttgtgaccac aagacaaaag gaaaagtcca atgtgaccaa cctgctcatt gccaacctgg    540

ccttctctga cttcctcatg tgcctcatct gccaaccact cacagtcacc tacaccatca    600

tggattactg gatctttggt gaagtccttt gcaagatgtt aactttcatc cagtgtatgt    660

cagtgacagt ctccatcctc tcactggtcc ttgtggccct ggagaggcac cagctcatta    720

tcaatccaac aggctggaaa cccagtattt tccaggccta cctggggatt gtggtcatct    780

ggttcgtctc ttgtttcctt tccttgccgt tcctggccaa cagcaccctg aatgacctct    840

tccactacaa ccactctaag gttgtagagt ttctggaaga caaggtcgtc tgctttgtgt    900

cctggtcttc agatcaccac cgtctcatct ataccacttt tctgctgctc tttcagtact    960

gcatccctct agccttcatc ctggtctgct acatacgcat ctaccatcgc ctgcagaggc   1020

agaagcatgt gttccatgcg cacgcttgca gctcacgagc gggacagatg aagcggatca   1080

acagcatgct catgacaatg gtgactgcct ttgcagttct ctggctaccc ctgcatgtgt   1140

tcaacactct ggaggactgg taccaggaag ccatccctgc ttgccatggc aacctcatct   1200

tcttgatgtg ccacctgttg gccatggctt ccacctgtgt caaccctttc atctatggct   1260

ttctcaacat caacttcaag aaggatatca aggctctggt gctgacctgc cattgcaggt   1320

cacctcgagg ggagtctgag catctgcccc tgtccactgt tcacacggac ctatccaagg   1380

gatcgatgag gatgggtagc aagtctaact tcatatagtc gtgtctgggc ttttccctac   1440

catttttga cacatccttt cacttagtta agaagacaca ttgcaggctg tgatagcatc   1500

ctgtcatttc tggcttttgg tgcccagata ggttggcaag agacttgaag cttggcattc   1560

agatggttta gccctttgct tctgagagat ctctgagtca ggattctgca gatcacagag   1620

ggaactttgt ggcttgagct gcaagggtat tagagtcaga agtggctggc tgactctcac   1680

agccactcag tacagatgcc tggcccaaaa gtcttcatct atgtcctgac cattcagcta   1740
```

```
acctgccttt ggtgatgtgc ttatgttctt tcaagggatg ttgggtgttt cagtatgggt   1800

tgggtgctgg tagaagcagg tgctgggagt tgggagtctg cttaataaag tgcttgctga   1860

aaagaacagg gacaatacga acgggctatg ataaatgtgg ctgccttacc tatggtggtc   1920

aaagttcagt gtccctcctg gctgctgaat ggggcccaag gcatcctcag tgtgtgtcct   1980

tagaaagaag gatatgccaa gattgctctt ggtccacata agataggatg ttgcagtcca   2040

gttctgactg aatagagcaa tcttcaatac agtaaacaca gtagtctcag gggagactta   2100

ccccacactg aacaggtctg atggactttc tggttctggt cccttaccga gcatgtgtgc   2160

gactgatgtc ctggacagtt gccctggagc caccacttct ttctacctgt ctcagctttt   2220

tggctgcatc tccagcttag tgtttttgtt cctggatttg agacaatttc ttttcttttg   2280

aagtaggatc ttaccgtata ggcaggcttg tctagcacgc ctgccaggct tcctttctga   2340

gcaccgatta aggcatacgc catcacatat gatgaaagat gagcttttaa accactcttg   2400

ttatctgata tagtctttag ctgactactt catatcatct actttgagca aaacccagac   2460

tctcaggccc accctggcaa gatgacattg tctgaactta ctgacctggg gccacagact   2520

tctcctcgtc tcagaagctc cagaatgtaa gcttttatta attaggctca atgagaccag   2580

gttgccagtg gtccagatga gatatttagt gaaggtgtta ggagtcaggg tgggatgtag   2640

aggctccacc tgacatcttc tgttttcctt cccacttagt tagggtgaca ttagcctacc   2700

cggatggttg tttcctgatc ctggtgtcct ggtgtctaat ggcccttgag atttcttggt   2760

tgccagctcc ttcgatgttt actatcctaa gtatggtctg aagaccagca gccctcgaaa   2820

ctggaggctg ttagatatac cgagtctttg tcgtcaccgc agatacgctg agtgcaaatc   2880

tgcatctggt caaaatatgc aggttaattg taggcacact gaaagcagga agctttgctt   2940

taggaaacaa actctgggac ttggggtatg gggtgagagt gtgcaaacac gcactctggg   3000

gtctggcgtg gatccctgtt ctgagcatct ttaaactttg gagtgctgca aaggtatgct   3060

gttttggctg tcatttctct gcctgcatgt ggacatagtt ctcatgagct tttcatcat    3120

ttcaataaat acttgccaaa tcagtagctt ataaaattcc acctacaggg agcccgccct   3180

ttgcattctg ctgcgtttca cttaaaactg tactgtgaac agttttccca tcagtttcca   3240

cggctgcgta ccagaaactg ccccagtaaa agctgggatc tcgcagtatt tctatgtaac   3300

tcctcacagg cctgctgggg agagctccta tggggaggtt ggtagctgct tcctctgtag   3360

gagtggtagg gttagagctg gagacatatt cctgtacgaa ggcctgggat ttctgagatt   3420

atgtgaagtc gtatcaaacc ctggcagcaa gagctcagct gtttaactct ggccttttcc   3480

tctcgacttg cttttccatt gtaaaagtaa tcatatggta aaataaactg aaaacaaagg   3540

taattgttgt ttttgggact catttttagt tattatatgc atatgtctgt tttgaaaatg   3600

tgattaaaac tgaacagtgt atgtattt                                      3628
```

```
<210> SEQ ID NO 41
<211> LENGTH: 1128
<212> TYPE: DNA
<213> ORGANISM: Mus musculus

<400> SEQUENCE: 41

atgaatacct ctcatttctt ggcccctctc ttcccaggat ccctacaggg taagaatggg     60

accaatccat tggattcccc ctataatttc tctgatggct gccaggattc ggcagagctg    120

ttggccttca tcatcaccac ctacagcatt gagaccatct tgggggtcct gggaaacctc    180
```

-continued

```
tgcttgatat ttgtgaccac aagacaaaag gaaaagtcca atgtgaccaa cctgctcatt    240

gccaacctgg ccttctctga cttcctcatg tgcctcatct gccaaccact cacagtcacc    300

tacaccatca tggattactg gatctttggt gaagtccttt gcaagatgtt aactttcatc    360

cagtgtatgt cagtgacagt ctccatcctc tcactggtcc ttgtggccct ggagaggcac    420

cagctcatta tcaatccaac aggctggaaa cccagtattt tccaggccta cctggggatt    480

gtggtcatct ggttcgtctc ttgtttcctt tccttgccgt tcctggccaa cagcaccctg    540

aatgacctct tccactacaa ccactctaag gttgtagagt ttctggaaga caaggtcgtc    600

tgctttgtgt cctggtcttc agatcaccac cgtctcatct ataccacttt tctgctgctc    660

tttcagtact gcatccctct agccttcatc ctggtctgct acatacgcat ctaccatcgc    720

ctgcagaggc agaagcatgt gttccatgcg cacgcttgca gctcacgagc gggacagatg    780

aagcggatca acagcatgct catgacaatg gtgactgcct ttgcagttct ctggctaccc    840

ctgcatgtgt tcaacactct ggaggactgg taccaggaag ccatccctgc ttgccatggc    900

aacctcatct tcttgatgtg ccacctgttg gccatggctt ccacctgtgt caacccttttc   960

atctatggct ttctcaacat caacttcaag aaggatatca aggctctggt gctgacctgc   1020

cattgcaggt cacctcgagg ggagtctgag catctgcccc tgtccactgt tcacacggac   1080

ctatccaagg gatcgatgag gatgggtagc aagtctaact tcatatag                 1128
```

<210> SEQ ID NO 42
<211> LENGTH: 375
<212> TYPE: PRT
<213> ORGANISM: Mus musculus

<400> SEQUENCE: 42

```
Met Asn Thr Ser His Phe Leu Ala Pro Leu Phe Pro Gly Ser Leu Gln
1               5                   10                  15

Gly Lys Asn Gly Thr Asn Pro Leu Asp Ser Pro Tyr Asn Phe Ser Asp
            20                  25                  30

Gly Cys Gln Asp Ser Ala Glu Leu Leu Ala Phe Ile Ile Thr Thr Tyr
        35                  40                  45

Ser Ile Glu Thr Ile Leu Gly Val Leu Gly Asn Leu Cys Leu Ile Phe
    50                  55                  60

Val Thr Thr Arg Gln Lys Glu Lys Ser Asn Val Thr Asn Leu Leu Ile
65                  70                  75                  80

Ala Asn Leu Ala Phe Ser Asp Phe Leu Met Cys Leu Ile Cys Gln Pro
                85                  90                  95

Leu Thr Val Thr Tyr Thr Ile Met Asp Tyr Trp Ile Phe Gly Glu Val
            100                 105                 110

Leu Cys Lys Met Leu Thr Phe Ile Gln Cys Met Ser Val Thr Val Ser
        115                 120                 125

Ile Leu Ser Leu Val Leu Val Ala Leu Glu Arg His Gln Leu Ile Ile
    130                 135                 140

Asn Pro Thr Gly Trp Lys Pro Ser Ile Phe Gln Ala Tyr Leu Gly Ile
145                 150                 155                 160

Val Val Ile Trp Phe Val Ser Cys Phe Leu Ser Leu Pro Phe Leu Ala
                165                 170                 175

Asn Ser Thr Leu Asn Asp Leu Phe His Tyr Asn His Ser Lys Val Val
            180                 185                 190

Glu Phe Leu Glu Asp Lys Val Val Cys Phe Val Ser Trp Ser Ser Asp
        195                 200                 205
```

```
His His Arg Leu Ile Tyr Thr Thr Phe Leu Leu Leu Phe Gln Tyr Cys
    210                 215                 220

Ile Pro Leu Ala Phe Ile Leu Val Cys Tyr Ile Arg Ile Tyr His Arg
225                 230                 235                 240

Leu Gln Arg Gln Lys His Val Phe His Ala His Ala Cys Ser Ser Arg
                245                 250                 255

Ala Gly Gln Met Lys Arg Ile Asn Ser Met Leu Met Thr Met Val Thr
            260                 265                 270

Ala Phe Ala Val Leu Trp Leu Pro Leu His Val Phe Asn Thr Leu Glu
        275                 280                 285

Asp Trp Tyr Gln Glu Ala Ile Pro Ala Cys His Gly Asn Leu Ile Phe
    290                 295                 300

Leu Met Cys His Leu Leu Ala Met Ala Ser Thr Cys Val Asn Pro Phe
305                 310                 315                 320

Ile Tyr Gly Phe Leu Asn Ile Asn Phe Lys Lys Asp Ile Lys Ala Leu
                325                 330                 335

Val Leu Thr Cys His Cys Arg Ser Pro Arg Gly Glu Ser Glu His Leu
            340                 345                 350

Pro Leu Ser Thr Val His Thr Asp Leu Ser Lys Gly Ser Met Arg Met
        355                 360                 365

Gly Ser Lys Ser Asn Phe Ile
    370                 375


<210> SEQ ID NO 43
<211> LENGTH: 1259
<212> TYPE: DNA
<213> ORGANISM: Rattus norvegicus

<400> SEQUENCE: 43

cggcaggcta cactcagaag tgggcccttt agtcttgaag ttcctggtct tctcacaccc     60

accatgaata cctctcatct catggcctcc ctttctccgg cattcctaca aggtaagaat    120

gggaccaact cactggattc cctctataat ctctctgacg gctgccagga ttcggcagat    180

ctgttggcct tcatcatcac cacctacagc gttgagaccg tcttggggt cctaggaaac    240

ctctgcttga tatttgtgac cacaaggcaa aaggaaaagt ccaatgtgac caacctactc    300

attgccaacc tggccttctc tgacttcctc atgtgtctca tctgccagcc gctcacggtc    360

acctacacca tcatggacta ctggatcttc ggcgaagtcc tttgcaagat gttaacgttc    420

atccagtgta tgtcggtgac agtctccatc ctctcactgg tccttgtggc cctggagagg    480

caccagctca ttatcaaccc gactggctgg aaacccagca tttcccaggc ctacctgggg    540

attgtggtca tctggttcat ttcttgtttc ctctccttgc ccttcctggc caatagcatc    600

ctgaacgacc tcttccacta caaccactct aaggttgtgg agtttctgga agacaaggtt    660

gtctgctttg tgtcctggtc ctcggatcac caccgcctca tctacaccac ctttctgctg    720

ctcttccaat actgcgtccc tctggccttc atcctggtct gctacatgcg tatctaccag    780

cgcctgcaga ggcagaggcg tgcgttccac acgcacactt gcagctcacg agtggggcag    840

atgaagcgga tcaatggcat gctcatggca atggtgactg cctttgcagt tctctggctg    900

cccctgcatg tgttcaacac tctggaggac tggtaccagg aagccatccc tgcttgccat    960

ggcaacctca tcttcttgat gtgccacctg tttgccatgg cttccacctg tgtcaaccct   1020

ttcatctatg gctttctcaa catcaacttc aagaaggaca tcaaggctct ggttctgacc   1080

tgccgttgca ggccacctca aggggagcct gagcctctgc ccctgtccac tgtgcacacg   1140
```

```
gacctctcca agggatctat gaggatgggt agcaagtcta acgtcatgta gtcatgtcta   1200

ggctcttccg ccattttctt tcgacacacc ctttcactga gctaagtaga cacaatgca    1259


<210> SEQ ID NO 44
<211> LENGTH: 1128
<212> TYPE: DNA
<213> ORGANISM: Rattus norvegicus

<400> SEQUENCE: 44

atgaatacct ctcatctcat ggcctccctt tctccggcat tcctacaagg taagaatggg     60

accaactcac tggattccct ctataatctc tctgacggct gccaggattc ggcagatctg    120

ttggccttca tcatcaccac ctacagcgtt gagaccgtct tgggggtcct aggaaacctc    180

tgcttgatat ttgtgaccac aaggcaaaag gaaaagtcca atgtgaccaa cctactcatt    240

gccaacctgg ccttctctga cttcctcatg tgtctcatct gccagccgct cacggtcacc    300

tacaccatca tggactactg gatcttcggc gaagtccttt gcaagatgtt aacgttcatc    360

cagtgtatgt cggtgacagt ctccatcctc tcactggtcc ttgtggccct ggagaggcac    420

cagctcatta tcaacccgac tggctggaaa cccagcattt cccaggccta cctggggatt    480

gtggtcatct ggttcatttc ttgtttcctc tccttgccct tcctggccaa tagcatcctg    540

aacgacctct tccactacaa ccactctaag gttgtggagt ttctggaaga caaggttgtc    600

tgctttgtgt cctggtcctc ggatcaccac cgcctcatct acaccacctt tctgctgctc    660

ttccaatact gcgtccctct ggccttcatc ctggtctgct acatgcgtat ctaccagcgc    720

ctgcagaggc agaggcgtgc gttccacacg cacacttgca gctcacgagt ggggcagatg    780

aagcggatca atggcatgct catggcaatg gtgactgcct ttgcagttct ctggctgccc    840

ctgcatgtgt tcaacactct ggaggactgg taccaggaag ccatccctgc ttgccatggc    900

aacctcatct tcttgatgtg ccacctgttt gccatggctt ccacctgtgt caaccctttc    960

atctatggct ttctcaacat caacttcaag aaggacatca aggctctggt tctgacctgc   1020

cgttgcaggc cacctcaagg ggagcctgag cctctgcccc tgtccactgt gcacacggac   1080

ctctccaagg gatctatgag gatgggtagc aagtctaacg tcatgtag                1128


<210> SEQ ID NO 45
<211> LENGTH: 375
<212> TYPE: PRT
<213> ORGANISM: Rattus norvegicus

<400> SEQUENCE: 45

Met Asn Thr Ser His Leu Met Ala Ser Leu Ser Pro Ala Phe Leu Gln
1               5                   10                  15

Gly Lys Asn Gly Thr Asn Ser Leu Asp Ser Leu Tyr Asn Leu Ser Asp
            20                  25                  30

Gly Cys Gln Asp Ser Ala Asp Leu Leu Ala Phe Ile Ile Thr Thr Tyr
        35                  40                  45

Ser Val Glu Thr Val Leu Gly Val Leu Gly Asn Leu Cys Leu Ile Phe
    50                  55                  60

Val Thr Thr Arg Gln Lys Glu Lys Ser Asn Val Thr Asn Leu Leu Ile
65                  70                  75                  80

Ala Asn Leu Ala Phe Ser Asp Phe Leu Met Cys Leu Ile Cys Gln Pro
                85                  90                  95

Leu Thr Val Thr Tyr Thr Ile Met Asp Tyr Trp Ile Phe Gly Glu Val
            100                 105                 110
```

```
Leu Cys Lys Met Leu Thr Phe Ile Gln Cys Met Ser Val Thr Val Ser
        115                 120                 125

Ile Leu Ser Leu Val Leu Val Ala Leu Glu Arg His Gln Leu Ile Ile
    130                 135                 140

Asn Pro Thr Gly Trp Lys Pro Ser Ile Ser Gln Ala Tyr Leu Gly Ile
145                 150                 155                 160

Val Val Ile Trp Phe Ile Ser Cys Phe Leu Ser Leu Pro Phe Leu Ala
                165                 170                 175

Asn Ser Ile Leu Asn Asp Leu Phe His Tyr Asn His Ser Lys Val Val
            180                 185                 190

Glu Phe Leu Glu Asp Lys Val Val Cys Phe Val Ser Trp Ser Ser Asp
        195                 200                 205

His His Arg Leu Ile Tyr Thr Thr Phe Leu Leu Leu Phe Gln Tyr Cys
    210                 215                 220

Val Pro Leu Ala Phe Ile Leu Val Cys Tyr Met Arg Ile Tyr Gln Arg
225                 230                 235                 240

Leu Gln Arg Gln Arg Arg Ala Phe His Thr His Thr Cys Ser Ser Arg
                245                 250                 255

Val Gly Gln Met Lys Arg Ile Asn Gly Met Leu Met Ala Met Val Thr
            260                 265                 270

Ala Phe Ala Val Leu Trp Leu Pro Leu His Val Phe Asn Thr Leu Glu
        275                 280                 285

Asp Trp Tyr Gln Glu Ala Ile Pro Ala Cys His Gly Asn Leu Ile Phe
    290                 295                 300

Leu Met Cys His Leu Phe Ala Met Ala Ser Thr Cys Val Asn Pro Phe
305                 310                 315                 320

Ile Tyr Gly Phe Leu Asn Ile Asn Phe Lys Lys Asp Ile Lys Ala Leu
                325                 330                 335

Val Leu Thr Cys Arg Cys Arg Pro Pro Gln Gly Glu Pro Glu Pro Leu
            340                 345                 350

Pro Leu Ser Thr Val His Thr Asp Leu Ser Lys Gly Ser Met Arg Met
        355                 360                 365

Gly Ser Lys Ser Asn Val Met
    370                 375
```

<210> SEQ ID NO 46
<211> LENGTH: 1936
<212> TYPE: DNA
<213> ORGANISM: Homo sapiens

<400> SEQUENCE: 46

```
agcgatcgcg ctgggccgcg ctcccgggag cccagggcct gcagcggccg gggcgccccg      60

aggtctgctc attgtgtttt tcaggaaaaa ggaagggaaa gggtgttaca aggaaaggct     120

atcggtaaca actgacctgc cacaaagtta gaagaaagga ttgattcaag aaagactata     180

atatggattt agagctcgac gagtattata acaagacact tgccacagag aataatactg     240

ctgccactcg gaattctgat ttcccagtct gggatgacta taaaagcagt gtagatgact     300

tacagtattt tctgattggg ctctatacat ttgtaagtct tcttggcttt atggggaatc     360

tacttatttt aatggctctc atgaaaaagc gtaatcagaa gactacggta aacttcctca     420

taggcaatct ggccttttct gatatcttgg ttgtgctgtt ttgctcacct ttcacactga     480

cgtctgtctt gctggatcag tggatgtttg gcaaagtcat gtgccatatt atgcctttttc    540

ttcaatgtgt gtcagttttg gtttcaactt taattttaat atcaattgcc attgtcaggt     600
```

```
atcatatgat aaaacatccc atatctaata atttaacagc aaaccatggc tactttctga    660

tagctactgt ctggacacta ggttttgcca tctgttctcc ccttccagtg tttcacagtc    720

ttgtggaact tcaagaaaca tttggttcag cattgctgag cagcaggtat ttatgtgttg    780

agtcatggcc atctgattca tacagaattg cctttactat ctctttattg ctagttcagt    840

atattctgcc cttagtttgt cttactgtaa gtcatacaag tgtctgcaga agtataagct    900

gtggattgtc caacaaagaa aacagacttg aagaaaatga gatgatcaac ttaactcttc    960

atccatccaa aaagagtggg cctcaggtga aactctctgg cagccataaa tggagttatt   1020

cattcatcaa aaaacacaga agaagatata gcaagaagac agcatgtgtg ttacctgctc   1080

cagaaagacc ttctcaagag aaccactcca gaatacttcc agaaaacttt ggctctgtaa   1140

gaagtcagct ctcttcatcc agtaagttca taccaggggt ccccacttgc tttgagataa   1200

aacctgaaga aaattcagat gttcatgaat tgagagtaaa acgttctgtt acaagaataa   1260

aaaagagatc tcgaagtgtt ttctacagac tgaccatact gatattagta tttgctgtta   1320

gttggatgcc actacacctt ttccatgtgg taactgattt taatgacaat cttatttcaa   1380

ataggcattt caagttggtg tattgcattt gtcatttgtt gggcatgatg tcctgttgtc   1440

ttaatccaat tctatatggg tttcttaata atgggattaa agctgattta gtgtccctta   1500

tacactgtct tcatatgtaa taattctcac tgtttaccaa ggaaagaaca aatgctgggg   1560

tcatataaaa tatatttatg ataactattt acatataata aatagaaatt ttgttaacat   1620

ggaatttaat ttatgtgaaa gagttctgga ttcaaatgtc agttcataat atatggaaga   1680

taattttatg tgttatagta ggattaattt atttagttgt gcagtcagtg tcaatccaat   1740

ctgtaatttc actttagaag gttgtattac cttccacttc catgttgtct tataaacaaa   1800

tgaattgtat tttttgttga aagtaaaagt tatatctaac caaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaa                                                   1936
```

<210> SEQ ID NO 47
<211> LENGTH: 1338
<212> TYPE: DNA
<213> ORGANISM: Homo sapiens

<400> SEQUENCE: 47

```
atggatttag agctcgacga gtattataac aagacacttg ccacagagaa taatactgct     60

gccactcgga attctgattt cccagtctgg gatgactata aagcagtgt agatgactta    120

cagtattttc tgattgggct ctatacattt gtaagtcttc ttggctttat ggggaatcta    180

cttattttaa tggctctcat gaaaaagcgt aatcagaaga ctacggtaaa cttcctcata    240

ggcaatctgg ccttttctga tatcttggtt gtgctgtttt gctcaccttt cacactgacg    300

tctgtcttgc tggatcagtg gatgtttggc aaagtcatgt gccatattat gccttttctt    360

caatgtgtgt cagttttggt ttcaacttta attttaatat caattgccat tgtcaggtat    420

catatgataa aacatcccat atctaataat ttaacagcaa accatggcta ctttctgata    480

gctactgtct ggacactagg ttttgccatc tgttctcccc ttccagtgtt tcacagtctt    540

gtggaacttc aagaaacatt tggttcagca ttgctgagca gcaggtattt atgtgttgag    600

tcatggccat ctgattcata cagaattgcc tttactatct ctttattgct agttcagtat    660

attctgccct tagtttgtct tactgtaagt catacaagtg tctgcagaag tataagctgt    720

ggattgtcca acaaagaaaa cagacttgaa gaaaatgaga tgatcaactt aactcttcat    780
```

```
ccatccaaaa agagtgggcc tcaggtgaaa ctctctggca gccataaatg gagttattca    840

ttcatcaaaa aacacagaag aagatatagc aagaagacag catgtgtgtt acctgctcca    900

gaaagacctt ctcaagagaa ccactccaga atacttccag aaaactttgg ctctgtaaga    960

agtcagctct cttcatccag taagttcata ccaggggtcc ccacttgctt tgagataaaa   1020

cctgaagaaa attcagatgt tcatgaattg agagtaaaac gttctgttac aagaataaaa   1080

aagagatctc gaagtgtttt ctacagactg accatactga tattagtatt tgctgttagt   1140

tggatgccac tacacctttt ccatgtggta actgatttta atgacaatct tatttcaaat   1200

aggcatttca agttggtgta ttgcatttgt catttgttgg gcatgatgtc ctgttgtctt   1260

aatccaattc tatatgggtt tcttaataat gggattaaag ctgatttagt gtcccttata   1320

cactgtcttc atatgtaa                                                 1338
```

```
<210> SEQ ID NO 48
<211> LENGTH: 445
<212> TYPE: PRT
<213> ORGANISM: Homo sapiens

<400> SEQUENCE: 48

Met Asp Leu Glu Leu Asp Glu Tyr Tyr Asn Lys Thr Leu Ala Thr Glu
1               5                   10                  15

Asn Asn Thr Ala Ala Thr Arg Asn Ser Asp Phe Pro Val Trp Asp Asp
            20                  25                  30

Tyr Lys Ser Ser Val Asp Asp Leu Gln Tyr Phe Leu Ile Gly Leu Tyr
        35                  40                  45

Thr Phe Val Ser Leu Leu Gly Phe Met Gly Asn Leu Leu Ile Leu Met
    50                  55                  60

Ala Leu Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Val
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Gln Glu Thr Phe Gly Ser Ala Leu Leu
            180                 185                 190

Ser Ser Arg Tyr Leu Cys Val Glu Ser Trp Pro Ser Asp Ser Tyr Arg
        195                 200                 205

Ile Ala Phe Thr Ile Ser Leu Leu Leu Val Gln Tyr Ile Leu Pro Leu
    210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                245                 250                 255

Leu Thr Leu His Pro Ser Lys Lys Ser Gly Pro Gln Val Lys Leu Ser
            260                 265                 270
```

```
Gly Ser His Lys Trp Ser Tyr Ser Phe Ile Lys Lys His Arg Arg Arg
        275                 280                 285

Tyr Ser Lys Lys Thr Ala Cys Val Leu Pro Ala Pro Glu Arg Pro Ser
    290                 295                 300

Gln Glu Asn His Ser Arg Ile Leu Pro Glu Asn Phe Gly Ser Val Arg
305                 310                 315                 320

Ser Gln Leu Ser Ser Ser Ser Lys Phe Ile Pro Gly Val Pro Thr Cys
                325                 330                 335

Phe Glu Ile Lys Pro Glu Glu Asn Ser Asp Val His Glu Leu Arg Val
            340                 345                 350

Lys Arg Ser Val Thr Arg Ile Lys Lys Arg Ser Arg Ser Val Phe Tyr
        355                 360                 365

Arg Leu Thr Ile Leu Ile Leu Val Phe Ala Val Ser Trp Met Pro Leu
    370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                405                 410                 415

Ser Cys Cys Leu Asn Pro Ile Leu Tyr Gly Phe Leu Asn Asn Gly Ile
            420                 425                 430

Lys Ala Asp Leu Val Ser Leu Ile His Cys Leu His Met
        435                 440                 445


<210> SEQ ID NO 49
<211> LENGTH: 1338
<212> TYPE: DNA
<213> ORGANISM: Macaca mulatta

<400> SEQUENCE: 49

atggatttag agctcgatga atattataac aagacacttg ccacagagaa taatactgct     60

gccactcgga attctgattt cccagtctgg gatgactata aaagcagtgt agatgactta    120

cagtattttc tgattgggct ctatacattt gtaagtcttc ttggctttat ggggaattta    180

cttattttaa tggctctcat gaaaaagcgt aatcagaaga ctacggtaaa cttccttata    240

ggaaatctgg ccttttctga tatcttggtt gtgctgtttt gctcaccttt cacactgaca    300

tctgtcttgc tggatcagtg gatgtttggc aaagtcatgt gccatattat gccttttctg    360

caatgcgtgt cagttttggt ttcaacttta attttaatat caattgccat tgtcaggtat    420

catatgataa aacatcccat ctctaataat ttaacagcaa accatggcta ctttctgata    480

gctactgtct ggacactagg ttttgccatc tgttctcccc ttccagtgtt tcacagtctt    540

gtggaacttc aagaaacatt tggttcagcg ttgctgagca gcaggtattt atgtgttgag    600

tcatggccat ctgattcata cagaattgcc tttactatct ctttattgct agttcagtat    660

attctgccct tagtttgtct tactgtaagt catacaagtg tctgcagaag cataagctgt    720

ggattgtcca acaaagaaaa cagacttgaa gaaaatgaga tgatcaactt aactcttcat    780

ccatccagaa agattgggcc tcaggtgaaa ctctctggca gccataaatg gagttattca    840

ttcatcaaaa aacacagaag gagatatagc aagaagacag catgtgtgtt acccgctcca    900

gaaagacctt ctcaagagaa ccactccaga atacttccag aaaactttgg ctctgtaaga    960

agtcagctct cttcatccag taagttcata ccaggggtcc ccacttgctt tgaaataaaa   1020

cctgaagaaa attcagatgt tcatgaattg agagtaaaac gttctgttac aagaataaaa   1080

aagagatctc gaagtgtttt ctacaggctg accatactga tattagtatt tgctgttagt   1140
```

```
tggatgccac tacacctttt ccatgtggta actgatttta atgacaatct tatttcaaat   1200

aggcatttca agttggtgta ttgcatttgt catttgttgg gcatgatgtc ctgttgtctt   1260

aatccaattc tgtatggatt tcttaataat gggattaaag ctgatttaat gtcccttata   1320

cactgtcttc atatgtaa                                                 1338


<210> SEQ ID NO 50
<211> LENGTH: 445
<212> TYPE: PRT
<213> ORGANISM: Macaca mulatta

<400> SEQUENCE: 50

Met Asp Leu Glu Leu Asp Glu Tyr Tyr Asn Lys Thr Leu Ala Thr Glu
1               5                   10                  15

Asn Asn Thr Ala Ala Thr Arg Asn Ser Asp Phe Pro Val Trp Asp Asp
            20                  25                  30

Tyr Lys Ser Ser Val Asp Asp Leu Gln Tyr Phe Leu Ile Gly Leu Tyr
        35                  40                  45

Thr Phe Val Ser Leu Leu Gly Phe Met Gly Asn Leu Leu Ile Leu Met
    50                  55                  60

Ala Leu Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Val
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Gln Glu Thr Phe Gly Ser Ala Leu Leu
            180                 185                 190

Ser Ser Arg Tyr Leu Cys Val Glu Ser Trp Pro Ser Asp Ser Tyr Arg
        195                 200                 205

Ile Ala Phe Thr Ile Ser Leu Leu Leu Val Gln Tyr Ile Leu Pro Leu
    210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                245                 250                 255

Leu Thr Leu His Pro Ser Arg Lys Ile Gly Pro Gln Val Lys Leu Ser
            260                 265                 270

Gly Ser His Lys Trp Ser Tyr Ser Phe Ile Lys Lys His Arg Arg Arg
        275                 280                 285

Tyr Ser Lys Lys Thr Ala Cys Val Leu Pro Ala Pro Glu Arg Pro Ser
    290                 295                 300

Gln Glu Asn His Ser Arg Ile Leu Pro Glu Asn Phe Gly Ser Val Arg
305                 310                 315                 320

Ser Gln Leu Ser Ser Ser Ser Lys Phe Ile Pro Gly Val Pro Thr Cys
                325                 330                 335
```

```
Phe Glu Ile Lys Pro Glu Glu Asn Ser Asp Val His Glu Leu Arg Val
            340                 345                 350

Lys Arg Ser Val Thr Arg Ile Lys Lys Arg Ser Arg Ser Val Phe Tyr
        355                 360                 365

Arg Leu Thr Ile Leu Ile Leu Val Phe Ala Val Ser Trp Met Pro Leu
    370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                405                 410                 415

Ser Cys Cys Leu Asn Pro Ile Leu Tyr Gly Phe Leu Asn Asn Gly Ile
            420                 425                 430

Lys Ala Asp Leu Met Ser Leu Ile His Cys Leu His Met
        435                 440                 445


<210> SEQ ID NO 51
<211> LENGTH: 2336
<212> TYPE: DNA
<213> ORGANISM: Mus musculus

<400> SEQUENCE: 51

ggagggccct tctttcccac cgccgcttcc aggtcctgct cctgctgcca ccgcttccat      60

ctcaagcaga agcgaccgca ttcagccgcg taccccggag tccaggcacc cgcagcggcc     120

agggcatccc gaggactcta gtatggaggt taaacttgaa gagcatttta acaagacatt     180

tgtcacggag aacaatactg ctgccagtca gaacacggcc tcccctgcct gggaggacta     240

cagaggcaca gagaacaata cttctgctgc tcggaacact gcctttccag tctgggagga     300

ctatagaggc agcgtagacg acttacaata cttcctgatt gggctctata catttgtaag     360

tcttctgggt tttatgggaa atctacttat cttaatggct gttatgaaaa agcgcaatca     420

gaagactaca gtgaactttc tcataggcaa cctggccttc tccgacattt tggttgtcct     480

gttttgctcc cctttcaccc tgacctctgt cttgttggat cagtggatgt tcggcaaagc     540

catgtgccat atcatgccat tccttcagtg tgtatcagtt ctggtttcaa ctctgatttt     600

aatatcgatt gccattgtca ggtatcatat gataaagcac cctatatcta acaatttaac     660

agcaaaccat ggctacttcc tgatagctac tgtctggaca ctgggctttg ccatctgttc     720

tcccctccca gtgtttcaca gccttgtgga acttaaggaa acctttggct cagcattgct     780

aagcagcaag tatttgtgtg ttgagtcatg gccctctgat tcatacagaa ttgctttcac     840

aatctcttta ttgttagttc agtatatcct gcctctagta tgtttaacag taagtcatac     900

tagtgtctgc aggagtataa gctgtggatt gtcccacaaa gaaaacagac tcgaagaaaa     960

tgagatgatc aacttaactc tacatccatc ccaaaagagt cgggaccagg caaaaccccc    1020

cagcactcaa aagtggagct actcattcat cagaaagcac cgaagaaggt acagcaagaa    1080

gacggcatgc gtgttacccg ccccagcagg accttcccag gagaagcacc taaccgttcc    1140

agaaaaccca ggctcggtcc gtagccagct gtcaccatcc agtaaggtta ttccaggggt    1200

cccgatctgc tttgaggtga aacctgaaga aagctcagat gctcaggaga tgagagtcaa    1260

gcgttccctc acgagaataa agaagagatc tcgcagtgtt ttctacagac tgactatatt    1320

gatattagtg ttcgctgtta gctggatgcc actccacgtc ttccacgtgg tgaccgattt    1380

caatgataac ctgatttcca ataggcattt caagctggtg tactgcatct gtcacttgtt    1440

aggcatgatg tcctgttgtc ttaatccgat cttatatgga ttccttaata atggtatcaa    1500
```

```
agcagacttg agagccctta tccactgcct acacatgtca tgattctctc tgtgcaccga   1560
ggagagaaga aatgtgagac tgcccacaat acatctgtgc taattgatgc ataatttaca   1620
taaacgtgtt ctggatctga atgccagttt gtaatctatg ttagatcatt tatgttataa   1680
tgtggttaat tccgtcactt gtgcagagtc catgtcgatc taaggaaatt tctgtcttga   1740
aatagttaca ttaccgtcca tttcatgtca ttggtaataa gttgagtgtc ttcggtgtcg   1800
agtaaaagtt atagctatcc aaattgttat tttgtacaaa aatgtaagaa gtgaaaaagt   1860
tgttccaaag aatatttaac ctcagattta aggaatttct tttatctaga tatctttatt   1920
tctatttcac atgcttcttg actttttttt tgtaaaacta caaaaatatt caaaagtcag   1980
aactctatta cagatgttag cataaaacat gatataaatt tataggagaa agatccactc   2040
ctattattgt tgactggtta aattgtcaga ttaatccagc tgttctgcta ctaatattta   2100
acttatcaaa tacgaaaggg ttttagcttt tgttcagatt tatatcacat taaacattgt   2160
ccaataaagg ctgttttcat atgcatcttt gatgttctaa aatgtgaagt ccatatggtg   2220
tgtatttcca attactatta ttagactatt tttaaaagtc catagattgt atgaatagct   2280
tgttgtttgt ttaaattaaa taaaaattga ttacttaaaa aaaaaaaaaa aaaaaa       2336
```

<210> SEQ ID NO 52
<211> LENGTH: 1401
<212> TYPE: DNA
<213> ORGANISM: Mus musculus

<400> SEQUENCE: 52

```
atggaggtta aacttgaaga gcattttaac aagacatttg tcacggagaa caatactgct     60
gccagtcaga acacggcctc ccctgcctgg gaggactaca gaggcacaga gaacaatact    120
tctgctgctc ggaacactgc ctttccagtc tgggaggact atagaggcag cgtagacgac    180
ttacaatact tcctgattgg gctctataca tttgtaagtc ttctgggttt tatgggaaat    240
ctacttatct taatggctgt tatgaaaaag cgcaatcaga agactacagt gaactttctc    300
ataggcaacc tggccttctc cgacattttg gttgtcctgt tttgctcccc tttcaccctg    360
acctctgtct tgttggatca gtggatgttc ggcaaagcca tgtgccatat catgccattc    420
cttcagtgtg tatcagttct ggtttcaact ctgattttaa tatcgattgc cattgtcagg    480
tatcatatga taaagcaccc tatatctaac aatttaacag caaaccatgg ctacttcctg    540
atagctactg tctggacact gggctttgcc atctgttctc cctcccagt gtttcacagc     600
cttgtggaac ttaaggaaac ctttggctca gcattgctaa gcagcaagta tttgtgtgtt    660
gagtcatggc cctctgattc atacagaatt gctttcacaa tctctttatt gttagttcag    720
tatatcctgc ctctagtatg tttaacagta agtcatacta gtgtctgcag gagtataagc    780
tgtggattgt cccacaaaga aaacagactc gaagaaaatg agatgatcaa cttaactcta    840
catccatccc aaaagagtcg ggaccaggca aaacccccca gcactcaaaa gtggagctac    900
tcattcatca gaaagcaccg aagaaggtac agcaagaaga cggcatgcgt gttacccgcc    960
ccagcaggac cttcccagga gaagcaccta accgttccag aaaacccagg ctcggtccgt   1020
agccagctgt caccatccag taaggttatt ccaggggtcc cgatctgctt tgaggtgaaa   1080
cctgaagaaa gctcagatgc tcaggagatg agagtcaagc gttccctcac gagaataaag   1140
aagagatctc gcagtgtttt ctacagactg actatattga tattagtgtt cgctgttagc   1200
tggatgccac tccacgtctt ccacgtggtg accgatttca atgataacct gatttccaat   1260
```

```
aggcatttca agctggtgta ctgcatctgt cacttgttag gcatgatgtc ctgttgtctt   1320

aatccgatct tatatggatt ccttaataat ggtatcaaag cagacttgag agcccttatc   1380

cactgcctac acatgtcatg a                                             1401


<210> SEQ ID NO 53
<211> LENGTH: 466
<212> TYPE: PRT
<213> ORGANISM: Mus musculus

<400> SEQUENCE: 53

Met Glu Val Lys Leu Glu Glu His Phe Asn Lys Thr Phe Val Thr Glu
1               5                   10                  15

Asn Asn Thr Ala Ala Ser Gln Asn Thr Ala Ser Pro Ala Trp Glu Asp
            20                  25                  30

Tyr Arg Gly Thr Glu Asn Asn Thr Ser Ala Ala Arg Asn Thr Ala Phe
        35                  40                  45

Pro Val Trp Glu Asp Tyr Arg Gly Ser Val Asp Asp Leu Gln Tyr Phe
    50                  55                  60

Leu Ile Gly Leu Tyr Thr Phe Val Ser Leu Leu Gly Phe Met Gly Asn
65                  70                  75                  80

Leu Leu Ile Leu Met Ala Val Met Lys Lys Arg Asn Gln Lys Thr Thr
                85                  90                  95

Val Asn Phe Leu Ile Gly Asn Leu Ala Phe Ser Asp Ile Leu Val Val
            100                 105                 110

Leu Phe Cys Ser Pro Phe Thr Leu Thr Ser Val Leu Leu Asp Gln Trp
        115                 120                 125

Met Phe Gly Lys Ala Met Cys His Ile Met Pro Phe Leu Gln Cys Val
    130                 135                 140

Ser Val Leu Val Ser Thr Leu Ile Leu Ile Ser Ile Ala Ile Val Arg
145                 150                 155                 160

Tyr His Met Ile Lys His Pro Ile Ser Asn Asn Leu Thr Ala Asn His
                165                 170                 175

Gly Tyr Phe Leu Ile Ala Thr Val Trp Thr Leu Gly Phe Ala Ile Cys
            180                 185                 190

Ser Pro Leu Pro Val Phe His Ser Leu Val Glu Leu Lys Glu Thr Phe
        195                 200                 205

Gly Ser Ala Leu Leu Ser Ser Lys Tyr Leu Cys Val Glu Ser Trp Pro
    210                 215                 220

Ser Asp Ser Tyr Arg Ile Ala Phe Thr Ile Ser Leu Leu Leu Val Gln
225                 230                 235                 240

Tyr Ile Leu Pro Leu Val Cys Leu Thr Val Ser His Thr Ser Val Cys
                245                 250                 255

Arg Ser Ile Ser Cys Gly Leu Ser His Lys Glu Asn Arg Leu Glu Glu
            260                 265                 270

Asn Glu Met Ile Asn Leu Thr Leu His Pro Ser Gln Lys Ser Arg Asp
        275                 280                 285

Gln Ala Lys Pro Pro Ser Thr Gln Lys Trp Ser Tyr Ser Phe Ile Arg
    290                 295                 300

Lys His Arg Arg Arg Tyr Ser Lys Lys Thr Ala Cys Val Leu Pro Ala
305                 310                 315                 320

Pro Ala Gly Pro Ser Gln Glu Lys His Leu Thr Val Pro Glu Asn Pro
                325                 330                 335

Gly Ser Val Arg Ser Gln Leu Ser Pro Ser Ser Lys Val Ile Pro Gly
            340                 345                 350
```

```
Val Pro Ile Cys Phe Glu Val Lys Pro Glu Glu Ser Ser Asp Ala Gln
        355                 360                 365

Glu Met Arg Val Lys Arg Ser Leu Thr Arg Ile Lys Lys Arg Ser Arg
    370                 375                 380

Ser Val Phe Tyr Arg Leu Thr Ile Leu Ile Leu Val Phe Ala Val Ser
385                 390                 395                 400

Trp Met Pro Leu His Val Phe His Val Val Thr Asp Phe Asn Asp Asn
                405                 410                 415

Leu Ile Ser Asn Arg His Phe Lys Leu Val Tyr Cys Ile Cys His Leu
            420                 425                 430

Leu Gly Met Met Ser Cys Cys Leu Asn Pro Ile Leu Tyr Gly Phe Leu
        435                 440                 445

Asn Asn Gly Ile Lys Ala Asp Leu Arg Ala Leu Ile His Cys Leu His
    450                 455                 460

Met Ser
465


<210> SEQ ID NO 54
<211> LENGTH: 2475
<212> TYPE: DNA
<213> ORGANISM: Rattus norvegicus

<400> SEQUENCE: 54

ttggactatg ggggccggga acaggcgatc ttgagccggg tgtccggggt ctcagggact     60

gtcacgtgtt cccgaggtgc ttctaaaacc ctggcggctc cggagcccct ccttcccacc    120

accgcctcca ggtcctgctc ctgccgccac cgcttccatc tggagcagaa gcgaccgcgc    180

tcagccacgt accccggagt ccaggcaccc gcagcggccg gggcatcccg aggattttag    240

tatggagttt aagcttgagg agcattttaa caagacattt gtcacagaga acaatacagc    300

tgctgctcgg aatgcagcct tccctgcctg ggaggactac agaggcagcg tagacgattt    360

acaatacttt ctgattgggc tctatacatt cgtaagtctt cttggcttta tgggcaatct    420

acttatttta atggctgtta tgaaaaagcg caatcagaag actacagtga actttctcat    480

aggcaacctg gccttctccg acatcttggt cgtcctgttt tgctcccctt tcaccctgac    540

ctctgtcttg ttggatcagt ggatgtttgg caaagccatg tgccatatca tgccgttcct    600

tcaatgtgtg tcagttctgg tttcaactct gattttaata tcaattgcca ttgtcaggta    660

tcatatgata aagcacccta tttctaacaa tttaacggca aaccatggct acttcctgat    720

agctactgtc tggacactgg gctttgccat ctgttctccc ctcccagtgt ttcacagtct    780

tgtggaactt aaggagacct ttggctcagc actgctgagt agcaaatatc tctgtgttga    840

gtcatggccc tctgattcat acagaattgc tttcacaatc tctttattgc tagtgcagta    900

tatcctgcct ctagtatgtt taacggtaag tcataccagc gtctgccgaa gcataagctg    960

tggattgtcc cacaaagaaa acagactcga agaaaatgag atgatcaact taaccctaca   1020

gccatccaaa aagagcagga accaggcaaa aacccccagc actcaaaagt ggagctactc   1080

attcatcaga aagcacagaa ggaggtacag caagaagacg gcctgtgtct tacccgcccc   1140

agcaggacct tcccagggga agcacctagc cgttccagaa aatccagcct ccgtccgtag   1200

ccagctgtcg ccatccagta aggtcattcc aggggtccca atctgctttg aggtgaaacc   1260

tgaagaaagc tcagatgctc atgagatgag agtcaagcgt tccatcacta gaataaaaaa   1320

gagatctcga agtgttttct acagactgac catactgata ctcgtgttcg ccgttagctg   1380
```

```
gatgccactc cacgtcttcc acgtggtgac tgacttcaat gataacttga tttccaatag   1440
gcatttcaag ctggtatact gcatctgtca cttgttaggc atgatgtcct gttgtctaaa   1500
tccgatccta tatggtttcc ttaataatgg tatcaaagca gacttgagag cccttatcca   1560
ctgcctacac atgtcatgat tctctctgtg caccaaagag agaagaaacg tggtaattga   1620
cacataattt atacagaagt attctggatc tgaatgccag ttcgtaatct acgtaagatc   1680
atcttcatgt tataatatgg ttaattcaat cagttgtgca gagtcaatgt ccatctaata   1740
caatttcatg tgttgaagta gtttacatta ttttccattt tatgtcattg gtaataagtt   1800
gagtgatact ctgtggttta gtgtaaaaga tatagctatc caaattgtta cgttgtacaa   1860
aaaatgtatg aagtgacaag ttgtcccaaa gagcatttaa ctacagattt aaggaatttc   1920
tattatctgg gtatcttcat ttctatttca caggcttctt aacatttttt tgtaaaagta   1980
caaaaatatt caaaagtcag aactctatta cagatgtatg cataaaagat gattataatt   2040
ttgtaggaga aagatctgct cctattagtg aagattggta aaattgtcag tttaacccgg   2100
ctgtcctact actaatattt aatttttcaa atatgaaaag gtttcagatt ttgtttagat   2160
ttatatcaca ttaaacactg tcaaataaag gctgttttta tatgcatcgt tgatgttcca   2220
aaatgtgaag tctaaatggt gtctgtattt ccaattatta aataacttct aagatcattt   2280
ttaaaagtct gtagatggta tggatagcta gttgtttgtt aatataaagt aaaagtagat   2340
agctgattta tgttgtacct atgtcgtatg tatattaggt atcgtgttgt ctcactaaag   2400
tgaaagcaaa cgaaaaaaaa aaaaaaaaaa aaaaaaaaaa aaaaaaaaaa aaaaaaaaaa   2460
aaaaaaaaaa aaaaa                                                    2475
```

```
<210> SEQ ID NO 55
<211> LENGTH: 1338
<212> TYPE: DNA
<213> ORGANISM: Rattus norvegicus

<400> SEQUENCE: 55
```

```
atggagttta agcttgagga gcattttaac aagacatttg tcacagagaa caatacagct     60
gctgctcgga atgcagcctt ccctgcctgg gaggactaca gaggcagcgt agacgattta    120
caatactttc tgattgggct ctatacattc gtaagtcttc ttggctttat gggcaatcta    180
cttattttaa tggctgttat gaaaaagcgc aatcagaaga ctacagtgaa ctttctcata    240
ggcaacctgg ccttctccga catcttggtc gtcctgtttt gctccccttt caccctgacc    300
tctgtcttgt tggatcagtg gatgtttggc aaagccatgt gccatatcat gccgttcctt    360
caatgtgtgt cagttctggt ttcaactctg attttaatat caattgccat tgtcaggtat    420
catatgataa agcaccctat ttctaacaat ttaacggcaa accatggcta cttcctgata    480
gctactgtct ggacactggg ctttgccatc tgttctcccc tcccagtgtt tcacagtctt    540
gtggaactta aggagacctt tggctcagca ctgctgagta gcaaatatct ctgtgttgag    600
tcatggccct ctgattcata cagaattgct ttcacaatct ctttattgct agtgcagtat    660
atcctgcctc tagtatgttt aacggtaagt cataccagcg tctgccgaag cataagctgt    720
ggattgtccc acaaagaaaa cagactcgaa gaaaatgaga tgatcaactt aaccctacag    780
ccatccaaaa agagcaggaa ccaggcaaaa acccccagca ctcaaaagtg gagctactca    840
ttcatcagaa agcacagaag gaggtacagc aagaagacgg cctgtgtctt acccgcccca    900
gcaggacctt cccaggggaa gcacctagcc gttccagaaa atccagcctc cgtccgtagc    960
cagctgtcgc catccagtaa ggtcattcca ggggtcccaa tctgctttga ggtgaaacct   1020
```

```
gaagaaagct cagatgctca tgagatgaga gtcaagcgtt ccatcactag aataaaaaag   1080

agatctcgaa gtgttttcta cagactgacc atactgatac tcgtgttcgc cgttagctgg   1140

atgccactcc acgtcttcca cgtggtgact gacttcaatg ataacttgat ttccaatagg   1200

catttcaagc tggtatactg catctgtcac ttgttaggca tgatgtcctg ttgtctaaat   1260

ccgatcctat atggtttcct taataatggt atcaaagcag acttgagagc ccttatccac   1320

tgcctacaca tgtcatga                                                 1338


<210> SEQ ID NO 56
<211> LENGTH: 445
<212> TYPE: PRT
<213> ORGANISM: Rattus norvegicus

<400> SEQUENCE: 56

Met Glu Phe Lys Leu Glu Glu His Phe Asn Lys Thr Phe Val Thr Glu
1               5                   10                  15

Asn Asn Thr Ala Ala Ala Arg Asn Ala Ala Phe Pro Ala Trp Glu Asp
            20                  25                  30

Tyr Arg Gly Ser Val Asp Asp Leu Gln Tyr Phe Leu Ile Gly Leu Tyr
        35                  40                  45

Thr Phe Val Ser Leu Leu Gly Phe Met Gly Asn Leu Leu Ile Leu Met
    50                  55                  60

Ala Val Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Ala
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Lys Glu Thr Phe Gly Ser Ala Leu Leu
            180                 185                 190

Ser Ser Lys Tyr Leu Cys Val Glu Ser Trp Pro Ser Asp Ser Tyr Arg
        195                 200                 205

Ile Ala Phe Thr Ile Ser Leu Leu Leu Val Gln Tyr Ile Leu Pro Leu
    210                 215                 220

Val Cys Leu Thr Val Ser His Thr Ser Val Cys Arg Ser Ile Ser Cys
225                 230                 235                 240

Gly Leu Ser His Lys Glu Asn Arg Leu Glu Glu Asn Glu Met Ile Asn
                245                 250                 255

Leu Thr Leu Gln Pro Ser Lys Lys Ser Arg Asn Gln Ala Lys Thr Pro
            260                 265                 270

Ser Thr Gln Lys Trp Ser Tyr Ser Phe Ile Arg Lys His Arg Arg Arg
        275                 280                 285

Tyr Ser Lys Lys Thr Ala Cys Val Leu Pro Ala Pro Ala Gly Pro Ser
    290                 295                 300

Gln Gly Lys His Leu Ala Val Pro Glu Asn Pro Ala Ser Val Arg Ser
```

```
305                 310                 315                 320

Gln Leu Ser Pro Ser Ser Lys Val Ile Pro Gly Val Pro Ile Cys Phe
                325                 330                 335

Glu Val Lys Pro Glu Glu Ser Ser Asp Ala His Glu Met Arg Val Lys
            340                 345                 350

Arg Ser Ile Thr Arg Ile Lys Lys Arg Ser Arg Ser Val Phe Tyr Arg
        355                 360                 365

Leu Thr Ile Leu Ile Leu Val Phe Ala Val Ser Trp Met Pro Leu His
    370                 375                 380

Val Phe His Val Val Thr Asp Phe Asn Asp Asn Leu Ile Ser Asn Arg
385                 390                 395                 400

His Phe Lys Leu Val Tyr Cys Ile Cys His Leu Leu Gly Met Met Ser
                405                 410                 415

Cys Cys Leu Asn Pro Ile Leu Tyr Gly Phe Leu Asn Asn Gly Ile Lys
            420                 425                 430

Ala Asp Leu Arg Ala Leu Ile His Cys Leu His Met Ser
        435                 440                 445


<210> SEQ ID NO 57
<211> LENGTH: 1957
<212> TYPE: DNA
<213> ORGANISM: Homo sapiens

<400> SEQUENCE: 57

ttgataggga tagaaacaca tttggctgct tctatagtta acaagatgct gttacattcc     60

ttgcctcact agctctgaag actatactag cgggacaaag aaagcacctg agatgagctg    120

agaggagggt aaaggtacac agagatcccc tggatatttg ttctatgtcc tctcaggggc    180

tttgctacca ctagagaatt atccatatta agaacttgca ttgatattct gggttctgtt    240

tcattttttta gggtctcaag agcacgctca agtcattcac atgtttccat caaatacaga    300

cacagatcag ggaagattaa accctactaa tttctcgtcg gatgcctcac aacaaggtgc    360

cttccaagaa ctaatggcca aaatatccac ccacaacaca aataagctta gaaaatctct    420

tcttacaatc ctgacacaat ggaagtttcc ctaaaccacc cagcatctaa tacaaccagc    480

acaaagaaca acaactcggc attttttttac tttgagtcct gtcaacctcc ttctccagct    540

ttactcctat tatgcatagc ctatactgtg gtcttaattg tgggcctttt tggaaacctc    600

tctctcatca tcatcatctt taagaagcag agaaaagctc agaatttcac cagcatactg    660

attgccaatc tctccctctc tgatacttg gtgtgtgtca tgtgcatcca ttttactatc    720

atctacactc tgatggacca ctggatattt ggggatacca tgtgcagact cacatcctat    780

gtgcagagtg tctcaatctc tgtgtccata ttctcacttg tattcactgc tgtcgaaaga    840

tatcagctaa ttgtgaaccc ccgtggctgg aagcccagtg tgactcatgc ctactggggc    900

atcacactga tttggctgtt ttcccttctg ctgtctattc ccttcttcct gtcctaccac    960

ctcactgatg agcccttccg caacctctct ctccccactg acctctacac ccaccaggtg   1020

gcctgtgtgg agaactggcc ctccaaaaag gaccggctgc tcttcaccac ctcccttttt   1080

ctgctgcagt attttgttcc tctaggcttc atcctcatct gctacttgaa gattgttatc   1140

tgcctccgca ggagaaatgc aaaggtagat aagaagaagg aaaatgaggg ccggctcaat   1200

gagaacaaga ggatcaacac aatgttgatt tccatcgtgg tgacctttgg agcctgctgg   1260

ctgccccgaa tatcttcaat gtcatctttg actggtatca tgaggtgctg atgagctgcc   1320

accacgacct ggtatttgta gtttgccact tggttgctat ggtttccaca tgtataaacc   1380
```

```
ctctctttta tggctttctc aacaaaaatt tccaaaagga cctggtagtg cttattcacc   1440

actgctggtg cttcacacct caggaaagat gtgaaaatat tgccatctcc actatgcaca   1500

cagactccaa gaggtcttta agattggctc gtataacaac aggtatatga aaattgataa   1560

tgctgaagct cttcttgaat gggagctgga caggtaatgg tgggaatagg gcaagatgca   1620

gaaagaagaa accagaacca aaaatagcaa ctttataccc acttttcctt taggctaaga   1680

ctgcctgtct catatgtcta tccaacacac cctccaacat acacgaacac acataccacc   1740

ccttttctct taagaaaata actctaataa ttcaaacaac ctgcccgcca tcatttgtgg   1800

caaagaatga gaatgagaaa gcagagagag aggcaaacag cagtgatggc tggggaacaa   1860

tgttcacaga tacttttatt caatggaata tctacaaaag ttatgactaa tgatatgcct   1920

agtaaaaaca ctgctatacc tccttagcac tgagaat                            1957
```

<210> SEQ ID NO 58
<211> LENGTH: 873
<212> TYPE: DNA
<213> ORGANISM: Homo sapiens

<400> SEQUENCE: 58

```
atggaagttt ccctaaacca cccagcatct aatacaacca gcacaaagaa caacaactcg     60

gcattttttt actttgagtc ctgtcaacct ccttctccag ctttactcct attatgcata    120

gcctatactg tggtcttaat tgtgggcctt tttggaaacc tctctctcat catcatcatc    180

tttaagaagc agagaaaagc tcagaatttc accagcatac tgattgccaa tctctccctc    240

tctgatacct tggtgtgtgt catgtgcatc catttttacta tcatctacac tctgatggac    300

cactggatat ttggggatac catgtgcaga ctcacatcct atgtgcagag tgtctcaatc    360

tctgtgtcca tattctcact tgtattcact gctgtcgaaa gatatcagct aattgtgaac    420

ccccgtggct ggaagcccag tgtgactcat gcctactggg gcatcacact gatttggctg    480

ttttcccttc tgctgtctat tcccttcttc ctgtcctacc acctcactga tgagcccttc    540

cgcaacctct ctctccccac tgacctctac acccaccagg tggcctgtgt ggagaactgg    600

ccctccaaaa aggaccggct gctcttcacc acctcccttt ttctgctgca gtattttgtt    660

cctctaggct tcatcctcat ctgctacttg aagattgtta tctgcctccg caggagaaat    720

gcaaaggtag ataagaagaa ggaaaatgag ggccggctca atgagaacaa gaggatcaac    780

acaatgttga tttccatcgt ggtgaccttt ggagcctgct ggctgccccg aatatcttca    840

atgtcatctt tgactggtat catgaggtgc tga                                 873
```

<210> SEQ ID NO 59
<211> LENGTH: 290
<212> TYPE: PRT
<213> ORGANISM: Homo sapiens

<400> SEQUENCE: 59

```
Met Glu Val Ser Leu Asn His Pro Ala Ser Asn Thr Thr Ser Thr Lys
1               5                   10                  15

Asn Asn Asn Ser Ala Phe Phe Tyr Phe Glu Ser Cys Gln Pro Pro Ser
            20                  25                  30

Pro Ala Leu Leu Leu Leu Cys Ile Ala Tyr Thr Val Val Leu Ile Val
        35                  40                  45

Gly Leu Phe Gly Asn Leu Ser Leu Ile Ile Ile Ile Phe Lys Lys Gln
    50                  55                  60
```

```
Arg Lys Ala Gln Asn Phe Thr Ser Ile Leu Ile Ala Asn Leu Ser Leu
65                  70                  75                  80

Ser Asp Thr Leu Val Cys Val Met Cys Ile His Phe Thr Ile Ile Tyr
                85                  90                  95

Thr Leu Met Asp His Trp Ile Phe Gly Asp Thr Met Cys Arg Leu Thr
            100                 105                 110

Ser Tyr Val Gln Ser Val Ser Ile Ser Val Ser Ile Phe Ser Leu Val
        115                 120                 125

Phe Thr Ala Val Glu Arg Tyr Gln Leu Ile Val Asn Pro Arg Gly Trp
    130                 135                 140

Lys Pro Ser Val Thr His Ala Tyr Trp Gly Ile Thr Leu Ile Trp Leu
145                 150                 155                 160

Phe Ser Leu Leu Leu Ser Ile Pro Phe Phe Leu Ser Tyr His Leu Thr
                165                 170                 175

Asp Glu Pro Phe Arg Asn Leu Ser Leu Pro Thr Asp Leu Tyr Thr His
            180                 185                 190

Gln Val Ala Cys Val Glu Asn Trp Pro Ser Lys Lys Asp Arg Leu Leu
        195                 200                 205

Phe Thr Thr Ser Leu Phe Leu Leu Gln Tyr Phe Val Pro Leu Gly Phe
    210                 215                 220

Ile Leu Ile Cys Tyr Leu Lys Ile Val Ile Cys Leu Arg Arg Arg Asn
225                 230                 235                 240

Ala Lys Val Asp Lys Lys Lys Glu Asn Glu Gly Arg Leu Asn Glu Asn
                245                 250                 255

Lys Arg Ile Asn Thr Met Leu Ile Ser Ile Val Val Thr Phe Gly Ala
            260                 265                 270

Cys Trp Leu Pro Arg Ile Ser Ser Met Ser Ser Leu Thr Gly Ile Met
        275                 280                 285

Arg Cys
    290
```

<210> SEQ ID NO 60
<211> LENGTH: 2570
<212> TYPE: DNA
<213> ORGANISM: Mus musculus

<400> SEQUENCE: 60

```
tggcctagat agtgactcca actccaggga atagcttctg aagtgaagct acgataaata     60

catcagggca ggaaaaagaa gtattggaac ttggagggat ggttattgtg acatctttct    120

gcaaggaagt aatctttaag aatagcacca ctgaagaaag caagcatgta gaagatgaaa    180

gcagagttac agactgaaaa tttctaacag gatctcaaga gcatgctgac gtcatttatg    240

tgtttccatc agatacagac agagatcata aacatttaac tcattgatta tatgttgaga    300

gttgtccctc aagaaccaat ggccaaacat ccactgagga tacacggaag cttagaaaat    360

ctctaattaa aatcctgaca taatggaagt gctcacaaac cagccaacac ctaataaaac    420

cagtggcaag agcaacaact cggcattttt ctactttgaa tcctgccaac cccctttct     480

agccatactc ttgctactca tagcatatac tgtgatccta atcatgggca tttttggaaa    540

cctctctctt atcatcatca tctttaagaa acagagagaa gctcaaaatg ttaccaacat    600

actgattgcc aacctgtccc tctctgacat cttggtgtgt gtcatgtgca tccctttttac   660

ggtcatctac actctgatgg accactgggt atttgggaac actatgtgta aactcacttc    720

ctacgtgcaa agtgtctcag tttctgtgtc catattctcc cttgtgttga ttgctattga    780
```

```
acgatatcag ctgattgtga acccccgtgg ctggaaaccc agagtagctc atgcctattg    840

ggggatcatc ttgatttggc tcatttctct gacattgtct attcccttat tcctgtccta    900

ccacctcacc aatgagccct ttcataatct ctctctccct actgacatct acacccacca    960

ggtagcttgt gtggagattt ggccttctaa actgaaccaa ctcctctttt ctacatcatt   1020

atttatgctc cagtattttg tccctctggg tttcattctt atctgctacc tgaagatcgt   1080

tctctgcctc cgaaaaagaa ctaggcaggt ggacaggaga aaggaaaata agagccgtct   1140

caatgagaac aagagggtaa atgtgatgtt gatttccatc gtagtgactt ttggagcctg   1200

ctggttgccc ttgaacattt tcaatgtcat cttcgactgg tatcatgaga tgctgatgag   1260

ctgccaccac gacctggtat ttgtagtttg ccacttgatt gctatggttt ctacttgcat   1320

aaatcctctc ttttatggat ttctcaacaa aaacttccag aaggatctaa tgatgcttat   1380

tcaccactgt tggtgtggtg aacctcagga aagttatgaa aatattgcca tgtctactat   1440

gcacacagat gaatccaagg gatcattaaa actggctcac ataccaacag gcatatagaa   1500

actggtaagc aaaatcaaag cccttctgtt atgaaagaaa gagaagaaat agtatggaat   1560

agggcaaggt gcagaggaag ccagacttaa acacataata tctttgggcc cagttttgct   1620

ttaagttaag catgtctact ccattcagcc atagaacaca cagagattta tccctaccct   1680

ttcttttttt cctttggaag aataataact taaacaacct agacatcatt actgaggaag   1740

agaacaaaaa tgagagagca tacaaggaca gcagagatgt ctggggtaca aaattcacgt   1800

tattcgctgg aatagctaga aagttattag ttgtgctgca ggcaggaaaa acccatacta   1860

tgcctccttt gcatcaaaga aattcaactt tcgcatatga gactataact tgcaatcaca   1920

taactattca attaattaga taaatcaaaa agcatactac cataaattat taattaatta   1980

tatctggatt ataattgaaa gcttgtttta acatgtatac tgaacactat agttataatt   2040

aatttccctg tctgtatctg actctgaagt tgttataatg ctccatttct tttacttaca   2100

atgctattaa gactaggaaa actagtcatt cattcaatag cactccaatt atagcagaga   2160

tcattttatc taatgaatgt tctgtgtcga tagagatttc attacaaaac ggccttttat   2220

cctgatgtct ttatgtatat taagcagggg ttcgttataa ctttgtaaac tgggagatta   2280

ttatcaacag tagcattata attaactcca gcattccaga aaattatcat ctatctcagt   2340

acttaaacat tattcaagaa tattcactaa ataagaccat cgggtagatt atttacaaca   2400

agataattga ccttttgttt aaacatctgt tagctcagag acttgtacta attcacacaa   2460

gctttaccat ttcctagggt aaacctccct gatacttatt aaatttgact gcagcctatg   2520

tgtgtcatat acaaatgtaa gcatgtcttc ttttcaataa atattctccc              2570
```

<210> SEQ ID NO 61
<211> LENGTH: 1116
<212> TYPE: DNA
<213> ORGANISM: Mus musculus

<400> SEQUENCE: 61

```
atggaagtgc tcacaaacca gccaacacct aataaaacca gtggcaagag caacaactcg     60

gcatttttct actttgaatc ctgccaaccc ccttttctag ccatactctt gctactcata    120

gcatatactg tgatcctaat catgggcatt tttggaaacc tctctcttat catcatcatc    180

tttaagaaac agagagaagc tcaaaatgtt accaacatac tgattgccaa cctgtccctc    240

tctgacatct tggtgtgtgt catgtgcatc ccttttacgg tcatctacac tctgatggac    300

cactgggtat ttgggaacac tatgtgtaaa ctcacttcct acgtgcaaag tgtctcagtt    360
```

```
tctgtgtcca tattctccct tgtgttgatt gctattgaac gatatcagct gattgtgaac    420

ccccgtggct ggaaacccag agtagctcat gcctattggg ggatcatctt gatttggctc    480

atttctctga cattgtctat tcccttattc ctgtcctacc acctcaccaa tgagcccttt    540

cataatctct ctctccctac tgacatctac acccaccagg tagcttgtgt ggagatttgg    600

ccttctaaac tgaaccaact cctcttttct acatcattat ttatgctcca gtattttgtc    660

cctctgggtt tcattcttat ctgctacctg aagatcgttc tctgcctccg aaaaagaact    720

aggcaggtgg acaggagaaa ggaaaataag agccgtctca atgagaacaa gagggtaaat    780

gtgatgttga tttccatcgt agtgactttt ggagcctgct ggttgccctt gaacattttc    840

aatgtcatct tcgactggta tcatgagatg ctgatgagct gccaccacga cctggtattt    900

gtagtttgcc acttgattgc tatggtttct acttgcataa atcctctctt ttatggattt    960

ctcaacaaaa acttccagaa ggatctaatg atgcttattc accactgttg gtgtggtgaa   1020

cctcaggaaa gttatgaaaa tattgccatg tctactatgc acacagatga atccaaggga   1080

tcattaaaac tggctcacat accaacaggc atatag                             1116
```

<210> SEQ ID NO 62
<211> LENGTH: 371
<212> TYPE: PRT
<213> ORGANISM: Mus musculus

<400> SEQUENCE: 62

```
Met Glu Val Leu Thr Asn Gln Pro Thr Pro Asn Lys Thr Ser Gly Lys
1               5                   10                  15

Ser Asn Asn Ser Ala Phe Phe Tyr Phe Glu Ser Cys Gln Pro Pro Phe
            20                  25                  30

Leu Ala Ile Leu Leu Leu Leu Ile Ala Tyr Thr Val Ile Leu Ile Met
        35                  40                  45

Gly Ile Phe Gly Asn Leu Ser Leu Ile Ile Ile Ile Phe Lys Lys Gln
    50                  55                  60

Arg Glu Ala Gln Asn Val Thr Asn Ile Leu Ile Ala Asn Leu Ser Leu
65                  70                  75                  80

Ser Asp Ile Leu Val Cys Val Met Cys Ile Pro Phe Thr Val Ile Tyr
                85                  90                  95

Thr Leu Met Asp His Trp Val Phe Gly Asn Thr Met Cys Lys Leu Thr
            100                 105                 110

Ser Tyr Val Gln Ser Val Ser Val Ser Val Ser Ile Phe Ser Leu Val
        115                 120                 125

Leu Ile Ala Ile Glu Arg Tyr Gln Leu Ile Val Asn Pro Arg Gly Trp
    130                 135                 140

Lys Pro Arg Val Ala His Ala Tyr Trp Gly Ile Ile Leu Ile Trp Leu
145                 150                 155                 160

Ile Ser Leu Thr Leu Ser Ile Pro Leu Phe Leu Ser Tyr His Leu Thr
                165                 170                 175

Asn Glu Pro Phe His Asn Leu Ser Leu Pro Thr Asp Ile Tyr Thr His
            180                 185                 190

Gln Val Ala Cys Val Glu Ile Trp Pro Ser Lys Leu Asn Gln Leu Leu
        195                 200                 205

Phe Ser Thr Ser Leu Phe Met Leu Gln Tyr Phe Val Pro Leu Gly Phe
    210                 215                 220

Ile Leu Ile Cys Tyr Leu Lys Ile Val Leu Cys Leu Arg Lys Arg Thr
225                 230                 235                 240
```

```
Arg Gln Val Asp Arg Arg Lys Glu Asn Lys Ser Arg Leu Asn Glu Asn
                245                 250                 255

Lys Arg Val Asn Val Met Leu Ile Ser Ile Val Val Thr Phe Gly Ala
            260                 265                 270

Cys Trp Leu Pro Leu Asn Ile Phe Asn Val Ile Phe Asp Trp Tyr His
        275                 280                 285

Glu Met Leu Met Ser Cys His His Asp Leu Val Phe Val Val Cys His
    290                 295                 300

Leu Ile Ala Met Val Ser Thr Cys Ile Asn Pro Leu Phe Tyr Gly Phe
305                 310                 315                 320

Leu Asn Lys Asn Phe Gln Lys Asp Leu Met Met Leu Ile His His Cys
                325                 330                 335

Trp Cys Gly Glu Pro Gln Glu Ser Tyr Glu Asn Ile Ala Met Ser Thr
            340                 345                 350

Met His Thr Asp Glu Ser Lys Gly Ser Leu Lys Leu Ala His Ile Pro
        355                 360                 365

Thr Gly Ile
    370


<210> SEQ ID NO 63
<211> LENGTH: 1299
<212> TYPE: DNA
<213> ORGANISM: Oryctolagus cuniculus

<400> SEQUENCE: 63

agagtttagg aaatttctca gaatcctgaa ataatggaag tttccctcaa tgacccagca      60

tctaataaaa ccagtgcaaa gagcaacagc tcagcatttt tttactttga atcctgtcaa     120

tccccttctc tagccttact cctattactc attgcctata ctgtggtttt aatcatgggc     180

atttgtggaa acctctctct catcaccatc atctttaaga agcagagaga agctcagaat     240

gtcaccaaca tactgattgc caacctctcc ctctctgaca tcttggtgtg tgtcatgtgc     300

atccctttta ctgctattta cactctgatg gatcgctgga tatttgggaa caccatgtgc     360

aaactcacct cctatgtaca gagtgtctcc atctctgtgt ctattttctc acttgtatta     420

attgctattg aaagatatca gctgattgtg aacccccgtg gctggaagcc gagtgcatcc     480

cacgcttact ggggcatcat gctgatttgg ctcttctccc ttctgttgtc cattcccttg     540

ttgctttcct accacctcac tgatgagccc ttccgcaacc tctctctccc cactgacctc     600

tacagtcacc atgtagtctg tgtagagcac tggccctcca agacaaacca gctcctctat     660

tccacctcct tgattatgct ccagtatttt gtcccgctgg gcttcatgtt catctgctac     720

ctgaagattg ttatctgcct ccacaagaga aacagcaaaa tagacagaag gagggaaaat     780

gaaagccggc tcactgagaa caagagaatc aacacaatgc tgatctccat cgttgtgact     840

tttgcagcct gctggctgcc cctgaacacc ttcaatgtta tctttgactg gtatcacgag     900

gtgctgatga gctgccacca tgatctggtg tttgcaatat gccacttggt tgctatggtt     960

tccacatgca taaaccctct cttttatgga tttctgaaca gaaatttcca gaaagatctg    1020

gtggtgctta ttcaccactg cttgtgcttt gcacttcggg aaagatatga aaatattgcc    1080

atctccactc tgcacacaga tgaatccaag ggatctttaa gagtggctca tataccagca    1140

ggtatataaa aattgctaac acttaacact aatgcccttc ctcactggga cacggaaagg    1200

taatggcagt ggataggaca agaaacaaaa tgaaggcaga accaagaaca taccaacttt    1260

atacacattt tgtttttggc taagcctgtc tgtctgacc                           1299
```

<210> SEQ ID NO 64
<211> LENGTH: 1116
<212> TYPE: DNA
<213> ORGANISM: Oryctolagus cuniculus

<400> SEQUENCE: 64
atggaagttt ccctcaatga cccagcatct aataaaacca gtgcaaagag caacagctca 60
gcattttttt actttgaatc ctgtcaatcc ccttctctag ccttactcct attactcatt 120
gcctatactg tggttttaat catgggcatt tgtggaaacc tctctctcat caccatcatc 180
tttaagaagc agagagaagc tcagaatgtc accaacatac tgattgccaa cctctccctc 240
tctgacatct tggtgtgtgt catgtgcatc ccttttactg ctatttacac tctgatggat 300
cgctggatat ttgggaacac catgtgcaaa ctcacctcct atgtacagag tgtctccatc 360
tctgtgtcta ttttctcact tgtattaatt gctattgaaa gatatcagct gattgtgaac 420
ccccgtggct ggaagccgag tgcatcccac gcttactggg gcatcatgct gatttggctc 480
ttctcccttc tgttgtccat tcccttgttg ctttcctacc acctcactga tgagcccttc 540
cgcaacctct ctctccccac tgacctctac agtcaccatg tagtctgtgt agagcactgg 600
ccctccaaga caaaccagct cctctattcc acctccttga ttatgctcca gtattttgtc 660
ccgctgggct tcatgttcat ctgctacctg aagattgtta tctgcctcca caagagaaac 720
agcaaaatag acagaaggag ggaaaatgaa agccggctca ctgagaacaa gagaatcaac 780
acaatgctga tctccatcgt tgtgactttt gcagcctgct ggctgcccct gaacaccttc 840
aatgttatct ttgactggta tcacgaggtg ctgatgagct gccaccatga tctggtgttt 900
gcaatatgcc acttggttgc tatggtttcc acatgcataa accctctctt ttatggattt 960
ctgaacagaa atttccagaa agatctggtg gtgcttattc accactgctt gtgctttgca 1020
cttcgggaaa gatatgaaaa tattgccatc tccactctgc acacagatga atccaaggga 1080
tctttaagag tggctcatat accagcaggt atataa 1116

<210> SEQ ID NO 65
<211> LENGTH: 371
<212> TYPE: PRT
<213> ORGANISM: Oryctolagus cuniculus

<400> SEQUENCE: 65

Met Glu Val Ser Leu Asn Asp Pro Ala Ser Asn Lys Thr Ser Ala Lys
1               5                   10                  15

Ser Asn Ser Ser Ala Phe Phe Tyr Phe Glu Ser Cys Gln Ser Pro Ser
            20                  25                  30

Leu Ala Leu Leu Leu Leu Leu Ile Ala Tyr Thr Val Val Leu Ile Met
        35                  40                  45

Gly Ile Cys Gly Asn Leu Ser Leu Ile Thr Ile Ile Phe Lys Lys Gln
    50                  55                  60

Arg Glu Ala Gln Asn Val Thr Asn Ile Leu Ile Ala Asn Leu Ser Leu
65                  70                  75                  80

Ser Asp Ile Leu Val Cys Val Met Cys Ile Pro Phe Thr Ala Ile Tyr
                85                  90                  95

Thr Leu Met Asp Arg Trp Ile Phe Gly Asn Thr Met Cys Lys Leu Thr
            100                 105                 110

Ser Tyr Val Gln Ser Val Ser Ile Ser Val Ser Ile Phe Ser Leu Val
        115                 120                 125

```
Leu Ile Ala Ile Glu Arg Tyr Gln Leu Ile Val Asn Pro Arg Gly Trp
    130                 135                 140

Lys Pro Ser Ala Ser His Ala Tyr Trp Gly Ile Met Leu Ile Trp Leu
145                 150                 155                 160

Phe Ser Leu Leu Leu Ser Ile Pro Leu Leu Leu Ser Tyr His Leu Thr
                165                 170                 175

Asp Glu Pro Phe Arg Asn Leu Ser Leu Pro Thr Asp Leu Tyr Ser His
            180                 185                 190

His Val Val Cys Val Glu His Trp Pro Ser Lys Thr Asn Gln Leu Leu
        195                 200                 205

Tyr Ser Thr Ser Leu Ile Met Leu Gln Tyr Phe Val Pro Leu Gly Phe
    210                 215                 220

Met Phe Ile Cys Tyr Leu Lys Ile Val Ile Cys Leu His Lys Arg Asn
225                 230                 235                 240

Ser Lys Ile Asp Arg Arg Arg Glu Asn Glu Ser Arg Leu Thr Glu Asn
                245                 250                 255

Lys Arg Ile Asn Thr Met Leu Ile Ser Ile Val Val Thr Phe Ala Ala
            260                 265                 270

Cys Trp Leu Pro Leu Asn Thr Phe Asn Val Ile Phe Asp Trp Tyr His
        275                 280                 285

Glu Val Leu Met Ser Cys His His Asp Leu Val Phe Ala Ile Cys His
    290                 295                 300

Leu Val Ala Met Val Ser Thr Cys Ile Asn Pro Leu Phe Tyr Gly Phe
305                 310                 315                 320

Leu Asn Arg Asn Phe Gln Lys Asp Leu Val Val Leu Ile His His Cys
                325                 330                 335

Leu Cys Phe Ala Leu Arg Glu Arg Tyr Glu Asn Ile Ala Ile Ser Thr
            340                 345                 350

Leu His Thr Asp Glu Ser Lys Gly Ser Leu Arg Val Ala His Ile Pro
        355                 360                 365

Ala Gly Ile
    370


<210> SEQ ID NO 66
<211> LENGTH: 778
<212> TYPE: DNA
<213> ORGANISM: Homo sapiens

<400> SEQUENCE: 66

atatagcagc ggcggcggtg gcggcggcca caccgggcgg cggacacgtg gagggacccg     60

gcccgcgcct tctgcccctg ctgccggccg cgccatgcgg tgagcgcccc aggccgccag    120

agcccacccg acccggcccg acgcccggac ctgccgccca gacccgccac cgcacccgga    180

ccccgacgct ccgaacccgg gcgcagccgc agctcaagat ggcccgaggc agcgccctcc    240

tgctcgcctc cctcctcctc gccgcggccc tttctgcctc tgcggggctc tggtcgccgg    300

ccaaggaaaa acgaggctgg accctgaaca gcgcgggcta cctgctgggc ccacatgccg    360

ttggcaacca caggtcattc agcgacaaga atggcctcac cagcaagcgg gagctgcggc    420

ccgaagatga catgaaacca ggaagctttg acaggtccat acctgaaaac aatatcatgc    480

gcacaatcat tgagtttctg tctttcttgc atctcaaaga ggccggtgcc ctcgaccgcc    540

tcctggatct ccccgccgca gcctcctcag aagacatcga gcggtcctga gagcctcctg    600

ggcatgtttg tctgtgtgct gtaacctgaa gtcaaacctt aagataatgg ataatcttcg    660

gccaatttat gcagagtcag ccattcctgt tctctttgcc ttgatgttgt gttgttatca    720
```

```
tttaagattt tttttttttg gtaattattt tgagtggcaa aataaagaat agcaatta      778


<210> SEQ ID NO 67
<211> LENGTH: 372
<212> TYPE: DNA
<213> ORGANISM: Homo sapiens

<400> SEQUENCE: 67

atggcccgag gcagcgccct cctgctcgcc tccctcctcc tcgccgcggc cctttctgcc     60

tctgcggggc tctggtcgcc ggccaaggaa aaacgaggct ggaccctgaa cagcgcgggc    120

tacctgctgg gcccacatgc cgttggcaac cacaggtcat tcagcgacaa gaatggcctc    180

accagcaagc gggagctgcg gcccgaagat gacatgaaac caggaagctt tgacaggtcc    240

atacctgaaa acaatatcat gcgcacaatc attgagtttc tgtctttctt gcatctcaaa    300

gaggccggtg ccctcgaccg cctcctggat ctccccgccg cagcctcctc agaagacatc    360

gagcggtcct ga                                                        372


<210> SEQ ID NO 68
<211> LENGTH: 123
<212> TYPE: PRT
<213> ORGANISM: Homo sapiens

<400> SEQUENCE: 68

Met Ala Arg Gly Ser Ala Leu Leu Leu Ala Ser Leu Leu Leu Ala Ala
1               5                   10                  15

Ala Leu Ser Ala Ser Ala Gly Leu Trp Ser Pro Ala Lys Glu Lys Arg
            20                  25                  30

Gly Trp Thr Leu Asn Ser Ala Gly Tyr Leu Leu Gly Pro His Ala Val
        35                  40                  45

Gly Asn His Arg Ser Phe Ser Asp Lys Asn Gly Leu Thr Ser Lys Arg
    50                  55                  60

Glu Leu Arg Pro Glu Asp Asp Met Lys Pro Gly Ser Phe Asp Arg Ser
65                  70                  75                  80

Ile Pro Glu Asn Asn Ile Met Arg Thr Ile Ile Glu Phe Leu Ser Phe
                85                  90                  95

Leu His Leu Lys Glu Ala Gly Ala Leu Asp Arg Leu Leu Asp Leu Pro
            100                 105                 110

Ala Ala Ala Ser Ser Glu Asp Ile Glu Arg Ser
        115                 120


<210> SEQ ID NO 69
<211> LENGTH: 165
<212> TYPE: DNA
<213> ORGANISM: Macaca nemestrina

<400> SEQUENCE: 69

ggctggaccc tgaacagcgc gggctacctg ctgggcccac atgctgttgg caaccacagg     60

tcattcagcg acaagaatgg cctcaccagc aagcgggagc tgcagcccca agacgacgtg    120

aaaccaggaa gctttgacag gtccatgcct gagaacaata tcatg                    165


<210> SEQ ID NO 70
<211> LENGTH: 55
<212> TYPE: PRT
<213> ORGANISM: Macaca nemestrina

<400> SEQUENCE: 70
```

```
Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser Lys Arg
            20                  25                  30

Glu Leu Gln Pro Gln Asp Asp Val Lys Pro Gly Ser Phe Asp Arg Ser
        35                  40                  45

Met Pro Glu Asn Asn Ile Met
    50                  55


<210> SEQ ID NO 71
<211> LENGTH: 716
<212> TYPE: DNA
<213> ORGANISM: Mus musculus

<400> SEQUENCE: 71

gatcctcgtg cgcttcccca tgccgctgag ctgcgccgtg cagtaagcga ccatccagcc      60

cgccactctt caccacgccc gacccggacc gagagagcct tgatcctgca ctgaccagcc     120

acgcccggtt ctcaccgctg ctcaagatgg ccagaggcag cgttatcctg ctaggctggc     180

tcctgttggt tgtgaccctg tcagccactc tgggacttgg gatgcctgca aaggagaaga     240

gaggttggac cctgaacagc gctggctacc ttctgggccc acatgccatt gacaaccaca     300

gatcatttag cgacaagcat ggcctcacag gcaagaggga gttacaactg gaggtggagg     360

aaaggagacc aggaagtgtt gatgtgcccc tgcctgagag caacattgtc cgcactataa     420

tggagtttct cagtttcttg caccttaaag aggccggggc cctcgacagc ctgcctggca     480

tccccttggc cacctcctca gaagacctag agaagtcctg agaccatgcc cactgtgcac     540

gtgtgtcctg tgctgtaatt taaagtcatt ctaggctaag aagaatcttc tgccaactcc     600

tcaagccaat cctctgttct ctgctttgaa gctgtgttat aattaagatg ttttgattgg     660

agtaattata ttgtgtgaca taataaaaac tagcaagtaa aaaaaaaaaa aaaaaa         716


<210> SEQ ID NO 72
<211> LENGTH: 375
<212> TYPE: DNA
<213> ORGANISM: Mus musculus

<400> SEQUENCE: 72

atggccagag gcagcgttat cctgctaggc tggctcctgt tggttgtgac cctgtcagcc      60

actctgggac ttgggatgcc tgcaaaggag aagagaggtt ggaccctgaa cagcgctggc     120

taccttctgg gcccacatgc cattgacaac cacagatcat ttagcgacaa gcatggcctc     180

acaggcaaga gggagttaca actggaggtg gaggaaagga gaccaggaag tgttgatgtg     240

cccctgcctg agagcaacat tgtccgcact ataatggagt ttctcagttt cttgcacctt     300

aaagaggccg gggccctcga cagcctgcct ggcatcccct tggccacctc ctcagaagac     360

ctagagaagt cctga                                                      375


<210> SEQ ID NO 73
<211> LENGTH: 124
<212> TYPE: PRT
<213> ORGANISM: Mus musculus

<400> SEQUENCE: 73

Met Ala Arg Gly Ser Val Ile Leu Leu Gly Trp Leu Leu Leu Val Val
1               5                   10                  15

Thr Leu Ser Ala Thr Leu Gly Leu Gly Met Pro Ala Lys Glu Lys Arg
            20                  25                  30
```

```
Gly Trp Thr Leu Asn Ser Ala Gly Tyr Leu Leu Gly Pro His Ala Ile
        35                  40                  45

Asp Asn His Arg Ser Phe Ser Asp Lys His Gly Leu Thr Gly Lys Arg
    50                  55                  60

Glu Leu Gln Leu Glu Val Glu Glu Arg Arg Pro Gly Ser Val Asp Val
65                  70                  75                  80

Pro Leu Pro Glu Ser Asn Ile Val Arg Thr Ile Met Glu Phe Leu Ser
                85                  90                  95

Phe Leu His Leu Lys Glu Ala Gly Ala Leu Asp Ser Leu Pro Gly Ile
            100                 105                 110

Pro Leu Ala Thr Ser Ser Glu Asp Leu Glu Lys Ser
        115                 120
```

<210> SEQ ID NO 74
<211> LENGTH: 699
<212> TYPE: DNA
<213> ORGANISM: Rattus norvegicus

<400> SEQUENCE: 74

```
cgagggatcc tcgtgcgctt ccctacgccg ctgatctgcg ccatgcagtg agcgaccctc     60

gcgcccgcca ctctacgcca cgcctggacg gagacacttg gacctgcact aaccagctac    120

gcccggttcc caccactgct caagatggcc aggggcagcg ttatcctgct agcctggctc    180

ctgttggttg caaccctgtc agccactctg ggctcggga tgccaacaaa ggagaagaga    240

ggctggaccc tgaacagcgc tggctacctt ctgggcccac atgccattga caaccacaga    300

tcatttagcg acaagcatgg cctcacaggc aagagggagt taccactgga agtggaggaa    360

gggagactag gaagtgttgc tgtgcccctg cctgagagca atatcgtccg cactataatg    420

gagtttctca gtttcttgca ccttaaagag gccggggccc tcgacagcct gcctggcatc    480

cccttggcca cctcctcaga agacctagag cagtcctgag accacaccca ctgtgcacct    540

gtgtcctctg ctataattta aagtcattct aggctaaaaa gaatcttccg ccaactcctc    600

aagccaacac tttgttctct gctttgatgc tgagttatta caattaagat gttttgattg    660

gagtaattat attgtgtgac ataataaaaa ctagcaagt                           699
```

<210> SEQ ID NO 75
<211> LENGTH: 375
<212> TYPE: DNA
<213> ORGANISM: Rattus norvegicus

<400> SEQUENCE: 75

```
atggccaggg gcagcgttat cctgctagcc tggctcctgt tggttgcaac cctgtcagcc     60

actctggggc tcgggatgcc aacaaaggag aagagaggct ggaccctgaa cagcgctggc    120

taccttctgg gcccacatgc cattgacaac cacagatcat ttagcgacaa gcatggcctc    180

acaggcaaga gggagttacc actggaagtg gaggaaggga gactaggaag tgttgctgtg    240

cccctgcctg agagcaatat cgtccgcact ataatggagt ttctcagttt cttgcacctt    300

aaagaggccg gggccctcga cagcctgcct ggcatcccct tggccacctc ctcagaagac    360

ctagagcagt cctga                                                     375
```

<210> SEQ ID NO 76
<211> LENGTH: 124
<212> TYPE: PRT
<213> ORGANISM: Rattus norvegicus

<400> SEQUENCE: 76

```
Met Ala Arg Gly Ser Val Ile Leu Leu Ala Trp Leu Leu Leu Val Ala
1               5                   10                  15

Thr Leu Ser Ala Thr Leu Gly Leu Gly Met Pro Thr Lys Glu Lys Arg
            20                  25                  30

Gly Trp Thr Leu Asn Ser Ala Gly Tyr Leu Leu Gly Pro His Ala Ile
        35                  40                  45

Asp Asn His Arg Ser Phe Ser Asp Lys His Gly Leu Thr Gly Lys Arg
    50                  55                  60

Glu Leu Pro Leu Glu Val Glu Glu Gly Arg Leu Gly Ser Val Ala Val
65                  70                  75                  80

Pro Leu Pro Glu Ser Asn Ile Val Arg Thr Ile Met Glu Phe Leu Ser
                85                  90                  95

Phe Leu His Leu Lys Glu Ala Gly Ala Leu Asp Ser Leu Pro Gly Ile
            100                 105                 110

Pro Leu Ala Thr Ser Ser Glu Asp Leu Glu Gln Ser
        115                 120
```

<210> SEQ ID NO 77
<211> LENGTH: 3056
<212> TYPE: DNA
<213> ORGANISM: Homo sapiens

<400> SEQUENCE: 77

```
atcccgctag aatccgtcca gtctctgctc gcgcaccgtg acttctaagg ggcgcggatt     60

tcagccgagc tgttttcgcc tctcagttgc agcagagaag cccctggcac ccgactctat    120

ccaccaccag gaagcctccc aaaagagctc tcgccctgtg gacgactcgg aatccctgga    180

aaagccggga gggagtcgga ggcgccagcc cactggggag gtggcgctgg gcgcgcggga    240

tgcgcgggga gccttctctg caggagccgc acagtgcact gctgcgcgct gggcagtgcg    300

gggaagcgcc gcgggaagga gcggctccga gcaacaggtg cagcacgcag ccgctccggg    360

agccagggaa aaccgccggc gaagatctgg agcggtaagg cggagagaag ggtctttcca    420

cctgcgcggc tgcagccggc ggatccctct tcccaggctc cgtggtcgcg cagcgggcgg    480

aggcgcccgg gcaggggacc ccagtgctct cgagatcacc gtcccttccc gagaaggtcc    540

agctccgggc tcccgaaccc accctctctc agaaggtcgc ggcgcaaaga cggtgccacc    600

aggcacggcc accggatccc cgctcccgct ggctcgcgcc tcgggggaag ctcagactcc    660

taaactcgca ctctccgtgc tttgcgccgg gacccctggc cacccccggc gcctgctatc    720

ccgccctccc tccccgcgcg ccccgccgct cgccgggaca gccccgcggg ccatggagct    780

ggcggtcggg aacctcagcg agggcaacgc gagctggccg gagcccccg ccccggagcc     840

cgggccgctg ttcggcatcg gcgtggagaa cttcgtcacg ctggtggtgt tcggcctgat    900

cttcgcgctg ggcgtgctgg gcaacagcct agtgatcacc gtgctggcgc gcagcaagcc    960

gggcaagccg cggagcacca ccaacctgtt catcctcaac ctgagcatcg ccgacctggc   1020

ctacctgctc ttctgcatcc ccttccaggc caccgtgtac gcgctgccca cctgggtgct   1080

gggcgccttc atctgcaagt tcatccacta cttcttcacc gtgtccatgc tggtgagcat   1140

cttcaccctg gccgcgatgt ccgtggaccg ctacgtggcc atcgtgcact cgcggcgctc   1200

ctcctccctc agggtgtccc gcaacgcgct gctgggcgtg ggctgcatct gggcgctgtc   1260

cattgccatg gcctcgcccg tggcctacca ccagggcctc ttccacccgc gcgccagcaa   1320

ccagaccttc tgctgggagc agtggcccga ccctcgccac aagaaggcct acgtggtgtg   1380
```

caccttcgtc ttcggctacc tgctgccgct cctgctcatc tgcttctgct atgccaaggt 1440
ccttaatcac ttgcataaaa agttgaagaa catgtcaaag aagtctgaag catccaagaa 1500
aaagactgca cagacagttc tggtggtggt tgtggtgttt ggaatctcct ggctgccgca 1560
ccacatcatc catctctggg ctgagtttgg agttttcccg ctgacgccgg cttccttcct 1620
cttcagaatc accgcccact gcctggcgta cagcaattcc tccgtgaatc ctatcattta 1680
tgcatttctc tctgaaaatt tcaggaaggc ctataaacaa gtgttcaagt gtcacattcg 1740
caaagattca cacctgagtg atactaaaga aaataaaagt cgaatagaca ccccaccatc 1800
aaccaattgt actcatgtgt gataaaagat agagtatcct tatggttgag tttccatata 1860
agtggaccag acacagaaac aaacagaatg agctagtaag cgatgctgca acttgttatc 1920
ttaacaagaa ttcaagtcgt tttaattaaa tcccacgtgt gttaaaaagt actttgatcc 1980
atttaggaaa ttcctaggtc tagtgagaat tatttttcaa ttttatttta gttctaaatt 2040
atgtttcaga aacaaaagac aatgctgtac agttttattc ctcttcagac atgaaaggga 2100
acatatatat tccatatata tgttcaactc ttcatagatt gtgaactggc ccatcaatat 2160
ggtcaggaat atttgcagtc tacattttaa agccaattta tttagaaaaa aaatttgagc 2220
tttaattctt taattttaag agaagtaata ttgtgaacta tgtattttaa aatatgatca 2280
tggacacaca atgatgaatt ttttggccat ttacatagac atatctatta agtggaaaga 2340
aggctttctg aagtctgttt gcacaggtgg catttgcttc caattgtagc tagcgcacag 2400
agctttggaa gcctgtcatt atgagataca gtcggtttac ctcaggagtc aattcagtgt 2460
tgtactggtg acctgggatg cagtagtagg cactgttgat tcaaatttat cctgtgaaac 2520
tggctttata gagttaacaa aacagagtca gagaccactg tcttaacagt ggaagatgca 2580
aataagtttt tgagaataaa actggatttt gaaattttac attagtactt gacaaaagtt 2640
ttcattttgc cttgaatgga acctactaaa aagagagatg aaaaaaaatc agcgaggttg 2700
atgtagataa taatttctat gggaccaaag actagacaga attcagtaag tcacatgaag 2760
taatggtcat gcctgtacat aaagcatatt tcatgtttga tttagatgac attcaaaaaa 2820
aatcatggga ctgaatatac ctggggtatc ctatcttgta caaatgcatg ctttttcatt 2880
aaatttgtaa tgatgtttaa tgaacatttc caccaaacat tatttcctct aaaaatgtta 2940
atttggggtt aaaaccatca ccatttgaat ttcaaatgta gttttcatga caattttata 3000
ttgatgtgtg tttacaatga gaaaatggca tgaaaatatt aaattgtctt gtatcg 3056

<210> SEQ ID NO 78
<211> LENGTH: 1050
<212> TYPE: DNA
<213> ORGANISM: Homo sapiens

<400> SEQUENCE: 78
atggagctgg cggtcgggaa cctcagcgag ggcaacgcga gctggccgga gccccccgcc 60
ccggagcccg ggccgctgtt cggcatcggc gtggagaact tcgtcacgct ggtggtgttc 120
ggcctgatct tcgcgctggg cgtgctgggc aacagcctag tgatcaccgt gctggcgcgc 180
agcaagccgg gcaagccgcg gagcaccacc aacctgttca tcctcaacct gagcatcgcc 240
gacctggcct acctgctctt ctgcatcccc ttccaggcca ccgtgtacgc gctgcccacc 300
tgggtgctgg gcgccttcat ctgcaagttc atccactact tcttcaccgt gtccatgctg 360
gtgagcatct tcaccctggc cgcgatgtcc gtggaccgct acgtggccat cgtgcactcg 420

```
cggcgctcct cctccctcag ggtgtcccgc aacgcgctgc tgggcgtggg ctgcatctgg     480

gcgctgtcca ttgccatggc ctcgcccgtg gcctaccacc agggcctctt ccacccgcgc     540

gccagcaacc agaccttctg ctgggagcag tggcccgacc ctcgccacaa gaaggcctac     600

gtggtgtgca ccttcgtctt cggctacctg ctgccgctcc tgctcatctg cttctgctat     660

gccaaggtcc ttaatcactt gcataaaaag ttgaagaaca tgtcaaagaa gtctgaagca     720

tccaagaaaa agactgcaca gacagttctg gtggtggttg tggtgtttgg aatctcctgg     780

ctgccgcacc acatcatcca tctctgggct gagtttggag ttttcccgct gacgccggct     840

tccttcctct tcagaatcac cgcccactgc ctggcgtaca gcaattcctc cgtgaatcct     900

atcatttatg catttctctc tgaaaatttc aggaaggcct ataaacaagt gttcaagtgt     960

cacattcgca aagattcaca cctgagtgat actaaagaaa ataaaagtcg aatagacacc    1020

ccaccatcaa ccaattgtac tcatgtgtga                                     1050
```

<210> SEQ ID NO 79
<211> LENGTH: 349
<212> TYPE: PRT
<213> ORGANISM: Homo sapiens

<400> SEQUENCE: 79

```
Met Glu Leu Ala Val Gly Asn Leu Ser Glu Gly Asn Ala Ser Trp Pro
1               5                   10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
        35                  40                  45

Leu Gly Asn Ser Leu Val Ile Thr Val Leu Ala Arg Ser Lys Pro Gly
    50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
        115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
                165                 170                 175

Phe His Pro Arg Ala Ser Asn Gln Thr Phe Cys Trp Glu Gln Trp Pro
            180                 185                 190

Asp Pro Arg His Lys Lys Ala Tyr Val Val Cys Thr Phe Val Phe Gly
        195                 200                 205

Tyr Leu Leu Pro Leu Leu Leu Ile Cys Phe Cys Tyr Ala Lys Val Leu
    210                 215                 220

Asn His Leu His Lys Lys Leu Lys Asn Met Ser Lys Lys Ser Glu Ala
225                 230                 235                 240

Ser Lys Lys Lys Thr Ala Gln Thr Val Leu Val Val Val Val Val Phe
                245                 250                 255

Gly Ile Ser Trp Leu Pro His His Ile Ile His Leu Trp Ala Glu Phe
```

```
            260                 265                 270

Gly Val Phe Pro Leu Thr Pro Ala Ser Phe Leu Phe Arg Ile Thr Ala
        275                 280                 285

His Cys Leu Ala Tyr Ser Asn Ser Ser Val Asn Pro Ile Ile Tyr Ala
    290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
            340                 345


<210> SEQ ID NO 80
<211> LENGTH: 2748
<212> TYPE: DNA
<213> ORGANISM: Pan troglodytes

<400> SEQUENCE: 80

atgtcagcca cgtctataga ggagctcacg cggccctttc cctttgcact tctctcctct     60

ctagcaggcc gcggggtgag ggtgggatta ggcggccaat tttacaaaac tccagggagc    120

gtcgccagcc tcgatttcct ggggttattc ctgggagaga ggcgttctca cggacagcca    180

ccctggggag gaggaggagg aggaaaggca ctgatggatg aggaggcccg cgcacccctc    240

cgcctcccac cccggcgcgc cctggaacgc cctggagcgc gcccggcttc cctcgcccgc    300

ctggcccgcg gcatccggca gccccgcctt cagcccgccg ggcaggtccg cactccgcgg    360

aggcgagcgc gctccggttc cagccgggag gtgggcggcg acccatcccg ccagaatccg    420

tccagtctct gctcgcgcac cgtgacttct agggggcgcg gatttcagcc gggctgtttt    480

cgcctctcag ttgcagcaga gaggcccctg gcacccgact ctatccacca ccaggaagcc    540

tcccaaaaga gctctcgccc tgtggacgac tcggaatccc tggaaaagcc gggagggagt    600

cggaggcgcc agcccactgg ggaggtggcg ctgggcgcgc aggatgcgcg gggagccctg    660

tctgtaggag ccgcacatgc tctcgagatc accgtccctt cccgagaagg tccagttccg    720

ggctcccgaa cccaccctct ctcagaaggt cgcggcgcaa agacggtgcc accaggcacg    780

gccaccggat ccccgctccc gctggctcgc gcctcggggg aagctcagac tcccaaactc    840

gcactctccg tgctttgcgc cgggaccccc ggccaccccc ggcgtctact atcccgccct    900

ccctccccgc gcgccccgcc gctcgccggg acagccccgc gggccatgga gctggcggtc    960

gggaacctca gcgagggcaa cgcgagctgg ccggagtccc ccgcccccgga gcccgggccg   1020

ctgttcggca tcggcgtgga gaacttcgtc acgctggtgg tgttcggcct gatcttcgcg   1080

ctgggcgtgc tgggcaacag cctagtgatc accgtgctgg cgcgcagcaa gccgggcaag   1140

ccgcggagca ccaccaacct gttcatcctc aacctgagca tcgccgacct ggcctacctg   1200

ctcttctgca tccccttcca ggccacggtg tacgcgctgc ccacctgggt gctgggcgcc   1260

ttcatctgca agttcatcca ctacttcttc accgtgtcca tgctggtgag catcttcacc   1320

ctggccgcga tgtccgtgga ccgctacgtg gccatcgtgc actcgcggcg ctcctcctcc   1380

ctcagggtgt cccgcaacgc gctgctgggc gtgggctgca tctgggcgct gtccattgcc   1440

atggcctcgc ccgtggccta ccaccagggc ctcttccacc cgcgcgccag caaccagacc   1500

ttctgctggg agcagtggcc cgaccctcgc cacaagaagg cctacgtggt gtgcaccttc   1560

gtcttcggct acctgctgcc gctcctgctc atctgcttct gctatgccaa ggtgcacgcc   1620
```

```
ggtcgcgggg ccgagacgcg cgagggaggg cggagggccg gtgggggccc tggggtctca   1680
gtgtcccgcg gccctgccgg agccttggcg gcagcctggc cccggtggtc cccactctgg   1740
cggcgctggt acggatctgt gcagagaggc ttcctggccg ctgctggagc gtgccattgg   1800
cttgcgcaag aaagttactt ggagtctgag agatgctggg gaaagtttgc agttcacttc   1860
gcatggtccg gtagaacaag tttctcctcc cctccccttc ctcggccctg cggcccttca   1920
acgcccccag gttgcctggg cgatcagctg ctcggggagg ttacagccgc ggcgctgtgg   1980
gacctgagga gagctctggt ggtcaccaga gcgcggacct tttgcgaggg tgacgggtcc   2040
ccacagctcc ctcccgggct ctcagctggc cgtggcgggg aggactcgcg gggcggcccc   2100
tctcccccgg gtgaattact gtccagaatc tccttggtct accatgagga taaactcaat   2160
gggcccactc gactaagtta ctccgaatcc ccaggatgta gccagcagga cctggtttgg   2220
tttgagctag caccttcctg tgcacactca gaaatttaca gactcaccaa gagaccccag   2280
tatgttatta tcactctcaa acatcgtcat accctatcat ggtacctgca ttcttcctcc   2340
tttgctgccg agaccttcag tggggtcctt aatcacttgc ataaaaagtt gaagaacatg   2400
tcaaagaagt ctgaagcatc caagaaaaag actgcacaga cagttctggt ggtggtcgtg   2460
gtgtttggaa tctcctggct gccgcaccac atcatccatc tctgggctga gttcggagtt   2520
ttcccgctga cgccggcttc cttcctcttc agaatcaccg cccactgcct ggcgtacagc   2580
aattcctccg tgaatcctat catttatgca tttctctctg aaaatttcag gaaggcctat   2640
aagcaagtgt tcaagtgtca cattcgcaaa gattcacccc tgagtgatac taaagaaaat   2700
aaaagtcgaa tagacacccc accatcaacc aattgtactc atgtgtga                2748
```

<210> SEQ ID NO 81
<211> LENGTH: 915
<212> TYPE: PRT
<213> ORGANISM: Pan troglodytes

<400> SEQUENCE: 81

```
Met Ser Ala Thr Ser Ile Glu Glu Leu Thr Arg Pro Phe Pro Phe Ala
1               5                   10                  15

Leu Leu Ser Ser Leu Ala Gly Arg Gly Val Arg Val Gly Leu Gly Gly
            20                  25                  30

Gln Phe Tyr Lys Thr Pro Gly Ser Val Ala Ser Leu Asp Phe Leu Gly
        35                  40                  45

Leu Phe Leu Gly Glu Arg Arg Ser His Gly Gln Pro Pro Trp Gly Gly
    50                  55                  60

Gly Gly Gly Gly Lys Ala Leu Met Asp Glu Glu Ala Arg Ala Pro Leu
65                  70                  75                  80

Arg Leu Pro Pro Arg Arg Ala Leu Glu Arg Pro Gly Ala Arg Pro Ala
                85                  90                  95

Ser Leu Ala Arg Leu Ala Arg Gly Ile Arg Gln Pro Arg Leu Gln Pro
            100                 105                 110

Ala Gly Gln Val Arg Thr Pro Arg Arg Arg Ala Arg Ser Gly Ser Ser
        115                 120                 125

Arg Glu Val Gly Gly Asp Pro Ser Arg Gln Asn Pro Ser Ser Leu Cys
    130                 135                 140

Ser Arg Thr Val Thr Ser Arg Gly Arg Gly Phe Gln Pro Gly Cys Phe
145                 150                 155                 160

Arg Leu Ser Val Ala Ala Glu Arg Pro Leu Ala Pro Asp Ser Ile His
                165                 170                 175
```

```
His Gln Glu Ala Ser Gln Lys Ser Ser Arg Pro Val Asp Asp Ser Glu
            180                 185                 190

Ser Leu Glu Lys Pro Gly Gly Ser Arg Arg Arg Gln Pro Thr Gly Glu
        195                 200                 205

Val Ala Leu Gly Ala Gln Asp Ala Arg Gly Ala Leu Ser Val Gly Ala
    210                 215                 220

Ala His Ala Leu Glu Ile Thr Val Pro Ser Arg Glu Gly Pro Val Pro
225                 230                 235                 240

Gly Ser Arg Thr His Pro Leu Ser Glu Gly Arg Gly Ala Lys Thr Val
                245                 250                 255

Pro Pro Gly Thr Ala Thr Gly Ser Pro Leu Pro Leu Ala Arg Ala Ser
            260                 265                 270

Gly Glu Ala Gln Thr Pro Lys Leu Ala Leu Ser Val Leu Cys Ala Gly
        275                 280                 285

Thr Pro Gly His Pro Arg Arg Leu Leu Ser Arg Pro Pro Ser Pro Arg
    290                 295                 300

Ala Pro Pro Leu Ala Gly Thr Ala Pro Arg Ala Met Glu Leu Ala Val
305                 310                 315                 320

Gly Asn Leu Ser Glu Gly Asn Ala Ser Trp Pro Glu Ser Pro Ala Pro
                325                 330                 335

Glu Pro Gly Pro Leu Phe Gly Ile Gly Val Glu Asn Phe Val Thr Leu
            340                 345                 350

Val Val Phe Gly Leu Ile Phe Ala Leu Gly Val Leu Gly Asn Ser Leu
        355                 360                 365

Val Ile Thr Val Leu Ala Arg Ser Lys Pro Gly Lys Pro Arg Ser Thr
    370                 375                 380

Thr Asn Leu Phe Ile Leu Asn Leu Ser Ile Ala Asp Leu Ala Tyr Leu
385                 390                 395                 400

Leu Phe Cys Ile Pro Phe Gln Ala Thr Val Tyr Ala Leu Pro Thr Trp
                405                 410                 415

Val Leu Gly Ala Phe Ile Cys Lys Phe Ile His Tyr Phe Phe Thr Val
            420                 425                 430

Ser Met Leu Val Ser Ile Phe Thr Leu Ala Ala Met Ser Val Asp Arg
        435                 440                 445

Tyr Val Ala Ile Val His Ser Arg Arg Ser Ser Ser Leu Arg Val Ser
    450                 455                 460

Arg Asn Ala Leu Leu Gly Val Gly Cys Ile Trp Ala Leu Ser Ile Ala
465                 470                 475                 480

Met Ala Ser Pro Val Ala Tyr His Gln Gly Leu Phe His Pro Arg Ala
                485                 490                 495

Ser Asn Gln Thr Phe Cys Trp Glu Gln Trp Pro Asp Pro Arg His Lys
            500                 505                 510

Lys Ala Tyr Val Val Cys Thr Phe Val Phe Gly Tyr Leu Leu Pro Leu
        515                 520                 525

Leu Leu Ile Cys Phe Cys Tyr Ala Lys Val His Ala Gly Arg Gly Ala
    530                 535                 540

Glu Thr Arg Glu Gly Gly Arg Arg Ala Gly Gly Gly Pro Gly Val Ser
545                 550                 555                 560

Val Ser Arg Gly Pro Ala Gly Ala Leu Ala Ala Ala Trp Pro Arg Trp
                565                 570                 575

Ser Pro Leu Trp Arg Arg Trp Tyr Gly Ser Val Gln Arg Gly Phe Leu
            580                 585                 590

Ala Ala Ala Gly Ala Cys His Trp Leu Ala Gln Glu Ser Tyr Leu Glu
```

```
        595                 600                 605

Ser Glu Arg Cys Trp Gly Lys Phe Ala Val His Phe Ala Trp Ser Gly
    610                 615                 620

Arg Thr Ser Phe Ser Ser Pro Pro Leu Pro Arg Pro Cys Gly Pro Ser
625                 630                 635                 640

Thr Pro Pro Gly Cys Leu Gly Asp Gln Leu Leu Gly Glu Val Thr Ala
                645                 650                 655

Ala Ala Leu Trp Asp Leu Arg Arg Ala Leu Val Val Thr Arg Ala Arg
            660                 665                 670

Thr Phe Cys Glu Gly Asp Gly Ser Pro Gln Leu Pro Pro Gly Leu Ser
        675                 680                 685

Ala Gly Arg Gly Gly Glu Asp Ser Arg Gly Gly Pro Ser Pro Pro Gly
    690                 695                 700

Glu Leu Leu Ser Arg Ile Ser Leu Val Tyr His Glu Asp Lys Leu Asn
705                 710                 715                 720

Gly Pro Thr Arg Leu Ser Tyr Ser Glu Ser Pro Gly Cys Ser Gln Gln
                725                 730                 735

Asp Leu Val Trp Phe Glu Leu Ala Pro Ser Cys Ala His Ser Glu Ile
            740                 745                 750

Tyr Arg Leu Thr Lys Arg Pro Gln Tyr Val Ile Ile Thr Leu Lys His
        755                 760                 765

Arg His Thr Leu Ser Trp Tyr Leu His Ser Ser Ser Phe Ala Ala Glu
    770                 775                 780

Thr Phe Ser Gly Val Leu Asn His Leu His Lys Lys Leu Lys Asn Met
785                 790                 795                 800

Ser Lys Lys Ser Glu Ala Ser Lys Lys Lys Thr Ala Gln Thr Val Leu
                805                 810                 815

Val Val Val Val Val Phe Gly Ile Ser Trp Leu Pro His His Ile Ile
            820                 825                 830

His Leu Trp Ala Glu Phe Gly Val Phe Pro Leu Thr Pro Ala Ser Phe
        835                 840                 845

Leu Phe Arg Ile Thr Ala His Cys Leu Ala Tyr Ser Asn Ser Ser Val
    850                 855                 860

Asn Pro Ile Ile Tyr Ala Phe Leu Ser Glu Asn Phe Arg Lys Ala Tyr
865                 870                 875                 880

Lys Gln Val Phe Lys Cys His Ile Arg Lys Asp Ser Pro Leu Ser Asp
                885                 890                 895

Thr Lys Glu Asn Lys Ser Arg Ile Asp Thr Pro Pro Ser Thr Asn Cys
            900                 905                 910

Thr His Val
        915
```

<210> SEQ ID NO 82
<211> LENGTH: 2859
<212> TYPE: DNA
<213> ORGANISM: Mus musculus

<400> SEQUENCE: 82

```
ggatccgtga gagaggctcg ccctgcagag gacccgggac taagagggag ccgcaggcca     60

gcgcagcgag gcagggaggt ggatcttagt gcgggaagct cagcgaccct cttcaccatt    120

gaaggtgtgc atcgctgggc tctcggacgt tcgggaagaa gagcgtcaaa gcaacaggtg    180

caacctcaag gcactgaaag caaggggacg cagctcacaa gggccaaggg attgaaccca    240

taaccgctca gaagattctc cgcctgcgga gagctgcgga ggagtcccac ccgtccagct    300
```

```
tgctgactgc gagcagtgag agtcgcctag acccgtacct ctgtgttctg gagcctgccg    360
cccccgcacg ggaaaggctt agctcgggac ttgcagcacc gcctcctctt tagccaggcc    420
aggcacgagg atagtgtgat cgggcacagc cagggtcgct cttccaggct ttcttgcggg    480
ttgcgggagg tactagttgg agacgcgcgc gctcgctctc gccgctctgt cctgggccac    540
tccgtgatcc taggctacct ccagagccag ttttccctgg ctggcacaac tctccagggc    600
gctccggtcc gttgcacagc gccccaaggg ggtatcccag taagtgatgg aactggctat    660
ggtgaacctc agtgaaggga atgggagcga cccagagccg ccagccccgg agtccaggcc    720
gctcttcggc attggcgtgg agaacttcat tacgctggta gtgtttggcc tgattttcgc    780
gatgggcgtg ctgggcaaca gcctggtgat caccgtgctg gcgcgcagca aaccaggcaa    840
gccgcgcagc accaccaacc tgtttatcct caatctgagc atcgcagacc tggcctacct    900
gctcttctgc atccctttc aggccaccgt gtatgcactg ccaacctggg tgctgggcgc    960
cttcatctgc aagtttatac actacttctt caccgtgtcc atgctggtga gcatcttcac   1020
cctggccgcg atgtctgtgg atcgctacgt ggccattgtg cactcgcggc gctcctcctc   1080
cctcagggtg tcccgcaacg cactgctggg cgtgggcttc atctgggcgc tgtccatcgc   1140
catggcctcg ccggtggcct accaccagcg tcttttccat cgggacagca accagacctt   1200
ctgctgggag cagtggccca acaagctcca caagaaggct tacgtggtgt gcactttcgt   1260
ctttgggtac cttctgccct tactgctcat ctgcttttgc tatgccaagg tccttaatca   1320
tctgcataaa aagctgaaaa acatgtcaaa aaagtctgaa gcatccaaga aaaagactgc   1380
acagaccgtc ctggtggtcg ttgtagtatt tggcatatcc tggctgcccc atcatgtcgt   1440
ccacctctgg gctgagtttg gagccttccc actgacgcca gcttccttct tcttcagaat   1500
caccgcccat tgcctggcat acagcaactc ctcagtgaac cccatcatat atgcctttct   1560
ctcagaaaac ttccggaagg cgtacaagca agtgttcaag tgtcatgttt gcgatgaatc   1620
tccacgcagt gaaactaagg aaaacaagag ccggatggac accccgccat ccaccaactg   1680
cacccacgtg tgaaggtttg cgggagcctc ccgacttcca gctcccatgt gtgttagaga   1740
gaggagggcg gagcgaatta tcaagtaaca tggcagctta ttctccacag caattcctat   1800
cgatccaact acattccaca gtggtaaaag gacgttgatt gttcagggaa ctcgtgggtc   1860
tactgaagat cattttccaa tttcatttta ctctataatt gtatatatga gacaaaagaa   1920
acttctgtat agtttctagc tctcaaggaa tgaaagtcct acagcactct gcaaatgttt   1980
tgatgcatgc cccagccttc cctcccagtc tgcctcagta tcctcgggct tccgccactc   2040
gtgcctcatt gtttttttgtt tgtttgtttg tttttggtat tttgaaatag ggtttctctg   2100
tgtagccctg gctgtcctga actcactctg tagaccaggc tggcctagaa ctcagaaatc   2160
tgcctgcctc tgcctcccaa gtgctgggat taaaggtgtg caccaccact gcccggccct   2220
gcctcattgt tttaactgca tgtgggacag tctctagtgg gccacatcct tttgtgggtg   2280
gagtctcctg tgagctcaga tctgctctgt tcagaaatac agaatcaaac agaaggggct   2340
gctgtagttg gccaactaat ctctactcga atcacccggc gatgctgggg tgttcctcac   2400
tattcacccc aatgttccag gttcccgaat gaaatacaca cagacagagg gagagggaga   2460
aggagaggga aagggagagg gagagggaga gggagaggga gagggagagg gagagggaaa   2520
gccatatttt ttaatgtttt ttaacagctc aacggctggg ctacttctta gcctccgtgc   2580
ggctaacaca ctctttcaat attcctgact caccacttac taaaatcctg ggcaccccag   2640
```

acccagacct gtagcccttc tgggccatgc cccgactctt tacacagtgg ttctgtgctc 2700
ttctgtacct ctcacgtctg gtttttacta ctttcctggc atggcagccc ctcccctgtc 2760
ccttgcccaa gaatcttaaa agtactgcct ttgtctccgt acccagccat ttgctgctgg 2820
caactttatt taccaataaa aaccaacttg gggcaagga 2859

<210> SEQ ID NO 83
<211> LENGTH: 1047
<212> TYPE: DNA
<213> ORGANISM: Mus musculus

<400> SEQUENCE: 83
atggaactgg ctatggtgaa cctcagtgaa gggaatggga gcgacccaga gccgccagcc 60
ccggagtcca ggccgctctt cggcattggc gtggagaact tcattacgct ggtagtgttt 120
ggcctgattt tcgcgatggg cgtgctgggc aacagcctgg tgatcaccgt gctggcgcgc 180
agcaaaccag gcaagccgcg cagcaccacc aacctgttta tcctcaatct gagcatcgca 240
gacctggcct acctgctctt ctgcatccct tttcaggcca ccgtgtatgc actgccaacc 300
tgggtgctgg gcgccttcat ctgcaagttt atacactact tcttcaccgt gtccatgctg 360
gtgagcatct tcaccctggc cgcgatgtct gtggatcgct acgtggccat tgtgcactcg 420
cggcgctcct cctccctcag ggtgtcccgc aacgcactgc tgggcgtggg cttcatctgg 480
gcgctgtcca tcgccatggc ctcgccggtg gcctaccacc agcgtctttt ccatcgggac 540
agcaaccaga ccttctgctg ggagcagtgg cccaacaagc tccacaagaa ggcttacgtg 600
gtgtgcactt tcgtctttgg gtaccttctg cccttactgc tcatctgctt ttgctatgcc 660
aaggtcctta atcatctgca taaaaagctg aaaaacatgt caaaaaagtc tgaagcatcc 720
aagaaaaaga ctgcacagac cgtcctggtg gtcgttgtag tatttggcat atcctggctg 780
ccccatcatg tcgtccacct ctgggctgag tttggagcct tcccactgac gccagcttcc 840
ttcttcttca gaatcaccgc ccattgcctg gcatacagca actcctcagt gaaccccatc 900
atatatgcct ttctctcaga aaacttccgg aaggcgtaca agcaagtgtt caagtgtcat 960
gtttgcgatg aatctccacg cagtgaaact aaggaaaaca agagccggat ggacaccccg 1020
ccatccacca actgcaccca cgtgtga 1047

<210> SEQ ID NO 84
<211> LENGTH: 348
<212> TYPE: PRT
<213> ORGANISM: Mus musculus

<400> SEQUENCE: 84

Met Glu Leu Ala Met Val Asn Leu Ser Glu Gly Asn Gly Ser Asp Pro
1 5 10 15

Glu Pro Pro Ala Pro Glu Ser Arg Pro Leu Phe Gly Ile Gly Val Glu
20 25 30

Asn Phe Ile Thr Leu Val Val Phe Gly Leu Ile Phe Ala Met Gly Val
35 40 45

Leu Gly Asn Ser Leu Val Ile Thr Val Leu Ala Arg Ser Lys Pro Gly
50 55 60

Lys Pro Arg Ser Thr Thr Asn Leu Phe Ile Leu Asn Leu Ser Ile Ala
65 70 75 80

Asp Leu Ala Tyr Leu Leu Phe Cys Ile Pro Phe Gln Ala Thr Val Tyr
85 90 95

Ala Leu Pro Thr Trp Val Leu Gly Ala Phe Ile Cys Lys Phe Ile His

```
            100                 105                 110

Tyr Phe Phe Thr Val Ser Met Leu Val Ser Ile Phe Thr Leu Ala Ala
        115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Phe Ile Trp
145                 150                 155                 160

Ala Leu Ser Ile Ala Met Ala Ser Pro Val Ala Tyr His Gln Arg Leu
                165                 170                 175

Phe His Arg Asp Ser Asn Gln Thr Phe Cys Trp Glu Gln Trp Pro Asn
            180                 185                 190

Lys Leu His Lys Lys Ala Tyr Val Val Cys Thr Phe Val Phe Gly Tyr
        195                 200                 205

Leu Leu Pro Leu Leu Leu Ile Cys Phe Cys Tyr Ala Lys Val Leu Asn
    210                 215                 220

His Leu His Lys Lys Leu Lys Asn Met Ser Lys Lys Ser Glu Ala Ser
225                 230                 235                 240

Lys Lys Lys Thr Ala Gln Thr Val Leu Val Val Val Val Val Phe Gly
                245                 250                 255

Ile Ser Trp Leu Pro His His Val Val His Leu Trp Ala Glu Phe Gly
            260                 265                 270

Ala Phe Pro Leu Thr Pro Ala Ser Phe Phe Phe Arg Ile Thr Ala His
        275                 280                 285

Cys Leu Ala Tyr Ser Asn Ser Ser Val Asn Pro Ile Ile Tyr Ala Phe
    290                 295                 300

Leu Ser Glu Asn Phe Arg Lys Ala Tyr Lys Gln Val Phe Lys Cys His
305                 310                 315                 320

Val Cys Asp Glu Ser Pro Arg Ser Glu Thr Lys Glu Asn Lys Ser Arg
                325                 330                 335

Met Asp Thr Pro Pro Ser Thr Asn Cys Thr His Val
            340                 345


<210> SEQ ID NO 85
<211> LENGTH: 2325
<212> TYPE: DNA
<213> ORGANISM: Rattus norvegicus

<400> SEQUENCE: 85

gaattcggca cgaggccagg ccagggaaga ggatagcgag atcaggcaca gcccgggtca      60

ctgtcctctg ctgtcttgcc ggttgcggga ggttctagct ggagacgcgc gctctctccg     120

cgctgtctag ggccatcctg tgaccctagg ctacctccag agctggcttt ccctggctgg     180

cacaactctc caaggagctc cggtccattg cacagcgccc caagggggtg tctcagtaag     240

tgatggaact ggctccggtg aacctcagtg aagggaatgg gagcgaccct gaacctccag     300

cggaacccag gccgctcttc ggcatcggcg tggagaactt catcacgctg gtggtgtttg     360

gccttatttt cgcgatgggc gtgctgggca acagcctggt gatcaccgtg ctggcgcgca     420

gcaaaccggg caagccgcgc agcaccacca acctgttcat cctcaacctg agcatcgcag     480

acctggccta cctgctcttc tgcatccctt tccaggccac cgtgtacgca ctgcccacct     540

gggtgctggg cgccttcatc tgcaagttta tacactactt cttcaccgtg tccatgctcg     600

tgagcatctt caccctggcc gcgatgtctg tggatcgcta tgtggccatt gtgcattcac     660

ggcgctcctc ctccctcagg gtgtcccgca acgcgctgct gggcgtgggc ttcatctggg     720
```

```
cgctgtccat cgctatggcc tcgccggtgg cctactacca gcgccttttt catcgggaca    780

gcaaccaaac cttctgctgg gagcactggc ccaaccaact ccacaagaag gcttacgtgg    840

tgtgcacttt cgtctttggt taccttctgc ccttactgct catctgcttt tgctatgcca    900

aggttctcaa tcatctgcat aaaaagttga agaacatgtc aaaaaagtca gaggcatcca    960

agaaaaagac tgcacagact gtcctggtgg tcgttgtggt atttggcata tcatggctgc   1020

cccatcatgt catccacctc tgggctgagt tcggagcatt cccgctgacc ccagcttcct   1080

tcttcttcag aatcactgcc cactgcctgg catacagcaa ctcctcggtg aaccccatca   1140

tctacgcctt tctctcagaa aacttccgga aggcgtacaa gcaagtgttc aagtgccgtg   1200

tttgcaatga gtcgccgcac ggcgatgcta aagaaaagaa ccgaatagat accccgccct   1260

ccaccaactg cacccacgtg tgaaggttgg ccagagcctc ctgtcctccg ctcccatgtg   1320

tgttagagag gggaggacac agtgaattat caagtaacat ggcagctcgt tctcctgcca   1380

gcaattccta tcattctaac aacattccac agcggtgaaa gcactttgat tgtccaggga   1440

actcctcggt ctactgaaga ttatttccca attttatttc attttatgat tgtatttatg   1500

aagcaaaaga aacttccata tagcttctat cttttaaggg atgaaagtcc aacagcgcac   1560

tgcagatatg ttctgatctc catgatacaa accaagttct aggaagcaat gaagattatt   1620

tgaaatccac attttaaggc cagttaatat agggaaacag ttctctttct tttaatgatg   1680

tagtattcta gttttgaaat acatttgtgg gcccagaata gtgaatttta ttttactgaa   1740

cctttgtgga ctggcacctc ttccgagtca ggggaggctt ttcaaagtct gttcccatag   1800

gtgtacagag ttctgtctgg gaacgtgaga ctcaccaagt tcatctcagg agatcattgg   1860

tgactccact ttgaagtaat cctgtggact aagacaccag ggagtctgct gtggacggct   1920

acaaacctgc ctgttgtagc tttaaggatg ttcttggcaa attattagct gggcctccaa   1980

agaacccagg aaaccagtca gccaacagtt tccacggggt tgaaaactgg acaaaactta   2040

gccacgtagt taatattcat gccgcatgga gaaagcagga aagatgcttg attccgaatg   2100

agcaaagaca aaggtatcct gtgggagaat agataaacac ttagagacgt gatgccttat   2160

gcagacttgt accgacaact gtttaatgat tgttttcccc aaacattatt ccctggggca   2220

attaatttag aattaaaatc accaccacgt gacttgcaaa tgtaaaaaaa aaaaaaaaaa   2280

aaaaaaaaaa aaaaaaaaaa aaaaaaaaaa aaaaagggcg gccgc                   2325
```

<210> SEQ ID NO 86
<211> LENGTH: 1041
<212> TYPE: DNA
<213> ORGANISM: Rattus norvegicus

<400> SEQUENCE: 86

```
atggaactgg ctccggtgaa cctcagtgaa gggaatggga gcgaccctga acctccagcg     60

gaacccaggc cgctcttcgg catcggcgtg gagaacttca tcacgctggt ggtgtttggc    120

cttattttcg cgatgggcgt gctgggcaac agcctggtga tcaccgtgct ggcgcgcagc    180

aaaccgggca agccgcgcag caccaccaac ctgttcatcc tcaacctgag catcgcagac    240

ctggcctacc tgctcttctg catccctttc caggccaccg tgtacgcact gcccacctgg    300

gtgctgggcg ccttcatctg caagtttata cactacttct tcaccgtgtc catgctcgtg    360

agcatcttca ccctggccgc gatgtctgtg gatcgctatg tggccattgt gcattcacgg    420

cgctcctcct ccctcagggt gtcccgcaac gcgctgctgg gcgtgggctt catctgggcg    480

ctgtccatcg ctatggcctc gccggtggcc tactaccagc gcctttttca tcgggacagc    540
```

```
aaccaaacct tctgctggga gcactggccc aaccaactcc acaagaaggc ttacgtggtg    600

tgcactttcg tctttggtta ccttctgccc ttactgctca tctgcttttg ctatgccaag    660

gttctcaatc atctgcataa aaagttgaag aacatgtcaa aaaagtcaga ggcatccaag    720

aaaaagactg cacagactgt cctggtggtc gttgtggtat ttggcatatc atggctgccc    780

catcatgtca tccacctctg ggctgagttc ggagcattcc cgctgacccc agcttccttc    840

ttcttcagaa tcactgccca ctgcctggca tacagcaact cctcggtgaa ccccatcatc    900

tacgcctttc tctcagaaaa cttccggaag gcgtacaagc aagtgttcaa gtgccgtgtt    960

tgcaatgagt cgccgcacgg cgatgctaaa gaaaagaacc gaatagatac cccgccctcc   1020

accaactgca cccacgtgtg a                                             1041
```

<210> SEQ ID NO 87
<211> LENGTH: 690
<212> TYPE: DNA
<213> ORGANISM: Rattus norvegicus

<400> SEQUENCE: 87

```
atggaactgg ctccggtgaa cctcagtgaa gggaatggga gcgaccctga acctccagcg     60

gaacccaggc cgctcttcgg catcggcgtg gagaacttca tcacgctggt ggtgtttggc    120

cttattttcg cgatgggcgt gctgggcaac agcctggtga tcaccgtgct ggcgcgcagc    180

aaaccgggca agccgcgcag caccaccaac ctgttcatcc tcaacctgag catcgcagac    240

ctgggctacc tgctcttctg catccctttc caggccaccg tgtacgcact gcccacctgg    300

gtgctgggcg ccttcatctg caagtttata cactacttct tcaccgtgtc catgctcgtg    360

agcatcttca ccctggccgc gatgtctgtg gatcgctatg tggccattgt gcattcacgg    420

cgctcctcct ccctcagggt gtcccgccaa cgcgctgctg ggcgtgggcc ttcatctggg    480

cgctgtccat cgctatggcc tcgccggtgg cctactacca gcgccttttt catcgggaca    540

gcaaccaaac cttctgctgg gagcactggc ccaaccaact ccacaagaag gcttacgtgg    600

tgtgcacttt cgtctttggt taccttctgc ccttactgct catctgcttt tgctatgcca    660

aggttctcaa tcatctgcat aaaaagttga                                    690
```

<210> SEQ ID NO 88
<211> LENGTH: 346
<212> TYPE: PRT
<213> ORGANISM: Rattus norvegicus

<400> SEQUENCE: 88

```
Met Glu Leu Ala Pro Val Asn Leu Ser Glu Gly Asn Gly Ser Asp Pro
1               5                   10                  15

Glu Pro Pro Ala Glu Pro Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110
```

```
Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205

Leu Pro Leu Leu Leu Ile Cys Phe Cys Tyr Ala Lys Val Leu Asn His
    210                 215                 220

Leu His Lys Lys Leu Lys Asn Met Ser Lys Lys Ser Glu Ala Ser Lys
225                 230                 235                 240

Lys Lys Thr Ala Gln Thr Val Leu Val Val Val Val Val Phe Gly Ile
                245                 250                 255

Ser Trp Leu Pro His His Val Ile His Leu Trp Ala Glu Phe Gly Ala
            260                 265                 270

Phe Pro Leu Thr Pro Ala Ser Phe Phe Phe Arg Ile Thr Ala His Cys
        275                 280                 285

Leu Ala Tyr Ser Asn Ser Ser Val Asn Pro Ile Ile Tyr Ala Phe Leu
    290                 295                 300

Ser Glu Asn Phe Arg Lys Ala Tyr Lys Gln Val Phe Lys Cys Arg Val
305                 310                 315                 320

Cys Asn Glu Ser Pro His Gly Asp Ala Lys Glu Lys Asn Arg Ile Asp
                325                 330                 335

Thr Pro Pro Ser Thr Asn Cys Thr His Val
            340                 345


<210> SEQ ID NO 89
<211> LENGTH: 229
<212> TYPE: PRT
<213> ORGANISM: Rattus norvegicus

<400> SEQUENCE: 89

Met Glu Leu Ala Pro Val Asn Leu Ser Glu Gly Asn Gly Ser Asp Pro
1               5                   10                  15

Glu Pro Pro Ala Glu Pro Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Gly Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
```

```
    130                 135                 140

Leu Arg Val Ser Arg Gln Arg Ala Ala Gly Arg Gly Pro Ser Ser Gly
145                 150                 155                 160

Arg Cys Pro Ser Leu Trp Pro Arg Arg Trp Pro Thr Thr Ser Ala Phe
                165                 170                 175

Phe Ile Gly Thr Ala Thr Lys Pro Ser Ala Gly Ser Thr Gly Pro Thr
            180                 185                 190

Asn Ser Thr Arg Arg Leu Thr Trp Cys Ala Leu Ser Ser Leu Val Thr
        195                 200                 205

Phe Cys Pro Tyr Cys Ser Ser Ala Phe Ala Met Pro Arg Phe Ser Ile
    210                 215                 220

Ile Cys Ile Lys Ser
225


<210> SEQ ID NO 90
<211> LENGTH: 1264
<212> TYPE: DNA
<213> ORGANISM: Homo sapiens

<400> SEQUENCE: 90

aagacccaga cggctgcagg agcccgggca gcctcggggt cagcggcacc atgaacgtct      60

cgggctgccc aggggccggg aacgcgagcc aggcgggcgg cgggggaggc tggcaccccg     120

aggcggtcat cgtgcccctg ctcttcgcgc tcatcttcct cgtgggcacc gtgggcaaca     180

cgctggtgct ggcggtgctg ctgcgcggcg gccaggcggt cagcactacc aacctgttca     240

tccttaacct gggcgtggcc gacctgtgtt tcatcctgtg ctgcgtgccc ttccaggcca     300

ccatctacac cctggacggc tgggtgttcg gctcgctgct gtgcaaggcg gtgcacttcc     360

tcatcttcct caccatgcac gccagcagct tcacgctggc cgccgtctcc ctggacaggt     420

atctggccat ccgctacccg ctgcactccc gcgagctgcg cacgcctcga aacgcgctgg     480

cagccatcgg gctcatctgg gggctgtcgc tgctcttctc cgggccctac ctgagctact     540

accgccagtc gcagctggcc aacctgaccg tgtgccatcc cgcgtggagc gcccctcgcc     600

gccgcgccat ggacatctgc accttcgtct tcagctacct gcttcctgtg ctggttctcg     660

gcctgaccta cgcgcgcacc ttgcgctacc tctggcgcgc cgtcgacccg gtggccgcgg     720

gctcgggtgc ccggcgcgcc aagcgcaagg tgacacgcat gatcctcatc gtggccgcgc     780

tcttctgcct ctgctggatg ccccaccacg cgctcatcct ctgcgtgtgg ttcggccagt     840

tcccgctcac gcgcgccact tatgcgcttc gcatcctctc gcacctggtc tcctacgcca     900

actcctgcgt caaccccatc gtttacgcgc tggtctccaa gcacttccgc aaaggcttcc     960

gcacgatctg cgcgggcctg ctgggccgtg ccccaggccg agcctcgggc cgtgtgtgcg    1020

ctgccgcgcg gggcacccac agtggcagcg tgttggagcg cgagtccagc gacctgttgc    1080

acatgagcga ggcggcgggg gcccttcgtc cctgccccgg cgcttcccag ccatgcatcc    1140

tcgagccctg tcctggcccg tcctggcagg gcccaaaggc aggcgacagc atcctgacgg    1200

ttgatgtggc ctgaaagcac ttagcgggcg cgctgggatg tcacagagtt ggagtcattg    1260

ttgg                                                                 1264


<210> SEQ ID NO 91
<211> LENGTH: 1164
<212> TYPE: DNA
<213> ORGANISM: Homo sapiens

<400> SEQUENCE: 91
```

```
atgaacgtct cgggctgccc aggggccggg aacgcgagcc aggcgggcgg cgggggaggc      60

tggcaccccg aggcggtcat cgtgcccctg ctcttcgcgc tcatcttcct cgtgggcacc     120

gtgggcaaca cgctggtgct ggcggtgctg ctgcgcggcg gccaggcggt cagcactacc     180

aacctgttca tccttaacct gggcgtggcc gacctgtgtt tcatcctgtg ctgcgtgccc     240

ttccaggcca ccatctacac cctggacggc tgggtgttcg gctcgctgct gtgcaaggcg     300

gtgcacttcc tcatcttcct caccatgcac gccagcagct tcacgctggc cgccgtctcc     360

ctggacaggt atctggccat ccgctacccg ctgcactccc gcgagctgcg cacgcctcga     420

aacgcgctgg cagccatcgg gctcatctgg gggctgtcgc tgctcttctc cgggccctac     480

ctgagctact accgccagtc gcagctggcc aacctgaccg tgtgccatcc cgcgtggagc     540

gcccctcgcc gccgcgccat ggacatctgc accttcgtct tcagctacct gcttcctgtg     600

ctggttctcg gcctgaccta cgcgcgcacc ttgcgctacc tctggcgcgc cgtcgacccg     660

gtggccgcgg gctcgggtgc ccggcgcgcc aagcgcaagg tgacacgcat gatcctcatc     720

gtggccgcgc tcttctgcct ctgctggatg ccccaccacg cgctcatcct ctgcgtgtgg     780

ttcggccagt tcccgctcac gcgcgccact tatgcgcttc gcatcctctc gcacctggtc     840

tcctacgcca actcctgcgt caaccccatc gtttacgcgc tggtctccaa gcacttccgc     900

aaaggcttcc gcacgatctg cgcgggcctg ctgggccgtg ccccaggccg agcctcgggc     960

cgtgtgtgcg ctgccgcgcg gggcacccac agtggcagcg tgttggagcg cgagtccagc    1020

gacctgttgc acatgagcga ggcggcgggg gcccttcgtc cctgccccgg cgcttcccag    1080

ccatgcatcc tcgagccctg tcctggcccg tcctggcagg gcccaaaggc aggcgacagc    1140

atcctgacgg ttgatgtggc ctga                                           1164
```

<210> SEQ ID NO 92
<211> LENGTH: 387
<212> TYPE: PRT
<213> ORGANISM: Homo sapiens

<400> SEQUENCE: 92

```
Met Asn Val Ser Gly Cys Pro Gly Ala Gly Asn Ala Ser Gln Ala Gly
1               5                   10                  15

Gly Gly Gly Gly Trp His Pro Glu Ala Val Ile Val Pro Leu Leu Phe
            20                  25                  30

Ala Leu Ile Phe Leu Val Gly Thr Val Gly Asn Thr Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ser Leu Leu Phe Ser Gly Pro Tyr
145                 150                 155                 160
```

```
Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Ile Cys Thr Phe
            180                 185                 190

Val Phe Ser Tyr Leu Leu Pro Val Leu Val Leu Gly Leu Thr Tyr Ala
        195                 200                 205

Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Ile Leu Glu Pro Cys Pro
        355                 360                 365

Gly Pro Ser Trp Gln Gly Pro Lys Ala Gly Asp Ser Ile Leu Thr Val
    370                 375                 380

Asp Val Ala
385
```

<210> SEQ ID NO 93
<211> LENGTH: 1164
<212> TYPE: DNA
<213> ORGANISM: Pan troglodytes

<400> SEQUENCE: 93

```
atgaacgtct cgggctgccc aggggccggg aacgcgagcc aggcgggcgg cgggggaggc      60

tggcaccccg aggcggtcat cgtgcccctg ctcttcgcgc tcatcttcct cgtgggcatc     120

gtgggcaaca cgctggtgct ggcggtgctg ctgcgcggcg gccaggcggt cagcaccacc     180

aacctgttca tccttaacct gggcgtagcc gacctgtgtt tcatcctgtg ctgcgtgccc     240

ttccaggcca ccatctacac cctggacggc tgggtgttcg gctcgctgct gtgcaaggcg     300

gtgcacttct tcatcttcct caccatgcac gccagcagct tcacgctggc cgccgtctcc     360

ctggacaggt atctggccat ccgctacccg ctgcactccc gcgagctgcg cacgcctcga     420

aacgcgctgg cagccatcgg gctcatctgg gggctgtcgc tgctcttctc cgggccctac     480

ctgagctact accgccagtc gcagctggcc aacctgaccg tgtgccatcc tgcgtggagc     540

gcccctcgcc gccgcgccat ggacatctgc accttcgtct tcagctacct gcttcctgtg     600

ctggttctcg gcctgaccta cgcgcgcacc ttgcgctacc tctggcgcgc cgtcgacccg     660

gtggccgcgg gctcgggtgc ccggcgcgcc aagcgcaagg tgacacgcat gatcctcatc     720

gtggccgcgc tcttctgcct ctgctggatg ccccaccacg cgctcatcct ctgcgtgtgg     780
```

```
ttcggccatt tcccgctcac gcgcgccact tatgcgcttc gcatcctctc gcacctggtc    840

tcctacgcca actcctgcgt caaccccatc gtttacgcgc tggtctccaa gcacttccgc    900

aaaggcttcc gcacgatctg cgcgggcctg ctgggccgtg ccccaggccg agcctcgggc    960

cgtgtgtgcg ctgccgcgcg gggcacccac agtggcagcg tgctggagcg cgagtccagc   1020

gacctgttgc acatgagcga ggcggcgggg gcccttcgtc cctgccccgg cgcttcccag   1080

ccatgcaccc tcgagccctg tcctggcccg tcctggcagg gcccaaaggc aggcgacagc   1140

atcctgacgg ttgatgtggc ctga                                          1164


<210> SEQ ID NO 94
<211> LENGTH: 387
<212> TYPE: PRT
<213> ORGANISM: Pan troglodytes

<400> SEQUENCE: 94

Met Asn Val Ser Gly Cys Pro Gly Ala Gly Asn Ala Ser Gln Ala Gly
1               5                   10                  15

Gly Gly Gly Gly Trp His Pro Glu Ala Val Ile Val Pro Leu Leu Phe
            20                  25                  30

Ala Leu Ile Phe Leu Val Gly Ile Val Gly Asn Thr Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Phe Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Ile Cys Thr Phe
            180                 185                 190

Val Phe Ser Tyr Leu Leu Pro Val Leu Val Leu Gly Leu Thr Tyr Ala
        195                 200                 205

Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly His Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300
```

```
Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Thr Leu Glu Pro Cys Pro
        355                 360                 365

Gly Pro Ser Trp Gln Gly Pro Lys Ala Gly Asp Ser Ile Leu Thr Val
    370                 375                 380

Asp Val Ala
385


<210> SEQ ID NO 95
<211> LENGTH: 1116
<212> TYPE: DNA
<213> ORGANISM: Mus musculus
<220> FEATURE:
<221> NAME/KEY: misc_feature
<222> LOCATION: (1078)..(1078)
<223> OTHER INFORMATION: n is a, c, g, or t

<400> SEQUENCE: 95

atgaatggct cggacagcca gggggcggag gactcgagcc aggaaggtgg cggcggctgg     60

cagcccgagg cggtcctcgt acccctattt ttcgcgctca tcttcctcgt gggcgctgtg    120

ggcaacgcgc tggtgctggc ggtgctgctg cgcggcggcc aggcggtcag caccacgaac    180

ctattcatcc tcaacctggg tgtggccgac ctgtgtttca tcctgtgctg cgtgcctttc    240

caggccacca tctataccct ggacgattgg gtgtttggct cactgctctg caaggccgtt    300

catttcctca tcttcctcac tatgcacgcc agcagcttca cgctggccgc tgtctccctg    360

gacaggtatc tggccatccg ctacccgctg cactcccgag agttgcgcac acctcgaaac    420

gcgctggcgg ccatcgggct catctggggg ctagcactgc tcttctccgg gccctacctg    480

agctactaca gtcagtcgca gctggccaat ctgacggtgt gccacccagc gtggagcgca    540

ccacgacgcc catggaactc ttgcactttt tgtcttagct acctgttgcc agtgctggtg    600

ctcagcctga cctatgcgcg caccttgcac tacctctggc gcacagttga cccagtagtt    660

gcaggctcag gttcccagcg cgccaagcgc aaggtgacac ggatgatcgt catcgtggcg    720

gtactcttct gcctctgttg gatgccccac cacgcgctta tcctctgcgt gtggtttggt    780

cgctttccgc tcacgcgtgc cacttacgcc ctgcgcatcc tttcacatct agtatcttat    840

gccaactcgt gtgtcaaccc catcgtttat gctctggtct ccaagcattt ccgcaaaggt    900

ttccgcaaaa tctgcgcggg cctgctacgc cgtgccccga ggagagcttc aggccgagtg    960

tgcatcctgg cgcytggaaa ccatagtggt ggcatgctgg aacctgagtc cacagacctg   1020

acacaggtga agcgaggcag ccgggcccct cgtccccgca cccgcacttc ccaaactngc   1080

acaaccttga gtagaaccct cgatccagcc tgttaa                             1116


<210> SEQ ID NO 96
<211> LENGTH: 371
<212> TYPE: PRT
<213> ORGANISM: Mus musculus
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
```

<222> LOCATION: (360)..(360)
<223> OTHER INFORMATION: Xaa can be any naturally occurring amino acid

<400> SEQUENCE: 96

```
Met Asn Gly Ser Asp Ser Gln Gly Ala Glu Asp Ser Ser Gln Glu Gly
1               5                   10                  15

Gly Gly Gly Trp Gln Pro Glu Ala Val Leu Val Pro Leu Phe Phe Ala
            20                  25                  30

Leu Ile Phe Leu Val Gly Ala Val Gly Asn Ala Leu Val Leu Ala Val
        35                  40                  45

Leu Leu Arg Gly Gly Gln Ala Val Ser Thr Thr Asn Leu Phe Ile Leu
    50                  55                  60

Asn Leu Gly Val Ala Asp Leu Cys Phe Ile Leu Cys Cys Val Pro Phe
65                  70                  75                  80

Gln Ala Thr Ile Tyr Thr Leu Asp Asp Trp Val Phe Gly Ser Leu Leu
                85                  90                  95

Cys Lys Ala Val His Phe Leu Ile Phe Leu Thr Met His Ala Ser Ser
            100                 105                 110

Phe Thr Leu Ala Ala Val Ser Leu Asp Arg Tyr Leu Ala Ile Arg Tyr
        115                 120                 125

Pro Leu His Ser Arg Glu Leu Arg Thr Pro Arg Asn Ala Leu Ala Ala
    130                 135                 140

Ile Gly Leu Ile Trp Gly Leu Ala Leu Leu Phe Ser Gly Pro Tyr Leu
145                 150                 155                 160

Ser Tyr Tyr Ser Gln Ser Gln Leu Ala Asn Leu Thr Val Cys His Pro
                165                 170                 175

Ala Trp Ser Ala Pro Arg Arg Pro Trp Asn Ser Cys Thr Phe Cys Leu
            180                 185                 190

Ser Tyr Leu Leu Pro Val Leu Val Leu Ser Leu Thr Tyr Ala Arg Thr
        195                 200                 205

Leu His Tyr Leu Trp Arg Thr Val Asp Pro Val Val Ala Gly Ser Gly
    210                 215                 220

Ser Gln Arg Ala Lys Arg Lys Val Thr Arg Met Ile Val Ile Val Ala
225                 230                 235                 240

Val Leu Phe Cys Leu Cys Trp Met Pro His His Ala Leu Ile Leu Cys
                245                 250                 255

Val Trp Phe Gly Arg Phe Pro Leu Thr Arg Ala Thr Tyr Ala Leu Arg
            260                 265                 270

Ile Leu Ser His Leu Val Ser Tyr Ala Asn Ser Cys Val Asn Pro Ile
        275                 280                 285

Val Tyr Ala Leu Val Ser Lys His Phe Arg Lys Gly Phe Arg Lys Ile
    290                 295                 300

Cys Ala Gly Leu Leu Arg Arg Ala Pro Arg Arg Ala Ser Gly Arg Val
305                 310                 315                 320

Cys Ile Leu Ala Xaa Gly Asn His Ser Gly Gly Met Leu Glu Pro Glu
                325                 330                 335

Ser Thr Asp Leu Thr Gln Val Lys Arg Gly Ser Arg Ala Pro Arg Pro
            340                 345                 350

Arg Thr Arg Thr Ser Gln Thr Xaa Thr Thr Leu Ser Arg Thr Leu Asp
        355                 360                 365

Pro Ala Cys
    370
```

<210> SEQ ID NO 97

<211> LENGTH: 1290
<212> TYPE: DNA
<213> ORGANISM: Rattus norvegicus

<400> SEQUENCE: 97

```
cggcccgcag ctgtccgggt cttggtgagc acgctgctcc ctcgctgcag cgccccagcg     60

agactgccga gctccaggag ccagggcagg ggtgcgcggg ggacgggagg aggagggagc    120

ggcgtccact ttggtgatac catgaatggc tccggcagcc agggcgcgga gaacacgagc    180

caggaaggcg gtagcggcgg ctggcagcct gaggcggtcc ttgtacccct atttttcgcg    240

ctcatcttcc tcgtgggcac cgtgggcaac gcgctggtgc tggcggtgct gctgcgcggc    300

ggccaggcgg tcagcaccac caacctgttc atcctcaacc tgggcgtggc cgacctgtgt    360

ttcatcctgt gctgcgtgcc tttccaggcc accatctaca ccctggacga ctgggtgttc    420

ggctcgctgc tctgcaaggc tgttcatttc ctcatctttc tcactatgca cgccagcagc    480

ttcacgctgg ccgccgtctc cctggacagg tatctggcca tccgctaccc gctgcactcc    540

cgagagttgc gcacacctcg aaacgcgctg gccgccatcg ggctcatctg ggggctagca    600

ctgctcttct ccgggcccta cctgagctac taccgtcagt cgcagctggc caacctgaca    660

gtatgccacc cagcatggag cgcacctcga cgtcgagcca tggacctctg caccttcgtc    720

tttagctacc tgctgccagt gctagtcctc agtctgacct atgcgcgtac cctgcgctac    780

ctctggcgca cagtcgaccc ggtgactgca ggctcaggtt cccagcgcgc caaacgcaag    840

gtgacacgga tgatcatcat cgtggcggtg cttttctgcc tctgttggat gccccaccac    900

gcgcttatcc tctgcgtgtg gtttggtcgc ttcccgctca cgcgtgccac ttacgcgttg    960

cgcatccttt cacacctagt ttcctatgcc aactcctgtg tcaaccccat cgtttacgct   1020

ctggtctcca agcatttccg taaaggtttc cgcaaaatct gcgcgggcct gctgcgccct   1080

gccccgaggc gagcttcggg ccgagtgagc atcctggcgc ctgggaacca tagtggcagc   1140

atgctggaac aggaatccac agacctgaca caggtgagcg aggcagccgg gccccttgtc   1200

ccaccacccg cacttcccaa ctgcacagcc tcgagtagaa ccctggatcc ggcttgttaa   1260

aggaccaaag ggcatctaac agcttctaga                                     1290
```

<210> SEQ ID NO 98
<211> LENGTH: 372
<212> TYPE: PRT
<213> ORGANISM: Rattus norvegicus

<400> SEQUENCE: 98

```
Met Asn Gly Ser Gly Ser Gln Gly Ala Glu Asn Thr Ser Gln Glu Gly
1               5                   10                  15

Gly Ser Gly Gly Trp Gln Pro Glu Ala Val Leu Val Pro Leu Phe Phe
            20                  25                  30

Ala Leu Ile Phe Leu Val Gly Thr Val Gly Asn Ala Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
            100                 105                 110
```

```
Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Thr Val Asp Pro Val Thr Ala Gly
    210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350

Val Pro Pro Pro Ala Leu Pro Asn Cys Thr Ala Ser Ser Arg Thr Leu
        355                 360                 365

Asp Pro Ala Cys
    370
```

<210> SEQ ID NO 99
<211> LENGTH: 1157
<212> TYPE: DNA
<213> ORGANISM: Homo sapiens

<400> SEQUENCE: 99

```
tcccaggtgc ccgtctgatg gggagatggc tgatgcccag aacatttcac tggacagccc     60

agggagtgtg gggccgtgg cagtgcctgt ggtctttgcc ctaatcttcc tgctgggcac    120

agtgggcaat gggctggtgc tggcagtgct cctgcagcct ggcccgagtg cctggcagga    180

gcctggcagc accacggacc tgttcatcct caacctggcg gtggctgacc tctgcttcat    240

cctgtgctgc gtgcccttcc aggccaccat ctacacgctg gatgcctggc tctttggggc    300

cctcgtctgc aaggccgtgc acctgctcat ctacctcacc atgtacgcca gcagctttac    360

gctggctgct gtctccgtgg acaggtacct ggccgtgcgg cacccgctgc gctcgcgcgc    420

cctgcgcacg ccgcgtaacg cccgcgccgc agtggggctg gtgtggctgc tggcggcgct    480

cttctcggcg ccctacctca gctactacgg caccgtgcgc tacggcgcgc tggagctctg    540

cgtgcccgcc tgggaggacg cgcgccgccg cgccctggac gtggccacct tcgctgccgg    600
```

```
ctacctgctg cccgtggctg tggtgagcct ggcctacggg cgcacgctgc gcttcctgtg    660
ggccgccgtg ggtcccgcgg gcgcggcggc ggccgaggcg cggcggaggg cgacgggccg    720
cgcggggcgc gccatgctgg cggtggccgc gctctacgcg ctctgctggg gtccgcacca    780
cgcgctcatc ctgtgcttct ggtacggccg cttcgccttc agcccggcca cctacgcctg    840
ccgcctggcc tcacactgcc tggcctacgc caactcctgc ctcaacccgc tcgtctacgc    900
gctcgcctcg cgccacttcc gcgcgcgctt ccgccgcctg tggccgtgcg gccgccgacg    960
ccgccaccgt gcccgccgcg ccttgcgtcg cgtccgcccc gcgtcctcgg gcccacccgg   1020
ctgccccgga gacgcccggc ctagcgggag gctgctggct ggtggcggcc agggcccgga   1080
gcccagggag ggacccgtcc acggcggaga ggctgcccga ggaccggaat aaaccctgcc   1140
gcctggactc cgcctgt                                                  1157
```

<210> SEQ ID NO 100
<211> LENGTH: 1107
<212> TYPE: DNA
<213> ORGANISM: Homo sapiens

<400> SEQUENCE: 100

```
atggctgatg cccagaacat ttcactggac agcccaggga gtgtgggggc cgtggcagtg     60
cctgtggtct ttgccctaat cttcctgctg ggcacagtgg gcaatgggct ggtgctggca    120
gtgctcctgc agcctggccc gagtgcctgg caggagcctg gcagcaccac ggacctgttc    180
atcctcaacc tggcggtggc tgacctctgc ttcatcctgt gctgcgtgcc cttccaggcc    240
accatctaca cgctggatgc ctggctcttt ggggccctcg tctgcaaggc cgtgcacctg    300
ctcatctacc tcaccatgta cgccagcagc tttacgctgg ctgctgtctc cgtggacagg    360
tacctggccg tgcggcaccc gctgcgctcg cgcgccctgc gcacgccgcg taacgcccgc    420
gccgcagtgg ggctggtgtg gctgctggcg gcgctcttct cggcgcccta cctcagctac    480
tacggcaccg tgcgctacgg cgcgctggag ctctgcgtgc ccgcctggga ggacgcgcgc    540
cgccgcgccc tggacgtggc caccttcgct gccggctacc tgctgcccgt ggctgtggtg    600
agcctggcct acgggcgcac gctgcgcttc ctgtgggccg ccgtgggtcc cgcgggcgcg    660
gcggcggccg aggcgcggcg gagggcgacg ggccgcgcgg ggcgcgccat gctggcggtg    720
gccgcgctct acgcgctctg ctggggtccg caccacgcgc tcatcctgtg cttctggtac    780
ggccgcttcg ccttcagccc ggccacctac gcctgccgcc tggcctcaca ctgcctggcc    840
tacgccaact cctgcctcaa cccgctcgtc tacgcgctcg cctcgcgcca cttccgcgcg    900
cgcttccgcc gcctgtggcc gtgcggccgc cgacgccgcc accgtgcccg ccgcgccttg    960
cgtcgcgtcc gccccgcgtc ctcgggccca cccggctgcc ccggagacgc ccggcctagc   1020
gggaggctgc tggctggtgg cggccagggc ccggagccca gggagggacc cgtccacggc   1080
ggagaggctg cccgaggacc ggaataa                                       1107
```

<210> SEQ ID NO 101
<211> LENGTH: 368
<212> TYPE: PRT
<213> ORGANISM: Homo sapiens

<400> SEQUENCE: 101

```
Met Ala Asp Ala Gln Asn Ile Ser Leu Asp Ser Pro Gly Ser Val Gly
1               5                   10                  15

Ala Val Ala Val Pro Val Val Phe Ala Leu Ile Phe Leu Leu Gly Thr
            20                  25                  30
```

```
Val Gly Asn Gly Leu Val Leu Ala Val Leu Leu Gln Pro Gly Pro Ser
        35                  40                  45

Ala Trp Gln Glu Pro Gly Ser Thr Thr Asp Leu Phe Ile Leu Asn Leu
    50                  55                  60

Ala Val Ala Asp Leu Cys Phe Ile Leu Cys Cys Val Pro Phe Gln Ala
65                  70                  75                  80

Thr Ile Tyr Thr Leu Asp Ala Trp Leu Phe Gly Ala Leu Val Cys Lys
                85                  90                  95

Ala Val His Leu Leu Ile Tyr Leu Thr Met Tyr Ala Ser Ser Phe Thr
            100                 105                 110

Leu Ala Ala Val Ser Val Asp Arg Tyr Leu Ala Val Arg His Pro Leu
        115                 120                 125

Arg Ser Arg Ala Leu Arg Thr Pro Arg Asn Ala Arg Ala Ala Val Gly
    130                 135                 140

Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Arg Ala Leu Asp Val Ala Thr Phe Ala Ala Gly
            180                 185                 190

Tyr Leu Leu Pro Val Ala Val Val Ser Leu Ala Tyr Gly Arg Thr Leu
        195                 200                 205

Arg Phe Leu Trp Ala Ala Val Gly Pro Ala Gly Ala Ala Ala Ala Glu
    210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
            260                 265                 270

Arg Leu Ala Ser His Cys Leu Ala Tyr Ala Asn Ser Cys Leu Asn Pro
        275                 280                 285

Leu Val Tyr Ala Leu Ala Ser Arg His Phe Arg Ala Arg Phe Arg Arg
    290                 295                 300

Leu Trp Pro Cys Gly Arg Arg Arg Arg His Arg Ala Arg Arg Ala Leu
305                 310                 315                 320

Arg Arg Val Arg Pro Ala Ser Ser Gly Pro Pro Gly Cys Pro Gly Asp
                325                 330                 335

Ala Arg Pro Ser Gly Arg Leu Leu Ala Gly Gly Gly Gln Gly Pro Glu
            340                 345                 350

Pro Arg Glu Gly Pro Val His Gly Gly Glu Ala Ala Arg Gly Pro Glu
        355                 360                 365
```

<210> SEQ ID NO 102
<211> LENGTH: 1113
<212> TYPE: DNA
<213> ORGANISM: Mus musculus

<400> SEQUENCE: 102

```
atggctgaca tccagaacat ttcgctggac agcccaggga gcgtaggggc tgtggcagtg      60

ccggtggtct ttgccctcat cttcctgttg ggcatggtgg gtaatgggct ggtgttggcc     120

gtgcttctgc agcctggccc aagtgcctgg caggaaccgg gcagtaccac ggatctcttc     180

atcctcaact tggcggtggc cgacctttgc ttcatcctgt gctgcgtgcc cttccaggcg     240
```

```
gccatctaca cactggatgc ctggctcttt ggggctttcg tgtgcaagac ggtacatctg    300

ctcatctacc tcaccatgta tgccagcagc ttcaccctgg cggccgtctc agtggatagg    360

tacctggcgg tgcgacaccc gctgcgctcc cgggccctcc gcaccccgcg caacgcgcgc    420

gccgccgtgg ggctcgtgtg gctgctggcg gcgctctttt ccgcgcccta cctaagctac    480

tacggcacgg tgcgctacgg cgcgctcgag ctctgcgtgc ccgcctggga ggacgcgcgg    540

cggcgcgcgc tggacgtggc caccttcgcc gcaggctacc tgctgccggt gaccgtggtg    600

agcctggcct acgggcgcac gctgtgcttc ctgtgggccg ccgtgggtcc cgcgggtgcg    660

gcggcggcag aggcacgcag acgggcaacc ggccgcgcgg ggcgcgccat gctggcggtg    720

gccgcgctct acgcactctg ctggggcccg caccacgcgc tcatcctctg cttctggtac    780

ggccgcttcg ccttcagccc ggccacctac gcctgtcgtc tggcttcgca ctgcctcgcc    840

tacgccaact cctgcctcaa cccgctcgtc tattcccttg cctcccgcca cttccgcgcg    900

cgcttccgcc gcctgtggcc ctgcggccac cgccgccacc gccaccacca ccaccgcctt    960

catcgagccc tccgtcgtgt ccagccggcg tcttcgggcc ccgccggcta tcccggcgac   1020

gccagacctc gcggttggag tatggagccc agaggggatg ccttgcgcgg tggagagact   1080

agactaaccc tgtccgccag gggaccgcaa taa                                1113
```

<210> SEQ ID NO 103
<211> LENGTH: 370
<212> TYPE: PRT
<213> ORGANISM: Mus musculus

<400> SEQUENCE: 103

```
Met Ala Asp Ile Gln Asn Ile Ser Leu Asp Ser Pro Gly Ser Val Gly
1               5                   10                  15

Ala Val Ala Val Pro Val Val Phe Ala Leu Ile Phe Leu Leu Gly Met
            20                  25                  30

Val Gly Asn Gly Leu Val Leu Ala Val Leu Leu Gln Pro Gly Pro Ser
        35                  40                  45

Ala Trp Gln Glu Pro Gly Ser Thr Thr Asp Leu Phe Ile Leu Asn Leu
    50                  55                  60

Ala Val Ala Asp Leu Cys Phe Ile Leu Cys Cys Val Pro Phe Gln Ala
65                  70                  75                  80

Ala Ile Tyr Thr Leu Asp Ala Trp Leu Phe Gly Ala Phe Val Cys Lys
                85                  90                  95

Thr Val His Leu Leu Ile Tyr Leu Thr Met Tyr Ala Ser Ser Phe Thr
            100                 105                 110

Leu Ala Ala Val Ser Val Asp Arg Tyr Leu Ala Val Arg His Pro Leu
        115                 120                 125

Arg Ser Arg Ala Leu Arg Thr Pro Arg Asn Ala Arg Ala Ala Val Gly
    130                 135                 140

Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Arg Ala Leu Asp Val Ala Thr Phe Ala Ala Gly
            180                 185                 190

Tyr Leu Leu Pro Val Thr Val Val Ser Leu Ala Tyr Gly Arg Thr Leu
        195                 200                 205

Cys Phe Leu Trp Ala Ala Val Gly Pro Ala Gly Ala Ala Ala Ala Glu
```

```
    210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
            260                 265                 270

Arg Leu Ala Ser His Cys Leu Ala Tyr Ala Asn Ser Cys Leu Asn Pro
        275                 280                 285

Leu Val Tyr Ser Leu Ala Ser Arg His Phe Arg Ala Arg Phe Arg Arg
    290                 295                 300

Leu Trp Pro Cys Gly His Arg Arg His Arg His His His His Arg Leu
305                 310                 315                 320

His Arg Ala Leu Arg Arg Val Gln Pro Ala Ser Ser Gly Pro Ala Gly
                325                 330                 335

Tyr Pro Gly Asp Ala Arg Pro Arg Gly Trp Ser Met Glu Pro Arg Gly
            340                 345                 350

Asp Ala Leu Arg Gly Gly Glu Thr Arg Leu Thr Leu Ser Ala Arg Gly
        355                 360                 365

Pro Gln
    370
```

<210> SEQ ID NO 104
<211> LENGTH: 1163
<212> TYPE: DNA
<213> ORGANISM: Rattus norvegicus

<400> SEQUENCE: 104

```
ggcccagtac ctaggactga ggaagatggc tgacatccag aacatttcgc tggacagccc     60

agggagcgta ggggctgtgg cagtgcctgt gatctttgcc ctcatcttcc tgttgggcat    120

ggtgggcaat gggctggtgt tggctgtgct actgcagcct ggcccaagtg cctggcagga    180

gccaagcagt accacagatc tcttcatcct caacttggcc gtggccgacc tttgcttcat    240

cctgtgctgc gtgcccttcc aggcagccat ctacacactg gatgcctggc tctttggggc    300

tttcgtgtgc aagacggtac atctgctcat ctacctcacc atgtatgcca gcagcttcac    360

cctggcggcc gtctccctgg acaggtacct ggctgtgcgg cacccactgc gctccagagc    420

cctgcgcacc ccgcgcaacg cgcgcgccgc cgtggggctc gtgtggctgc tggcggctct    480

cttttccgcg ccctacctaa gctattacgg cacggtgcgc tacggcgcgc tcgagctctg    540

cgtgcccgct tgggaggacg cgcggcggcg cgcgctggac gtggccacct tcgccgcggg    600

ctacctgctg ccggtggccg tggtgagcct ggcctacgga cgcacgctat gtttcctatg    660

ggccgccgtg ggtcccgcgg gcgcggcggc agcagaggcg cgcagacggg cgaccggccg    720

ggcgggacgc gccatgctgg cagtggccgc gctctacgcg ctttgctggg gcccgcacca    780

cgcgctcatc ctctgcttct ggtacggccg cttcgccttc agcccggcca cctacgcctg    840

tcgcctggcc tcgcactgcc tcgcctacgc caactcctgc cttaacccgc tcgtctactc    900

gctcgcctcg cgccacttcc gcgcgcgctt ccgccgcctg tggccctgcg gccgtcgccg    960

ccaccgccac caccaccgcg ctcatcgagc cctccgtcgt gtccagccgg cgtcttcggg   1020

ccccgccggt tatcccggcg acgccaggcc tcgtggttgg agtatggagc ccagagggga   1080

tgctctgcgt ggtggtggag agactagact aaccctgtcc cccaggggac ctcaataacc   1140

ctgcccgctt ggactctgac gtc                                           1163
```

<210> SEQ ID NO 105
<211> LENGTH: 370
<212> TYPE: PRT
<213> ORGANISM: Rattus norvegicus

<400> SEQUENCE: 105

```
Met Ala Asp Ile Gln Asn Ile Ser Leu Asp Ser Pro Gly Ser Val Gly
1               5                   10                  15

Ala Val Ala Val Pro Val Ile Phe Ala Leu Ile Phe Leu Leu Gly Met
            20                  25                  30

Val Gly Asn Gly Leu Val Leu Ala Val Leu Leu Gln Pro Gly Pro Ser
        35                  40                  45

Ala Trp Gln Glu Pro Ser Ser Thr Thr Asp Leu Phe Ile Leu Asn Leu
    50                  55                  60

Ala Val Ala Asp Leu Cys Phe Ile Leu Cys Cys Val Pro Phe Gln Ala
65                  70                  75                  80

Ala Ile Tyr Thr Leu Asp Ala Trp Leu Phe Gly Ala Phe Val Cys Lys
                85                  90                  95

Thr Val His Leu Leu Ile Tyr Leu Thr Met Tyr Ala Ser Ser Phe Thr
            100                 105                 110

Leu Ala Ala Val Ser Leu Asp Arg Tyr Leu Ala Val Arg His Pro Leu
        115                 120                 125

Arg Ser Arg Ala Leu Arg Thr Pro Arg Asn Ala Arg Ala Ala Val Gly
    130                 135                 140

Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Arg Ala Leu Asp Val Ala Thr Phe Ala Ala Gly
            180                 185                 190

Tyr Leu Leu Pro Val Ala Val Val Ser Leu Ala Tyr Gly Arg Thr Leu
        195                 200                 205

Cys Phe Leu Trp Ala Ala Val Gly Pro Ala Gly Ala Ala Ala Ala Glu
    210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
            260                 265                 270

Arg Leu Ala Ser His Cys Leu Ala Tyr Ala Asn Ser Cys Leu Asn Pro
        275                 280                 285

Leu Val Tyr Ser Leu Ala Ser Arg His Phe Arg Ala Arg Phe Arg Arg
    290                 295                 300

Leu Trp Pro Cys Gly Arg Arg Arg His Arg His His His Arg Ala His
305                 310                 315                 320

Arg Ala Leu Arg Arg Val Gln Pro Ala Ser Ser Gly Pro Ala Gly Tyr
                325                 330                 335

Pro Gly Asp Ala Arg Pro Arg Gly Trp Ser Met Glu Pro Arg Gly Asp
            340                 345                 350

Ala Leu Arg Gly Gly Gly Glu Thr Arg Leu Thr Leu Ser Pro Arg Gly
        355                 360                 365

Pro Gln
```

370

<210> SEQ ID NO 106
<211> LENGTH: 633
<212> TYPE: DNA
<213> ORGANISM: Homo sapiens

<400> SEQUENCE: 106
ctccagctcg gctttcgcgg cgccgagatg ctgtcctgcc gcctccagtg cgcgctggct 60
gcgctgtcca tcgtcctggc cctgggctgt gtcaccggcg ctccctcgga ccccagactc 120
cgtcagtttc tgcagaagtc cctggctgct gccgcgggga agcaggaact ggccaagtac 180
ttcttggcag agctgctgtc tgaacccaac cagacggaga atgatgccct ggaacctgaa 240
gatctgtccc aggctgctga gcaggatgaa atgaggcttg agctgcagag atctgctaac 300
tcaaacccgg ctatggcacc ccgagaacgc aaagctggct gcaagaattt cttctggaag 360
actttcacat cctgttagct ttcttaacta gtattgtcca tatcagacct ctgatccctc 420
gcccccacac cccatctctc ttccctaatc ctccaagtct tcagcgagac ccttgcatta 480
gaaactgaaa actgtaaata caaaataaaa ttatggtgaa attatgaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaa 633

<210> SEQ ID NO 107
<211> LENGTH: 351
<212> TYPE: DNA
<213> ORGANISM: Homo sapiens

<400> SEQUENCE: 107
atgctgtcct gccgcctcca gtgcgcgctg gctgcgctgt ccatcgtcct ggccctgggc 60
tgtgtcaccg gcgctccctc ggaccccaga ctccgtcagt ttctgcagaa gtccctggct 120
gctgccgcgg ggaagcagga actggccaag tacttcttgg cagagctgct gtctgaaccc 180
aaccagacgg agaatgatgc cctggaacct gaagatctgt cccaggctgc tgagcaggat 240
gaaatgaggc ttgagctgca gagatctgct aactcaaacc cggctatggc accccgagaa 300
cgcaaagctg gctgcaagaa tttcttctgg aagactttca catcctgtta g 351

<210> SEQ ID NO 108
<211> LENGTH: 116
<212> TYPE: PRT
<213> ORGANISM: Homo sapiens

<400> SEQUENCE: 108

Met Leu Ser Cys Arg Leu Gln Cys Ala Leu Ala Ala Leu Ser Ile Val
1 5 10 15

Leu Ala Leu Gly Cys Val Thr Gly Ala Pro Ser Asp Pro Arg Leu Arg
20 25 30

Gln Phe Leu Gln Lys Ser Leu Ala Ala Ala Ala Gly Lys Gln Glu Leu
35 40 45

Ala Lys Tyr Phe Leu Ala Glu Leu Leu Ser Glu Pro Asn Gln Thr Glu
50 55 60

Asn Asp Ala Leu Glu Pro Glu Asp Leu Ser Gln Ala Ala Glu Gln Asp
65 70 75 80

Glu Met Arg Leu Glu Leu Gln Arg Ser Ala Asn Ser Asn Pro Ala Met
85 90 95

Ala Pro Arg Glu Arg Lys Ala Gly Cys Lys Asn Phe Phe Trp Lys Thr

```
            100                 105                 110

Phe Thr Ser Cys
        115


<210> SEQ ID NO 109
<211> LENGTH: 604
<212> TYPE: DNA
<213> ORGANISM: Macaca fascicularis

<400> SEQUENCE: 109

acacaagccg ctttaggagt cgcgaggttc ggagccatcg ctgctgcctg ctgatccgcg     60

cctagagttt gaccagccac tcttcagctc agctttcccg gcgccgagat gctgtcctgc    120

cgcctccagt gcgcgctggc tgcgctgtcc atcgtcctgg ccctgggctg tgtcaccggc    180

gctccctcgg accccagact ccgtcagttt ctgcagaagt ccctggcggc tgccgcgggg    240

aagcaggaac tggccaagta cttcttggca gagctgctct ctgaacccaa ccagacggag    300

aatgatgccc tggaacccga agatctgtcc caggctgctg agcaggatga aatgaggctt    360

gagttgcaga gatctgctaa ctcaaaccca gctatggcac cccgagaacg caaagctggc    420

tgcaagaatt tcttctggaa gactttcaca tcctgttagc tttcttaatt agtaaagtcc    480

ataccagacc tctgatccct caccccctaaa ccccatctct cttccctaat cctccaaatc    540

ctcagcgaga cccttgcatt agaaattgaa gactgtaaat ataaaataaa attatggtga    600

aatt                                                                 604


<210> SEQ ID NO 110
<211> LENGTH: 351
<212> TYPE: DNA
<213> ORGANISM: Macaca fascicularis

<400> SEQUENCE: 110

atgctgtcct gccgcctcca gtgcgcgctg gctgcgctgt ccatcgtcct ggccctgggc     60

tgtgtcaccg gcgctccctc ggaccccaga ctccgtcagt ttctgcagaa gtccctggcg    120

gctgccgcgg ggaagcagga actggccaag tacttcttgg cagagctgct ctctgaaccc    180

aaccagacgg agaatgatgc cctggaaccc gaagatctgt cccaggctgc tgagcaggat    240

gaaatgaggc ttgagttgca gagatctgct aactcaaacc cagctatggc accccgagaa    300

cgcaaagctg gctgcaagaa tttcttctgg aagactttca catcctgtta g             351


<210> SEQ ID NO 111
<211> LENGTH: 116
<212> TYPE: PRT
<213> ORGANISM: Macaca fascicularis

<400> SEQUENCE: 111

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

Gln Phe Leu Gln Lys Ser Leu Ala Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
```

```
                85                  90                  95

Ala Pro Arg Glu Arg Lys Ala Gly Cys Lys Asn Phe Phe Trp Lys Thr
            100                 105                 110

Phe Thr Ser Cys
        115


<210> SEQ ID NO 112
<211> LENGTH: 599
<212> TYPE: DNA
<213> ORGANISM: Mus musculus

<400> SEQUENCE: 112

agcggctgaa ggagacgcta ccgaagccgt cgctgctgcc tgaggacctg cgactagact     60

gacccaccgc gctccagctt ggctgcctga ggcaaggaag atgctgtcct gccgtctcca    120

gtgcgccctg gctgcgctct gcatcgtcct ggctttgggc ggtgtcaccg gcgcgccctc    180

ggaccccaga ctccgtcagt ttctgcagaa gtctctggcg gctgccaccg ggaaacagga    240

actggccaag tacttcttgg cagagctgct gtccgagccc aaccagacag agaatgatgc    300

cctggagccc gaggatttgc cccaggcagc tgagcaggac gagatgaggc tggagctgca    360

gaggtctgcc aactcgaacc cagcaatggc accccgggaa cgcaaagctg gctgcaagaa    420

cttcttctgg aagacattca catcctgtta gctttaatat tgttgtccta gccagacctc    480

tgatccctct cccccaaacc ccatatctct tccttaactc ctggcccccg atgctcaact    540

tgaccctgca ttagaaattg aagactgtaa atacaaaata aaattatggt gagattatg     599


<210> SEQ ID NO 113
<211> LENGTH: 351
<212> TYPE: DNA
<213> ORGANISM: Mus musculus

<400> SEQUENCE: 113

atgctgtcct gccgtctcca gtgcgccctg gctgcgctct gcatcgtcct ggctttgggc     60

ggtgtcaccg gcgcgccctc ggaccccaga ctccgtcagt ttctgcagaa gtctctggcg    120

gctgccaccg ggaaacagga actggccaag tacttcttgg cagagctgct gtccgagccc    180

aaccagacag agaatgatgc cctggagccc gaggatttgc cccaggcagc tgagcaggac    240

gagatgaggc tggagctgca gaggtctgcc aactcgaacc cagcaatggc accccgggaa    300

cgcaaagctg gctgcaagaa cttcttctgg aagacattca catcctgtta g             351


<210> SEQ ID NO 114
<211> LENGTH: 116
<212> TYPE: PRT
<213> ORGANISM: Mus musculus

<400> SEQUENCE: 114

Met Leu Ser Cys Arg Leu Gln Cys Ala Leu Ala Ala Leu Cys Ile Val
1               5                   10                  15

Leu Ala Leu Gly Gly Val Thr Gly Ala Pro Ser Asp Pro Arg Leu Arg
            20                  25                  30

Gln Phe Leu Gln Lys Ser Leu Ala Ala Ala Thr Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Pro Gln Ala Ala Glu Gln Asp
65                  70                  75                  80
```

```
Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115


<210> SEQ ID NO 115
<211> LENGTH: 564
<212> TYPE: DNA
<213> ORGANISM: Rattus norvegicus

<400> SEQUENCE: 115

tgcggacctg cgtctagact gacccaccgc gctcaagctc ggctgtctga ggcaggggag      60

atgctgtcct gccgtctcca gtgcgcgctg gccgcgctct gcatcgtcct ggctttgggc     120

ggtgtcaccg gggcgccctc ggaccccaga ctccgtcagt ttctgcagaa gtctctggcg     180

gctgccaccg ggaaacagga actggccaag tacttcttgg cagaactgct gtctgagccc     240

aaccagacag agaacgatgc cctggagcct gaggatttgc cccaggcagc tgagcaggac     300

gagatgaggc tggagctgca gaggtctgcc aactcgaacc cagccatggc accccgggaa     360

cgcaaagctg gctgcaagaa cttcttctgg aagacattca catcctgtta gctttaatat     420

tgttgtctca gccagacctc tgatccctct cctccaaatc ccatatctct tccttaactc     480

ccagcccccc ccccaatgct caactagacc ctgcgttaga aattgaagac tgtaaataca     540

aaataaaatt atggtgaaat tatg                                            564


<210> SEQ ID NO 116
<211> LENGTH: 351
<212> TYPE: DNA
<213> ORGANISM: Rattus norvegicus

<400> SEQUENCE: 116

atgctgtcct gccgtctcca gtgcgcgctg gccgcgctct gcatcgtcct ggctttgggc      60

ggtgtcaccg gggcgccctc ggaccccaga ctccgtcagt ttctgcagaa gtctctggcg     120

gctgccaccg ggaaacagga actggccaag tacttcttgg cagaactgct gtctgagccc     180

aaccagacag agaacgatgc cctggagcct gaggatttgc cccaggcagc tgagcaggac     240

gagatgaggc tggagctgca gaggtctgcc aactcgaacc cagccatggc accccgggaa     300

cgcaaagctg gctgcaagaa cttcttctgg aagacattca catcctgtta g              351


<210> SEQ ID NO 117
<211> LENGTH: 116
<212> TYPE: PRT
<213> ORGANISM: Rattus norvegicus

<400> SEQUENCE: 117

Met Leu Ser Cys Arg Leu Gln Cys Ala Leu Ala Ala Leu Cys Ile Val
1               5                   10                  15

Leu Ala Leu Gly Gly Val Thr Gly Ala Pro Ser Asp Pro Arg Leu Arg
            20                  25                  30

Gln Phe Leu Gln Lys Ser Leu Ala Ala Ala Thr Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Pro Gln Ala Ala Glu Gln Asp
65                  70                  75                  80
```

```
Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115


<210> SEQ ID NO 118
<211> LENGTH: 4343
<212> TYPE: DNA
<213> ORGANISM: Homo sapiens

<400> SEQUENCE: 118

tggtcatcgc acggcggcag ctcctcacct ggatttagaa gagctggcgt ccccgcccgc     60

ccaagccttt aaactctcgt ctgccagaac ccgccaactc tccaggctta gggccagttt    120

ccgcgattct aagagtaatt gcgtgggcac ctgtgctggg gccaggcgca aagaagggag    180

ttggtctgcg cgaagatcgt caacctgcta acagaccgca catgcacttt gcaccgacca    240

tctacgtctc agtctggagg ttgcgcactt tggctgctga cgcgctggtg gtgcctatta    300

atcatttacc agtccagagc cgcgccagtt aatggctgtg ccgtgcggtg ctcccacatc    360

ctggcctctc ctctccacgg tcgcctgtgc ccgggcaccc cggagctgca aactgcagag    420

cccaggcaac cgctgggctg tgcgccccgc cggcgccggt aggagccgcg ctccccgcag    480

cggttgcgct ctacccggag gcgctgggcg gctgtgggct gcaggcaagc ggtcgggtgg    540

ggagggaggg cgcaggcggc gggtgcgcga ggagaaagcc ccagccctgg cagccccact    600

ggccccccctc agctgggatg ttccccaatg gcaccgcctc ctctccttcc tcctctccta    660

gccccagccc gggcagctgc ggcgaaggcg gcggcagcag gggccccggg gccggcgctg    720

cggacggcat ggaggagcca gggcgaaatg cgtcccagaa cgggaccttg agcgagggcc    780

agggcagcgc catcctgatc tctttcatct actccgtggt gtgcctggtg gggctgtgtg    840

ggaactctat ggtcatctac gtgatcctgc gctatgccaa gatgaagacg gccaccaaca    900

tctacatcct aaatctggcc attgctgatg agctgctcat gctcagcgtg cccttcctag    960

tcacctccac gttgttgcgc cactggccct tcggtgcgct gctctgccgc ctcgtgctca   1020

gcgtggacgc ggtcaacatg ttcaccagca tctactgtct gactgtgctc agcgtggacc   1080

gctacgtggc cgtggtgcat cccatcaagg cggcccgcta ccgccggccc accgtggcca   1140

aggtagtaaa cctgggcgtg tgggtgctat cgctgctcgt catcctgccc atcgtggtct   1200

tctctcgcac cgcggccaac agcgacggca cggtggcttg caacatgctc atgccagagc   1260

ccgctcaacg ctggctggtg ggcttcgtgt tgtacacatt tctcatgggc ttcctgctgc   1320

ccgtgggggc tatctgcctg tgctacgtgc tcatcattgc taagatgcgc atggtggccc   1380

tcaaggccgg ctggcagcag cgcaagcgct cggagcgcaa gatcacctta atggtgatga   1440

tggtggtgat ggtgtttgtc atctgctgga tgcctttcta cgtggtgcag ctggtcaacg   1500

tgtttgctga gcaggacgac gccacggtga gtcagctgtc ggtcatcctc ggctatgcca   1560

acagctgcgc caaccccatc ctctatggct ttctctcaga caacttcaag cgctctttcc   1620

aacgcatcct atgcctcagc tggatggaca acgccgcgga ggagccggtt gactattacg   1680

ccaccgcgct caagagccgt gcctacagtg tggaagactt ccaacctgag aacctggagt   1740

ccggcggcgt cttccgtaat ggcacctgca cgtcccggat cacgacgctc tgagcccggg   1800

ccacgcaggg gctctgagcc cgggccacgc aggggccctg agccaaaaga gggggagaat   1860
```

```
gagaagggaa ggccgggtgc gaaagggacg gtatccaggg cgccagggtg ctgtcgggat   1920
aacgtggggc taggacactg acagcctttg atggaggaac ccaagaaagg cgcgcgacaa   1980
tggtagaagt gagagctttg cttataaact gggaaggctt tcaggctacc tttttctggg   2040
tctcccactt tctgttcctt cctccactgc gcttactcct ctgaccctcc ttctattttc   2100
cctaccctgc aacttctatc ctttcttccg caccgtcccg ccagtgcaga tcacgaactc   2160
attaacaact cattctgatc ctcagcccct ccagtcgtta tttctgtttg tttaagctga   2220
gccacggata ccgccacggg tttccctcgg cgttagtccc tagccgcgcg gggccgctgt   2280
ccaggttctg tctggtgccc ctactggagt cccgggaatg accgctctcc ctttgcgcag   2340
ccctacctta aggaaagttg gacttgagaa agatctaagc agctggtctt ttctcctact   2400
cttgggtgaa ggtgcatctt tccctgccct cccctgtccc cctctcgccg cccgcccgcc   2460
accaccactc tcactccacc cagagtagag ccaggtgctt agtaaaatag gtcccgcgct   2520
tcgaactcca ggctttctgg agttcccacc caagccctcc tttggagcaa agaaggagct   2580
gagaacaagc cgaatgagga gtttttataa gattgcgggg tcggagtgtg ggcgcgtaat   2640
aggaatcacc ctcctactgc gcgttttcaa agaccaagcg ctgggcgctc ccgggccgcg   2700
cgtctgcgtt aggcagggca gggtagtgca gggcacacct tccccggggt tcggggttcg   2760
gggttcggtt gcagggctgc agcccgcctt ggctttctcc ctcacccaag tttccggagg   2820
agccgaccta aaagtaacaa tagataaggt ttcctgctcc agtgtatctc aaaagaccgg   2880
gcgccagggg cgggggacct agggcgacgt cttcagagtc cgccagtgtt ggcggtgtcg   2940
ccgcaacctg caggctcccg agtggggcct gcctggtctc tagagggttg ctgcctttca   3000
agcggtgcct aagaagttat tttcttgttt aacatatata tttattaatt tatttgtcgt   3060
gttggaaaat gtgtctctgc tttccttttc tctgcttgcc tagccccagg tcttttcttt   3120
gggaccctgg gggcgggcat ggaagtggaa gtaggggcaa gctcttgccc cactccctgg   3180
ccatctcaac gcctctcctc aatgctgggc cctcttatct catcctttcc tctagctttt   3240
ctatttttga ttgtgttgag tgaagtttgg agatttttca tacttttctt actatagtct   3300
cttgtttgtc ttattaggat aatacataaa tgataatgtg ggttatcctc ctctccatgc   3360
acagtggaaa gtcctgaact cctggctttc caggagacat atatagggga acatcaccct   3420
atatataatt tgagtgtata tatatttata tatatgatgt ggacatatgt atacttatct   3480
tgctccattg tcatgagtcc atgagtctaa gtatagccac tgatggtgac aggtgtgagt   3540
ctggctggaa cactttcagt ttcaggagtg caagcagcac tcaaacctgg agctgaggaa   3600
tctaattcag acagagactt taatcactgc tgaagatgcc cctgctccct ctgggttcca   3660
gcagaggtga ttcttacata tgatccagtt aacatcatca cttttttttga ggacattgaa   3720
agtgaaataa tttgtgtctg tgtttaatat taccaactac attggaagcc tgagcagggc   3780
gaggaccaat aattttaatt atttatattt cctgtattgc tttagtatgc tggcttgtac   3840
atagtaggca ctaaatacat gtttgttggt tgattgttta agccagagtg tattacaaca   3900
atctggagat actaaatctg gggttctcag gttcactcat tgacatgata tacaatggtt   3960
aaaatcacta ttgaaaaata cgttttgtgt atatttgctt caacaacttt gtgctttcct   4020
gaaagcagta accaagagtt aagatatccc taatgttttg cttaaactaa tgaacaaata   4080
tgctttgggt cataaatcag aaagtttaga tctgtccctt aataaaaata tatattacta   4140
ctcctttgga aaatagattt ttaatggtta agaactgtga aatttacaaa tcaaaatctt   4200
```

```
aatcattatc cttctaagag gatacaaatt tagtgctctt aacttgttac cattgtaata   4260
ttaactaaat aaacagatgt attatgctgt taaaaaaaaa aaaaaaaaaa aaaaaaaaaa   4320
aaaaaaaaaa aaaaaaaaaa aaa                                            4343
```

<210> SEQ ID NO 119
<211> LENGTH: 1176
<212> TYPE: DNA
<213> ORGANISM: Homo sapiens

<400> SEQUENCE: 119

```
atgttcccca atggcaccgc ctcctctcct tcctcctctc ctagccccag cccgggcagc     60
tgcggcgaag gcggcggcag caggggcccc ggggccggcg ctgcggacgg catggaggag    120
ccagggcgaa atgcgtccca gaacgggacc ttgagcgagg gccagggcag cgccatcctg    180
atctctttca tctactccgt ggtgtgcctg gtggggctgt gtgggaactc tatggtcatc    240
tacgtgatcc tgcgctatgc caagatgaag acggccacca acatctacat cctaaatctg    300
gccattgctg atgagctgct catgctcagc gtgcccttcc tagtcacctc cacgttgttg    360
cgccactggc ccttcggtgc gctgctctgc cgcctcgtgc tcagcgtgga cgcggtcaac    420
atgttcacca gcatctactg tctgactgtg ctcagcgtgg accgctacgt ggccgtggtg    480
catcccatca aggcggcccg ctaccgccgg cccaccgtgg ccaaggtagt aaacctgggc    540
gtgtgggtgc tatcgctgct cgtcatcctg cccatcgtgg tcttctctcg caccgcggcc    600
aacagcgacg gcacggtggc ttgcaacatg ctcatgccag agcccgctca acgctggctg    660
gtgggcttcg tgttgtacac atttctcatg ggcttcctgc tgcccgtggg ggctatctgc    720
ctgtgctacg tgctcatcat tgctaagatg cgcatggtgg ccctcaaggc cggctggcag    780
cagcgcaagc gctcggagcg caagatcacc ttaatggtga tgatggtggt gatggtgttt    840
gtcatctgct ggatgccttt ctacgtggtg cagctggtca acgtgtttgc tgagcaggac    900
gacgccacgg tgagtcagct gtcggtcatc ctcggctatg ccaacagctg cgccaacccc    960
atcctctatg gctttctctc agacaacttc aagcgctctt tccaacgcat cctatgcctc   1020
agctggatgg acaacgccgc ggaggagccg gttgactatt acgccaccgc gctcaagagc   1080
cgtgcctaca gtgtggaaga cttccaacct gagaacctgg agtccggcgg cgtcttccgt   1140
aatggcacct gcacgtcccg gatcacgacg ctctga                             1176
```

<210> SEQ ID NO 120
<211> LENGTH: 391
<212> TYPE: PRT
<213> ORGANISM: Homo sapiens

<400> SEQUENCE: 120

```
Met Phe Pro Asn Gly Thr Ala Ser Ser Pro Ser Ser Ser Pro Ser Pro
1               5                   10                  15

Ser Pro Gly Ser Cys Gly Glu Gly Gly Gly Ser Arg Gly Pro Gly Ala
            20                  25                  30

Gly Ala Ala Asp Gly Met Glu Glu Pro Gly Arg Asn Ala Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95
```

```
Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Thr Ser Arg Ile Thr Thr Leu
385                 390
```

```
<210> SEQ ID NO 121
<211> LENGTH: 1176
<212> TYPE: DNA
<213> ORGANISM: Pan troglodytes

<400> SEQUENCE: 121

atgttcccca atggcaccgc ctcctctcct tcctcctctc ctagccccag cccgggcagc      60

tgcggcgaag gcggcggcag caggggcccc ggggccggcg ctgcggacgg catggaggag     120

ccagggcgaa atgcgtccca gaacgggacc ttgagcgagg gccagggcag cgccatcctg     180

atctctttca tctactccgt ggtgtgcctg gtggggctgt gtgggaactc tatggtcatc     240

tacgtgatcc tgcgctatgc caagatgaag acggccacca acatctacat cctaaatctg     300

gccattgctg atgagctgct catgctcagc gtgcccttcc tggtcacctc cacgttgttg     360

cgccactggc ccttcggtgc gctgctctgc cgcctcgtgc tcagcgtgga cgcggtcaac     420
```

```
atgttcacca gcatctactg tctgactgtg ctcagcgtgg accgctacgt ggccgtggtg    480

catcccatca aggcggcccg ctaccgccgg cccaccgtgg ccaaggtagt aaacctgggc    540

gtgtgggtgc tatcgctgct cgtcatcctg cccatcgtgg tcttctctcg caccgcggcc    600

aacagcgacg gcacggtggc ttgcaacatg ctcatgccag agcccgctca acgctggctg    660

gtgggcttcg tgctgtacac atttctcatg ggcttcctgc tgcccgtcgg ggctatctgc    720

ctgtgctacg tgctcatcat tgctaagatg cgcatggtgg ccctcaaggc cggctggcag    780

cagcgcaagc gctcggagcg caagatcacc ttaatggtga tgatggtggt gatggtgttt    840

gtcatctgct ggatgccttt ctacgtggtg cagctggtca acgtgtttgc tgagcaggac    900

gacgccacgg tgagccagct gtcggtcatc ctcggctatg ccaacagctg cgccaacccc    960

atcctctatg gctttctctc agacaacttc aagcgctctt tccaacgcat cctatgcctc   1020

agctggatgg acaacgccgc ggaggagccg gttgactatt acgccaccgc gctcaaaagc   1080

cgtgcctaca gtgtggaaga cttccaacct gagaacctgg agtccggcgg cgtcttccgt   1140

aatggcacct gcacgtcccg gatcacgacg ctctga                             1176
```

<210> SEQ ID NO 122
<211> LENGTH: 391
<212> TYPE: PRT
<213> ORGANISM: Pan troglodytes

<400> SEQUENCE: 122

```
Met Phe Pro Asn Gly Thr Ala Ser Ser Pro Ser Ser Ser Pro Ser Pro
1               5                   10                  15

Ser Pro Gly Ser Cys Gly Glu Gly Gly Gly Ser Arg Gly Pro Gly Ala
            20                  25                  30

Gly Ala Ala Asp Gly Met Glu Glu Pro Gly Arg Asn Ala Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240
```

```
Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Thr Ser Arg Ile Thr Thr Leu
385                 390


<210> SEQ ID NO 123
<211> LENGTH: 2014
<212> TYPE: DNA
<213> ORGANISM: Mus musculus

<400> SEQUENCE: 123

gagacatcat tgacttgggg atctgaaggc ctgaaatctc caggtacagg tttaaagaac      60

tggcaagcag gaaaggagct gctgacgcga tggtgccgct tattaatcat tcatcagtcc     120

agagcctttc cacttaatgg atgtgccgcg ctgggctcta gcctcttggc ctctcctctc     180

cactctccag tgtgcccagg acccccggag ctgcaagaga gacagcgctc aagcaagctg     240

ccgctgggtg atgctcccgg cggcctcagt cggagccgcg ctcgccacag ctgctgcgct     300

ctgccgggtg gcgccaggcg gcggtgagct gtgagcttgg ggccttgagc ctagggaggg     360

cgcagacagc aagggcgcaa ggtgagcgcc ccagccggca gccgcaccgg cccacttcag     420

ctgggatgtt ccccaatggc accgcctcct ctccctcctc ttctccaagc cccagcccag     480

gcagctgcgg ggaaggagcc tgcagcaggg gtccggggtc cggcgctgcg gacggcatgg     540

aagagcctgg acgaaacgct tcccagaatg ggaccttaag cgagggacag ggtagcgcca     600

ttctcatctc tttcatctac tccgtggtat gcttggtggg actgtgtggg aactctatgg     660

tcatctatgt gatcctgcgc tacgccaaga tgaagaccgc taccaacatc tacattctaa     720

acctggctat tgctgatgag ctgctcatgc tcagcgtgcc ctttctggtc acttccacgc     780

tgttgcgcca ctggcccttc ggcgcgctac tttgccgcct ggtgctcagc gtggatgcgg     840

tcaacatgtt caccagcatc tactgtctga ctgtgcttag tgtggaccgc tatgtggctg     900

tggtgcaccc gatcaaggca gcgcgctacc gtcggcccac tgtggccaaa gtagtgaacc     960

tgggcgtgtg ggtcctgtca ttactggtta tcttgcccat cgtggtcttc tcacgcaccg    1020

cagccaacag cgatggcacg gtagcctgca acatgctcat gcccgagccc gcccagcgct    1080

ggttggtggg cttcgtctta tacacatttc tcatgggctt cctgctgcct gtcggggcca    1140

tttgcctgtg ttatgtgctc atcattgcca agatgcgcat ggtggccctc aaggctggct    1200
```

ggcagcagcg caagcgctca gagcgcaaga tcactctaat ggtgatgatg gtggtgatgg 1260
tttttgtcat ctgctggatg cctttctacg tggtacagct ggtcaacgtg ttcgccgagc 1320
aagacgacgc caccgtgagc cagttgtctg tcatcctggg ctatgccaac agctgtgcca 1380
accccatcct ctacggcttc ctgtcggaca acttcaagcg ctctttccag cgcatcctgt 1440
gcctcagctg gatggataac gctgcggagg aaccagtcga ctactatgcc actgccctga 1500
agagtcgagc ctacagcgtg gaggacttcc agcccgagaa tctggagtct ggaggcgttt 1560
tccgtaatgg cacctgcgct tccaggatca gcacgctttg aggccgggca ctgccgggag 1620
ggggggagtg gtcagaaaga tggagctggg aagcgggtgg gagggaatgg taacccgaca 1680
ccaggtgctg aagtcatagt gcatgacagc gatgcagcgc ccctgcgctg aaccctgttc 1740
cgctgcgcag gtcagcgggc cagactcttt tcagagtggc tacaagacag tccctaatca 1800
ccgctctcct ttcgcagagc cttactgtca aggaagcaca gctcgaggat gtctaggcaa 1860
cttgtctttt ctactctcag agaaggaagg cacattttcc cttgggccct tcctctgctc 1920
cactccatcc cgagcagagc taggcgctta agaaaaagtt ctgtgccctg atctccagtc 1980
ttggtatagt accacacata tgcttctttg gagc 2014

<210> SEQ ID NO 124
<211> LENGTH: 1176
<212> TYPE: DNA
<213> ORGANISM: Mus musculus

<400> SEQUENCE: 124
atgttcccca atggcaccgc ctcctctccc tcctcttctc caagccccag cccaggcagc 60
tgcggggaag gagcctgcag caggggtccg gggtccggcg ctgcggacgg catggaagag 120
cctggacgaa acgcttccca gaatgggacc ttaagcgagg gacagggtag cgccattctc 180
atctctttca tctactccgt ggtatgcttg gtgggactgt gtgggaactc tatggtcatc 240
tatgtgatcc tgcgctacgc caagatgaag accgctacca acatctacat tctaaacctg 300
gctattgctg atgagctgct catgctcagc gtgccctttc tggtcacttc cacgctgttg 360
cgccactggc ccttcggcgc gctactttgc cgcctggtgc tcagcgtgga tgcggtcaac 420
atgttcacca gcatctactg tctgactgtg cttagtgtgg accgctatgt ggctgtggtg 480
cacccgatca aggcagcgcg ctaccgtcgg cccactgtgg ccaaagtagt gaacctgggc 540
gtgtgggtcc tgtcattact ggttatcttg cccatcgtgg tcttctcacg caccgcagcc 600
aacagcgatg gcacggtagc ctgcaacatg ctcatgcccg agcccgccca gcgctggttg 660
gtgggcttcg tcttatacac atttctcatg ggcttcctgc tgcctgtcgg ggccatttgc 720
ctgtgttatg tgctcatcat tgccaagatg cgcatggtgg ccctcaaggc tggctggcag 780
cagcgcaagc gctcagagcg caagatcact ctaatggtga tgatggtggt gatggttttt 840
gtcatctgct ggatgccttt ctacgtggta cagctggtca acgtgttcgc cgagcaagac 900
gacgccaccg tgagccagtt gtctgtcatc ctgggctatg ccaacagctg tgccaacccc 960
atcctctacg gcttcctgtc ggacaacttc aagcgctctt tccagcgcat cctgtgcctc 1020
agctggatgg ataacgctgc ggaggaacca gtcgactact atgccactgc cctgaagagt 1080
cgagcctaca gcgtggagga cttccagccc gagaatctgg agtctggagg cgttttccgt 1140
aatggcacct gcgcttccag gatcagcacg ctttga 1176

<210> SEQ ID NO 125
<211> LENGTH: 391

```
<212> TYPE: PRT
<213> ORGANISM: Mus musculus

<400> SEQUENCE: 125

Met Phe Pro Asn Gly Thr Ala Ser Ser Pro Ser Ser Ser Pro Ser Pro
1               5                   10                  15

Ser Pro Gly Ser Cys Gly Glu Gly Ala Cys Ser Arg Gly Pro Gly Ser
            20                  25                  30

Gly Ala Ala Asp Gly Met Glu Glu Pro Gly Arg Asn Ala Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Ala Ser Arg Ile Ser Thr Leu
385                 390
```

<210> SEQ ID NO 126
<211> LENGTH: 3615
<212> TYPE: DNA
<213> ORGANISM: Rattus norvegicus

<400> SEQUENCE: 126
gctcgccaca gctgctgcgc gctgccggga gggccaggcg cggtgagctg tgagcttgga 60
gccttgagcc tagggagggc gcaggcagca agggcgcaag gtgagcgtcc caaccggcgg 120
ccacaccggc ccacttcagc tgggatgttc cccaatggca ccgccccctc tcccacctct 180
tctcccagct ccagcccagg cggctgcggg gaaggagtct gcagcagggg tcccgggtcc 240
ggcgctgcgg acggcatgga agaacctgga cgaaactctt cccagaacgg gactttaagc 300
gagggtcagg gtagcgccat tctcatctct ttcatctact ccgtggtatg cttggtggga 360
ctgtgtggga actccatggt catttacgtg atcctgcgct acgccaagat gaagaccgca 420
accaacatct acattctaaa cctggccatt gctgatgagc tgctcatgct cagcgtgccc 480
tttctggtca cttccacgct gttgcgccac tggccctttg gcgcgctact ttgccgcctg 540
gtgctcagcg tggatgcagt caacatgttc accagcatct actgtctgac tgtgcttagt 600
gtggaccgct atgtggctgt ggtgcacccg atcaaggcag cgcgctaccg tcggcccact 660
gtggccaaag tagtgaacct gggcgtgtgg gtgctgtcgc tactggttat cttgcccatc 720
gtggtcttct cacgcaccgc agccaacagc gatggcacgg tggcctgcaa catgctcatg 780
cccgagcccg cccagcgctg gttggtgggc ttcgtcttat acacatttct catgggcttc 840
ctgctgcctg tcggggccat ctgcctgtgt tacgtgctca tcattgccaa gatgcgcatg 900
gtggccctca aggccggctg gcagcagcgc aagcgctcag agcgcaagat cactctaatg 960
gtgatgatgg tggtgatggt ttttgtcatc tgctggatgc ctttctacgt ggtacagcta 1020
gtcaacgtgt tcgccgagca agacgacgcc acggtgagcc agttgtctgt catcctcggc 1080
tatgccaata gctgtgccaa ccccatcctc tacggcttcc tgtcggacaa cttcaagcgc 1140
tctttccagc gcatcctgtg cctcagctgg atggataacg ctgcggagga gcctgttgac 1200
tactacgcca ctgccctgaa gagtcgtgcc tacagtgtgg aggacttcca gcctgagaat 1260
ctggaatctg gaggcgtttt ccgtaatggc acctgcgctt ccaggatcag cacgctttga 1320
ggccggacgc taaccggagg gggagagtgg tcagaaaggt ggagagggga agcaggtggg 1380
agggaatgat agccgcacac caggtgctat gggagtagtg cgtgacagcg atgcagcgcc 1440
cctgtttagc aaagctatgt gactaaggta aacgggagag atttgagaat gttttcgggc 1500
catctggtat tctgaactgt gttctccaaa cccgataatt tccatcctcc ctcccagttc 1560
tgctagtaca aactgcaaac ttaacgtcgc caactccgtt tgaccctttc cctctcaagc 1620
tgttatttct gcttctttaa actgagccat cttgtgtttc ttttgggctg agtccccacc 1680
ttgcgctgaa ccccctgcgc aggtcagcgg gccagactct tcagagcggc taccagactg 1740
tccccagtta ccgctcccct tttgcacagc cttactgtca agtaagccca gctccaggat 1800
gaccaggcaa ctggtctttt ctactctcaa agaaggcacc atcttccctt gggccctttc 1860
tctgcttcac tgcatccaga gcagagctgg gtgcttaaga aaaagtcctg tgcccagatg 1920
gccagacttg gtgtagtccc acccattccc tcctttggag cacaaaaagg agctaagagc 1980
cagcagaagg gcaagtttct aagattcctg ggctgtggtt gtgggtgcca gagaagccac 2040
cctcccatag agctcaggac ctgagcacta ggcttggagg tcccagctag ggagctcccc 2100

```
ggcttgtgaa taacttatgc accctggtgt gtgaacctga attgcacagc agttcccctt   2160
ggaggtctcc ctagaataac aaaggattgg gttgcctgct ccctttccta gtccagctcc   2220
tgttccagtg acaaaccgca gagcccttgc caaagctgga tggctaactt cagcttgtct   2280
ggtccctgac atttttgcc tttcaagcgg tgcctaataa gttatttctt gtttgacata   2340
tttatttatt tatttatggt gttgaaaaaa aaagtgtgtt tccactttct ttttctgtat   2400
ttgcctaaca gggctgttct tgagaatcct ctggcaggca cgtggtggtg tggaggtgtg   2460
gaggggagca ggggtggaga aagttctctc accccaagac tccctcagaa gtttcccttc   2520
ttttgcactc cattggcctt ttcttgatcc ttcttggttt tgcttgtgtc cagtgaagtt   2580
tggagatttt aaaaatatat ttttactgta gttttgtctt gttaaaataa gtacatggca   2640
atttggttta acttttgtca gtgtggagtg gaaggcctga atccctggca tcccagaaaa   2700
cacaggggaa caaatcacat gatccgtgat gtatgtctgt atatgtgctg tcacacacaa   2760
gtcacatata tacgtgtata tatatatcat atatgtacac acacatataa aggtagattt   2820
gtcaatcttg acaactgtca ctagttcatg acaattataa ggacacccac aatgtgtgac   2880
ctgagctgta gcactccagc tgggatctga gaaacgtcag agattggagt cgctgctgaa   2940
gatgctgctg cccttttcta tcccctcaga ggtgattctt acccagtaag tctagtcact   3000
tttgttgagg aatggaagcg aaacaattgt gtctgcattt actgactacc gtggaaacct   3060
gaacacggaa ggacccatct cttcacttgt tgcatttgct gtgttcctgt gtatgctcgt   3120
ttgtacatag gggccactga aaggatatct tgcttggttg tttaaggaag ccagtgtata   3180
tcagtggtct tagaacaatg aacctggggt tctcgggtcc acagtgacct gacatctaac   3240
ctgcaatggt cgaatgcact gttgaaaatg gtgttttgtg tacatttgct tcaagaacac   3300
atccatgctt ttcctaaaag caggaaccaa gagttaaact gtctcttctg ttttgtttaa   3360
ataaatgaac aaatatgctt ttgatcataa gtgagaaagt ttagatcttt tcctaagaat   3420
agtatatata tatatatata tgtatatata tatatatata tatgtatata tatatacttt   3480
tctgttaatt agatttttta accgataaga agagtgaact ttataaactg aaatctccat   3540
cattatcatc tcgacaggat aaaaatgtag tgctcttacc ctgtaatagt aactgaataa   3600
aaagatgtat tatgc                                                    3615
```

<210> SEQ ID NO 127
<211> LENGTH: 1176
<212> TYPE: DNA
<213> ORGANISM: Rattus norvegicus

<400> SEQUENCE: 127

```
atgttcccca atggcaccgc cccctctccc acctcttctc ccagctccag cccaggcggc     60
tgcggggaag gagtctgcag caggggtccc gggtccggcg ctgcggacgg catggaagaa    120
cctggacgaa actcttccca gaacgggact ttaagcgagg gtcagggtag cgccattctc    180
atctctttca tctactccgt ggtatgcttg gtgggactgt gtgggaactc catggtcatt    240
tacgtgatcc tgcgctacgc caagatgaag accgcaacca acatctacat tctaaacctg    300
gccattgctg atgagctgct catgctcagc gtgccctttc tggtcacttc cacgctgttg    360
cgccactggc cctttggcgc gctactttgc cgcctggtgc tcagcgtgga tgcagtcaac    420
atgttcacca gcatctactg tctgactgtg cttagtgtgg accgctatgt ggctgtggtg    480
cacccgatca aggcagcgcg ctaccgtcgg cccactgtgg ccaaagtagt gaacctgggc    540
gtgtgggtgc tgtcgctact ggttatcttg cccatcgtgg tcttctcacg caccgcagcc    600
```

```
aacagcgatg gcacggtggc ctgcaacatg ctcatgcccg agcccgccca gcgctggttg    660

gtgggcttcg tcttatacac atttctcatg ggcttcctgc tgcctgtcgg ggccatctgc    720

ctgtgttacg tgctcatcat tgccaagatg cgcatggtgg ccctcaaggc cggctggcag    780

cagcgcaagc gctcagagcg caagatcact ctaatggtga tgatggtggt gatggttttt    840

gtcatctgct ggatgccttt ctacgtggta cagctagtca acgtgttcgc cgagcaagac    900

gacgccacgg tgagccagtt gtctgtcatc ctcggctatg ccaatagctg tgccaacccc    960

atcctctacg gcttcctgtc ggacaacttc aagcgctctt tccagcgcat cctgtgcctc   1020

agctggatgg ataacgctgc ggaggagcct gttgactact acgccactgc cctgaagagt   1080

cgtgcctaca gtgtggagga cttccagcct gagaatctgg aatctggagg cgttttccgt   1140

aatggcacct gcgcttccag gatcagcacg ctttga                              1176


<210> SEQ ID NO 128
<211> LENGTH: 391
<212> TYPE: PRT
<213> ORGANISM: Rattus norvegicus

<400> SEQUENCE: 128

Met Phe Pro Asn Gly Thr Ala Pro Ser Pro Thr Ser Ser Pro Ser Ser
1               5                   10                  15

Ser Pro Gly Gly Cys Gly Glu Gly Val Cys Ser Arg Gly Pro Gly Ser
            20                  25                  30

Gly Ala Ala Asp Gly Met Glu Glu Pro Gly Arg Asn Ser Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270
```

```
Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Ala Ser Arg Ile Ser Thr Leu
385                 390


<210> SEQ ID NO 129
<211> LENGTH: 2996
<212> TYPE: DNA
<213> ORGANISM: Homo sapiens

<400> SEQUENCE: 129

cgcagccacc catgcgcgcg cgctcgcaag accaccagcg cccagagccc cagtctgagg     60

cttggcgccg gggtctgcgg ggcgaggga gctctctacg tgcgaggggc tagcgggagc    120

cggcacaaga gggtcgagga gccaggaacc ccaaacgtcc ggcgccaggc gctagccaag    180

ctgctgcgcg ccccggcgcc cagctggctc ggggacagcc gctgggtgtc ggagaccgga    240

gctagcggat tgcagcggaa aagcaaagat gtcacactgg atccttggcc tccagggtcc    300

attaaggtga gaataagatc tctgggctgg ctggaactag cctaagactg aaaagcagcc    360

atggacatgg cggatgagcc actcaatgga agccacacat ggctatccat tccatttgac    420

ctcaatggct ctgtggtgtc aaccaacacc tcaaaccaga cagagccgta ctatgacctg    480

acaagcaatg cagtcctcac attcatctat tttgtggtct gcatcattgg gttgtgtggc    540

aacacacttg tcatttatgt catcctccgc tatgccaaga tgaagaccat caccaacatt    600

tacatcctca acctggccat cgcagatgag ctcttcatgc tgggtctgcc tttcttggct    660

atgcaggtgg ctctggtcca ctggcccttt ggcaaggcca tttgccgggt ggtcatgact    720

gtggatggca tcaatcagtt caccagcatc ttctgcctga cagtcatgag catcgaccga    780

tacctggctg tggtccaccc catcaagtcg gccaagtgga ggagaccccg gacggccaag    840

atgatcacca tggctgtgtg ggagtctct ctgctggtca tcttgcccat catgatatat    900

gctgggctcc ggagcaacca gtgggggaga agcagctgca ccatcaactg gccaggtgaa    960

tctggggctt ggtacacagg gttcatcatc tacactttca ttctggggtt cctggtaccc   1020

ctcaccatca tctgtctttg ctacctgttc attatcatca aggtgaagtc ctctggaatc   1080

cgagtgggct cctctaagag gaagaagtct gagaagaagg tcacccgaat ggtgtccatc   1140

gtggtggctg tcttcatctt ctgctggctt cccttctaca tattcaacgt ttcttccgtc   1200

tccatggcca tcagccccac cccagccctt aaaggcatgt ttgactttgt ggtggtcctc   1260

acctatgcta acagctgtgc caaccctatc ctatatgcct tcttgtctga caacttcaag   1320

aagagcttcc agaatgtcct ctgcttggtc aaggtgagcg gcacagatga tggggagcgg   1380
```

```
agtgacagta agcaggacaa atcccggctg aatgagacca cggagaccca gaggaccctc   1440
ctcaatggag acctccaaac cagtatctga actgcttggg gggtgggaaa gaaccaagcc   1500
atgctctgtc tactggcaat gggctcccta cccacactgg cttcctgcct cccacccctc   1560
acacctggct tctagaatag aggattgctc agcatgagtc caattcagag aacggtgttt   1620
gagtcagctt gtctgattga atgataatgt gctaaattga ttacctcccc cttaaagcga   1680
acactgaaat gcaggtagac aattcaaagt ctggagaaga gggatcatgc ctggatatga   1740
tctttagaaa caacaaaaat agaaaaaaat aagtatctgt gtgtttgtgt attgaaaact   1800
caatatgtaa tcttgtgttt ttatatgtat acttgtatat tcctatttat tctctgtata   1860
ggcattacct acgttcctgt gtttacatac acaagtagca aattcgagta tgcatagtgt   1920
agatggacat ttgccacaac acactgcccg cagaaatgga cttaccgtga agccaataaa   1980
gttcaagctt cagggatctc tcttgcacgg gccttgccaa ggcccaggag ggacttgggc   2040
agtatgttca tgtggtcata tgtttttgta aaaaattgtg aaagtaagat atgtttgtat   2100
tgtttttctt aaagaggaac ctcgtataag cttcaagcct cacaaacctt ctagcctctg   2160
cccttgggga tttgcttcat taatttcagg caagtgaggt caatgtaaga agggaaaggg   2220
agaagatatt tgaagaacca gaatgtaaat tcatgtgttt ccacttctca gatatagtca   2280
gagaattatt catttgccca aaaggactta agtggttgtg gtcatccatc attgtattta   2340
tcaagacaaa gccaactttg ttataagatt gcattttttt cttttcaaat tgctttagtt   2400
tttcttaggg agctatgagg gggaaaaatc actaacatga aaggcaaaaa atggactatg   2460
attcctgtgg ggaaacaatt tcattctctc catcgtgaaa ataagtgaat aagagtgaag   2520
caaaattaca cctttatgag aaaccataaa attgttttta tttttcaggc cagacatagc   2580
ttcctaatga aagaaaatgg aaatgtaatt cgacgactcc tcaaagggga ctttagagga   2640
cttcatacaa agctgggcat taagaaaacc acaatgcatg gccgggcgtg gtggcttaca   2700
cctgtaatcc cagcactttg ggaggccgag gtgggtggat cacccgaggt caggagttcg   2760
agaccagcct ggccaacatg gtgaaacccc atcactacta aaaatatgta aattagtcgg   2820
gcgtggtgtc acgtgcctgt aatcctagct gctcgggagg ctgaggcagg agaatcactt   2880
gaacttggga ggtggaggtt gcagtaagct gagattgtgc cactgcactc tagcctgagc   2940
aacaagagca aaactcagtc tcaaaaaaaa aaaaaaaaaa aaaaaaaaaa aaaaaa       2996
```

```
<210> SEQ ID NO 130
<211> LENGTH: 1110
<212> TYPE: DNA
<213> ORGANISM: Homo sapiens

<400> SEQUENCE: 130

atggacatgg cggatgagcc actcaatgga agccacacat ggctatccat tccatttgac     60
ctcaatggct ctgtggtgtc aaccaacacc tcaaaccaga cagagccgta ctatgacctg    120
acaagcaatg cagtcctcac attcatctat tttgtggtct gcatcattgg gttgtgtggc    180
aacacacttg tcatttatgt catcctccgc tatgccaaga tgaagaccat caccaacatt    240
tacatcctca acctggccat cgcagatgag ctcttcatgc tgggtctgcc tttcttggct    300
atgcaggtgg ctctggtcca ctggcccttt ggcaaggcca tttgccgggt ggtcatgact    360
gtggatggca tcaatcagtt caccagcatc ttctgcctga cagtcatgag catcgaccga    420
tacctggctg tggtccaccc catcaagtcg gccaagtgga ggagaccccg gacggccaag    480
atgatcacca tggctgtgtg ggagtctct ctgctggtca tcttgcccat catgatatat    540
```

```
gctgggctcc ggagcaacca gtgggggaga agcagctgca ccatcaactg gccaggtgaa    600

tctggggctt ggtacacagg gttcatcatc tacactttca ttctggggtt cctggtaccc    660

ctcaccatca tctgtctttg ctacctgttc attatcatca aggtgaagtc ctctggaatc    720

cgagtgggct cctctaagag gaagaagtct gagaagaagg tcacccgaat ggtgtccatc    780

gtggtggctg tcttcatctt ctgctggctt cccttctaca tattcaacgt ttcttccgtc    840

tccatggcca tcagccccac cccagccctt aaaggcatgt ttgactttgt ggtggtcctc    900

acctatgcta acagctgtgc caaccctatc ctatatgcct tcttgtctga caacttcaag    960

aagagcttcc agaatgtcct ctgcttggtc aaggtgagcg gcacagatga tggggagcgg   1020

agtgacagta agcaggacaa atcccggctg aatgagacca cggagaccca gaggaccctc   1080

ctcaatggag acctccaaac cagtatctga                                    1110


<210> SEQ ID NO 131
<211> LENGTH: 369
<212> TYPE: PRT
<213> ORGANISM: Homo sapiens

<400> SEQUENCE: 131

Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
            20                  25                  30

Gln Thr Glu Pro Tyr Tyr Asp Leu Thr Ser Asn Ala Val Leu Thr Phe
        35                  40                  45

Ile Tyr Phe Val Val Cys Ile Ile Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160

Met Ile Thr Met Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Thr Phe Ile Leu Gly Phe Leu Val Pro Leu Thr Ile Ile
    210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270
```

```
Tyr Ile Phe Asn Val Ser Ser Val Ser Met Ala Ile Ser Pro Thr Pro
        275                 280                 285

Ala Leu Lys Gly Met Phe Asp Phe Val Val Val Leu Thr Tyr Ala Asn
    290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Asp
                325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Ser
        355                 360                 365

Ile
```

<210> SEQ ID NO 132
<211> LENGTH: 1297
<212> TYPE: DNA
<213> ORGANISM: Pan troglodytes

<400> SEQUENCE: 132

```
aagcaaagat gtcacactgg atccttggcc tccagggtcc attaaggtga gaataagatc     60

tctgggctgg ctggaactag cctaaaactg aaaagcagcc atggacatgg cggatgagcc    120

actcaatgga agccacacat ggctatccat tccatttgac ctcaatggct ctgtggtgtc    180

aaccaacacc tcaaaccaga cagagccgta ctatgacctg acaagcaatg cagtcctcac    240

attcatctat tttgtggtct gcatcattgg gttgtgtggc aacacacttg tcatttacgt    300

catcctccgc tatgccaaga tgaagaccat caccaacatt tacatcctca acctggccat    360

cgcagatgag ctcttcatgc tgggtctgcc tttcttagct atgcaggtgg ctctggtcca    420

ctggcccttt ggcaaggcca tttgccgggt ggtcatgact gtggatggca tcaatcagtt    480

caccagcatc ttctgcctga cagtcatgag catcgaccga tacctggctg tggtccaccc    540

cattaagtcg gccaagtgga ggagaccccg gacggccaag atgatcacca tggctgtgtg    600

gggagtctct ctgctggtca tcttgcccat catgatatat gctgggctcc ggagcaacca    660

gtgggggaga agcagctgca ccatcaactg gccaggtgaa tctggggctt ggtacacagg    720

gttcatcatc tacactttca ttctggggtt cctggtgccc ctcaccatca tctgtctttg    780

ctacctgttc attatcatca aggtgaagtc ctctggaatc cgagtggggt cctctaagag    840

gaagaagtct gagaagaagg tcacccgaat ggtgtccatc gtggtggctg tcttcatctt    900

ctgctggctt cccttctaca tattcaacgt ttcttccgtc tccatggcca tcagccccac    960

cccgcccctt aaaggcatgt ttgactttgt ggtggtccta acctatgcta acagctgtgc   1020

cacccctatc ctatatgcct tcttgtctga caacttcaag aagagcttcc agaatgtcct   1080

ctgcttggtc aaggtgagcg gcacagatga tggggagcgg agtgacagta agcaggacaa   1140

atcccggctg aatgagacca cggagaccca gaggaccctc ctcaatggag acctccaaac   1200

cacgaacact gaaatgcagg tagacaattc aaagtctgga gaagagggat catgcctgga   1260

tatgatcttt agaaacaaca aaaatagaaa aaaataa                              1297
```

<210> SEQ ID NO 133
<211> LENGTH: 1197
<212> TYPE: DNA
<213> ORGANISM: Pan troglodytes

<400> SEQUENCE: 133

```
atggacatgg cggatgagcc actcaatgga agccacacat ggctatccat tccatttgac     60
ctcaatggct ctgtggtgtc aaccaacacc tcaaaccaga cagagccgta ctatgacctg    120
acaagcaatg cagtcctcac attcatctat tttgtggtct gcatcattgg gttgtgtggc    180
aacacacttg tcatttacgt catcctccgc tatgccaaga tgaagaccat caccaacatt    240
tacatcctca acctggccat cgcagatgag ctcttcatgc tgggtctgcc tttcttagct    300
atgcaggtgg ctctggtcca ctggcccttt ggcaaggcca tttgccgggt ggtcatgact    360
gtggatggca tcaatcagtt caccagcatc ttctgcctga cagtcatgag catcgaccga    420
tacctggctg tggtccaccc cattaagtcg gccaagtgga ggagaccccg gacggccaag    480
atgatcacca tggctgtgtg gggagtctct ctgctggtca tcttgcccat catgatatat    540
gctgggctcc ggagcaacca gtgggggaga agcagctgca ccatcaactg gccaggtgaa    600
tctggggctt ggtacacagg gttcatcatc tacactttca ttctggggtt cctggtgccc    660
ctcaccatca tctgtctttg ctacctgttc attatcatca aggtgaagtc ctctggaatc    720
cgagtggggt cctctaagag gaagaagtct gagaagaagg tcacccgaat ggtgtccatc    780
gtggtggctg tcttcatctt ctgctggctt cccttctaca tattcaacgt ttcttccgtc    840
tccatggcca tcagccccac ccccgccctt aaaggcatgt ttgactttgt ggtggtccta    900
acctatgcta acagctgtgc caccccctatc ctatatgcct tcttgtctga caacttcaag    960
aagagcttcc agaatgtcct ctgcttggtc aaggtgagcg gcacagatga tggggagcgg   1020
agtgacagta agcaggacaa atcccggctg aatgagacca cggagaccca gaggaccctc   1080
ctcaatggag acctccaaac cacgaacact gaaatgcagg tagacaattc aaagtctgga   1140
gaagagggat catgcctgga tatgatcttt agaaacaaca aaaatagaaa aaaataa      1197
```

<210> SEQ ID NO 134
<211> LENGTH: 398
<212> TYPE: PRT
<213> ORGANISM: Pan troglodytes

<400> SEQUENCE: 134

```
Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
            20                  25                  30

Gln Thr Glu Pro Tyr Tyr Asp Leu Thr Ser Asn Ala Val Leu Thr Phe
        35                  40                  45

Ile Tyr Phe Val Val Cys Ile Ile Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160
```

```
Met Ile Thr Met Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Thr Phe Ile Leu Gly Phe Leu Val Pro Leu Thr Ile Ile
    210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Met Ala Ile Ser Pro Thr Pro
        275                 280                 285

Ala Leu Lys Gly Met Phe Asp Phe Val Val Val Leu Thr Tyr Ala Asn
    290                 295                 300

Ser Cys Ala Thr Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Asp
                325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Thr
        355                 360                 365

Asn Thr Glu Met Gln Val Asp Asn Ser Lys Ser Gly Glu Glu Gly Ser
    370                 375                 380

Cys Leu Asp Met Ile Phe Arg Asn Asn Lys Asn Arg Lys Lys
385                 390                 395
```

<210> SEQ ID NO 135
<211> LENGTH: 1904
<212> TYPE: DNA
<213> ORGANISM: Mus musculus

<400> SEQUENCE: 135

```
ggaattccgg ctggaggtag tcattgagct ttaggaaggt ctgacatgca gcggcgatct      60

cagcctctgt gtacttgacc gagcagccct tcacgggcca gggcaccgtg aagagtctgg     120

tgttcaagta cttgtaggtg cagcctgggt ccccgatgag gatgcgagac actggggtga     180

gcacatcttt gccttggatc ctcaccacgt cccgaaacaa gcagccatgc ttatcgagtg     240

tgagaaaggc ctcgggcacc tccttatgca gctcctctgg tatgctgccg gcctctcgga     300

aaaccagttt agggtatttc agctgccact gctgatagaa ctcatcatct ttgggtgtca     360

ggtaaggaag ctgggagccc cgggagccac tgctgagcgc caaacacccg ctaagcctgc     420

tgtgctcctg gacgcccagc tgggtaaaag aacagcttct gggtgctaga gaacacaggg     480

aagcgagtgc tcgaggaaaa ccaagatgtc acagtagact cttggccccc agagccctgt     540

gaggcgagag gaagatctct aggcagcttg gttctagacg gagtggaaag cagccatgga     600

gatgagctct gagcagttga atgggagcca agtatgggtg tcctctccat ttgacctcaa     660

cggttcactg ggccaagcca atggctccaa ccagaccgag ccatactacg acatgacaag     720

caacgccgtc ctcacgttca tctacttcgt ggtgtgcgtc gtcgggctgt gcggcaacac     780
```

```
gctggtcatt tacgtcatcc tccgctacgc caagatgaag accatcacca acatctacat     840
ccttaacctg gccattgcag atgaactctt catgctaggg ctgcccttct tggccatgca     900
ggtggcgcta gtccactggc cttttggcaa ggccatctgc cgggtggtca tgactgtaga     960
tggcatcaat cagttcacca gtatcttctg cttgacggtc atgagcatcg accgctacct    1020
ggccgtggtg caccccatta agtcagccaa atggaggcga ccccggacag ccaagatgat    1080
caatgtggct gtgtggtgtg tgtctctgct cgtcattttg cccatcatgt tatacgccgg    1140
cctccggagc aaccagtggg gcagaagcag ctgtaccatc aactggccag gcgaatccgg    1200
ggcgtggtac acaggtttca ttatctacgc cttcatcctg ggttcctgg taccccttac     1260
catcatttgt ctctgctacc tgttcatcat catcaaggtg aagtcctctg gaatccgagt    1320
gggatcatcc aagaggaaaa agtcagagaa aaaggtgacc cgcatggtgt ccatcgtagt    1380
ggctgtcttc atcttctgct ggctcccttt ctacatcttc aacgtctctt ccgtgtctgt    1440
ggccatcagt cccaccccag ccctgaaagg aatgtttgac tttgtggtga tcctcaccta    1500
tgccaacacg tgcgccaacc ccatcctgta cgccttcttg tctgacaact tcaagaagag    1560
cttccagaat gttctttgct tggtcaaggc agacaattca caatccggag cggaagacat    1620
cattgcctgg gtgtgacctg gtggaaaaca gctgcccggc agaaaccgga aaaaccaaaa    1680
ctaaatcaaa gtcctgtgtg tatgtgtgct aacacgttac gtaaatcttg tgatctgata    1740
tttacatttg tatattctcc cctccccggt cacacaaaca tgtcccgtgt ttgtaagccc    1800
aagtagctag ttcgtgtgcg tctagtatag gtggacagtt accacaacgc tgaacctgaa    1860
gaaaaggact cgccacgtca cagtcagtcc aatctccgga attc                     1904
```

<210> SEQ ID NO 136
<211> LENGTH: 1041
<212> TYPE: DNA
<213> ORGANISM: Mus musculus

<400> SEQUENCE: 136

```
atggagatga gctctgagca gttgaatggg agccaagtat gggtgtcctc tccatttgac      60
ctcaacggtt cactggggcc aagcaatggc tccaaccaga ccgagccata ctacgacatg     120
acaagcaacg ccgtcctcac gttcatctac ttcgtggtgt gcgtcgtcgg gctgtgcggc     180
aacacgctgg tcatttacgt catcctccgc tacgccaaga tgaagaccat caccaacatc     240
tacatcctta acctggccat tgcagatgaa ctcttcatgc tagggctgcc cttcttggcc     300
atgcaggtgg cgctagtcca ctggcctttt ggcaaggcca tctgccgggt ggtcatgact     360
gtagatggca tcaatcagtt caccagtatc ttctgcttga cggtcatgag catcgaccgc     420
tacctggccg tggtgcaccc cattaagtca gccaaatgga ggcgaccccg gacagccaag     480
atgatcaatg tggctgtgtg gtgtgtgtct ctgctcgtca ttttgcccat catgttatac     540
gccggcctcc ggagcaacca gtggggcaga agcagctgta ccatcaactg gccaggcgaa     600
tccggggcgt ggtacacagg tttcattatc tacgccttca tcctggggtt cctggtaccc     660
cttaccatca tttgtctctg ctacctgttc atcatcatca aggtgaagtc ctctggaatc     720
cgagtgggat catccaagag gaaaaagtca gagaaaaagg tgacccgcat ggtgtccatc     780
gtagtggctg tcttcatctt ctgctggctc cctttctaca tcttcaacgt ctcttccgtg     840
tctgtggcca tcagtcccac cccagccctg aaaggaatgt ttgactttgt ggtgatcctc     900
acctatgcca acacgtgcgc caaccccatc ctgtacgcct tcttgtctga caacttcaag     960
```

```
aagagcttcc agaatgttct ttgcttggtc aaggcagaca attcacaatc cggagcggaa   1020

gacatcattg cctgggtgtg a                                            1041


<210> SEQ ID NO 137
<211> LENGTH: 346
<212> TYPE: PRT
<213> ORGANISM: Mus musculus

<400> SEQUENCE: 137

Met Glu Met Ser Ser Glu Gln Leu Asn Gly Ser Gln Val Trp Val Ser
1               5                   10                  15

Ser Pro Phe Asp Leu Asn Gly Ser Leu Gly Pro Ser Asn Gly Ser Asn
            20                  25                  30

Gln Thr Glu Pro Tyr Tyr Asp Met Thr Ser Asn Ala Val Leu Thr Phe
        35                  40                  45

Ile Tyr Phe Val Val Cys Val Val Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160

Met Ile Asn Val Ala Val Trp Cys Val Ser Leu Leu Val Ile Leu Pro
                165                 170                 175

Ile Met Leu Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Ala Phe Ile Leu Gly Phe Leu Val Pro Leu Thr Ile Ile
    210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Val Ala Ile Ser Pro Thr Pro
        275                 280                 285

Ala Leu Lys Gly Met Phe Asp Phe Val Val Ile Leu Thr Tyr Ala Asn
    290                 295                 300

Thr Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Ala Asp Asn Ser Gln
                325                 330                 335

Ser Gly Ala Glu Asp Ile Ile Ala Trp Val
            340                 345
```

<210> SEQ ID NO 138
<211> LENGTH: 2056
<212> TYPE: DNA
<213> ORGANISM: Rattus norvegicus

<400> SEQUENCE: 138

```
gccaccggca cgctggcgag gccaccggcc ctggagcacc agtccgccgc tgggcgtcga     60

tgatctacag gccagggtag ctctactggg gcccaggcaa gctctctcag acgccaggag    120

ggccagcacg agccagactg ggaagctgcg agcccgagag ctactgcgga gcgccaaaca    180

ccccctaaac ctgctgcgct cccgggcgcc cggctgggta aaggacagct tctgggagct    240

agagaacaca gagaagcgag tgctcgtgga aaagcaagat gtcacgatag acccttggcc    300

ccagagtcca ctgaggtgag aggaagatct ctgggctgct tggttctagg cggactgaag    360

agcagccatg gagttgacct ctgagcagtt caatgggagc caagtgtgga taccttctcc    420

ctttgacctc aacggctcac tggggccaag caatggctcc aaccagacag agccatacta    480

cgacatgaca agcaacgcgg tcctcacgtt catctacttc gtggtgtgcg tggtggggct    540

gtgcggcaac acgctcgtca tctacgtcat cctccgctac gccaagatga aaaccatcac    600

caacatttac atcctcaacc tggccatcgc agatgaactc ttcatgctgg ggctgccctt    660

cttggccatg caggtggcgc tggtccactg gccttttggc aaggccatct gccgggtggt    720

catgactgtg gacggtatca accagttcac cagtatcttc tgcttgacgg tcatgagcat    780

cgaccgttac ctggccgtgg tccaccccat taagtcagcc aaatggaggc gaccccggac    840

agccaagatg atcaacgtgg ctgtgtgggg tgtgtccctg cttgtcattt tgcccatcat    900

gatatacgct ggcctccgga gcaaccagtg ggtaggagc agctgcacca tcaactggcc     960

gggcgaatcc ggggcatggt acacgggttt cattatctat gccttcatcc tggggttcct   1020

ggtaccccta accatcatct gtctctgcta cctgttcatc atcatcaagg tgaagtcctc   1080

tgggatccga gtggggtcgt ccaagaggaa aaagtcagag aaaaaggtga cccgaatggt   1140

atccatcgtg gtggctgtct tcatcttctg ctggctcccc ttctatatct tcaatgtctc   1200

gtccgtgtct gtggccatca gccccacccc tgccctgaaa ggcatgtttg actttgtggt   1260

tatcctcacc tacgccaaca gctgcgccaa ccccatcctg tacgccttct tgtccgacaa   1320

cttcaagaag agcttccaga atgttctttg cttggtcaag gtgagtggtg cggaggatgg   1380

ggagcggagc gacagtaagc aggacaaatc ccggctgaat gagaccacgg agacccagag   1440

gaccctcctc aatggagacc tccaaaccag tatctgaaac aacccgggaa cgcaacgtgc   1500

acacgcacta gccaagcccc gcctcctggc agtgcgagcc ccattcaccc gcttcctgcc   1560

tcccctaccc atcacacccg gcttttctag agcagagcgg atttgagtct ggcttgtccg   1620

aaagtatacc cctctggtca catctacccc taaagtgaac gttttcgtgc aggcagacaa   1680

ttcaaagact ggagaagagg acacgatggc ctgggtgtga cccggtggaa agcagctacc   1740

cggcagaaac cggaaaaacc aaaactaaaa tcaaagttcc gcgcgtgtac gtgtgcttgc   1800

ccgctatgta atctcgtgat ctgatatttc cgtttgtaca tcacctcccc acccccaccc   1860

cggtctctgc ggagccagta tacacgtgtc ctgtgtttgt aaacccaagt agctagttca   1920

atgtcagagt caatctaatc taagcttcca gcatccctct tgcatgggcc tttcccagac   1980

ccaggaggag catgagcagt atgttcatat aataatacat ttttgtaaaa agaaaaaaaa   2040

aaaaaaaaaa aaaaaa                                                   2056
```

<210> SEQ ID NO 139

<211> LENGTH: 1110
<212> TYPE: DNA
<213> ORGANISM: Rattus norvegicus

<400> SEQUENCE: 139

```
atggagttga cctctgagca gttcaatggg agccaagtgt ggataccttc tccctttgac     60

ctcaacggct cactggggcc aagcaatggc tccaaccaga cagagccata ctacgacatg    120

acaagcaacg cggtcctcac gttcatctac ttcgtggtgt gcgtggtggg gctgtgcggc    180

aacacgctcg tcatctacgt catcctccgc tacgccaaga tgaaaaccat caccaacatt    240

tacatcctca acctggccat cgcagatgaa ctcttcatgc tggggctgcc cttcttggcc    300

atgcaggtgg cgctggtcca ctggcctttt ggcaaggcca tctgccgggt ggtcatgact    360

gtggacggta tcaaccagtt caccagtatc ttctgcttga cggtcatgag catcgaccgt    420

tacctggccg tggtccaccc cattaagtca gccaaatgga ggcgaccccg gacagccaag    480

atgatcaacg tggctgtgtg ggtgtgtcc ctgcttgtca ttttgcccat catgatatac     540

gctggcctcc ggagcaacca gtggggtagg agcagctgca ccatcaactg gccgggcgaa    600

tccggggcat ggtacacggg tttcattatc tatgccttca tcctggggtt cctggtaccc    660

ctaaccatca tctgtctctg ctacctgttc atcatcatca aggtgaagtc ctctgggatc    720

cgagtggggt cgtccaagag gaaaaagtca gagaaaaagg tgacccgaat ggtatccatc    780

gtggtggctg tcttcatctt ctgctggctc cccttctata tcttcaatgt ctcgtccgtg    840

tctgtggcca tcagccccac ccctgccctg aaaggcatgt ttgactttgt ggttatcctc    900

acctacgcca acagctgcgc caaccccatc ctgtacgcct tcttgtccga caacttcaag    960

aagagcttcc agaatgttct ttgcttggtc aaggtgagtg gtgcggagga tggggagcgg   1020

agcgacagta agcaggacaa atcccggctg aatgagacca cggagaccca gaggaccctc   1080

ctcaatggag acctccaaac cagtatctga                                    1110
```

<210> SEQ ID NO 140
<211> LENGTH: 369
<212> TYPE: PRT
<213> ORGANISM: Rattus norvegicus

<400> SEQUENCE: 140

```
Met Glu Leu Thr Ser Glu Gln Phe Asn Gly Ser Gln Val Trp Ile Pro
1               5                   10                  15

Ser Pro Phe Asp Leu Asn Gly Ser Leu Gly Pro Ser Asn Gly Ser Asn
            20                  25                  30

Gln Thr Glu Pro Tyr Tyr Asp Met Thr Ser Asn Ala Val Leu Thr Phe
        35                  40                  45

Ile Tyr Phe Val Val Cys Val Val Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
    130                 135                 140
```

```
Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Ala Phe Ile Leu Gly Phe Leu Val Pro Leu Thr Ile Ile
    210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Val Ala Ile Ser Pro Thr Pro
        275                 280                 285

Ala Leu Lys Gly Met Phe Asp Phe Val Val Ile Leu Thr Tyr Ala Asn
    290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Ala Glu
                325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Ser
        355                 360                 365

Ile
```

<210> SEQ ID NO 141
<211> LENGTH: 2123
<212> TYPE: DNA
<213> ORGANISM: Homo sapiens

<400> SEQUENCE: 141

```
cgcatctctc atcactcccc ctcattctgc ctttcctcct actcacggtc tcctctccct     60

ctccctctct ctctctcccc ctccctcttt ctctctctct ctctttctcc acctcctccc    120

gacccccttt cccctctatt tctattggct tctgtgtccc ttgctcccct cttctcttcc    180

tcaccctggg aagcttctcc cccctatcct tgcccctgcc cccccaggat gtgtcctgga    240

gatggggggt gacgtaccag gctctggttg ggaagtcagg gccggagacc agatgggaga    300

ggctctgtgg acagccgtgg ccgagggcct gggagggaac ctgagcccgc aagcggtcta    360

gaagtgggtg ccgtgtgggg accctagtta ggagtgccct gggggcacct ggggactggg    420

cagggagagg ggacagcaga atgataacca gcctggcggc aaggagggaa gccctcaccc    480

catgggcagg caaatagctg actgctgacc accctcccct cagccatgga catgcttcat    540

ccatcatcgg tgtccacgac ctcagaacct gagaatgcct cctcggcctg gcccccagat    600

gccaccctgg gcaacgtgtc ggcgggccca agcccggcag ggctggccgt cagtggcgtt    660

ctgatccccc tggtctacct ggtggtgtgc gtggtgggcc tgctgggtaa ctcgctggtc    720

atctatgtgg tcctgcggca cacggccagc ccttcagtca ccaacgtcta catcctcaac    780

ctggcgctgg ccgacgagct cttcatgctg gggctgccct tcctggccgc ccagaacgcc    840
```

```
ctgtcctact ggcccttcgg ctccctcatg tgccgcctgg tcatggcggt ggatggcatc    900
aaccagttca ccagcatatt ctgcctgact gtcatgagcg tggaccgcta cctggccgtg    960
gtacatccca cccgctcggc ccgctggcgc acagctccgg tggcccgcac ggtcagcgcg   1020
gctgtgtggg tggcctcagc cgtggtggtg ctgcccgtgg tggtcttctc gggagtgccc   1080
cgcggcatga gcacctgcca catgcagtgg cccgagccgg cggcggcctg gcgagccggc   1140
ttcatcatct acacggccgc actgggcttc ttcgggccgc tgctggtcat ctgcctctgc   1200
tacctgctca tcgtggtgaa ggtgcgctca gctgggcgcc gggtgtgggc accctcgtgc   1260
cagcggcggc ggcgctccga acgcagggtc acgcgcatgg tggtggccgt ggtggcgctc   1320
ttcgtgctct gctggatgcc cttctacgtg ctcaacatcg tcaacgtggt gtgcccactg   1380
cccgaggagc ctgccttctt tgggctctac ttcctggtgg tggcgctgcc ctatgccaac   1440
agctgtgcca accccatcct ttatggcttc ctctcctacc gcttcaagca gggcttccgc   1500
agggtcctgc tgcggccctc ccgccgtgtg cgcagccagg agcccactgt ggggcccccg   1560
gagaagactg aggaggagga tgaggaggag gaggatgggg aggagagcag ggagggggc    1620
aaggggaagg agatgaacgg ccgggtcagc cagatcacgc agcctggcac cagcgggcag   1680
gagcggccgc ccagcagagt ggccagcaag gagcagcagc tcctacccca agaggcttcc   1740
actggggaga agtccagcac gatgcgcatc agctacctgt agggcctggg gaaagccagg   1800
atggcccgag gaagaggcag aagccgtggg tgtgcctagg gcctacttcc caaggtgcca   1860
caggcccatg atgggatgtt gaggggcctg gactttgatg ctattgctgc caggtcttgc   1920
tgtgtgacct tgggtaggtt gcttctactc tctgggcctt gttttctcct ctgtgactca   1980
gggataggag tcatcagcct ggatgagcta tgtcagatga gaggtttgga gggcactgtt   2040
gctgggctga cctggctgag caggcaaaag gtgggtgcag actggcctcc ccccagggat   2100
ggagtgtctt ggggcatcaa cta                                           2123
```

<210> SEQ ID NO 142
<211> LENGTH: 1257
<212> TYPE: DNA
<213> ORGANISM: Homo sapiens

<400> SEQUENCE: 142

```
atggacatgc ttcatccatc atcggtgtcc acgacctcag aacctgagaa tgcctcctcg     60
gcctggcccc cagatgccac cctgggcaac gtgtcggcgg gcccaagccc ggcagggctg    120
gccgtcagtg gcgttctgat ccccctggtc tacctggtgg tgtgcgtggt gggcctgctg    180
ggtaactcgc tggtcatcta tgtggtcctg cggcacacgg ccagcccttc agtcaccaac    240
gtctacatcc tcaacctggc gctggccgac gagctcttca tgctggggct gcccttcctg    300
gccgcccaga acgccctgtc ctactggccc ttcggctccc tcatgtgccg cctggtcatg    360
gcggtggatg gcatcaacca gttcaccagc atattctgcc tgactgtcat gagcgtggac    420
cgctacctgg ccgtggtaca tcccacccgc tcggcccgct ggcgcacagc tccggtggcc    480
cgcacggtca gcgcggctgt gtgggtggcc tcagccgtgg tggtgctgcc cgtggtggtc    540
ttctcgggag tgccccgcgg catgagcacc tgccacatgc agtggcccga gccggcggcg    600
gcctggcgag ccggcttcat catctacacg gccgcactgg gcttcttcgg gccgctgctg    660
gtcatctgcc tctgctacct gctcatcgtg gtgaaggtgc gctcagctgg gcgccgggtg    720
tgggcaccct cgtgccagcg gcggcggcgc tccgaacgca gggtcacgcg catggtggtg    780
```

```
gccgtggtgg cgctcttcgt gctctgctgg atgcccttct acgtgctcaa catcgtcaac     840

gtggtgtgcc cactgcccga ggagcctgcc ttctttgggc tctacttcct ggtggtggcg     900

ctgccctatg ccaacagctg tgccaacccc atcctttatg gcttcctctc ctaccgcttc     960

aagcagggct tccgcagggt cctgctgcgg ccctcccgcc gtgtgcgcag ccaggagccc    1020

actgtggggc ccccggagaa gactgaggag gaggatgagg aggaggagga tggggaggag    1080

agcagggagg ggggcaaggg gaaggagatg aacggccggg tcagccagat cacgcagcct    1140

ggcaccagcg ggcaggagcg gccgcccagc agagtggcca gcaaggagca gcagctccta    1200

ccccaagagg cttccactgg ggagaagtcc agcacgatgc gcatcagcta cctgtag       1257


<210> SEQ ID NO 143
<211> LENGTH: 418
<212> TYPE: PRT
<213> ORGANISM: Homo sapiens

<400> SEQUENCE: 143

Met Asp Met Leu His Pro Ser Ser Val Ser Thr Thr Ser Glu Pro Glu
1               5                   10                  15

Asn Ala Ser Ser Ala Trp Pro Pro Asp Ala Thr Leu Gly Asn Val Ser
            20                  25                  30

Ala Gly Pro Ser Pro Ala Gly Leu Ala Val Ser Gly Val Leu Ile Pro
        35                  40                  45

Leu Val Tyr Leu Val Val Cys Val Val Gly Leu Leu Gly Asn Ser Leu
    50                  55                  60

Val Ile Tyr Val Val Leu Arg His Thr Ala Ser Pro Ser Val Thr Asn
65                  70                  75                  80

Val Tyr Ile Leu Asn Leu Ala Leu Ala Asp Glu Leu Phe Met Leu Gly
                85                  90                  95

Leu Pro Phe Leu Ala Ala Gln Asn Ala Leu Ser Tyr Trp Pro Phe Gly
            100                 105                 110

Ser Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
    130                 135                 140

Val Val His Pro Thr Arg Ser Ala Arg Trp Arg Thr Ala Pro Val Ala
145                 150                 155                 160

Arg Thr Val Ser Ala Ala Val Trp Val Ala Ser Ala Val Val Val Leu
                165                 170                 175

Pro Val Val Val Phe Ser Gly Val Pro Arg Gly Met Ser Thr Cys His
            180                 185                 190

Met Gln Trp Pro Glu Pro Ala Ala Ala Trp Arg Ala Gly Phe Ile Ile
        195                 200                 205

Tyr Thr Ala Ala Leu Gly Phe Phe Gly Pro Leu Leu Val Ile Cys Leu
    210                 215                 220

Cys Tyr Leu Leu Ile Val Val Lys Val Arg Ser Ala Gly Arg Arg Val
225                 230                 235                 240

Trp Ala Pro Ser Cys Gln Arg Arg Arg Arg Ser Glu Arg Arg Val Thr
                245                 250                 255

Arg Met Val Val Ala Val Val Ala Leu Phe Val Leu Cys Trp Met Pro
            260                 265                 270

Phe Tyr Val Leu Asn Ile Val Asn Val Val Cys Pro Leu Pro Glu Glu
        275                 280                 285

Pro Ala Phe Phe Gly Leu Tyr Phe Leu Val Val Ala Leu Pro Tyr Ala
```

```
    290                 295                 300

Asn Ser Cys Ala Asn Pro Ile Leu Tyr Gly Phe Leu Ser Tyr Arg Phe
305                 310                 315                 320

Lys Gln Gly Phe Arg Arg Val Leu Leu Arg Pro Ser Arg Arg Val Arg
                325                 330                 335

Ser Gln Glu Pro Thr Val Gly Pro Pro Glu Lys Thr Glu Glu Glu Asp
            340                 345                 350

Glu Glu Glu Glu Asp Gly Glu Glu Ser Arg Glu Gly Gly Lys Gly Lys
        355                 360                 365

Glu Met Asn Gly Arg Val Ser Gln Ile Thr Gln Pro Gly Thr Ser Gly
    370                 375                 380

Gln Glu Arg Pro Pro Ser Arg Val Ala Ser Lys Glu Gln Gln Leu Leu
385                 390                 395                 400

Pro Gln Glu Ala Ser Thr Gly Glu Lys Ser Ser Thr Met Arg Ile Ser
                405                 410                 415

Tyr Leu


<210> SEQ ID NO 144
<211> LENGTH: 1278
<212> TYPE: DNA
<213> ORGANISM: Canis familiaris

<400> SEQUENCE: 144

atggataccc ttggctatcc tgcatcggtg cccacaaccc tggagcccgg gaacacctcc     60

tcggcctggc ccctggatgc cactgtggga aatgtgtcgg cagccccgag tgtggcaggg    120

ctggccgtca gcggtgttct gatccccctg gtctacctgg tggtgtgcgt ggtgggcctg    180

ctgggcaact cactggtcat ctacgtggtc ctgcggcaca cggccagccc gtcggtcacc    240

aacgtctaca tcctcaacct ggcactggcc gacgagctct tcatgctggg gctgcccttc    300

ctggctgccc agaacgccct gtcctactgg ccctttggct ccctcatgtg ccgcctggtc    360

atggccgtgg atggcatcaa ccagttcacc agcatcttct gcctcacggt catgagcgtg    420

gaccgctacc tagcagtggt gcatcccacc cgctcggccc gctggcgcac ggcgcccgtg    480

gcccgcacgg tgagcgtggc tgtgtgggtg gcctcggccg tggtggtgct gcccgtggtg    540

gtcttctcgg gggtgcccca cggcatgagc acctgccaca tgcagtggcc cgagccggcg    600

gcagcctggc gggcgggctt catcatctac acggccgcgc tgggcttctt cgggccgctg    660

ctggtcatct gcctctgcta cctgctcatc gtggtcaagg tgcgctcggc ggggcggcgg    720

gtgcgggcgc cctcgtgcca gcggcggcgg cactcggagc gcaaggtcac gcgcatggtg    780

gtggccgtgg tggcgctctt cgtcctctgc tggatgccct tctacgtgct caacatcgtc    840

aacgtggtgt gcccgctgcc cgaggagccg gccttcttcg gcctctactt cctggtggtg    900

gcactgccct acgccaacag ctgcgccaac cccatcctct acggcttcct ctcctaccgc    960

ttcaagcagg gcttccgccg ggtcctgcta cggccctccc gccgcgtgcg cagccaggag   1020

cccgccggag gacctccaga gaagacggtg gaggagcagg gggaagaccg ggagggggag   1080

gaccgggagg gggaggacgg ggccgggaag cagggggagg ggaaggggat gaacggccgg   1140

gtcagcctca tcacccagcc tggcaccagc gggcaggagc ggccgcccag cgggaaggcc   1200

agcaaggaca agcagcccct acccctagag gcctcggctg cagacaagcc gggcgcgctg   1260

cacatcagct atctgtag                                                 1278


<210> SEQ ID NO 145
```

```
<211> LENGTH: 425
<212> TYPE: PRT
<213> ORGANISM: Canis familiaris

<400> SEQUENCE: 145

Met Asp Thr Leu Gly Tyr Pro Ala Ser Val Pro Thr Thr Leu Glu Pro
1               5                   10                  15

Gly Asn Thr Ser Ser Ala Trp Pro Leu Asp Ala Thr Val Gly Asn Val
            20                  25                  30

Ser Ala Ala Pro Ser Val Ala Gly Leu Ala Val Ser Gly Val Leu Ile
        35                  40                  45

Pro Leu Val Tyr Leu Val Val Cys Val Val Gly Leu Leu Gly Asn Ser
    50                  55                  60

Leu Val Ile Tyr Val Val Leu Arg His Thr Ala Ser Pro Ser Val Thr
65                  70                  75                  80

Asn Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
            100                 105                 110

Gly Ser Leu Met Cys Arg Leu Val Met Ala Val Asp Gly Ile Asn Gln
        115                 120                 125

Phe Thr Ser Ile Phe Cys Leu Thr Val Met Ser Val Asp Arg Tyr Leu
    130                 135                 140

Ala Val Val His Pro Thr Arg Ser Ala Arg Trp Arg Thr Ala Pro Val
145                 150                 155                 160

Ala Arg Thr Val Ser Val Ala Val Trp Val Ala Ser Ala Val Val Val
                165                 170                 175

Leu Pro Val Val Val Phe Ser Gly Val Pro His Gly Met Ser Thr Cys
            180                 185                 190

His Met Gln Trp Pro Glu Pro Ala Ala Ala Trp Arg Ala Gly Phe Ile
        195                 200                 205

Ile Tyr Thr Ala Ala Leu Gly Phe Phe Gly Pro Leu Leu Val Ile Cys
    210                 215                 220

Leu Cys Tyr Leu Leu Ile Val Val Lys Val Arg Ser Ala Gly Arg Arg
225                 230                 235                 240

Val Arg Ala Pro Ser Cys Gln Arg Arg Arg His Ser Glu Arg Lys Val
                245                 250                 255

Thr Arg Met Val Val Ala Val Val Ala Leu Phe Val Leu Cys Trp Met
            260                 265                 270

Pro Phe Tyr Val Leu Asn Ile Val Asn Val Val Cys Pro Leu Pro Glu
        275                 280                 285

Glu Pro Ala Phe Phe Gly Leu Tyr Phe Leu Val Val Ala Leu Pro Tyr
    290                 295                 300

Ala Asn Ser Cys Ala Asn Pro Ile Leu Tyr Gly Phe Leu Ser Tyr Arg
305                 310                 315                 320

Phe Lys Gln Gly Phe Arg Arg Val Leu Leu Arg Pro Ser Arg Arg Val
                325                 330                 335

Arg Ser Gln Glu Pro Ala Gly Gly Pro Pro Glu Lys Thr Val Glu Glu
            340                 345                 350

Gln Gly Glu Asp Arg Glu Gly Glu Asp Arg Glu Gly Glu Asp Gly Ala
        355                 360                 365

Gly Lys Gln Gly Glu Gly Lys Gly Met Asn Gly Arg Val Ser Leu Ile
    370                 375                 380

Thr Gln Pro Gly Thr Ser Gly Gln Glu Arg Pro Pro Ser Gly Lys Ala
```

```
385                 390                 395                 400

Ser Lys Asp Lys Gln Pro Leu Pro Leu Glu Ala Ser Ala Ala Asp Lys
                405                 410                 415

Pro Gly Ala Leu His Ile Ser Tyr Leu
            420                 425


<210> SEQ ID NO 146
<211> LENGTH: 3930
<212> TYPE: DNA
<213> ORGANISM: Mus musculus

<400> SEQUENCE: 146

gaggtgcggg tgacaagtca gggccgagga ccagatggga gaggcgacgt gggctgacgt     60

ggcccccaag gacctaggaa gggtccacgc ccacgaacgc tggacgagtg tgcaccgtgt    120

ggcaccccag ctggctgtgc tctggtggta cctggctgca gaatgctaac cagcctggca    180

actacaaagg gagttcttgc ccagtgggca gagtcttgga gcctctgtgc agcagcatgt    240

cagaactgga ccaaaccaga cgcaagctac catctggcct cccgggcctc gagcatccct    300

tgaagctggc agtggtgcct ctgaagagcc ccctccacct ctgcagcaac cctgtaaggt    360

tagggctggt tggctgctga ctgatcctca tctcagccat ggccactgtt acctatcctt    420

catctgagcc tacgaccttg gaccctggga acgcatcctc gacctggccc ctggatacca    480

ccctggggaa cacatccgct ggcgctagcc tgacaggcct ggctgtcagt ggcatcttga    540

tctctctggt gtacctggtg gtgtgcgtgg tgggtttgct gggcaactcg ctggtgatct    600

acgtggtcct gcggcacacg tccagcccat cagtgaccag tgtctatatc ctcaacctgg    660

ctctggctga tgagctcttc atgctagggc taccctttcct ggctgctcag aacgccctgt    720

cctactggcc cttcggatct ctcatgtgcc gtctggtcat ggccgtggat ggcatcaacc    780

agttcaccag catcttctgc ctcaccgtca tgagtgtgga ccgctatctg gctgtggtgc    840

accccacacg ctcagcccgc tggcgcacgg caccagtggc tcgcacggtc agtgcagctg    900

tctgggtggc ctcagctgtg gtggtgctgc ctgtggttgt gttctcagga gtgccccggg    960

gcatgagcac gtgccacatg cagtggccag agccagcggc tgcctggcga acagccttca   1020

tcatctacac ggccgcactg ggcttctttg ggcccctgct ggtcatctgc ttgtgctact   1080

tgctcattgt ggtaaaggtg cggtcgacca cccggcgggt gcgggcgccc tcgtgtcagt   1140

gggtacaggc acccgcatgc cagcggcgac gccgctctga gcgcagggtc acacgcatgg   1200

tggtggccgt ggtggcactc ttcgtcctct gctggatgcc tttctatctg ctcaacatcg   1260

tcaatgtggt gtgcccgctg ccggaggagc ccgccttctt cggcctctac ttcctggtgg   1320

tggcgctgcc ctacgccaac agctgcgcaa accccatcct ctacggcttc ctctcctacc   1380

gcttcaagca gggctttcgc aggatcctgc taagaccatc acgtcgcatt cggagccagg   1440

agccagggtc gggacctcca gagaagactg aagaggagga ggatgaagaa gaagaagaga   1500

gaagggaaga ggaggagcgg aggatgcaga gagggcagga gatgaacggg aggctcagtc   1560

agatcgcaca ggctggcact agtggacaac agccacggcc ctgcacaggg actgctaagg   1620

agcagcagct tctgccccag gaggccacag ctggggacaa ggccagcaca ctgagccatc   1680

tgtaaggacc ttcaaagaac cagcgtggtt cagaaaagag cagaagctgg gcttgacctc   1740

ggggctcgaa cacccacatg cagtgatctg agcagcagcg agaatgacct tatgtacatg   1800

gctgtcctgg tcctctctgg accgctgtgg taccagggtc cagtgatgga atgtttatag   1860

gcttgaactc tgtgccactg tgccaggact tgctgtgtgt cctttggccg gtcatttacc   1920
```

```
ctttctgggc cttgttttct tcttttgact cagggatggg taaactgagc ctggatgggc   1980

cctgtcagaa gaggggtctg gaatccttac caggatcact ctcctttcag atcagggccc   2040

aagttaagag aatttgggcc atctggccaa gaaacaagat atcttggtga tcagtctgtg   2100

tcttggccct caaggagata taccaggact tgggaaatca gagatgcggg tgagccaggg   2160

gcttacttgg ctgaaaccta aaggaagtgt tagttggcgc tgtgggatgc cacagcttag   2220

gacccaggtg agccctcccc atgctgctgt gtggtctcgg ccaatctgtt catgcccagg   2280

cctcctacct cttctgcagg acagtccagt gtcctacaga ccctcacccc agcctctgag   2340

cactgggcct tctatgctcc tggacatgag gggaagaatt ttccagaagg caaatgaaac   2400

caagtttcag gggttcttac tgcttgggcc cctctggggc ctacagctga ctcgtcttct   2460

aattttgtat tccttctctg gtggtggtga tggggttgag gggactgcac accacacagg   2520

ctcaggccac cggagatctg actcacccta ttaaggctat tcaggtcagc tacctggtcc   2580

ccagggcaga caccatgcag cagcctgagg caagaagagg gagaaagaag gagagggaga   2640

tgaggtagta ggaagagggt gggggatggg agaggaggga ggagagaaca gaacttggtg   2700

gtgatcctga gccaacctcc tgctcccctt aggctaagct cagttgcagt gttgatggct   2760

tcaggcagaa tctgaagaag acacgtggcc aggatcccct ggagggtgca tggggctggt   2820

gagaggggca caggccatga tagagtcctg ggaatgggct tggctcctca agacacttgg   2880

gagggatgat aagccctttg ggtgggtcag acctcccatc ctctgtattc ccaaggctcc   2940

agctgatgtg aagactaaag ggctgttgtc agggagtagc cactgttcca gctggttcag   3000

gacttcatcc tccccttccc agagatggtc cttctgggtc cagcaaggct ggccctggag   3060

aggttggagc ttctgcccaa acccccgccc taccctgcag agaggcaggg ctctcaggga   3120

acccacaaat ccagacattg agaaagctgg atcttctagt cacctcaagc cacttggcca   3180

caccctctgt ctctgcacct cagtatcctc atcataacga gaatggggtt cctcagttcg   3240

ccagtctgct ggaatttggg agggaattga gtcttgctgg ggaagctact gctggccaca   3300

acagggctgc ctcgggatac aaagtggcaa ggatacatag tggcaaggat acaaagtggc   3360

aaggttacaa agtggctagg acacaacata gcaagagtac aaagtagcaa ggttgcaaat   3420

gtggcaagga tacaaagtag caaggttaca aagtagcaag gatgcaaagt agcaaggatg   3480

caaagtggca aggatgcatc atgtcaagga tacaaagtgg caagggtagc aaggatagaa   3540

agtagcaagg atgcaaggtg gcaaggatgc aaagtggcaa ggatacaaag aggaggtgac   3600

cctacctcag gttcagccca taccctgccc cttcagtggg tggtttctgt gtcagctact   3660

ggaggtgaag gtattcatga aaaatggggg ccaagaggtc cgaagccaag ggccagggag   3720

aatgcaaagc accccagaag gaggaagttt gcaaacgtag gcatgtgtgg ggcctgaggc   3780

cagtccaggg cttcctctga gaaggaatgg gatcaggaag tgagcaggcc agccttcctg   3840

gatggggcag gtaagggagg aggatggtca gttgagaaat tcttcgctgc ttctgacctg   3900

agcgcctatc aataaagaca gtgactaagg                                    3930
```

<210> SEQ ID NO 147
<211> LENGTH: 1227
<212> TYPE: DNA
<213> ORGANISM: Mus musculus

<400> SEQUENCE: 147

```
atggccactg ttacctatcc ttcatctgag cctacgacct tggaccctgg gaacgcatcc     60
```

-continued

```
tcgacctggc ccctggatac caccctgggg aacacatccg ctggcgctag cctgacaggc    120

ctggctgtca gtggcatctt gatctctctg gtgtacctgg tggtgtgcgt ggtgggtttg    180

ctgggcaact cgctggtgat ctacgtggtc ctgcggcaca cgtccagccc atcagtgacc    240

agtgtctata tcctcaacct ggctctggct gatgagctct tcatgctagg gctacccttc    300

ctggctgctc agaacgccct gtcctactgg cccttcggat ctctcatgtg ccgtctggtc    360

atggccgtgg atggcatcaa ccagttcacc agcatcttct gcctcaccgt catgagtgtg    420

gaccgctatc tggctgtggt gcaccccaca cgctcagccc gctggcgcac ggcaccagtg    480

gctcgcacgg tcagtgcagc tgtctgggtg gcctcagctg tggtggtgct gcctgtggtt    540

gtgttctcag gagtgccccg gggcatgagc acgtgccaca tgcagtggcc agagccagcg    600

gctgcctggc gaacagcctt catcatctac acggccgcac tgggcttctt tgggcccctg    660

ctggtcatct gcttgtgcta cttgctcatt gtggtaaagg tgcggtcgac cacccggcgg    720

gtgcgggcgc cctcgtgtca gtgggtacag gcacccgcat gccagcggcg acgccgctct    780

gagcgcaggg tcacacgcat ggtggtggcc gtggtggcac tcttcgtcct ctgctggatg    840

cctttctatc tgctcaacat cgtcaatgtg gtgtgcccgc tgccggagga gcccgccttc    900

ttcggcctct acttcctggt ggtggcgctg ccctacgcca acagctgcgc aaaccccatc    960

ctctacggct tcctctccta ccgcttcaag cagggctttc gcaggatcct gctaagacca   1020

tcacgtcgca ttcggagcca ggagccaggg tcgggacctc cagagaagac tgaagaggag   1080

gaggatgaag aagaagaaga gagaagggaa gaggaggagc ggaggatgca gagagggcag   1140

gagatgaacg ggaggctcag tcagatcgca caggctggca ctagtggaca acagccacgg   1200

aaggccagca cactgagcca tctgtaa                                       1227
```

<210> SEQ ID NO 148
<211> LENGTH: 428
<212> TYPE: PRT
<213> ORGANISM: Mus musculus

<400> SEQUENCE: 148

```
Met Ala Thr Val Thr Tyr Pro Ser Ser Glu Pro Thr Thr Leu Asp Pro
1               5                   10                  15

Gly Asn Ala Ser Ser Thr Trp Pro Leu Asp Thr Thr Leu Gly Asn Thr
            20                  25                  30

Ser Ala Gly Ala Ser Leu Thr Gly Leu Ala Val Ser Gly Ile Leu Ile
        35                  40                  45

Ser Leu Val Tyr Leu Val Val Cys Val Val Gly Leu Leu Gly Asn Ser
    50                  55                  60

Leu Val Ile Tyr Val Val Leu Arg His Thr Ser Ser Pro Ser Val Thr
65                  70                  75                  80

Ser Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
            100                 105                 110

Gly Ser Leu Met Cys Arg Leu Val Met Ala Val Asp Gly Ile Asn Gln
        115                 120                 125

Phe Thr Ser Ile Phe Cys Leu Thr Val Met Ser Val Asp Arg Tyr Leu
    130                 135                 140

Ala Val Val His Pro Thr Arg Ser Ala Arg Trp Arg Thr Ala Pro Val
145                 150                 155                 160

Ala Arg Thr Val Ser Ala Ala Val Trp Val Ala Ser Ala Val Val Val
```

```
                165                 170                 175

Leu Pro Val Val Val Phe Ser Gly Val Pro Arg Gly Met Ser Thr Cys
            180                 185                 190

His Met Gln Trp Pro Glu Pro Ala Ala Ala Trp Arg Thr Ala Phe Ile
        195                 200                 205

Ile Tyr Thr Ala Ala Leu Gly Phe Phe Gly Pro Leu Leu Val Ile Cys
    210                 215                 220

Leu Cys Tyr Leu Leu Ile Val Val Lys Val Arg Ser Thr Thr Arg Arg
225                 230                 235                 240

Val Arg Ala Pro Ser Cys Gln Trp Val Gln Ala Pro Ala Cys Gln Arg
                245                 250                 255

Arg Arg Arg Ser Glu Arg Arg Val Thr Arg Met Val Val Ala Val Val
            260                 265                 270

Ala Leu Phe Val Leu Cys Trp Met Pro Phe Tyr Leu Leu Asn Ile Val
        275                 280                 285

Asn Val Val Cys Pro Leu Pro Glu Glu Pro Ala Phe Phe Gly Leu Tyr
    290                 295                 300

Phe Leu Val Val Ala Leu Pro Tyr Ala Asn Ser Cys Ala Asn Pro Ile
305                 310                 315                 320

Leu Tyr Gly Phe Leu Ser Tyr Arg Phe Lys Gln Gly Phe Arg Arg Ile
                325                 330                 335

Leu Leu Arg Pro Ser Arg Arg Ile Arg Ser Gln Glu Pro Gly Ser Gly
            340                 345                 350

Pro Pro Glu Lys Thr Glu Glu Glu Glu Asp Glu Glu Glu Glu Glu Arg
        355                 360                 365

Arg Glu Glu Glu Glu Arg Arg Met Gln Arg Gly Gln Glu Met Asn Gly
    370                 375                 380

Arg Leu Ser Gln Ile Ala Gln Ala Gly Thr Ser Gly Gln Gln Pro Arg
385                 390                 395                 400

Pro Cys Thr Gly Thr Ala Lys Glu Gln Gln Leu Leu Pro Gln Glu Ala
                405                 410                 415

Thr Ala Gly Asp Lys Ala Ser Thr Leu Ser His Leu
            420                 425
```

<210> SEQ ID NO 149
<211> LENGTH: 3985
<212> TYPE: DNA
<213> ORGANISM: Rattus norvegicus

<400> SEQUENCE: 149

```
caggcgtctc tccttactcc ccctcattct gcctttccgc ccacacactg tctcctctcc      60

ctctcctctc tctctctcca cctccgaccc tccccctcct ttccttattt tcctcggcct     120

tcttatgtcc cctgctatct cacatttctg tcatctttgg aagtgccttc tgtcaccccc     180

aactgggtgc catctgaaga cccccatcct gtgtccggca cccgccacgt gtcctggaga     240

tggggggtga cgtatcaggt gcgggtggca agtcaggact gaggaccaga tgggagaggc     300

gacgtgggct gacgtggccc ccgaggacct aggaagggcc caaccaagcc cacaagcact     360

ggaggagtgg gcactgtgtg tcaccccagc tggctgtgct ctggtggtac ctggctgcag     420

aaggttatcc agcctggcga ctgcaaaggg aattcttgcc ctgtgggcag aatcttggaa     480

cctccatgca gcagaatgtc agaactggac caaagagatg caagctaccc atggcttccc     540

aggccttgag cacccccctca tgctggcagt ggtgcatctg aagagtccct tccacctttg     600

cagcaacccc gtaaggtttg ggctagttgg ctgctgactg atcctcatcc ctgccatggc     660
```

```
cgctgttacc tatccttcat ccgtgcctac gaccttggac cctgggaatg catcctcagc    720
ctggcccctg gacacgtccc tggggaatgc atctgctggc actagcctgg caggactggc    780
tgtcagtggc atcttgatct ctctggtgta cctggtggtg tgtgtggtgg gtttgctggg    840
caattcactg gtgatctacg tggttctgcg gcacacgtcc agcccatcag tgaccagtgt    900
ctatatcctc aacctggcac tggctgacga actcttcatg ctggggctac ctttcctggc    960
tgctcagaac gccctgtcct actggccttt cggctctctc atgtgtcgtc tggtcatggc   1020
cgtggatggc atcaaccagt tcaccagcat cttctgcctc accgtcatga gtgtggaccg   1080
ctacctggct gtggtgcacc ccacacgctc tgcccgctgg cgcacggcac ctgtggctcg   1140
aatggtcagt gcagctgtct gggtggcctc agctgtggtc gtgctgcctg tggttgtgtt   1200
ctcaggagtg ccccgaggga tgagcacgtg ccacatgcag tggccagagc cagcggctgc   1260
ctggcgaaca gccttcatca tctatacggc cgcactgggc tttttgggc ccctgctggt   1320
catctgctta tgctacctgc ttattgtggt gaaggtgcgg tcgaccacac ggcgggtgcg   1380
ggcgccctcg tgccagtggg tacaggcacc cgcttgccag cggcggcggc gctctgagcg   1440
cagggtgaca cgcatggtgg tggctgtggt ggcactcttc gtcctctgct ggatgccttt   1500
ctatttactc aacatcgtta atgtggtgtg cccgctgccg gaggagcccg ccttctttgg   1560
cctctacttc ctggtggtcg cgctgcccta cgccaacagc tgcgcaaacc ccatcctcta   1620
cggcttcctc tcctaccgct tcaagcaggg cttccgcagg atcctgctaa gaccttctcg   1680
gcgagtacgg agccaggagc cagggtctgg ccctccagag aagacggagg aggaggagga   1740
tgaagaggaa gaagagagaa gggaagagga agagcggagg atgcagagag ggcaggagat   1800
gaatgggagg ctcagtcaga tcgcacagcc aggccccagt ggacagcagc aacggccttg   1860
cacagggact gccaaggaac agcagcttct accccaggaa gccacagctg gggacaaggc   1920
cagcacgctg agccatctgt aagaaccttc aaagagccag catgatcctg aagagagcag   1980
aagctatgct tgacctaagg cacgagtacc agacacatgg cagtgttcta agcaagcaac   2040
agctagagtg agcttattta catggctgtc ctggccctct ctggaccgtt gtggtactag   2100
ggtccagtga tggaatgtcc ataggcctgg gctctgtccc actgtgccag ggcttgctgt   2160
gtatactttg gccagtcact agccctctct gggtcttgtt ttcttctttt gactcaggga   2220
tgggtaaaat gagccctgtc agaagagggg tctggaatcc ttattgggat taatctccta   2280
atcagagccc aagttaagaa tttgcacagt ctgaccaaga aacaagatat cttggggatc   2340
agtctgtatc ttggccctca aggagataca ccagggcttg ggaaatcaga gatgcagatg   2400
acctgggggt gggtgcttgg ctgaaaccta aaggaagtgt tagttggtgt ggtgggatgc   2460
cacggcttag gacgcaagtg agccctttcc atgctgctct gtggcctcag ccactctgtt   2520
catgtgcagg cctcctacct cttctgcagg gcagtccggg tgtcctacag accctcaccc   2580
cagcgtctga gcattgggcc ttctgtgctc ctggacacca ggggaagaac ttcccagaag   2640
gcaggtgaaa ccaagtttca ggggttcttg ctgcttgggc ccccctggga cctacgtgtg   2700
actggtcttc taattttgta ttccttctct ggagggaaga ttgcacacca ccaggctcag   2760
gccacccgga gactgactca ccctattcag gtcagctacc tagtccccag ggctatgcag   2820
cagcctgagg gaaggagagg gagaaaggag gagagggagc tgaggcagta agaagaggag   2880
ggggatggga tcggagggag aagagaacag aactttgtgg tgatcttgag tcaaccttct   2940
ccccttgag ctaagctcag tttgcagcac tgatggtttc aggaaggatc tgaaggagac   3000
```

```
atgtgaccag gatcccctgg agggtgcgtg gggctggtga gaggggcaca ggtcatgatg   3060
gagtcgtggg aatgggcttg gctcctcagg agggatggta agtcctttgt gtgggtcagt   3120
cctcccatcc tctattccca gggctccagc tgatgtagag actaacaggc tgtcatgggg   3180
agtagccact gtcccagctg ggtcaggact tcattcttcc cctcccagag atggtccttc   3240
tggtcccagc agtgatggcc ctggaaaggt tgaggcttct gctcaaaccc ccaccctacc   3300
ctgcagaggc agggttctca gggaacccac aaatccagat gttgagaaag ctggatcttc   3360
tattcacctc aagcctcttg gccataccct ctgtctctgc gcctcagtat cctcatcata   3420
gtgagaatgt gatcccccag ttctccagtc tgttagaatc caggagggaa ctgagtcatg   3480
ccaggcaagc tactgctcac cacaatgggg ctgcgtaagg atacaaagcg gccgtgttgt   3540
acctcaggct cagcccacac cttgcccttt aagtgagtgg cttcggtgtc agctactgga   3600
ggtgaaggta ttcatgagaa atggagtgca ggaggtcaga agccaaggac catggagaat   3660
gcaagccacc ccagaaggag gaagtttgca aacataggca tgtatggggc ctgaggccca   3720
gcccaggggt tcctctgaga aggagctggg tcaggaagta agcagtccaa ccttcctgga   3780
tggggtaggt gagccacgtc ttgcaaaggg gtgggtgacc agttgagaag ttctttgctg   3840
cttctgacct gagctcctgt caataaagat agtgactaag aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaa                                         3985
```

<210> SEQ ID NO 150
<211> LENGTH: 1287
<212> TYPE: DNA
<213> ORGANISM: Rattus norvegicus

<400> SEQUENCE: 150

```
atggccgctg ttacctatcc ttcatccgtg cctacgacct tggaccctgg gaatgcatcc     60
tcagcctggc ccctggacac gtccctgggg aatgcatctg ctggcactag cctggcagga    120
ctggctgtca gtggcatctt gatctctctg gtgtacctgg tggtgtgtgt ggtgggtttg    180
ctgggcaatt cactggtgat ctacgtggtt ctgcggcaca cgtccagccc atcagtgacc    240
agtgtctata tcctcaacct ggcactggct gacgaactct tcatgctggg gctacctttc    300
ctggctgctc agaacgccct gtcctactgg cctttcggct ctctcatgtg tcgtctggtc    360
atggccgtgg atggcatcaa ccagttcacc agcatcttct gcctcaccgt catgagtgtg    420
gaccgctacc tggctgtggt gcaccccaca cgctctgccc gctggcgcac ggcacctgtg    480
gctcgaatgg tcagtgcagc tgtctgggtg gcctcagctg tggtcgtgct gcctgtggtt    540
gtgttctcag gagtgccccg agggatgagc acgtgccaca tgcagtggcc agagccagcg    600
gctgcctggc gaacagcctt catcatctat acggccgcac tgggcttttt tgggcccctg    660
ctggtcatct gcttatgcta cctgcttatt gtggtgaagg tgcggtcgac cacacggcgg    720
gtgcgggcgc cctcgtgcca gtgggtacag gcacccgctt gccagcggcg gcggcgctct    780
gagcgcaggg tgacacgcat ggtggtggct gtggtggcac tcttcgtcct ctgctggatg    840
cctttctatt tactcaacat cgttaatgtg gtgtgcccgc tgccggagga gcccgccttc    900
tttggcctct acttcctggt ggtcgcgctg ccctacgcca acagctgcgc aaaccccatc    960
ctctacggct tcctctccta ccgcttcaag cagggcttcc gcaggatcct gctaagacct   1020
tctcggcgag tacggagcca ggagccaggg tctggccctc cagagaagac ggaggaggag   1080
gaggatgaag aggaagaaga gagaagggaa gaggaagagc ggaggatgca gagagggcag   1140
```

```
gagatgaatg ggaggctcag tcagatcgca cagccaggcc ccagtggaca gcagcaacgg   1200

ccttgcacag ggactgccaa ggaacagcag cttctacccc aggaagccac agctggggac   1260

aaggccagca cgctgagcca tctgtaa                                       1287


<210> SEQ ID NO 151
<211> LENGTH: 428
<212> TYPE: PRT
<213> ORGANISM: Rattus norvegicus

<400> SEQUENCE: 151

Met Ala Ala Val Thr Tyr Pro Ser Ser Val Pro Thr Thr Leu Asp Pro
1               5                   10                  15

Gly Asn Ala Ser Ser Ala Trp Pro Leu Asp Thr Ser Leu Gly Asn Ala
            20                  25                  30

Ser Ala Gly Thr Ser Leu Ala Gly Leu Ala Val Ser Gly Ile Leu Ile
        35                  40                  45

Ser Leu Val Tyr Leu Val Val Cys Val Val Gly Leu Leu Gly Asn Ser
    50                  55                  60

Leu Val Ile Tyr Val Val Leu Arg His Thr Ser Ser Pro Ser Val Thr
65                  70                  75                  80

Ser Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
            100                 105                 110

Gly Ser Leu Met Cys Arg Leu Val Met Ala Val Asp Gly Ile Asn Gln
        115                 120                 125

Phe Thr Ser Ile Phe Cys Leu Thr Val Met Ser Val Asp Arg Tyr Leu
    130                 135                 140

Ala Val Val His Pro Thr Arg Ser Ala Arg Trp Arg Thr Ala Pro Val
145                 150                 155                 160

Ala Arg Met Val Ser Ala Ala Val Trp Val Ala Ser Ala Val Val Val
                165                 170                 175

Leu Pro Val Val Val Phe Ser Gly Val Pro Arg Gly Met Ser Thr Cys
            180                 185                 190

His Met Gln Trp Pro Glu Pro Ala Ala Ala Trp Arg Thr Ala Phe Ile
        195                 200                 205

Ile Tyr Thr Ala Ala Leu Gly Phe Phe Gly Pro Leu Leu Val Ile Cys
    210                 215                 220

Leu Cys Tyr Leu Leu Ile Val Val Lys Val Arg Ser Thr Thr Arg Arg
225                 230                 235                 240

Val Arg Ala Pro Ser Cys Gln Trp Val Gln Ala Pro Ala Cys Gln Arg
                245                 250                 255

Arg Arg Arg Ser Glu Arg Arg Val Thr Arg Met Val Val Ala Val Val
            260                 265                 270

Ala Leu Phe Val Leu Cys Trp Met Pro Phe Tyr Leu Leu Asn Ile Val
        275                 280                 285

Asn Val Val Cys Pro Leu Pro Glu Glu Pro Ala Phe Phe Gly Leu Tyr
    290                 295                 300

Phe Leu Val Val Ala Leu Pro Tyr Ala Asn Ser Cys Ala Asn Pro Ile
305                 310                 315                 320

Leu Tyr Gly Phe Leu Ser Tyr Arg Phe Lys Gln Gly Phe Arg Arg Ile
                325                 330                 335

Leu Leu Arg Pro Ser Arg Arg Val Arg Ser Gln Glu Pro Gly Ser Gly
```

```
            340                 345                 350

Pro Pro Glu Lys Thr Glu Glu Glu Glu Asp Glu Glu Glu Glu Glu Arg
        355                 360                 365

Arg Glu Glu Glu Glu Arg Arg Met Gln Arg Gly Gln Glu Met Asn Gly
    370                 375                 380

Arg Leu Ser Gln Ile Ala Gln Pro Gly Pro Ser Gly Gln Gln Gln Arg
385                 390                 395                 400

Pro Cys Thr Gly Thr Ala Lys Glu Gln Gln Leu Leu Pro Gln Glu Ala
                405                 410                 415

Thr Ala Gly Asp Lys Ala Ser Thr Leu Ser His Leu
            420                 425


<210> SEQ ID NO 152
<211> LENGTH: 1167
<212> TYPE: DNA
<213> ORGANISM: Homo sapiens

<400> SEQUENCE: 152

atgagcgccc cctcgacgct gcccccgggg ggcgaggaag ggctggggac ggcctggccc      60

tctgcagcca atgccagtag cgctccggcg gaggcggagg aggcggtggc ggggcccggg     120

gacgcgcggg cggcgggcat ggtcgctatc cagtgcatct acgcgctggt gtgcctggtg     180

gggctggtgg gcaacgccct ggtcatcttc gtgatccttc gctacgccaa gatgaagacg     240

gctaccacca tctacctgct caacctggcc gtagccgacg agctcttcat gctgagcgtg     300

cccttcgtgg cctcgtcggc cgccctgcgc cactggccct tcggctccgt gctgtgccgc     360

gcggtgctca gcgtcgacgg cctcaacatg ttcaccagcg tcttctgtct caccgtgctc     420

agcgtggacc gctacgtggc cgtggtgcac cctctgcgcg cggcgaccta ccggcggccc     480

agcgtggcca agctcatcaa cctgggcgtg tggctggcat ccctgttggt cactctcccc     540

atcgccatct tcgcagacac cagaccggct cgcggcggcc aggccgtggc ctgcaacctg     600

cagtggccac acccggcctg gtcggcagtc ttcgtggtct acactttcct gctgggcttc     660

ctgctgcccg tgctggccat tggcctgtgc tacctgctca tcgtgggcaa gatgcgcgcc     720

gtggccctgc gcgctggctg gcagcagcgc aggcgctcgg agaagaaaat caccaggctg     780

gtgctgatgg tcgtggtcgt ctttgtgctc tgctggatgc ctttctacgt ggtgcagctg     840

ctgaacctcg tcgtgaccag ccttgatgcc accgtcaacc acgtgtccct tatcctcagc     900

tatgccaaca gctgcgccaa ccctattctc tatggcttcc tctccgacaa cttccgccga     960

tccttccagc gggttctctg cctgcgctgc tgcctcctgg aaggtgctgg aggtgctgag    1020

gaggagcccc tggactacta tgccactgct ctcaagagca aaggtggggc agggtgcatg    1080

tgcccccccac taaaatgcca gcaggaagcc ctgcaaccag aacccggccg caagcgcatc    1140

cccctcacca ggaccaccac cttctga                                        1167


<210> SEQ ID NO 153
<211> LENGTH: 388
<212> TYPE: PRT
<213> ORGANISM: Homo sapiens

<400> SEQUENCE: 153

Met Ser Ala Pro Ser Thr Leu Pro Pro Gly Gly Glu Glu Gly Leu Gly
1               5                   10                  15

Thr Ala Trp Pro Ser Ala Ala Asn Ala Ser Ser Ala Pro Ala Glu Ala
            20                  25                  30
```

```
Glu Glu Ala Val Ala Gly Pro Gly Asp Ala Arg Ala Ala Gly Met Val
        35                  40                  45

Ala Ile Gln Cys Ile Tyr Ala Leu Val Cys Leu Val Gly Leu Val Gly
    50                  55                  60

Asn Ala Leu Val Ile Phe Val Ile Leu Arg Tyr Ala Lys Met Lys Thr
65                  70                  75                  80

Ala Thr Thr Ile Tyr Leu Leu Asn Leu Ala Val Ala Asp Glu Leu Phe
                85                  90                  95

Met Leu Ser Val Pro Phe Val Ala Ser Ser Ala Ala Leu Arg His Trp
            100                 105                 110

Pro Phe Gly Ser Val Leu Cys Arg Ala Val Leu Ser Val Asp Gly Leu
        115                 120                 125

Asn Met Phe Thr Ser Val Phe Cys Leu Thr Val Leu Ser Val Asp Arg
    130                 135                 140

Tyr Val Ala Val Val His Pro Leu Arg Ala Ala Thr Tyr Arg Arg Pro
145                 150                 155                 160

Ser Val Ala Lys Leu Ile Asn Leu Gly Val Trp Leu Ala Ser Leu Leu
                165                 170                 175

Val Thr Leu Pro Ile Ala Ile Phe Ala Asp Thr Arg Pro Ala Arg Gly
            180                 185                 190

Gly Gln Ala Val Ala Cys Asn Leu Gln Trp Pro His Pro Ala Trp Ser
        195                 200                 205

Ala Val Phe Val Val Tyr Thr Phe Leu Leu Gly Phe Leu Leu Pro Val
    210                 215                 220

Leu Ala Ile Gly Leu Cys Tyr Leu Leu Ile Val Gly Lys Met Arg Ala
225                 230                 235                 240

Val Ala Leu Arg Ala Gly Trp Gln Gln Arg Arg Arg Ser Glu Lys Lys
                245                 250                 255

Ile Thr Arg Leu Val Leu Met Val Val Val Val Phe Val Leu Cys Trp
            260                 265                 270

Met Pro Phe Tyr Val Val Gln Leu Leu Asn Leu Val Val Thr Ser Leu
        275                 280                 285

Asp Ala Thr Val Asn His Val Ser Leu Ile Leu Ser Tyr Ala Asn Ser
    290                 295                 300

Cys Ala Asn Pro Ile Leu Tyr Gly Phe Leu Ser Asp Asn Phe Arg Arg
305                 310                 315                 320

Ser Phe Gln Arg Val Leu Cys Leu Arg Cys Cys Leu Leu Glu Gly Ala
                325                 330                 335

Gly Gly Ala Glu Glu Glu Pro Leu Asp Tyr Tyr Ala Thr Ala Leu Lys
            340                 345                 350

Ser Lys Gly Gly Ala Gly Cys Met Cys Pro Pro Leu Lys Cys Gln Gln
        355                 360                 365

Glu Ala Leu Gln Pro Glu Pro Gly Arg Lys Arg Ile Pro Leu Thr Arg
    370                 375                 380

Thr Thr Thr Phe
385
```

```
<210> SEQ ID NO 154
<211> LENGTH: 1167
<212> TYPE: DNA
<213> ORGANISM: Pan troglodytes

<400> SEQUENCE: 154

atgagcgccc cctcgacgct gccccccggg ggcgaggaag ggctggggac ggcctggccc      60
```

```
tctgcagcca atgccagtag cgctccggcg gaggcggagg aggcggtggc ggggcccggg    120

gacgcgcggg cggcgggcat ggtcgccatc cagtgcatct acgcgctggt gtgcctggtg    180

gggctggtgg gcaacgccct ggtcatcttc gtgatccttc gctacgccaa gatgaagacg    240

gctaccaaca tctacctgct caacctggcc gtagccgatg agctcttcat gctgagcgtg    300

cccttcgtgg cctcgtcggc cgccctgcgc cactggccct tcggctccgt gctgtgccgc    360

gtggtgctca gcgtcgacgg cctcaacatg ttcaccagcg tcttctgtct cacggtgctc    420

agcgtggacc gctacgtggc cgtggtgcac cctctgcgcg cagcgaccta ccggcggccc    480

agcgtggcca agttcatcaa cctgggcgtg tggctggcgt ccctgttggt cactctcccc    540

atcgccatct tcgcagacac tagaccgact cgcggcggcc aggccgtggc ctgcaacctg    600

cagtggccac acccggcctg gtcggcagtc ttcgtggtct acactttcct gctgggcttc    660

ctgctgcccg tgctggccat tggcctgtgc tacctgctca tcgtgggcaa gatgcgcgcc    720

gtggccctgc gtgctggctg gcagcagcgc aggcgctcgg agaagaaaat caccaggctg    780

gtgctgatgg tcgtggccgt ctttgtgctc tgctggatgc ctttctacgt ggtgcagctg    840

ctgaacctct tcgtgaccag ccttgatgcc accgtcaacc acgtgtccct tatcctcagc    900

tatgccaaca gctgcgccaa ccccattctc tatggcttcc tctccgacaa cttccgccga    960

tccttccagc gggttctctg cctgcgctgc tgcctcctgg aaggtgctgg aggtgctgag   1020

gaggagcccc tggactacta tgccactgct ctcaagagca aaggtggggc agggtgcatg   1080

tgcccccccac tcccctgcca gcaggaagcc ctgcaaccag aacccggccg caagcgcatc   1140

cccctcacca ggaccaccac cttctga                                       1167
```

```
<210> SEQ ID NO 155
<211> LENGTH: 388
<212> TYPE: PRT
<213> ORGANISM: Pan troglodytes

<400> SEQUENCE: 155

Met Ser Ala Pro Ser Thr Leu Pro Pro Gly Gly Glu Glu Gly Leu Gly
1               5                   10                  15

Thr Ala Trp Pro Ser Ala Ala Asn Ala Ser Ser Ala Pro Ala Glu Ala
            20                  25                  30

Glu Glu Ala Val Ala Gly Pro Gly Asp Ala Arg Ala Ala Gly Met Val
        35                  40                  45

Ala Ile Gln Cys Ile Tyr Ala Leu Val Cys Leu Val Gly Leu Val Gly
    50                  55                  60

Asn Ala Leu Val Ile Phe Val Ile Leu Arg Tyr Ala Lys Met Lys Thr
65                  70                  75                  80

Ala Thr Asn Ile Tyr Leu Leu Asn Leu Ala Val Ala Asp Glu Leu Phe
                85                  90                  95

Met Leu Ser Val Pro Phe Val Ala Ser Ser Ala Ala Leu Arg His Trp
            100                 105                 110

Pro Phe Gly Ser Val Leu Cys Arg Val Val Leu Ser Val Asp Gly Leu
        115                 120                 125

Asn Met Phe Thr Ser Val Phe Cys Leu Thr Val Leu Ser Val Asp Arg
    130                 135                 140

Tyr Val Ala Val Val His Pro Leu Arg Ala Ala Thr Tyr Arg Arg Pro
145                 150                 155                 160

Ser Val Ala Lys Phe Ile Asn Leu Gly Val Trp Leu Ala Ser Leu Leu
                165                 170                 175
```

```
Val Thr Leu Pro Ile Ala Ile Phe Ala Asp Thr Arg Pro Thr Arg Gly
            180                 185                 190

Gly Gln Ala Val Ala Cys Asn Leu Gln Trp Pro His Pro Ala Trp Ser
        195                 200                 205

Ala Val Phe Val Val Tyr Thr Phe Leu Leu Gly Phe Leu Leu Pro Val
    210                 215                 220

Leu Ala Ile Gly Leu Cys Tyr Leu Leu Ile Val Gly Lys Met Arg Ala
225                 230                 235                 240

Val Ala Leu Arg Ala Gly Trp Gln Gln Arg Arg Arg Ser Glu Lys Lys
                245                 250                 255

Ile Thr Arg Leu Val Leu Met Val Val Ala Val Phe Val Leu Cys Trp
            260                 265                 270

Met Pro Phe Tyr Val Val Gln Leu Leu Asn Leu Phe Val Thr Ser Leu
        275                 280                 285

Asp Ala Thr Val Asn His Val Ser Leu Ile Leu Ser Tyr Ala Asn Ser
    290                 295                 300

Cys Ala Asn Pro Ile Leu Tyr Gly Phe Leu Ser Asp Asn Phe Arg Arg
305                 310                 315                 320

Ser Phe Gln Arg Val Leu Cys Leu Arg Cys Cys Leu Leu Glu Gly Ala
                325                 330                 335

Gly Gly Ala Glu Glu Glu Pro Leu Asp Tyr Tyr Ala Thr Ala Leu Lys
            340                 345                 350

Ser Lys Gly Gly Ala Gly Cys Met Cys Pro Pro Leu Pro Cys Gln Gln
        355                 360                 365

Glu Ala Leu Gln Pro Glu Pro Gly Arg Lys Arg Ile Pro Leu Thr Arg
    370                 375                 380

Thr Thr Thr Phe
385


<210> SEQ ID NO 156
<211> LENGTH: 2432
<212> TYPE: PRT
<213> ORGANISM: Mus musculus

<400> SEQUENCE: 156

Gly Gly Gly Cys Ala Cys Thr Thr Cys Thr Thr Ala Gly Gly Cys Gly
1               5                   10                  15

Gly Ala Gly Cys Gly Gly Cys Thr Gly Ala Gly Cys Cys Gly Ala Gly
            20                  25                  30

Cys Gly Thr Gly Thr Gly Cys Gly Cys Gly Cys Gly Cys Gly Ala Cys
        35                  40                  45

Cys Cys Cys Ala Gly Cys Cys Cys Gly Cys Cys Thr Cys Thr Thr Gly
    50                  55                  60

Gly Thr Cys Cys Thr Thr Gly Gly Cys Thr Cys Ala Gly Cys Gly Cys
65                  70                  75                  80

Thr Cys Cys Gly Cys Thr Gly Cys Thr Cys Thr Cys Cys Ala Cys Cys
                85                  90                  95

Gly Cys Ala Thr Thr Cys Cys Gly Cys Thr Gly Cys Cys Cys Gly Gly
            100                 105                 110

Gly Gly Thr Gly Gly Gly Cys Ala Cys Cys Cys Cys Gly Ala Gly Ala
        115                 120                 125

Cys Ala Thr Gly Ala Ala Cys Gly Cys Gly Cys Cys Ala Gly Cys Ala
    130                 135                 140

Ala Cys Thr Cys Thr Gly Cys Cys Thr Cys Cys Gly Gly Gly Gly Gly
145                 150                 155                 160
```

```
Thr Cys Gly Ala Gly Gly Ala Cys Ala Cys Cys Ala Cys Cys Thr Gly
                165                 170                 175

Gly Ala Cys Cys Cys Cys Thr Gly Gly Gly Ala Thr Cys Ala Ala Cys
            180                 185                 190

Gly Cys Cys Ala Gly Cys Thr Gly Gly Gly Cys Thr Cys Cys Gly Gly
        195                 200                 205

Ala Cys Gly Ala Gly Gly Ala Gly Gly Ala Gly Gly Ala Gly Gly Ala
    210                 215                 220

Thr Gly Cys Gly Ala Thr Gly Gly Gly Gly Thr Cys Cys Gly Ala Cys
225                 230                 235                 240

Gly Gly Cys Ala Cys Ala Gly Gly Gly Ala Cys Ala Gly Cys Gly Gly
                245                 250                 255

Gly Cys Ala Thr Gly Gly Thr Cys Ala Cys Thr Ala Thr Cys Cys Ala
            260                 265                 270

Gly Thr Gly Cys Ala Thr Cys Thr Ala Thr Gly Cys Gly Cys Thr Cys
        275                 280                 285

Gly Thr Gly Thr Gly Thr Cys Thr Gly Gly Thr Gly Gly Gly Cys Cys
    290                 295                 300

Thr Gly Gly Thr Gly Gly Gly Ala Ala Ala Cys Gly Cys Cys Cys Thr
305                 310                 315                 320

Gly Gly Thr Cys Ala Thr Cys Thr Thr Cys Gly Thr Gly Ala Thr Cys
                325                 330                 335

Cys Thr Ala Cys Gly Cys Thr Ala Thr Gly Cys Cys Ala Ala Gly Ala
            340                 345                 350

Thr Gly Ala Ala Gly Ala Cys Ala Gly Cys Cys Ala Cys Cys Ala Ala
        355                 360                 365

Cys Ala Thr Cys Thr Ala Cys Cys Thr Ala Cys Thr Cys Ala Ala Cys
    370                 375                 380

Cys Thr Gly Gly Cys Cys Gly Thr Cys Gly Cys Cys Gly Ala Thr Gly
385                 390                 395                 400

Ala Gly Cys Thr Cys Thr Thr Cys Ala Thr Gly Cys Thr Cys Ala Gly
                405                 410                 415

Cys Gly Thr Gly Cys Cys Ala Thr Thr Cys Gly Thr Gly Gly Cys Cys
            420                 425                 430

Thr Cys Gly Gly Cys Gly Gly Cys Thr Gly Cys Cys Cys Thr Gly Cys
        435                 440                 445

Gly Cys Cys Ala Cys Thr Gly Gly Cys Cys Gly Thr Thr Cys Gly Gly
    450                 455                 460

Gly Gly Cys Gly Gly Thr Gly Cys Thr Gly Thr Gly Thr Cys Gly Cys
465                 470                 475                 480

Gly Cys Ala Gly Thr Gly Cys Thr Thr Ala Gly Cys Gly Thr Gly Gly
                485                 490                 495

Ala Cys Gly Gly Cys Cys Thr Gly Ala Ala Cys Ala Thr Gly Thr Thr
            500                 505                 510

Cys Ala Cys Thr Ala Gly Thr Gly Thr Cys Thr Thr Cys Thr Gly Cys
        515                 520                 525

Cys Thr Cys Ala Cys Cys Gly Thr Gly Cys Thr Cys Ala Gly Cys Gly
    530                 535                 540

Thr Gly Gly Ala Cys Cys Gly Cys Thr Ala Thr Gly Thr Gly Gly Cys
545                 550                 555                 560

Thr Gly Thr Thr Gly Thr Gly Cys Ala Cys Cys Cys Thr Cys Thr Gly
                565                 570                 575
```

```
Cys Gly Cys Gly Cys Cys Gly Cys Cys Ala Cys Cys Thr Ala Cys Cys
            580                 585                 590

Gly Gly Cys Gly Gly Cys Cys Cys Ala Gly Cys Gly Thr Gly Gly Cys
        595                 600                 605

Cys Ala Ala Gly Cys Thr Ala Ala Thr Cys Ala Ala Cys Cys Thr Gly
    610                 615                 620

Gly Gly Ala Gly Thr Gly Thr Gly Gly Cys Thr Ala Gly Cys Ala Thr
625                 630                 635                 640

Cys Cys Thr Thr Gly Cys Thr Gly Gly Thr Cys Ala Cys Cys Cys Thr
                645                 650                 655

Gly Cys Cys Cys Ala Thr Cys Gly Cys Ala Gly Thr Cys Thr Thr Cys
            660                 665                 670

Gly Cys Thr Gly Ala Cys Ala Cys Cys Ala Gly Gly Cys Cys Ala Gly
        675                 680                 685

Cys Thr Cys Gly Thr Gly Gly Gly Gly Cys Gly Ala Gly Gly Cys
    690                 695                 700

Cys Gly Thr Gly Gly Cys Thr Thr Gly Cys Ala Ala Cys Cys Thr Gly
705                 710                 715                 720

Cys Ala Cys Thr Gly Gly Cys Cys Thr Cys Ala Cys Cys Cys Gly Gly
                725                 730                 735

Cys Cys Thr Gly Gly Thr Cys Thr Gly Cys Gly Gly Thr Cys Thr Thr
            740                 745                 750

Thr Gly Thr Gly Ala Thr Cys Thr Ala Thr Ala Cys Thr Thr Thr Thr
        755                 760                 765

Thr Thr Gly Thr Thr Gly Gly Gly Cys Thr Thr Cys Cys Thr Ala Cys
    770                 775                 780

Thr Cys Cys Cys Gly Gly Thr Thr Cys Thr Gly Gly Cys Cys Ala Thr
785                 790                 795                 800

Cys Gly Gly Ala Thr Thr Ala Thr Gly Cys Thr Ala Cys Cys Thr Gly
                805                 810                 815

Cys Thr Thr Ala Thr Thr Gly Thr Gly Gly Gly Cys Ala Ala Gly Ala
            820                 825                 830

Thr Gly Cys Gly Cys Gly Cys Thr Gly Thr Gly Gly Cys Cys Cys Thr
        835                 840                 845

Gly Cys Gly Gly Gly Cys Thr Gly Gly Cys Thr Gly Gly Cys Ala Ala
    850                 855                 860

Cys Ala Ala Cys Gly Gly Ala Gly Gly Cys Gly Cys Thr Cys Ala Gly
865                 870                 875                 880

Ala Gly Ala Ala Gly Ala Ala Gly Ala Thr Cys Ala Cys Thr Ala Gly
                885                 890                 895

Gly Cys Thr Cys Gly Thr Gly Cys Thr Ala Ala Thr Gly Gly Thr Gly
            900                 905                 910

Gly Thr Gly Ala Cys Cys Gly Thr Cys Thr Thr Thr Gly Thr Gly Cys
        915                 920                 925

Thr Ala Thr Gly Cys Thr Gly Gly Ala Thr Gly Cys Cys Thr Thr Thr
    930                 935                 940

Cys Thr Ala Thr Gly Thr Gly Gly Thr Gly Cys Ala Gly Cys Thr Thr
945                 950                 955                 960

Cys Thr Gly Ala Ala Cys Cys Thr Gly Thr Thr Thr Gly Thr Cys Ala
                965                 970                 975

Cys Cys Ala Gly Cys Cys Thr Cys Gly Ala Thr Gly Cys Cys Ala Cys
            980                 985                 990

Thr Gly Thr Cys Ala Ala Cys Cys  Ala Thr Gly Thr Gly  Thr Cys Cys
```

```
        995                 1000                1005

Cys Thr  Cys Ala Thr Cys Cys  Thr Gly Ala Gly Cys  Thr Ala Thr
    1010                 1015                1020

Gly Cys  Cys Ala Ala Cys Ala  Gly Cys Thr Gly Thr  Gly Cys Cys
    1025                 1030                1035

Ala Ala  Thr Cys Cys Cys Ala  Thr Thr Cys Thr Cys  Thr Ala Thr
    1040                 1045                1050

Gly Gly  Cys Thr Thr Cys Cys  Thr Cys Thr Cys Thr  Gly Ala Cys
    1055                 1060                1065

Ala Ala  Cys Thr Thr Cys Cys  Gly Gly Cys Gly Cys  Thr Cys Thr
    1070                 1075                1080

Thr Thr  Cys Cys Ala Gly Cys  Gly Gly Gly Thr Thr  Cys Thr Gly
    1085                 1090                1095

Thr Gly  Cys Cys Thr Gly Cys  Gly Cys Thr Gly Cys  Thr Gly Thr
    1100                 1105                1110

Cys Thr  Cys Cys Thr Gly Gly  Ala Ala Ala Cys Ala  Ala Cys Thr
    1115                 1120                1125

Gly Gly  Ala Gly Gly Thr Gly  Cys Thr Gly Ala Gly  Gly Ala Ala
    1130                 1135                1140

Gly Ala  Gly Cys Cys Cys Cys  Thr Gly Gly Ala Cys  Thr Ala Cys
    1145                 1150                1155

Thr Ala  Thr Gly Cys Cys Ala  Cys Thr Gly Cys Thr  Cys Thr Cys
    1160                 1165                1170

Ala Ala  Ala Ala Gly Cys Ala  Gly Ala Gly Gly Gly  Gly Gly Thr
    1175                 1180                1185

Gly Cys  Ala Gly Gly Ala Thr  Gly Cys Ala Thr Ala  Thr Gly Cys
    1190                 1195                1200

Cys Cys  Thr Cys Cys Thr Cys  Thr Gly Cys Cys Cys  Thr Gly Cys
    1205                 1210                1215

Cys Ala  Gly Cys Ala Gly Gly  Ala Gly Cys Cys Cys  Gly Thr Gly
    1220                 1225                1230

Cys Ala  Ala Gly Cys Ala Gly  Ala Ala Cys Cys Thr  Gly Gly Cys
    1235                 1240                1245

Thr Gly  Cys Ala Ala Gly Cys  Ala Ala Gly Thr Cys  Cys Cys Thr
    1250                 1255                1260

Thr Thr  Cys Ala Cys Cys Ala  Ala Gly Ala Cys Cys  Ala Cys Thr
    1265                 1270                1275

Ala Cys  Thr Thr Thr Cys Thr  Gly Ala Ala Ala Ala  Cys Cys Ala
    1280                 1285                1290

Thr Thr  Thr Thr Ala Cys Cys  Cys Thr Cys Cys Cys  Thr Cys Ala
    1295                 1300                1305

Cys Cys  Thr Cys Gly Cys Cys  Thr Gly Cys Ala Ala  Ala Cys Gly
    1310                 1315                1320

Gly Gly  Thr Cys Thr Gly Cys  Gly Cys Cys Ala Cys  Ala Cys Thr
    1325                 1330                1335

Cys Thr  Cys Ala Ala Gly Cys  Cys Ala Gly Cys Ala  Ala Cys Thr
    1340                 1345                1350

Thr Cys  Ala Ala Gly Ala Ala  Cys Ala Ala Cys Thr  Cys Cys Thr
    1355                 1360                1365

Gly Thr  Thr Thr Thr Cys Ala  Cys Thr Ala Ala Gly  Cys Cys Ala
    1370                 1375                1380

Gly Gly  Cys Cys Cys Thr Thr  Thr Cys Ala Gly Cys  Ala Gly Cys
    1385                 1390                1395
```

```
Cys Thr Gly Thr Gly Thr Gly Cys Thr Gly Thr Cys Cys Cys Cys
    1400                1405                1410

Ala Gly Gly Ala Gly Cys Cys Thr Cys Ala Gly Gly Ala Cys Thr
    1415                1420                1425

Ala Gly Gly Gly Thr Gly Gly Thr Gly Thr Gly Gly Ala Gly Gly
    1430                1435                1440

Cys Thr Cys Cys Thr Cys Thr Gly Thr Gly Thr Gly Cys Thr Ala
    1445                1450                1455

Thr Thr Ala Thr Thr Cys Ala Ala Ala Cys Thr Gly Gly Cys Thr
    1460                1465                1470

Thr Thr Thr Cys Thr Gly Thr Ala Gly Thr Cys Ala Cys Thr Thr
    1475                1480                1485

Cys Gly Thr Gly Cys Ala Gly Gly Cys Ala Gly Thr Gly Cys Cys
    1490                1495                1500

Ala Thr Cys Thr Cys Thr Thr Cys Thr Thr Cys Thr Ala Thr Thr
    1505                1510                1515

Thr Thr Gly Ala Thr Gly Ala Ala Ala Gly Cys Ala Cys Cys Ala
    1520                1525                1530

Cys Thr Thr Gly Cys Ala Cys Ala Thr Gly Ala Thr Ala Ala Ala
    1535                1540                1545

Ala Thr Cys Cys Ala Cys Cys Cys Thr Thr Thr Gly Cys Ala Ala
    1550                1555                1560

Gly Thr Ala Thr Gly Cys Ala Gly Thr Thr Cys Thr Gly Thr Gly
    1565                1570                1575

Ala Thr Gly Cys Ala Gly Thr Thr Ala Cys Ala Ala Thr Cys Cys
    1580                1585                1590

Thr Gly Ala Ala Gly Thr Thr Gly Ala Cys Ala Cys Cys Cys Cys
    1595                1600                1605

Ala Ala Thr Cys Ala Ala Gly Ala Gly Ala Gly Gly Cys Cys Cys
    1610                1615                1620

Cys Ala Thr Thr Thr Cys Thr Ala Thr Cys Cys Thr Cys Ala Thr
    1625                1630                1635

Thr Gly Cys Thr Thr Thr Cys Thr Thr Thr Gly Thr Gly Ala Thr
    1640                1645                1650

Cys Thr Gly Thr Ala Gly Cys Cys Thr Ala Cys Ala Gly Ala Ala
    1655                1660                1665

Gly Gly Gly Gly Gly Cys Cys Ala Cys Ala Gly Gly Gly Ala Ala
    1670                1675                1680

Gly Ala Cys Ala Gly Gly Ala Ala Gly Cys Ala Gly Ala Ala Thr
    1685                1690                1695

Thr Cys Thr Gly Gly Thr Gly Ala Gly Gly Cys Thr Thr Thr Cys
    1700                1705                1710

Cys Cys Thr Ala Ala Ala Thr Cys Thr Thr Thr Ala Gly Gly Gly
    1715                1720                1725

Gly Cys Cys Gly Cys Thr Cys Cys Thr Thr Thr Cys Cys Thr Gly
    1730                1735                1740

Cys Cys Ala Gly Cys Thr Cys Thr Gly Gly Ala Thr Thr Cys Thr
    1745                1750                1755

Thr Cys Cys Cys Ala Cys Thr Gly Thr Cys Ala Gly Gly Gly Gly
    1760                1765                1770

Gly Ala Ala Cys Thr Cys Ala Gly Cys Thr Gly Ala Gly Ala Gly
    1775                1780                1785
```

```
Ala Thr  Gly Cys Ala Gly Ala  Cys Ala Gly Cys Thr  Gly Cys Thr
    1790                 1795                 1800

Cys Cys  Cys Thr Gly Cys Cys  Cys Thr Thr Thr Ala  Gly Thr Cys
    1805                 1810                 1815

Cys Thr  Ala Ala Ala Cys Thr  Thr Gly Gly Ala Ala  Gly Ala Ala
    1820                 1825                 1830

Gly Thr  Gly Cys Thr Cys Thr  Gly Ala Cys Thr Thr  Cys Ala Gly
    1835                 1840                 1845

Ala Ala  Gly Cys Cys Thr Cys  Cys Thr Ala Ala Ala  Cys Ala Ala
    1850                 1855                 1860

Ala Cys  Thr Gly Gly Gly Gly  Cys Thr Thr Thr Ala  Ala Ala Thr
    1865                 1870                 1875

Ala Ala  Gly Thr Thr Cys Cys  Thr Gly Gly Gly Cys  Ala Ala Ala
    1880                 1885                 1890

Gly Thr  Thr Gly Thr Gly Ala  Ala Thr Thr Cys Cys  Cys Thr Ala
    1895                 1900                 1905

Thr Gly  Gly Ala Cys Thr Thr  Gly Gly Thr Ala Ala  Cys Cys Thr
    1910                 1915                 1920

Thr Thr  Thr Gly Ala Ala Thr  Ala Cys Cys Gly Ala  Ala Cys Ala
    1925                 1930                 1935

Thr Ala  Ala Ala Cys Thr Ala  Thr Thr Gly Gly Ala  Gly Gly Ala
    1940                 1945                 1950

Gly Thr  Gly Thr Gly Gly Thr  Thr Thr Cys Cys Thr  Thr Cys Cys
    1955                 1960                 1965

Ala Gly  Gly Thr Cys Gly Gly  Gly Ala Ala Cys Cys  Cys Ala Thr
    1970                 1975                 1980

Gly Cys  Thr Thr Thr Cys Thr  Thr Thr Cys Thr Gly  Gly Ala Ala
    1985                 1990                 1995

Gly Ala  Ala Cys Ala Gly Thr  Ala Ala Gly Gly Ala  Thr Ala Thr
    2000                 2005                 2010

Thr Cys  Cys Thr Cys Thr Ala  Gly Ala Cys Thr Cys  Thr Gly Thr
    2015                 2020                 2025

Cys Thr  Thr Thr Gly Cys Thr  Gly Cys Ala Gly Thr  Cys Thr Gly
    2030                 2035                 2040

Cys Cys  Ala Cys Thr Ala Cys  Cys Thr Gly Cys Thr  Ala Ala Cys
    2045                 2050                 2055

Thr Gly  Cys Thr Gly Gly Cys  Ala Thr Gly Ala Ala  Gly Ala Cys
    2060                 2065                 2070

Ala Ala  Thr Thr Gly Cys Ala  Cys Thr Gly Gly Gly  Thr Thr Thr
    2075                 2080                 2085

Gly Thr  Gly Thr Cys Ala Cys  Thr Cys Thr Gly Thr  Thr Thr Ala
    2090                 2095                 2100

Gly Gly  Thr Thr Thr Ala Thr  Thr Thr Ala Ala Gly  Thr Gly Gly
    2105                 2110                 2115

Cys Thr  Thr Cys Cys Thr Gly  Thr Gly Cys Thr Thr  Thr Gly Gly
    2120                 2125                 2130

Ala Ala  Gly Gly Thr Cys Ala  Gly Gly Ala Ala Ala  Gly Cys Thr
    2135                 2140                 2145

Gly Thr  Ala Thr Cys Thr Cys  Cys Cys Thr Cys Thr  Ala Gly Cys
    2150                 2155                 2160

Cys Cys  Ala Thr Cys Thr Thr  Ala Gly Cys Cys Ala  Ala Cys Thr
    2165                 2170                 2175

Thr Cys  Ala Gly Thr Thr Thr  Cys Thr Cys Cys Thr  Gly Gly Thr
```

```
    2180                2185                2190

Gly Thr  Cys Ala Gly Thr Gly  Cys Thr Gly Ala Ala  Thr Thr Thr
    2195                2200                2205

Cys Thr  Gly Cys Ala Gly Ala  Ala Cys Cys Ala Cys  Cys Thr Thr
    2210                2215                2220

Thr Gly  Gly Gly Gly Gly Gly  Gly Cys Ala Gly Gly  Ala Ala Gly
    2225                2230                2235

Gly Gly  Gly Ala Ala Ala Thr  Ala Cys Thr Gly Ala  Thr Gly Gly
    2240                2245                2250

Cys Ala  Gly Thr Thr Ala Ala  Ala Cys Ala Thr Cys  Thr Ala Cys
    2255                2260                2265

Ala Ala  Ala Gly Ala Ala Thr  Cys Thr Thr Gly Gly  Ala Thr Gly
    2270                2275                2280

Thr Thr  Thr Gly Thr Gly Gly  Thr Gly Thr Ala Thr  Ala Cys Cys
    2285                2290                2295

Thr Cys  Ala Gly Thr Ala Gly  Gly Thr Thr Ala Cys  Cys Cys Thr
    2300                2305                2310

Thr Cys  Cys Ala Gly Cys Thr  Cys Thr Thr Ala Gly  Gly Cys Thr
    2315                2320                2325

Ala Gly  Ala Gly Ala Gly Thr  Gly Ala Ala Gly Gly  Cys Ala Ala
    2330                2335                2340

Ala Ala  Thr Thr Ala Gly Cys  Ala Thr Gly Thr Gly  Ala Ala Ala
    2345                2350                2355

Gly Ala  Ala Ala Cys Thr Gly  Thr Cys Thr Gly Ala  Thr Thr Ala
    2360                2365                2370

Ala Gly  Gly Gly Gly Ala Ala  Gly Thr Ala Ala Cys  Thr Cys Cys
    2375                2380                2385

Thr Cys  Cys Cys Cys Ala Cys  Cys Ala Ala Ala Gly  Cys Thr Gly
    2390                2395                2400

Ala Gly  Gly Thr Thr Gly Thr  Ala Ala Cys Ala Ala  Ala Cys Ala
    2405                2410                2415

Thr Ala  Cys Thr Cys Thr Gly  Thr Gly Thr Ala Ala  Thr Cys
    2420                2425                2430
```

<210> SEQ ID NO 157
<211> LENGTH: 1158
<212> TYPE: DNA
<213> ORGANISM: Mus musculus

<400> SEQUENCE: 157

```
atgaacgcgc cagcaactct gcctccgggg gtcgaggaca ccacctggac ccctgggatc      60

aacgccagct gggctccgga cgaggaggag gaggatgcga tggggtccga cggcacaggg     120

acagcgggca tggtcactat ccagtgcatc tatgcgctcg tgtgtctggt gggcctggtg     180

ggaaacgccc tggtcatctt cgtgatccta cgctatgcca agatgaagac agccaccaac     240

atctacctac tcaacctggc cgtcgccgat gagctcttca tgctcagcgt gccattcgtg     300

gcctcggcgg ctgccctgcg ccactggccg ttcggggcgg tgctgtgtcg cgcagtgctt     360

agcgtggacg gcctgaacat gttcactagt gtcttctgcc tcaccgtgct cagcgtggac     420

cgctatgtgg ctgttgtgca ccctctgcgc gccgccacct accggcggcc cagcgtggcc     480

aagctaatca acctgggagt gtggctagca tccttgctgg tcaccctgcc catcgcagtc     540

ttcgctgaca ccaggccagc tcgtgggggc gaggccgtgg cttgcaacct gcactggcct     600

cacccggcct ggtctgcggt ctttgtgatc tatacttttt tgttgggctt cctactcccg     660
```

gttctggcca tcggattatg ctacctgctt attgtgggca agatgcgcgc tgtggccctg 720
cgggctggct ggcaacaacg gaggcgctca gagaagaaga tcactaggct cgtgctaatg 780
gtggtgaccg tctttgtgct atgctggatg cctttctatg tggtgcagct tctgaacctg 840
tttgtcacca gcctcgatgc cactgtcaac catgtgtccc tcatcctgag ctatgccaac 900
agctgtgcca atcccattct ctatggcttc ctctctgaca acttccggcg ctctttccag 960
cgggttctgt gcctgcgctg ctgtctcctg gaaacaactg gaggtgctga ggaagagccc 1020
ctggactact atgccactgc tctcaaaagc agagggggtg caggatgcat atgccctcct 1080
ctgccctgcc agcaggagcc cgtgcaagca gaacctggct gcaagcaagt ccctttcacc 1140
aagaccacta ctttctga 1158

<210> SEQ ID NO 158
<211> LENGTH: 385
<212> TYPE: PRT
<213> ORGANISM: Mus musculus

<400> SEQUENCE: 158

Met Asn Ala Pro Ala Thr Leu Pro Pro Gly Val Glu Asp Thr Thr Trp
1 5 10 15

Thr Pro Gly Ile Asn Ala Ser Trp Ala Pro Asp Glu Glu Glu Glu Asp
20 25 30

Ala Met Gly Ser Asp Gly Thr Gly Thr Ala Gly Met Val Thr Ile Gln
35 40 45

Cys Ile Tyr Ala Leu Val Cys Leu Val Gly Leu Val Gly Asn Ala Leu
50 55 60

Val Ile Phe Val Ile Leu Arg Tyr Ala Lys Met Lys Thr Ala Thr Asn
65 70 75 80

Ile Tyr Leu Leu Asn Leu Ala Val Ala Asp Glu Leu Phe Met Leu Ser
85 90 95

Val Pro Phe Val Ala Ser Ala Ala Ala Leu Arg His Trp Pro Phe Gly
100 105 110

Ala Val Leu Cys Arg Ala Val Leu Ser Val Asp Gly Leu Asn Met Phe
115 120 125

Thr Ser Val Phe Cys Leu Thr Val Leu Ser Val Asp Arg Tyr Val Ala
130 135 140

Val Val His Pro Leu Arg Ala Ala Thr Tyr Arg Arg Pro Ser Val Ala
145 150 155 160

Lys Leu Ile Asn Leu Gly Val Trp Leu Ala Ser Leu Leu Val Thr Leu
165 170 175

Pro Ile Ala Val Phe Ala Asp Thr Arg Pro Ala Arg Gly Gly Glu Ala
180 185 190

Val Ala Cys Asn Leu His Trp Pro His Pro Ala Trp Ser Ala Val Phe
195 200 205

Val Ile Tyr Thr Phe Leu Leu Gly Phe Leu Leu Pro Val Leu Ala Ile
210 215 220

Gly Leu Cys Tyr Leu Leu Ile Val Gly Lys Met Arg Ala Val Ala Leu
225 230 235 240

Arg Ala Gly Trp Gln Gln Arg Arg Arg Ser Glu Lys Lys Ile Thr Arg
245 250 255

Leu Val Leu Met Val Val Thr Val Phe Val Leu Cys Trp Met Pro Phe
260 265 270

Tyr Val Val Gln Leu Leu Asn Leu Phe Val Thr Ser Leu Asp Ala Thr

```
        275                 280                 285

Val Asn His Val Ser Leu Ile Leu Ser Tyr Ala Asn Ser Cys Ala Asn
    290                 295                 300

Pro Ile Leu Tyr Gly Phe Leu Ser Asp Asn Phe Arg Arg Ser Phe Gln
305                 310                 315                 320

Arg Val Leu Cys Leu Arg Cys Cys Leu Leu Glu Thr Thr Gly Gly Ala
                325                 330                 335

Glu Glu Glu Pro Leu Asp Tyr Tyr Ala Thr Ala Leu Lys Ser Arg Gly
            340                 345                 350

Gly Ala Gly Cys Ile Cys Pro Pro Leu Pro Cys Gln Gln Glu Pro Val
        355                 360                 365

Gln Ala Glu Pro Gly Cys Lys Gln Val Pro Phe Thr Lys Thr Thr Thr
    370                 375                 380

Phe
385


<210> SEQ ID NO 159
<211> LENGTH: 1865
<212> TYPE: DNA
<213> ORGANISM: Rattus norvegicus

<400> SEQUENCE: 159

gttcagcgtt cggctgctct ccacggcaat ccgctgcccc gggtgggcac cccgaagcat     60

gaacacgcct gcaactctgc ccctgggggg cgaggacacc acctggaccc ctgggatcaa    120

cgccagctgg gctccggatg aggaggagga tgcagtgcgg tccgacggca cggggacagc    180

gggcatggta actatccagt gcatctatgc gctcgtgtgt ctggtgggcc tggtaggaaa    240

cgccctggtc atattcgtga tcctacgcta tgccaaaatg aagacagcca ccaacatcta    300

cctgctcaac ctggccgtcg ctgatgagct cttcatgctc agtgtgccat ttgtggcctc    360

ggcggctgcc ctgcgccact ggccgttcgg ggcggtgctg tgccgcgcag tgcttagtgt    420

ggacggcctt aacatgttca cgagtgtctt ctgcctcaca gtgctcagcg tggatcgcta    480

tgtggctgta gtgcaccctc tgcgagctgc cacctaccgg cggcccagcg tggccaagct    540

aatcaacctg ggagtgtggc tagcatcctt gctggtcacc ctgcccatcg cagtcttcgc    600

tgacactagg ccagctcgtg gggggtgaggc agtagcttgc aacctgcact ggcctcaccc    660

ggcctggtct gcagtctttg tgatctatac ttttttgctg ggcttcctac tcccggttct    720

ggctatcgga ttatgttacc tgcttatcgt gggcaagatg cgtgctgtgg ccctgcgggc    780

tggctggcaa caacggaggc gctcagagaa gaagatcact aggctcgtgc taatggtggt    840

gactgtcttt gtgctatgct ggatgccatt ctatgtagtg cagcttctga atctgtttgt    900

caccagcctc gatgccactg tcaaccatgt gtccctcatc ctcagctatg ccaacagctg    960

tgccaacccg attctctatg gtttcctctc agacaacttc cgacgctctt tccagcgggt   1020

tctgtgcctg cgctgctgtc tcctggaaac aactggaggt gctgaggaag agcccctgga   1080

ctactatgct actgctctca aaagcagagg tggcccagga tgcatatgcc ctccattgcc   1140

ctgccagcag gagcccatgc aagcagaacc tgcctgcaag cgagtccctt tcaccaagac   1200

cactactttc tgaaaaccat ttcaccctcc ctcagcccac ctgcaagcag gtctgcacca   1260

cactctcaag ccagcaactt caagaaaact cctgttgtca ctaagccagg ccctttcagc   1320

agcctgtgtt ctgtccctag gagcctcagg actcctgcta gcccctgcct ctcctaggac   1380

tgactggctc caaggacaac tccgtggggg taggacttct ctgggttttg ggctagagta   1440
```

```
ccatccatcc tttcctggac ctctagcaat ttttcaagag gcaggaagca ggtggtggtc   1500

agaaagggat gcctaccctt gtgtgacttg tgacagtgac tgcttggaag agcgctggga   1560

gggtgaggta ggcagagcta ggctctctgc tgtgtggtag catagggcat acggtgatac   1620

aggggagaag atatgatacc tccaagtgtt ttccctctgt gtctgtctga gtctcttgtt   1680

gctaaatgag atgtctacgc aacagctgaa agcatttgct ttcccaaggc aaatgtttct   1740

ccagttgtca aaggaccagt agcagacttc ctgcgaatgc aaatgtttaa agaaggatgg   1800

tgtggggcgt tttttgaaaa aaaaaataat tctgatttct ggtcaggaat taaaaggcag   1860

aaagg                                                               1865
```

<210> SEQ ID NO 160
<211> LENGTH: 1155
<212> TYPE: DNA
<213> ORGANISM: Rattus norvegicus

<400> SEQUENCE: 160

```
atgaacacgc ctgcaactct gcccctgggg ggcgaggaca ccacctggac ccctgggatc     60

aacgccagct gggctccgga tgaggaggag gatgcagtgc ggtccgacgg cacggggaca    120

gcgggcatgg taactatcca gtgcatctat gcgctcgtgt gtctggtggg cctggtagga    180

aacgccctgg tcatattcgt gatcctacgc tatgccaaaa tgaagacagc caccaacatc    240

tacctgctca acctggccgt cgctgatgag ctcttcatgc tcagtgtgcc atttgtggcc    300

tcggcggctg ccctgcgcca ctggccgttc ggggcggtgc tgtgccgcgc agtgcttagt    360

gtggacggcc ttaacatgtt cacgagtgtc ttctgcctca cagtgctcag cgtggatcgc    420

tatgtggctg tagtgcaccc tctgcgagct gccacctacc ggcggcccag cgtggccaag    480

ctaatcaacc tgggagtgtg gctagcatcc ttgctggtca ccctgcccat cgcagtcttc    540

gctgacacta ggccagctcg tgggggtgag gcagtagctt gcaacctgca ctggcctcac    600

ccggcctggt ctgcagtctt tgtgatctat actttttgc tgggcttcct actcccggtt    660

ctggctatcg gattatgtta cctgcttatc gtgggcaaga tgcgtgctgt ggccctgcgg    720

gctggctggc aacaacggag gcgctcagag aagaagatca ctaggctcgt gctaatggtg    780

gtgactgtct ttgtgctatg ctggatgcca ttctatgtag tgcagcttct gaatctgttt    840

gtcaccagcc tcgatgccac tgtcaaccat gtgtccctca tcctcagcta tgccaacagc    900

tgtgccaacc cgattctcta tggtttcctc tcagacaact tccgacgctc tttccagcgg    960

gttctgtgcc tgcgctgctg tctcctggaa acaactggag gtgctgagga agagcccctg   1020

gactactatg ctactgctct caaaagcaga ggtggcccag gatgcatatg ccctccattg   1080

ccctgccagc aggagcccat gcaagcagaa cctgcctgca agcgagtccc tttcaccaag   1140

accactactt tctga                                                    1155
```

<210> SEQ ID NO 161
<211> LENGTH: 384
<212> TYPE: PRT
<213> ORGANISM: Rattus norvegicus

<400> SEQUENCE: 161

```
Met Asn Thr Pro Ala Thr Leu Pro Leu Gly Gly Glu Asp Thr Thr Trp
1               5                   10                  15

Thr Pro Gly Ile Asn Ala Ser Trp Ala Pro Asp Glu Glu Glu Asp Ala
            20                  25                  30

Val Arg Ser Asp Gly Thr Gly Thr Ala Gly Met Val Thr Ile Gln Cys
```

```
        35                  40                  45

Ile Tyr Ala Leu Val Cys Leu Val Gly Leu Val Gly Asn Ala Leu Val
    50                  55                  60

Ile Phe Val Ile Leu Arg Tyr Ala Lys Met Lys Thr Ala Thr Asn Ile
65                  70                  75                  80

Tyr Leu Leu Asn Leu Ala Val Ala Asp Glu Leu Phe Met Leu Ser Val
                85                  90                  95

Pro Phe Val Ala Ser Ala Ala Ala Leu Arg His Trp Pro Phe Gly Ala
            100                 105                 110

Val Leu Cys Arg Ala Val Leu Ser Val Asp Gly Leu Asn Met Phe Thr
        115                 120                 125

Ser Val Phe Cys Leu Thr Val Leu Ser Val Asp Arg Tyr Val Ala Val
    130                 135                 140

Val His Pro Leu Arg Ala Ala Thr Tyr Arg Arg Pro Ser Val Ala Lys
145                 150                 155                 160

Leu Ile Asn Leu Gly Val Trp Leu Ala Ser Leu Leu Val Thr Leu Pro
                165                 170                 175

Ile Ala Val Phe Ala Asp Thr Arg Pro Ala Arg Gly Gly Glu Ala Val
            180                 185                 190

Ala Cys Asn Leu His Trp Pro His Pro Ala Trp Ser Ala Val Phe Val
        195                 200                 205

Ile Tyr Thr Phe Leu Leu Gly Phe Leu Leu Pro Val Leu Ala Ile Gly
    210                 215                 220

Leu Cys Tyr Leu Leu Ile Val Gly Lys Met Arg Ala Val Ala Leu Arg
225                 230                 235                 240

Ala Gly Trp Gln Gln Arg Arg Arg Ser Glu Lys Lys Ile Thr Arg Leu
                245                 250                 255

Val Leu Met Val Val Thr Val Phe Val Leu Cys Trp Met Pro Phe Tyr
            260                 265                 270

Val Val Gln Leu Leu Asn Leu Phe Val Thr Ser Leu Asp Ala Thr Val
        275                 280                 285

Asn His Val Ser Leu Ile Leu Ser Tyr Ala Asn Ser Cys Ala Asn Pro
    290                 295                 300

Ile Leu Tyr Gly Phe Leu Ser Asp Asn Phe Arg Arg Ser Phe Gln Arg
305                 310                 315                 320

Val Leu Cys Leu Arg Cys Cys Leu Leu Glu Thr Thr Gly Gly Ala Glu
                325                 330                 335

Glu Glu Pro Leu Asp Tyr Tyr Ala Thr Ala Leu Lys Ser Arg Gly Gly
            340                 345                 350

Pro Gly Cys Ile Cys Pro Pro Leu Pro Cys Gln Gln Glu Pro Met Gln
        355                 360                 365

Ala Glu Pro Ala Cys Lys Arg Val Pro Phe Thr Lys Thr Thr Thr Phe
    370                 375                 380
```

```
<210> SEQ ID NO 162
<211> LENGTH: 1245
<212> TYPE: DNA
<213> ORGANISM: Homo sapiens

<400> SEQUENCE: 162

cgtcctccct tcttctcttg cagagcctga cgcaccccag ggctgccgcc atggagcccc      60

tgttcccagc ctccacgccc agctggaacg cctcctcccc gggggctgcc tctggaggcg     120

gtgacaacag gacgctggtg gggccggcgc cctcggcagg ggcccgggcg gtgctggtgc     180
```

-continued

```
ccgtgctgta cctgctggtg tgtgcggccg ggctgggcgg gaacacgctg gtcatctacg    240
tggtgctgcg cttcgccaag atgaagaccg tcaccaacat ctacattctc aacctggcag    300
tggccgacgt cctgtacatg ctggggctgc ctttcctggc cacgcagaac gccgcgtcct    360
tctggccctt cggccccgtc ctgtgccgcc tggtcatgac gctggacggc gtcaaccagt    420
tcaccagtgt cttctgcctg acagtcatga gcgtggaccg ctacctggca gtggtgcacc    480
cgctgagctc ggcccgctgg cgccgcccgc gtgtggccaa gctggcgagc gccgcggcct    540
gggtcctgtc tctgtgcatg tcgctgccgc tcctggtgtt cgcggacgtg caggagggcg    600
gtacctgcaa cgccagctgg ccggagcccg tggggctgtg ggcgccgtc ttcatcatct    660
acacggccgt gctgggcttc ttcgcgccgc tgctggtcat ctgcctgtgc tacctgctca    720
tcgtggtgaa ggtgagggcg gcgggcgtgc gcgtgggctg cgtgcggcgg cgctcggagc    780
ggaaggtgac gcgcatggtg ttggtggtgg tgctggtgtt tgcgggatgt tggctgccct    840
tcttcaccgt caacatcgtc aacctggccg tggcgctgcc ccaggagccc gcctccgccg    900
gcctctactt cttcgtggtc atcctctcct acgccaacag ctgtgccaac cccgtcctct    960
acggcttcct ctctgacaac ttccgccaga gcttccagaa ggttctgtgc ctccgcaagg   1020
gctctggtgc caaggacgct gacgccacgg agccgcgtcc agacaggatc cggcagcagc   1080
aggaggccac gccgcccgcg caccgcgccg cagccaacgg gcttatgcag accagcaagc   1140
tgtgagagtg caggcggggg gtgggcggcc ccgtgtcacc cccaggagcg gaggttgcac   1200
tgcggtgacc cccacccatg acctgccagt caggatgctc cccgg                   1245
```

```
<210> SEQ ID NO 163
<211> LENGTH: 1095
<212> TYPE: DNA
<213> ORGANISM: Homo sapiens

<400> SEQUENCE: 163

atggagcccc tgttcccagc ctccacgccc agctggaacg cctcctcccc gggggctgcc     60
tctggaggcg gtgacaacag gacgctggtg ggccggcgc cctcggcagg ggcccgggcg    120
gtgctggtgc ccgtgctgta cctgctggtg tgtgcggccg ggctgggcgg gaacacgctg    180
gtcatctacg tggtgctgcg cttcgccaag atgaagaccg tcaccaacat ctacattctc    240
aacctggcag tggccgacgt cctgtacatg ctggggctgc ctttcctggc cacgcagaac    300
gccgcgtcct tctggccctt cggccccgtc ctgtgccgcc tggtcatgac gctggacggc    360
gtcaaccagt tcaccagtgt cttctgcctg acagtcatga gcgtggaccg ctacctggca    420
gtggtgcacc cgctgagctc ggcccgctgg cgccgcccgc gtgtggccaa gctggcgagc    480
gccgcggcct gggtcctgtc tctgtgcatg tcgctgccgc tcctggtgtt cgcggacgtg    540
caggagggcg gtacctgcaa cgccagctgg ccggagcccg tggggctgtg ggcgccgtc    600
ttcatcatct acacggccgt gctgggcttc ttcgcgccgc tgctggtcat ctgcctgtgc    660
tacctgctca tcgtggtgaa ggtgagggcg gcgggcgtgc gcgtgggctg cgtgcggcgg    720
cgctcggagc ggaaggtgac gcgcatggtg ttggtggtgg tgctggtgtt tgcgggatgt    780
tggctgccct tcttcaccgt caacatcgtc aacctggccg tggcgctgcc ccaggagccc    840
gcctccgccg gcctctactt cttcgtggtc atcctctcct acgccaacag ctgtgccaac    900
cccgtcctct acggcttcct ctctgacaac ttccgccaga gcttccagaa ggttctgtgc    960
ctccgcaagg gctctggtgc caaggacgct gacgccacgg agccgcgtcc agacaggatc   1020
cggcagcagc aggaggccac gccgcccgcg caccgcgccg cagccaacgg gcttatgcag   1080
```

```
accagcaagc tgtga                                                    1095


<210> SEQ ID NO 164
<211> LENGTH: 364
<212> TYPE: PRT
<213> ORGANISM: Homo sapiens

<400> SEQUENCE: 164

Met Glu Pro Leu Phe Pro Ala Ser Thr Pro Ser Trp Asn Ala Ser Ser
1               5                   10                  15

Pro Gly Ala Ala Ser Gly Gly Gly Asp Asn Arg Thr Leu Val Gly Pro
            20                  25                  30

Ala Pro Ser Ala Gly Ala Arg Ala Val Leu Val Pro Val Leu Tyr Leu
        35                  40                  45

Leu Val Cys Ala Ala Gly Leu Gly Gly Asn Thr Leu Val Ile Tyr Val
    50                  55                  60

Val Leu Arg Phe Ala Lys Met Lys Thr Val Thr Asn Ile Tyr Ile Leu
65                  70                  75                  80

Asn Leu Ala Val Ala Asp Val Leu Tyr Met Leu Gly Leu Pro Phe Leu
                85                  90                  95

Ala Thr Gln Asn Ala Ala Ser Phe Trp Pro Phe Gly Pro Val Leu Cys
            100                 105                 110

Arg Leu Val Met Thr Leu Asp Gly Val Asn Gln Phe Thr Ser Val Phe
        115                 120                 125

Cys Leu Thr Val Met Ser Val Asp Arg Tyr Leu Ala Val Val His Pro
    130                 135                 140

Leu Ser Ser Ala Arg Trp Arg Arg Pro Arg Val Ala Lys Leu Ala Ser
145                 150                 155                 160

Ala Ala Ala Trp Val Leu Ser Leu Cys Met Ser Leu Pro Leu Leu Val
                165                 170                 175

Phe Ala Asp Val Gln Glu Gly Gly Thr Cys Asn Ala Ser Trp Pro Glu
            180                 185                 190

Pro Val Gly Leu Trp Gly Ala Val Phe Ile Ile Tyr Thr Ala Val Leu
        195                 200                 205

Gly Phe Phe Ala Pro Leu Leu Val Ile Cys Leu Cys Tyr Leu Leu Ile
    210                 215                 220

Val Val Lys Val Arg Ala Ala Gly Val Arg Val Gly Cys Val Arg Arg
225                 230                 235                 240

Arg Ser Glu Arg Lys Val Thr Arg Met Val Leu Val Val Val Leu Val
                245                 250                 255

Phe Ala Gly Cys Trp Leu Pro Phe Phe Thr Val Asn Ile Val Asn Leu
            260                 265                 270

Ala Val Ala Leu Pro Gln Glu Pro Ala Ser Ala Gly Leu Tyr Phe Phe
        275                 280                 285

Val Val Ile Leu Ser Tyr Ala Asn Ser Cys Ala Asn Pro Val Leu Tyr
    290                 295                 300

Gly Phe Leu Ser Asp Asn Phe Arg Gln Ser Phe Gln Lys Val Leu Cys
305                 310                 315                 320

Leu Arg Lys Gly Ser Gly Ala Lys Asp Ala Asp Ala Thr Glu Pro Arg
                325                 330                 335

Pro Asp Arg Ile Arg Gln Gln Gln Glu Ala Thr Pro Pro Ala His Arg
            340                 345                 350

Ala Ala Ala Asn Gly Leu Met Gln Thr Ser Lys Leu
        355                 360
```

<210> SEQ ID NO 165
<211> LENGTH: 2181
<212> TYPE: DNA
<213> ORGANISM: Pan troglodytes

<400> SEQUENCE: 165
atgtcagggc accctgtgct cttggggacg ctctgcgtta gctccctgag gatctcagac 60
accaggacac cctcccagcc cagtcccagc gacacatgcc ggcagcgcct gcgccagtgt 120
ttcttctcct gtcgggaggc tggtgacccg ctgtgctgcc ccggtggggg gctgatctct 180
gacctcctgt ctggcaggct gtgctacacc agccagggcc gggaggtgca cgtggacccg 240
tgtttattgg aatcctgctg tgatcagacc cgggggcgac gtcgagaccc accaggcccc 300
gtggcctcct gtgaacatct gcaggctgtt gggggcagcg gtcgaccgaa caagtgtggg 360
gtggcccggg cttcccggag gaagtgttgc ttgagctgcc aggggagtta cctgcagaaa 420
gggaggagcg gagggagagc cctgttggct gcagggcaga gtgccccaca ctcctcctgg 480
ccgccacccc cagggcccag cccagtccgg ggactaagac gagaggcctc tggggtgttc 540
cagactctcg acgagggacc ccctggactc ctgctggcgg caggaccccc acccccagct 600
ggggtctacc acagagcgga cagcaagaaa ataggaccca cccacgtgcc cgacccgctg 660
tccccagcct gccagcctgc ctggggcccc ctcaagggcg agagagcgga gtgcatggtg 720
acagaagttg ggatggttc cagcgaggct gagccctttc tgaagggagt gattctggcc 780
tatatttcag tggccttggc ccagccccac agcccccagc caggactgtg gcctttcctg 840
gcagctgctg gggtggtcct gtgctctgag gtgcctccgg ggtcagggcc gatgtctgtc 900
attgctgtgg gggtgacggt ccctgcgctg gcctggagag aggttcgggg ccgacgggca 960
gcgggcaccc cggcggggct ggggcccagg aggaaggaat gcctgcatgt gccggttcag 1020
ggactcacca ccctggcatc ctcccttctt ctcttgcaga gcccgacgca ccccggggct 1080
gccgccatgg agcccctgtt cccagcctcc acgcccagct ggaacgcctc ctccccgggg 1140
gctgcctctg gaggcggtga caacaggacg ctggtggggc cggcgccctc ggcgggggcc 1200
tgggcggtgc tggtgcccgt gctgtacctg ctggtgtgtg cggccgggct gggcgggaac 1260
acgctggtca tctacgtggt gctgcgcttc gccaagatga agaccgtcac caacatctac 1320
attctcaacc tggcagtggc cgacgtcctg tacatgctgg ggctgccttt cctggccacg 1380
cagaacgccg cgtccttctg gcccttcggc cccgtcctgt gccgcctggt catgacgctg 1440
gacggcgtca accagttcac cagtgtcttc tgcctgacag tcatgagcgt ggaccgctac 1500
ctggcggtgg tgcacccgct gagctccgcc cgctggcgcc gcccgcgtgt ggccaagctg 1560
gcgagcgccg cagcctgggt cctgtctctg tgcatgtcgc tgccgctcct ggtgttcgcg 1620
gacgtgcagg agggcggtac ctgcaacgcc agctggccgg agcccgtggg gctgtggggc 1680
gccgtcttca tcatctacac ggccgtgctg ggcttcttcg caccgctgct ggtcatctgc 1740
ctgtgctacc tgctcattgt ggtgaaggtg agggcggcgg gcgtgcgcgt gggctgcgtg 1800
cggcggcgct cggagcggaa ggtgacgcgc atggtgttgg tggtggtgct ggtgtttgcg 1860
ggatgttggc tgcccttctt caccgtcaac atcgtcaacc tggccgtggc gctgccccag 1920
gagcccgcct ccgccggcct ctacttcttc gtggtcatcc tctcctacgc caacagctgc 1980
gccaaccccg tcctctacgg cttcctctct gacaacttcc gccagagctt ccagaaggtt 2040
ctgtgcctcc gcaagggctc tggtgccaag gacgctgatg ccacggagcc gcgaccagac 2100

```
aggagccggc agcagcagga ggccacgccg cccgcgcacc gcgccgaagc caacgggctt   2160

atgcagacca gcaagctgtg a                                             2181


<210> SEQ ID NO 166
<211> LENGTH: 726
<212> TYPE: PRT
<213> ORGANISM: Pan troglodytes

<400> SEQUENCE: 166

Met Ser Gly His Pro Val Leu Leu Gly Thr Leu Cys Val Ser Ser Leu
1               5                   10                  15

Arg Ile Ser Asp Thr Arg Thr Pro Ser Gln Pro Ser Pro Ser Asp Thr
            20                  25                  30

Cys Arg Gln Arg Leu Arg Gln Cys Phe Phe Ser Cys Arg Glu Ala Gly
        35                  40                  45

Asp Pro Leu Cys Cys Pro Gly Gly Gly Leu Ile Ser Asp Leu Leu Ser
    50                  55                  60

Gly Arg Leu Cys Tyr Thr Ser Gln Gly Arg Glu Val His Val Asp Pro
65                  70                  75                  80

Cys Leu Leu Glu Ser Cys Cys Asp Gln Thr Arg Gly Arg Arg Arg Asp
                85                  90                  95

Pro Pro Gly Pro Val Ala Ser Cys Glu His Leu Gln Ala Val Gly Gly
            100                 105                 110

Ser Gly Arg Pro Asn Lys Cys Gly Val Ala Arg Ala Ser Arg Arg Lys
        115                 120                 125

Cys Cys Leu Ser Cys Gln Gly Ser Tyr Leu Gln Lys Gly Arg Ser Gly
    130                 135                 140

Gly Arg Ala Leu Leu Ala Ala Gly Gln Ser Ala Pro His Ser Ser Trp
145                 150                 155                 160

Pro Pro Pro Pro Gly Pro Ser Pro Val Arg Gly Leu Arg Arg Glu Ala
                165                 170                 175

Ser Gly Val Phe Gln Thr Leu Asp Glu Gly Pro Pro Gly Leu Leu Leu
            180                 185                 190

Ala Ala Gly Pro Pro Pro Pro Ala Gly Val Tyr His Arg Ala Asp Ser
        195                 200                 205

Lys Lys Ile Gly Pro Thr His Val Pro Asp Pro Leu Ser Pro Ala Cys
    210                 215                 220

Gln Pro Ala Trp Gly Pro Leu Lys Gly Glu Arg Ala Glu Cys Met Val
225                 230                 235                 240

Thr Glu Val Gly Asp Gly Ser Ser Glu Ala Glu Pro Phe Leu Lys Gly
                245                 250                 255

Val Ile Leu Ala Tyr Ile Ser Val Ala Leu Ala Gln Pro His Ser Pro
            260                 265                 270

Gln Pro Gly Leu Trp Pro Phe Leu Ala Ala Ala Gly Val Val Leu Cys
        275                 280                 285

Ser Glu Val Pro Pro Gly Ser Gly Pro Met Ser Val Ile Ala Val Gly
    290                 295                 300

Val Thr Val Pro Ala Leu Ala Trp Arg Glu Val Arg Gly Arg Arg Ala
305                 310                 315                 320

Ala Gly Thr Pro Ala Gly Leu Gly Pro Arg Arg Lys Glu Cys Leu His
                325                 330                 335

Val Pro Val Gln Gly Leu Thr Thr Leu Ala Ser Ser Leu Leu Leu Leu
            340                 345                 350

Gln Ser Pro Thr His Pro Gly Ala Ala Ala Met Glu Pro Leu Phe Pro
```

```
        355                 360                 365

Ala Ser Thr Pro Ser Trp Asn Ala Ser Ser Pro Gly Ala Ala Ser Gly
    370                 375                 380

Gly Gly Asp Asn Arg Thr Leu Val Gly Pro Ala Pro Ser Ala Gly Ala
385                 390                 395                 400

Trp Ala Val Leu Val Pro Val Leu Tyr Leu Leu Val Cys Ala Ala Gly
                405                 410                 415

Leu Gly Gly Asn Thr Leu Val Ile Tyr Val Val Leu Arg Phe Ala Lys
            420                 425                 430

Met Lys Thr Val Thr Asn Ile Tyr Ile Leu Asn Leu Ala Val Ala Asp
        435                 440                 445

Val Leu Tyr Met Leu Gly Leu Pro Phe Leu Ala Thr Gln Asn Ala Ala
    450                 455                 460

Ser Phe Trp Pro Phe Gly Pro Val Leu Cys Arg Leu Val Met Thr Leu
465                 470                 475                 480

Asp Gly Val Asn Gln Phe Thr Ser Val Phe Cys Leu Thr Val Met Ser
                485                 490                 495

Val Asp Arg Tyr Leu Ala Val Val His Pro Leu Ser Ser Ala Arg Trp
            500                 505                 510

Arg Arg Pro Arg Val Ala Lys Leu Ala Ser Ala Ala Ala Trp Val Leu
        515                 520                 525

Ser Leu Cys Met Ser Leu Pro Leu Leu Val Phe Ala Asp Val Gln Glu
    530                 535                 540

Gly Gly Thr Cys Asn Ala Ser Trp Pro Glu Pro Val Gly Leu Trp Gly
545                 550                 555                 560

Ala Val Phe Ile Ile Tyr Thr Ala Val Leu Gly Phe Phe Ala Pro Leu
                565                 570                 575

Leu Val Ile Cys Leu Cys Tyr Leu Leu Ile Val Val Lys Val Arg Ala
            580                 585                 590

Ala Gly Val Arg Val Gly Cys Val Arg Arg Arg Ser Glu Arg Lys Val
        595                 600                 605

Thr Arg Met Val Leu Val Val Val Leu Val Phe Ala Gly Cys Trp Leu
    610                 615                 620

Pro Phe Phe Thr Val Asn Ile Val Asn Leu Ala Val Ala Leu Pro Gln
625                 630                 635                 640

Glu Pro Ala Ser Ala Gly Leu Tyr Phe Phe Val Val Ile Leu Ser Tyr
                645                 650                 655

Ala Asn Ser Cys Ala Asn Pro Val Leu Tyr Gly Phe Leu Ser Asp Asn
            660                 665                 670

Phe Arg Gln Ser Phe Gln Lys Val Leu Cys Leu Arg Lys Gly Ser Gly
        675                 680                 685

Ala Lys Asp Ala Asp Ala Thr Glu Pro Arg Pro Asp Arg Ser Arg Gln
    690                 695                 700

Gln Gln Glu Ala Thr Pro Pro Ala His Arg Ala Glu Ala Asn Gly Leu
705                 710                 715                 720

Met Gln Thr Ser Lys Leu
                725


<210> SEQ ID NO 167
<211> LENGTH: 2699
<212> TYPE: DNA
<213> ORGANISM: Mus musculus

<400> SEQUENCE: 167
```

```
gctagcctga gggcgggcgc cgacttcgta cagcaatcca gtgagcgctc tgctctttga     60
gctcgagggc gctgcctgac cgctaagtac cgccgcctcg tccgccccgg cgtgggcatc    120
ctgtcctgca caggagaggt ctccacggct gtccacggga catgtgagga taacttttaa    180
agtgccataa agatacttcc tgagaccagc ccctgtgagc caacctctgt gagcagttcc    240
acctactgag ctccaaggag gctcctctaa cattgtcttt ttaagagata catgtgctct    300
ggcatcctga acctgacagc atggagcccc tctctttgac ttccacacct agctggaatg    360
cctcagctgc ttccagcagt agccataact ggtcactagt ggacccggtg tcacccatgg    420
gagcccgggc ggtattagtg cctgtgctct acttgttggt atgcaccgtg ggactgggtg    480
gaaacacact ggtcatctat gtggtgttgc ggtacgccaa gatgaagaca gttactaacg    540
tgtatatcct gaacctggcc gtggctgacg tgttgtttat gttggggctt cctttcctgg    600
caacgcagaa tgctgtctcc tactggccct ttggctcctt cttgtgccgc ctggtcatga    660
cgctggacgg catcaaccag ttcaccagta tcttctgcct gatggtcatg agtgtcgacc    720
gctacctggc cgtggtccac cctctccgct cagcccggtg gcgtcgccca cgggtagcca    780
agctggctag tgctgccgtc tgggtcttct cgctgctcat gtctctgccg ctcttggtct    840
ttgcggatgt ccaggagggc tggggcacct gcaacctgag ctggccagag cctgtgggac    900
tgtggggtgc agccttcatc acttacacgt ctgtgctggg cttctttggg cccctgctgg    960
tcatctgctt gtgctatttg ctcatcgtag tgaaggtgaa ggctgcaggt atgcgtgtgg   1020
gctcctcacg gcggaggcgc tcagaacgca aggtgactcg catggtggtg gtagtggtgc   1080
tggtgttcgt gggctgctgg ctgccttttct tcatcgtcaa catcgtcaac ctggccttca  1140
cgctacccga ggagcccacc tctgccggcc tctacttctt tgtggtggtc ctgtcttatg   1200
ccaatagctg tgccaacccc ctgctctatg gctttctctc tgataacttc cgccagagtt   1260
tccggaaggc tctgtgccta cgtagaggat acggtgtgga ggatgcagat gccatagagc   1320
cacggccaga caagagtggg cggccacaga ccacactgcc cacacgcagc tgtgaggcca   1380
acgggctcat gcagaccagc aggctttgag tgtcccagta acacctgggg ggtcctgcgg   1440
ggcctctgtg gtgttgtctt ctgggatatg agagtttgct gagatgcact cgcccccagg   1500
cctataagtt ggactcctct tggtggcagt gtgaagacag ctgtctgcgg ctaagccatg   1560
ggtgactgat catctctctc accaaaacgt tctgctagac cagggtctga gagtttggag   1620
accatgtgat aggcttggca gggagaaagg gctggttttt gcccctggta atattcaggc   1680
accttcaccc gtactgtggc atcatttttg tcagtctctc aggccaagaa gcaatttttc   1740
agaagagagc caagaaatga ttctcttgta gactattggt gtgtgctggc gattacccac   1800
cctgaagctg tgctggcctg ctggcccctc agccactgtt ccttgttctg gtcagcgtgg   1860
gagacaaatg aaaggtatcc atgtgtgttc agccccagcc tctgcgaacc tgcagctaca   1920
tgtacttcga ggcgacagtt ttaacaaaga tgcactggcc ctggggcagc agagatgaaa   1980
ccttgggccc tattctggct gcttcccatc tttctccagc acaaggaaaa gcaaggtctt   2040
ggcctttatg atgggagcag gtaggcgggg cagacgcatg gtgaagactg gaaagagaat   2100
ggacacacca cgatctggtc tctgcagagt ggcccagtga agaaggttct attgaggctt   2160
ccctgggact gagagacgac gaggacacac aggggactta acagccttcc atctctttaa   2220
ggcaggttgc tggggctctg tccctggaga aggagcaggg tgggcaggta gcaggcagga   2280
acaaacagca gagcctggaa agacctacca ttcgagagag tgcaaatgcc agccagtgcc   2340
agggagggcc aagtccctgg ggaatctgtg atcccgcctc agcagcttct ctacgccaga   2400
```

```
cccagaatgt gctcaaagcc cccatgtcca cattttgcca tggtgtcccc ggggctggag   2460

aaaagttaat cctactattt attcttctgc tctgggctgc cctgcctggc atgcctggct   2520

ccctgggagg gtgcagagac caggacagca ggatctggca gagggaaggc tgtgggggtt   2580

gctctgtctc aaatgtgacc ccctcccccg gcaaatgcta gccctgtaag ctcattcctc   2640

ataatgaggg cacttgtgct ccacaacctg cctctgaata aattagaaaa taagctgtt    2699


<210> SEQ ID NO 168
<211> LENGTH: 1089
<212> TYPE: DNA
<213> ORGANISM: Mus musculus

<400> SEQUENCE: 168

atggagcccc tctctttgac ttccacacct agctggaatg cctcagctgc ttccagcagt     60

agccataact ggtcactagt ggacccggtg tcacccatgg gagcccgggc ggtattagtg    120

cctgtgctct acttgttggt atgcaccgtg ggactgggtg gaaacacact ggtcatctat    180

gtggtgttgc ggtacgccaa gatgaagaca gttactaacg tgtatatcct gaacctggcc    240

gtggctgacg tgttgtttat gttggggctt cctttcctgg caacgcagaa tgctgtctcc    300

tactggccct ttggctcctt cttgtgccgc ctggtcatga cgctggacgg catcaaccag    360

ttcaccagta tcttctgcct gatggtcatg agtgtcgacc gctacctggc cgtggtccac    420

cctctccgct cagcccggtg gcgtcgccca cgggtagcca agctggctag tgctgccgtc    480

tgggtcttct cgctgctcat gtctctgccg ctcttggtct ttgcggatgt ccaggagggc    540

tggggcacct gcaacctgag ctggccagag cctgtgggac tgtggggtgc agccttcatc    600

acttacacgt ctgtgctggg cttctttggg cccctgctgg tcatctgctt gtgctatttg    660

ctcatcgtag tgaaggtgaa ggctgcaggt atgcgtgtgg gctcctcacg gcggaggcgc    720

tcagaacgca aggtgactcg catggtggtg gtagtggtgc tggtgttcgt gggctgctgg    780

ctgcctttct tcatcgtcaa catcgtcaac ctggccttca cgctacccga ggagcccacc    840

tctgccggcc tctacttctt tgtggtggtc ctgtcttatg ccaatagctg tgccaacccc    900

ctgctctatg gctttctctc tgataacttc cgccagagtt tccggaaggc tctgtgccta    960

cgtagaggat acggtgtgga ggatgcagat gccatagagc cacggccaga caagagtggg   1020

cggccacaga ccacactgcc cacacgcagc tgtgaggcca acgggctcat gcagaccagc   1080

aggctttga                                                           1089


<210> SEQ ID NO 169
<211> LENGTH: 362
<212> TYPE: PRT
<213> ORGANISM: Mus musculus

<400> SEQUENCE: 169

Met Glu Pro Leu Ser Leu Thr Ser Thr Pro Ser Trp Asn Ala Ser Ala
1               5                   10                  15

Ala Ser Ser Ser Ser His Asn Trp Ser Leu Val Asp Pro Val Ser Pro
            20                  25                  30

Met Gly Ala Arg Ala Val Leu Val Pro Val Leu Tyr Leu Leu Val Cys
        35                  40                  45

Thr Val Gly Leu Gly Gly Asn Thr Leu Val Ile Tyr Val Val Leu Arg
    50                  55                  60

Tyr Ala Lys Met Lys Thr Val Thr Asn Val Tyr Ile Leu Asn Leu Ala
65                  70                  75                  80
```

```
Val Ala Asp Val Leu Phe Met Leu Gly Leu Pro Phe Leu Ala Thr Gln
                85                  90                  95

Asn Ala Val Ser Tyr Trp Pro Phe Gly Ser Phe Leu Cys Arg Leu Val
            100                 105                 110

Met Thr Leu Asp Gly Ile Asn Gln Phe Thr Ser Ile Phe Cys Leu Met
        115                 120                 125

Val Met Ser Val Asp Arg Tyr Leu Ala Val Val His Pro Leu Arg Ser
    130                 135                 140

Ala Arg Trp Arg Arg Pro Arg Val Ala Lys Leu Ala Ser Ala Ala Val
145                 150                 155                 160

Trp Val Phe Ser Leu Leu Met Ser Leu Pro Leu Leu Val Phe Ala Asp
                165                 170                 175

Val Gln Glu Gly Trp Gly Thr Cys Asn Leu Ser Trp Pro Glu Pro Val
            180                 185                 190

Gly Leu Trp Gly Ala Ala Phe Ile Thr Tyr Thr Ser Val Leu Gly Phe
        195                 200                 205

Phe Gly Pro Leu Leu Val Ile Cys Leu Cys Tyr Leu Leu Ile Val Val
    210                 215                 220

Lys Val Lys Ala Ala Gly Met Arg Val Gly Ser Ser Arg Arg Arg Arg
225                 230                 235                 240

Ser Glu Arg Lys Val Thr Arg Met Val Val Val Val Val Leu Val Phe
                245                 250                 255

Val Gly Cys Trp Leu Pro Phe Phe Ile Val Asn Ile Val Asn Leu Ala
            260                 265                 270

Phe Thr Leu Pro Glu Glu Pro Thr Ser Ala Gly Leu Tyr Phe Phe Val
        275                 280                 285

Val Val Leu Ser Tyr Ala Asn Ser Cys Ala Asn Pro Leu Leu Tyr Gly
    290                 295                 300

Phe Leu Ser Asp Asn Phe Arg Gln Ser Phe Arg Lys Ala Leu Cys Leu
305                 310                 315                 320

Arg Arg Gly Tyr Gly Val Glu Asp Ala Asp Ala Ile Glu Pro Arg Pro
                325                 330                 335

Asp Lys Ser Gly Arg Pro Gln Thr Thr Leu Pro Thr Arg Ser Cys Glu
            340                 345                 350

Ala Asn Gly Leu Met Gln Thr Ser Arg Leu
        355                 360
```

<210> SEQ ID NO 170
<211> LENGTH: 1384
<212> TYPE: DNA
<213> ORGANISM: Rattus norvegicus

<400> SEQUENCE: 170

```
ccgacttcgt acagcaatcg agtgagcaca ctgctctttg agcccgagtg cgctgcctaa      60

ctgcgaagta ccgccgccgt gcccgccccg gcgtgggcac cctgtcctgc acagagacac     120

gcgtggtctg gcacccggcc tgaagctgac agcatggagc ccctctctct ggcctccaca     180

ccaagctgga atgcctcggc tgcttccagt ggtaaccata actggtcact ggtgggctca     240

gcatcgccaa tgggagcccg ggcagtatta gtgcctgtgc tctacctgtt ggtgtgcacc     300

gtgggactga gtggaaatac actggtcatt tatgtggtgc tgcggcacgc caagatgaag     360

acagttacta acgtgtacat cctgaacctg gccgtggctg acgtattatt tatgttggga     420

cttcctttcc tggccacgca gaacgccgtc gtctcctact ggcccttcgg ctccttcttg     480
```

```
tgccgcctgg tcatgacact ggatggcatc aaccagttca ccagtatctt ctgcctgatg    540

gtcatgagtg ttgaccgcta cctggccgtg gtccaccctc tccgctcagc ccggtggcgt    600

cgcccacggg tagccaagat ggccagcgcg gccgtctggg tcttttcgct gctcatgtct    660

ctgccgctct tggtcttcgc ggatgtccag gagggctggg gcacctgcaa cctgagctgg    720

ccagagcctg tggggctgtg ggtgcagcc ttcatcacct acacgtctgt gttgggcttc    780

tttgggcccc tgctggtcat ctgcttgtgc tacctgctca ttgtggtcaa ggtgaaggct    840

gcaggcatgc gcgtaggctc ctcaaggcgg aggcgctcgg agccgaaggt gactcgcatg    900

gtggtggtcg tggtgctggt gtttgtgggc tgctggctgc ctttcttcat tgtcaacatc    960

gtcaacctgg ccttcacact gcccgaggaa cccacatctg ccggcctcta tttctttgtg   1020

gtggtcctat cttatgccaa tagctgtgcc aaccccctgc tctacggctt tctctcggac   1080

aacttccgcc agagcttccg gaaggttctg tgcctacgta gaggatacgg tatggaggat   1140

gcggacgcca tagagccacg gccagacaag agtgggcggc ctcaggccac actgcccaca   1200

cgcagctgcg aggccaatgg gctcatgcag accagcagga tttgaatgcc cctgtaacac   1260

cctgggggtc ctccaggcct ccacggtgtt gtcttctggg atctgagagt ttgctgagat   1320

gcattcaccc ccaggcctac aagttggact cctctcggtg gcagtgtgaa gacaggacct   1380

gcag                                                                1384


<210> SEQ ID NO 171
<211> LENGTH: 1092
<212> TYPE: DNA
<213> ORGANISM: Rattus norvegicus

<400> SEQUENCE: 171

atggagcccc tctctctggc ctccacacca agctggaatg cctcggctgc ttccagtggt     60

aaccataact ggtcactggt gggctcagca tcgccaatgg gagcccgggc agtattagtg    120

cctgtgctct acctgttggt gtgcaccgtg ggactgagtg gaaatacact ggtcatttat    180

gtggtgctgc ggcacgccaa gatgaagaca gttactaacg tgtacatcct gaacctggcc    240

gtggctgacg tattatttat gttgggactt cctttcctgg ccacgcagaa cgccgtcgtc    300

tcctactggc ccttcggctc cttcttgtgc cgcctggtca tgacactgga tggcatcaac    360

cagttcacca gtatcttctg cctgatggtc atgagtgttg accgctacct ggccgtggtc    420

caccctctcc gctcagcccg gtggcgtcgc ccacgggtag ccaagatggc cagcgcggcc    480

gtctgggtct tttcgctgct catgtctctg ccgctcttgg tcttcgcgga tgtccaggag    540

ggctggggca cctgcaacct gagctggcca gagcctgtgg ggctgtgggg tgcagccttc    600

atcacctaca cgtctgtgtt gggcttcttt gggcccctgc tggtcatctg cttgtgctac    660

ctgctcattg tggtcaaggt gaaggctgca ggcatgcgcg taggctcctc aaggcggagg    720

cgctcggagc cgaaggtgac tcgcatggtg gtggtcgtgg tgctggtgtt tgtgggctgc    780

tggctgcctt tcttcattgt caacatcgtc aacctggcct tcacactgcc cgaggaaccc    840

acatctgccg gcctctattt ctttgtggtg gtcctatctt atgccaatag ctgtgccaac    900

cccctgctct acggctttct ctcggacaac ttccgccaga gcttccggaa ggttctgtgc    960

ctacgtagag gatacggtat ggaggatgcg gacgccatag agccacggcc agacaagagt   1020

gggcggcctc aggccacact gcccacacgc agctgcgagg ccaatgggct catgcagacc   1080

agcaggattt ga                                                       1092
```

<210> SEQ ID NO 172
<211> LENGTH: 363
<212> TYPE: PRT
<213> ORGANISM: Rattus norvegicus

<400> SEQUENCE: 172

```
Met Glu Pro Leu Ser Leu Ala Ser Thr Pro Ser Trp Asn Ala Ser Ala
1               5                   10                  15

Ala Ser Ser Gly Asn His Asn Trp Ser Leu Val Gly Ser Ala Ser Pro
            20                  25                  30

Met Gly Ala Arg Ala Val Leu Val Pro Val Leu Tyr Leu Leu Val Cys
        35                  40                  45

Thr Val Gly Leu Ser Gly Asn Thr Leu Val Ile Tyr Val Val Leu Arg
    50                  55                  60

His Ala Lys Met Lys Thr Val Thr Asn Val Tyr Ile Leu Asn Leu Ala
65                  70                  75                  80

Val Ala Asp Val Leu Phe Met Leu Gly Leu Pro Phe Leu Ala Thr Gln
                85                  90                  95

Asn Ala Val Val Ser Tyr Trp Pro Phe Gly Ser Phe Leu Cys Arg Leu
            100                 105                 110

Val Met Thr Leu Asp Gly Ile Asn Gln Phe Thr Ser Ile Phe Cys Leu
        115                 120                 125

Met Val Met Ser Val Asp Arg Tyr Leu Ala Val Val His Pro Leu Arg
    130                 135                 140

Ser Ala Arg Trp Arg Arg Pro Arg Val Ala Lys Met Ala Ser Ala Ala
145                 150                 155                 160

Val Trp Val Phe Ser Leu Leu Met Ser Leu Pro Leu Leu Val Phe Ala
                165                 170                 175

Asp Val Gln Glu Gly Trp Gly Thr Cys Asn Leu Ser Trp Pro Glu Pro
            180                 185                 190

Val Gly Leu Trp Gly Ala Ala Phe Ile Thr Tyr Thr Ser Val Leu Gly
        195                 200                 205

Phe Phe Gly Pro Leu Leu Val Ile Cys Leu Cys Tyr Leu Leu Ile Val
    210                 215                 220

Val Lys Val Lys Ala Ala Gly Met Arg Val Gly Ser Ser Arg Arg Arg
225                 230                 235                 240

Arg Ser Glu Pro Lys Val Thr Arg Met Val Val Val Val Val Leu Val
                245                 250                 255

Phe Val Gly Cys Trp Leu Pro Phe Phe Ile Val Asn Ile Val Asn Leu
            260                 265                 270

Ala Phe Thr Leu Pro Glu Glu Pro Thr Ser Ala Gly Leu Tyr Phe Phe
        275                 280                 285

Val Val Val Leu Ser Tyr Ala Asn Ser Cys Ala Asn Pro Leu Leu Tyr
    290                 295                 300

Gly Phe Leu Ser Asp Asn Phe Arg Gln Ser Phe Arg Lys Val Leu Cys
305                 310                 315                 320

Leu Arg Arg Gly Tyr Gly Met Glu Asp Ala Asp Ala Ile Glu Pro Arg
                325                 330                 335

Pro Asp Lys Ser Gly Arg Pro Gln Ala Thr Leu Pro Thr Arg Ser Cys
            340                 345                 350

Glu Ala Asn Gly Leu Met Gln Thr Ser Arg Ile
        355                 360
```

USE OF NUCLEIC ACID SEQUENCES FOR THE TREATMENT OF EPILEPSY

RELATED APPLICATIONS

This application is a nationalization under 35 U.S.C. 371 of PCT/SE2007/050494, filed Jul. 4, 2007 and published as WO 2008/004972 A2, on Jan. 10, 2008, which claimed priority under 35 U.S.C. 119 to Sweden Patent Application Serial No. 0601456-7, filed Jul. 4, 2006; which applications and publication are incorporated herein by reference and made a part hereof.

FIELD OF THE INVENTION

The present invention relates to the use of one or more expression vectors comprising certain nucleic acid sequences encoding a combination of neuropeptide Y (NPY) and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the preparation of a medicament for treatment of a disorder of the nervous system. The invention further relates to vectors that comprise nucleic acid sequences encoding the above combination, to compositions comprising such vectors and to a method of delivery and expression of the above combination of nucleic acid sequences into cells of the nervous system to treat neurological or psychiatric diseases in humans or animals.

BACKGROUND OF THE INVENTION

To describe the invention in greater detail, a number of publications and documents are referenced in the present application. The disclosure of each of these publications and documents is incorporated by reference in its entirety.

In general, the invention relates to methods for treating neurological and psychiatric diseases. Neurological and psychiatric diseases/disorders often progress rapidly and can be disruptive of essentially all aspects of a human or animal patient's life. Thus, these diseases present profound challenges for the patients, care givers, and attending physicians. In addition, the progressive nature of these diseases makes the passage of time a crucial consideration in the treatment process. Treatment of neurological or psychiatric diseases, particularly those affecting cognitive function, can be complicated by the duration of time which is frequently required to determine the efficacy of a therapeutic regimen. Depending on the disease involved, a considerable proportion of affected patients may present with an intractable form of disease.

Methodology directed at human and animal gene therapy renders feasible the treatment of numerous neurological and psychiatric diseases via delivery of a combination of nucleic acid sequences directly to the nervous system, wherein their expression can be manipulated in a therapeutically beneficial manner. This is a particularly valuable option for patients with intractable neurological disease, who may, for example, have a form of the disease that is not responsive to available drugs or may not be able to tolerate the unwanted side effects associated with many therapeutics. However, gene transfer into the central nervous system (CNS) is impeded by several features of the system, including the largely post-mitotic nature of most neurons in the brain, obstacles pertaining to the blood-brain-barrier or constraints related to low accessibility into several brain areas.

Applying retroviral vectors that are routinely used for somatic cell gene transfer is not useful, in general, for applications in post-mitotic neural cells because retrovirally mediated gene transfer requires at least one cell division in target brain cells for integration and expression. To address this challenge of gene transfer into the CNS, a number of vectors and non-viral methods have been developed. A number of studies have achieved varying degrees of success for gene transfer into the CNS using either an ex vivo approach, involving transplantation of cells retrovirally-transduced in vitro, or an in vivo approach. HSV-1 and adenoviral vectors, as well as non-viral methods, including cationic lipid mediated transfection, have also been utilized for gene transfer into neural cells of the CNS.

For instance, oligodendrocytes that were infected ex vivo with retroviral vectors have been transplanted into a syngenic rat model for a demyelinating disorder. Fibro and primary muscle cells have also been used successfully to introduce exogenous nucleic acid sequences and their encoded products into the CNS.

Herpes Simplex Virus (HSV-1) and a number of adenoviral vectors have been used in vivo causing persistent expression (i.e., at least two months) of marker genes in the rat brain. Besides viral vector approaches, some investigators have directly injected a cationic liposome:plasmid complex and have shown low levels and transient expression of a marker gene using this approach.

Nonetheless, relatively few studies have aimed at introducing "therapeutic" genes into cells of the CNS and the majority of these studies employed an ex vivo approach with transduction of fibroblasts and muscle cells with the human tyrosine hydroxylase gene that provided a source of L-dopa-secreting cells in models of Parkinson's disease. In vivo approaches have used HSV vectors to induce expression of beta-glucuronidase, glucose transporter, and nerve growth factor and an adenoviral vector to induce low-level transient expression of human alfa1-antitrypsin.

Few clinical studies documenting gene transfer into the brain have been reported. In one of these, rats were basically cured after intracerebral implantation of glioma cell lines infected with a retrovirus expressing the HSV-1 thymidine kinase gene following subsequent treatment with ganciclovir.

More recently, as described in patent PCT WO 2005/037211 A2, using an AAV vector, injection of the NPY gene into hippocampal formation of the rat caused overexpression of NPY that significantly reduced epileptic activity (Richichi et al. (2004) J. Neurosci. 24:3051-9). Injection of AAV-vectors containing NPY was studied in three rat epilepsy models, (1) intrahippocampal kainate injection, (2) intraventricular kainate, and (3) rapid kindling. Intrahippocampal injection of the NPY-AAV vector in rats caused long-lasting (at least 3 months) expression of NPY and decreased seizure activity in all three models, but, importantly, did not abolish seizure activity.

Also using AAV vectors, induced expression of galanin, another inhibitory neuropeptide, in the hippocampal formation has been shown to reduce epileptic activity and kainate-induced cell death in the hippocampal formation (Haberman et al. (2003) Nature Med. 9:1076-80; Lin et al. (2003) Eur. J. Neurosci. 18:2087-92). Thus, as with AAV-mediated hippocampal NPY expression, epileptic activity was reduced but not abolished.

Increased release of a neurotransmitter often leads to compensatory downregulation of the receptors mediating the effects of the neurotransmitter. Accordingly, overexpression of neuropeptides like NPY, galanin, or somatostatin might lead to downregulation of the corresponding receptors of these neuropeptides. Indeed, in patent PCT WO 2005/037211 A2, a prominent reduction in Y1 receptor binding sites was reported following overexpression of NPY via AAV vectors. Thus a therapeutic effect of overexpressing neuropeptides could taper off with time due to changes in receptors mediating the therapeutic effect. In conclusion, previous studies show that targeted expression of NPY and galanin are not sufficient to abolish seizures. In addition, compensatory downregulation of neuropeptide receptors in response to induced expression of neuropeptides via administration of viral vectors is likely to limit a potential therapeutic effect with time. Based on these considerations, the present invention aims at treating epilepsy and other neuropsychiatric diseases by inducing expression of a combination of one or more neuropeptides (NPY, galanin, somatostatin) and/or one or more of their corresponding receptors (Y1, Y2, Y4, Y5, y6, GALR1, GALR2, GALR3, SST1, SST2, SST3, SST4, SST5) via viral vectors acting in key brain regions.

SUMMARY OF THE INVENTION

The present invention, in one aspect, relates to the use of one or more expression vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the preparation of a medicament for treatment of a disorder of the nervous system.

In an embodiment of the invention said disorder of the nervous system is a neurological or a psychiatric disease.

In another embodiment said disorder is epilepsy, affective disorder, anxiety disorder or OCD. Said epilepsy can further be intractable epilepsy or temporal lobe epilepsy and said affective disorder can be treatment-resistant or not treatment-resistant depression or bipolar affective disorder. The anxiety disorder to be treated may further be panic disorder or generalized anxiety.

In an embodiment of the invention said medicament is intended for administration by stereotaxic microinjection.

In another embodiment of the invention the one or more expression vectors are viral and/or non-viral expression vectors, said one or more of the viral expression vectors can be AAV vectors and/or lentivirus vectors and/or HSV vectors. The AAV vectors and/or lentivirus vectors and/or HSV vectors can be free of both wildtype and helper virus. In another embodiment of the invention said one or more of the AAV vectors are serotype 2 and/or 5 AAV vectors and/or chimeric serotype ½ AAV vectors.

The present invention relates, in another aspect, to delivering nucleic acid sequences to mammalian nervous system target cells, wherein said nucleic acid sequences are expressible in the target cells for more than three months, said method comprising the administration of one or more expression vectors to the target cells, wherein said expression vectors comprise nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof.

In an embodiment of the invention, though not exclusively, said expression vectors will most often comprise nucleic acid sequences encoding one or more of the NPY receptors (Y1, Y2, Y4, Y5, y6) when also a nucleic acid sequence encoding NPY is delivered to target cells of the mammalian nervous system. Likewise, said expression vectors will most often comprise nucleic acid sequences encoding one or more of the galanin receptors (GALR1, GALR2, GALR3) when also a nucleic acid sequence encoding galanin is delivered to target cells of the mammalian nervous system. Finally, said expression vectors will most often comprise nucleic acid sequences encoding one or more of the somatostatin receptors (SST1, SST2, SST3, SST4, SST5) when also a nucleic acid sequence encoding somatostatin is delivered to target cells of the mammalian nervous system.

In an aspect of the method of the invention, the nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, are expressed in target cells either constitutively or under regulatable conditions.

In an embodiment of the method of the invention, expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in target cells reduces neuronal excitability. In yet another embodiment of the method, expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, reduces symptoms associated with neuronal hyperexcitability.

Thus, the present invention encompasses use of one or more expression vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the preparation of a medicament for delivery to human or animal nervous system target cells, wherein delivery of the medicament results in expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof in the nervous system target cells for greater than three months. In a particular embodiment, the medicament is delivered stereotactically. Expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof in the nervous system target cells is capable of altering neuronal excitability. In a particular embodiment, expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof in a nervous system target cell reduces neuronal excitability. In another embodiment, expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in nervous system target cells reduces symptoms associated with neuronal hyperexcitability.

In accordance with the method of the invention, the expression vectors are viral and/or a non-viral expression vectors. Viral expression vectors that may be used advantageously in the method of the invention include, but are not limited to, one or more lentivirus vectors, and/or one or more adeno-associated virus (AAV) vectors, and/or one or more herpes simplex virus (HSV) vectors.

In an aspect of the method wherein one or more of the viral expression vectors are AAV vectors capable of transducing the target cell, the AAV vectors are free of both wildtype and helper virus. Exemplary types of AAV vectors useful in the present invention include serotype 2 and 5 AAV vectors as well as chimeric serotype ½ AAV vectors.

In an aspect of the method wherein one or more of the viral expression vectors are lentivirus vectors capable of transducing the target cell, the lentivirus vectors are free of wild type and helper virus. Exemplary types of lentivirus vectors useful in the present invention include human immunodeficiency virus (HIV-1, HIV-2), feline immunodeficiency virus (FIV), and equine infectious anemia virus (EIAV).

In an aspect of the present method, wherein the nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, are each operably linked to an inducible regulatory sequence. Activation of the inducible regulatory sequence effects transcription of messenger RNA encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof. In an embodiment, an inducible regulatory sequence renders expression of a combination of NPY and/or one or more of its receptors (Y1, Y2, Y4, Y5, y6), and/or galanin and/or one or more of its receptors (GALR1, GALR2, GALR3), or derivatives or functional fragments thereof, nervous system-specific or central nervous system-specific. For some applications, expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, is specific to a medial temporal lobe or temporal cortex or frontal cortex of the CNS. In a further aspect, expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, may be directed to the medial temporal lobe, wherein it is localized to the hippocampal formation and/or amygdala. In yet another aspect, expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, may be directed to the raphe nuclei and/or periaqueductal gray of the brain stem.

In one aspect of the method, a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, is neuronal and/or glial specific.

In another aspect of the present method, the target cell is a mammalian cell of a mammalian order selected from the group consisting of Primata, Rodenta, Lagomorpha, Carnivora, Arteriodactyla, and Perissodactyla. More particularly, the target cell may be a human cell. A target cell may exist in a cell culture or within a living mammal.

In an embodiment of the method, one or more expression vectors of the invention are delivered to essentially all nervous system cells of the mammal. Alternatively, one or more expression vectors are specifically delivered to particular cell types or regions of the nervous system of the mammal. In a particular embodiment, one or more expression vectors of the invention are delivered via stereotaxic injection.

In an aspect of the method, delivering nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, to cells of the nervous system to affect expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, treats a disorder of the nervous system. Nervous system disorders treatable using the method of the invention, include, but are not limited to, epilepsy, affective disorder, anxiety disorder, and obsessive-compulsive disorder (OCD). Particular examples of epilepsy treatable by the present methods include, but are not limited to, intractable epilepsy and temporal lobe epilepsy. Particular examples of affective disorder treatable by the present methods include, but are not limited to, treatment-resistant depression and bipolar affective disorder. Particular examples of anxiety disorder treatable by the present methods include, but are not limited to, treatment-resistant anxiety disorder. Particular examples of OCD treatable by the present methods include, but are not limited to, treatment-resistant OCD.

Accordingly, the present invention is directed to use of one or more expression vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the preparation of a medicament for the treatment of a disorder of the nervous system, wherein expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, is targeted to a mammalian nervous system and is long-lived (e.g., greater than three months). Disorders of the nervous system for which such medicaments may by used include, but are not limited to, epilepsy, affective disorder, anxiety disorder, and OCD. Particular examples of epilepsy include, but are not limited to, intractable epilepsy and temporal lobe epilepsy. Particular examples of affective disorder include, but are not limited to, treatment-resistant depression and bipolar affective disorder. Particular examples of anxiety disorder include, but are not limited to, treatment-resistant anxiety disorder. Particular examples of OCD include, but are not limited to, treatment-resistant OCD. In a particular embodiment, the medicament is delivered stereotactically.

In accordance with the use or method of the invention, nucleic acid sequences encoding NPY and/or one or more of its receptors (Y2, Y5) are nucleic acid sequences encoding an amino acid sequence comprising SEQ ID NO: 3, SEQ ID NO: 6, SEQ ID NO: 9, or SEQ ID NO: 12, and/or one or more amino acid sequences comprising one or more of SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or derivatives or functional fragments thereof.

In an embodiment of the method or use of the invention, nucleic acid sequences encoding NPY and/or one or more of its receptors (Y2, Y5) are nucleic acid sequences encoding an amino acid sequence comprising SEQ ID NO: 3, SEQ ID NO: 6, SEQ ID NO: 9, or SEQ ID NO: 12, or a derivative or functional fragment thereof, or an amino acid sequence at least 90% homologous to SEQ ID NO: 3, SEQ ID NO: 6, SEQ ID NO: 9, or SEQ ID NO: 12, or a derivative or functional fragment thereof, and/or one or more amino acid sequences comprising one or more of SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or one or more derivatives or functional fragments thereof, or one or more amino acid sequences at least 90% homologous to SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or one or more derivatives or functional fragments thereof. In a further aspect of the method, nucleic acid sequences encoding NPY and/or one or more of its receptors (Y2, Y5) are nucleic acid sequences encoding an amino acid sequence comprising SEQ ID NO: 3, SEQ ID NO: 6, SEQ ID NO: 9, or SEQ ID NO: 12, or a derivative or functional fragment thereof, or an amino acid sequence at least 85% homologous to SEQ ID NO: 3, SEQ ID NO: 6, SEQ ID NO: 9, or SEQ ID NO: 12, or a derivative or functional fragment thereof, and/or one or more amino acid sequences comprising one or more of SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or one or more derivatives or functional fragments thereof, or one or more amino acid sequences at least 85% homologous to SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or one or more derivatives or functional fragments thereof.

In another aspect of the method or the use of the invention, nucleic acid sequences encoding NPY and/or one or more of its receptors (Y2, Y5) are nucleic acid sequences comprising SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, and/or one or more nucleic acid sequences comprising one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or derivatives or functional fragments thereof.

In another aspect of the method or the use, nucleic acid sequences encoding NPY and/or one or more of its receptors (Y2, Y5) are nucleic acid sequences comprising SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, or a derivative or functional fragment thereof, or a nucleic acid sequence at least 90% homologous to SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, or a derivative or functional fragment thereof, and/or one or more nucleic acid sequences comprising one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or one or more derivatives or functional fragments thereof, or one or more nucleic acid sequences at least 90% homologous to SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or one or more derivatives or functional fragments thereof. In a further aspect of the method, nucleic acid sequences encoding NPY and/or one or more of its receptors (Y2, Y5) are nucleic acid sequences comprising SEQ ID SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, or a derivative or functional fragment thereof, or a nucleic acid sequence at least 85% homologous to SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, or a derivative or functional fragment thereof, and/or one or more nucleic acid sequences comprising one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or one or more derivatives or functional fragments thereof, or one or more nucleic acid sequences at least 85% homologous to SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or one or more derivatives or functional fragments thereof.

In a particular embodiment of the method, one or more expression vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, may be administered by stereotaxic injection.

Also encompassed by the present invention are one or more lentivirus vectors and/or AAV vectors, and/or HSV vectors which retain only the replication and packaging signals of lentivirus, and/or AAV, and/or HSV, respectively, and which comprise nucleic acid sequences encoding a combination of NPY and/or one or more of its receptors (Y2, Y5) or derivatives or functional fragments thereof. A nucleic acid sequence encoding NPY may, for example, comprise a nucleic acid sequence of SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, or a derivative or functional fragment thereof; one or more nucleic acid sequences encoding one or more of NPY's receptors may, for example, comprise nucleic acid sequences of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or one or more derivatives or functional fragments thereof.

A nucleic acid sequence encoding NPY may comprise a nucleic acid sequence encoding an amino acid sequence comprising SEQ ID NO: 3, SEQ ID NO: 6, SEQ ID NO: 9, or SEQ ID NO: 12, or a derivative or functional fragment thereof; one or more nucleic acid sequences encoding one or more of NPY's receptors may comprise nucleic acid sequences encoding one or more amino acid sequences comprising SEQ ID NO: SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56.

The present invention also includes a composition comprising one or more lentivirus vectors and/or AAV vectors, and/or HSV vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, and a pharmaceutically acceptable carrier or excipient.

The present invention is also directed to a method for treating a mammal with a neurological or psychiatric disease, said method comprising administering one or more expression vectors to target cells in the mammal, wherein said expression vector comprise nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, and wherein said administering results in expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in said target cells and expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, reduces the symptoms of the neurological or psychiatric disease, thereby treating the mammal with the neurological or psychiatric disease. In an aspect of the method, the expression vector may be a viral and/or non-viral expression vector. In aspects of the method wherein viral vectors are utilized, such vectors include, but are not limited to, one or more lentivirus, and/or AAV, and/or HSV vectors.

Accordingly, the present invention encompasses the use of an expression vector comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the preparation of a medicament for the treatment of a mammal with a neurological or psychiatric disease. An expression vector of the present invention may be a viral or a non-viral expression vector. Useful viral vectors include, without limitation, lentivirus vectors, AAV vectors, HSV vectors. Neurological and psychiatric diseases for which such medicaments are efficacious include, but are not limited to epilepsy, affective disorder, anxiety disorder, or OCD. In specific embodiments, the epilepsy treated is intractable epilepsy or temporal lobe epilepsy, and the depression treated is treatment-resistant depression. In a particular embodiment, the medicament is delivered stereotactically.

In an embodiment of the method, nucleic acid sequences encoding a combination of NPY and/or one or more of its receptors (Y2, Y5), or derivatives or functional fragments thereof, are nucleic acid sequences encoding amino acid sequences comprising one of SEQ ID NO: 3, SEQ ID NO: 6, SEQ ID NO: 9, or SEQ ID NO: 12, and/or one or more of SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or derivatives or functional fragments thereof. In another embodiment, nucleic acid sequences encoding a combination of NPY and/or one or more of its receptors (Y2, Y5), or derivatives or functional fragments thereof, are nucleic acid sequences comprising one of SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, and/or one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55.

In yet another embodiment of the method, nucleic acid sequences encoding a combination of NPY and/or one or more of its receptors (Y2, Y5), or derivatives or functional fragments thereof, are nucleic acid sequences comprising one of SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, and/or one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, and/or derivatives or functional fragments thereof, or are nucleic acid sequences at least 90% homologous to one of SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, and/or one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, and/or derivatives or functional fragments thereof. The method also encompasses the use of nucleic acid sequences encoding a combination of NPY and/or one or more of its receptors (Y2, Y5) or derivatives or functional fragments thereof, wherein the nucleic acid sequences comprise one of SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, and/or one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, and/or derivatives or functional fragments thereof, or nucleic acid sequences at least 85% homologous to one of SEQ ID NO: 1, SEQ ID NO: 2, SEQ ID NO: 4, SEQ ID NO: 5, SEQ ID NO: 7, SEQ ID NO: 8, SEQ ID NO: 10, or SEQ ID NO: 11, and/or one or more of SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or derivatives or functional fragments thereof.

Neurological diseases treatable using the method of the present invention, include, but are not limited to, epilepsy. In specific embodiments, the epilepsy to be treated is intractable epilepsy or temporal lobe epilepsy. Psychiatric diseases treatable using the method of the present invention, include, but are not limited to, depression, bipolar affective disorder, anxiety disorder, and OCD. In specific embodiments, depression, bipolar affective disorder, anxiety disorder, OCD are treatment resistant.

In accordance with the method, one or more expression vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, are administered by stereotaxic microinjection to affect treatment of a mammal with a neurological disease. In one aspect, stereotaxic microinjection is targeted to the medial temporal lobe or temporal cortex and/or brain stem of the CNS. In a further aspect, administering to the medial temporal lobe may be localized to the hippocampal formation and/or amygdala. In further accordance with the method, one or more expression vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, are administered by stereotaxic microinjection to affect treatment of a mammal with a psychiatric disease. In one aspect, stereotaxic microinjection is targeted to the medial temporal lobe or temporal cortex and/or brain stem of the CNS. In a further aspect, administering to the medial temporal lobe may be localized to the hippocampal formation and/or amygdala and administering to the brain stem may be localized to the raphe nuclei and/or periaqueductal gray.

The present invention also encompasses a method for delivering nucleic acid sequences to mammalian nervous system target cells, wherein the nucleic acid sequences are expressible in the target cells for more than three months, the method comprising administering one or more lentivirus vectors and/or AAV vectors, and/or HSV vectors to the target cells; and the vectors comprise nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, and are free of both wildtype and helper virus. Alternatively, and in accordance with the method, a composition of the invention comprising one or more lentivirus vectors and/or AAV vectors, and/or HSV vectors which encodes a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, may be administered.

The present invention also includes a method for treating a mammal with a neurological or psychiatric disease, the method comprising administering one or more lentivirus vectors and/or AAV vectors, and/or HSV vectors to target cells in the mammal, wherein the vectors comprise nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, and wherein administering results in the expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the target cells and this expression reduces the symptoms of the neurological or psychiatric disease, thereby treating the mammal with the neurological or psychiatric disease. In accordance with the method, a composition of the invention comprising one or more lentivirus vectors and/or AAV vectors, and/or HSV vectors which encode a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, may also be administered to affect expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, the expression of which reduces the symptoms or the neurological or psychiatric disease, and thereby treats the mammal with the neurological or psychiatric disease.

Accordingly, the present invention encompasses the use of one or more lentivirus vectors and/or AAV vectors, and/or HSV vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the preparation of a medicament for the treatment of a neurological or psychiatric disease, wherein expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, reduces the symptoms of the neurological or psychiatric disease. With regard to epilepsy, for example, symptoms associated with the disease include epileptic seizures and reduction of disease symptoms may refer to a reduction in the frequency, severity, and/or duration of epileptic seizures. In a particular embodiment, the medicament is delivered to the nervous system of a mammal with a neurological or psychiatric disease. In another particular embodiment, the medicament is delivered stereotactically.

DETAILED DESCRIPTION OF THE INVENTION

Figure 1:
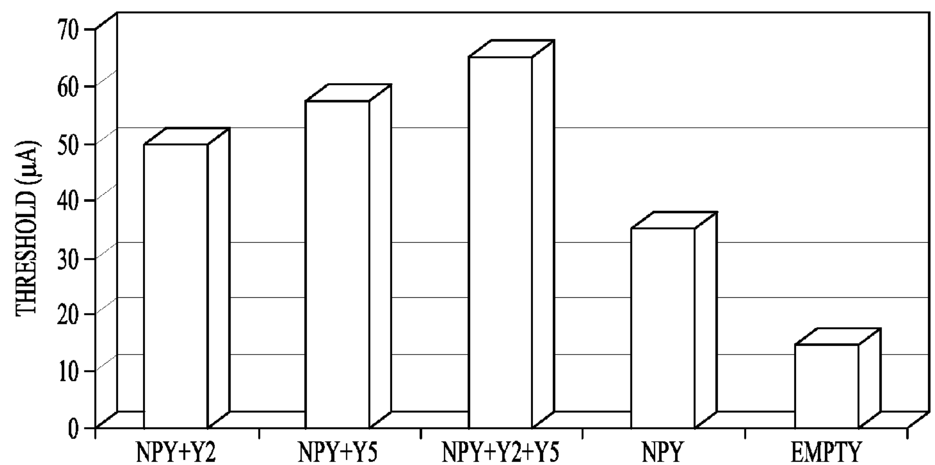
FIG. 1 depicts that mice kindled electrically by traditional one-stimulation-per-day protocol after viral vector infusion will increase the threshold for seizure induction at four to five weeks later.

Traditional medical drugs have been used for epilepsy and psychiatric diseases for several years. Administering these drugs is often associated with considerable life-long side effects for the patients. In addition, the drugs are not sufficiently effective in a fairly large proportion of patients with these diseases and novel treatments are called for. New alternative treatment strategies not based on traditional medical drugs could be based on selective and region-specific alterations of endogenous agents that are normally expressed in the brain and can attenuate excitatory synaptic transmission. The neuropeptides NPY, galanin, and somatostatin are lately emerging as such novel inhibitory neurotransmitters with antiepileptic effects and anxiolytic-/antidepressant-like effects (Kokaia et al. (2001) PNAS 98:14006-11; Woldbye & Kokaia (2004) Neuropeptides 38:253-60; Vezzani & Hoyer (1999) Eur. J. Neurosci. 11:3767-76).

NPY.

NPY is a neuropeptide that is widely expressed in the brain and has been shown to be involved in numerous functions, such as regulation of blood pressure, circadian rhythms, feeding behaviour, anxiety, depression, memory, and cognition. NPY is often colocalized with classical neurotransmitters in neurons and is predominantly released during high frequency activity. The effects of NPY are mediated via a number of G-protein-coupled receptor subtypes, including Y1, Y2, Y4, Y5 and y6 identified so far. In the hippocampal formation, Y2 receptors are present presynaptically on the mossy fibres and Schaffer collaterals, and Y1 receptors are found in the molecular layer on the dendrites of granule cells. Y5 receptor mRNA has also been detected in the dentate gyrus and CA3. Seizures increase NPY expression in the frontal, piriform and entorhinal cortices, as well as in the amygdala and hippocampal formation. In the hippocampal formation, NPY levels increase after seizures in the GABAergic interneurons, and granule cells and mossy fibres, where normally NPY is not detected. In line with these observations, changes in Y2, Y5, and Y1 NPY receptor densities and expression are observed in the hippocampal formation and other brain regions after seizures.

Taken together, these data indicate that NPY might be involved in adaptation mechanisms and/or pathophysiology of epileptogenesis (Vezzani et al. (1999) Trends Neurosci. 22:25-30). In agreement with this notion, NPY has been shown to have anticonvulsant action in vivo, e.g., when injected into the hippocampal formation or intracerebroventricularly in picrotoxin- and kainate-induced seizure models (Woldbye & Kokaia (2004) Neuropeptides 38:253-60). Similarly, NPY has been shown to inhibit epileptiform interictal activity in hippocampal and cortical slices perfused by extracellular solutions containing bicuculline, picrotoxin, or zero concentration magnesium (Vezzani et al. (1999) Trends Neurosci. 22:25-30). As revealed by using distinct NPY agonists and antagonists selectively acting on different subtypes of receptors, the seizure-suppressant effects of NPY might be mediated mostly via Y2 receptors, but Y5 and Y1 receptors also appear to be involved in regulation of seizures (Vezzani et al. (1999) Trends Neurosci. 22:25-30; Woldbye & Kokaia (2004) Neuropeptides 38:253-60). At present, it cannot be excluded that Y4 and y6 receptors might also have a role in regulation of seizures.

NPY administered intracerebroventricularly and into the brain region, amygdala, has anxiolytic-like effects in animal models, including the behavioural models, the open field test and elevated plus maze. This effect appears to be mediated via Y1 and Y5 receptors. In accordance with the present invention, increasing the expression of NPY and one or more of its receptors, especially Y1 and Y5, via viral vectors administered to the amygdala and/or other brain regions, should have a prominent anxiolytic effect in human and animal patients with anxiety disorders.

NPY also has antidepressant-like effects in the animal model of depression, the forced swim test. This effect appears predominantly to be mediated via Y1 receptors, though other NPY receptors cannot, at present, be fully excluded. Moreover, electroconvulsive therapy (ECT), a widely used efficacious treatment for severe depression, causes prominent increases in NPY gene expression in the hippocampal formation and other brain regions. Several drugs used for depression also cause changes in hippocampal NPY neurotransmission. In accordance with the present invention, increased expression of NPY and one/or more of its receptors should have a substantial antidepressant effect in human and animal patients with depression.

The therapeutic effects of NPY seems to be due to decreased glutamate release from the excitatory presynaptic terminals, as described in the hippocampal formation. Increased NPY gene expression and NPY protein synthesis found in animal models after seizures are accompanied by changes in NPY receptor binding sites and expression. Indeed, expression of NPY as described in patent PCT WO 2005/037211 A2 was also associated with prominent changes in NPY receptors. It is likely that these changes could limit the therapeutic effects of increasing NPY gene expression over time. Thus the present invention of combining expression of NPY and one or more of its corresponding receptors in target brain regions should have a much more pronounced therapeutic effect.

Galanin.

Galanin is another neuropeptide distributed throughout the brain, mainly in fibres arising from septal cholinergic and locus coeruleus noradrenergic neurons, in which it serves as a co-transmitter. It stimulates food consumption, as well as regulates insulin and hypothalamo-adrenal hormone release. Effects are mediated via binding to three G-protein coupled receptors (GALR1, GALR2, GALR3) Recently, powerful anticonvulsant effects were observed after intrahippocampal injection of galanin during status epilepticus (SE) in rats. In line with these observations, galnon, a non-peptide agonist of galanin, and overexpression of galanin in the noradrenergic fibers under dopamine-beta-hydroxylase promoter have been shown to increase resistance of mice to status epilepticus (SE), kainate, and pentylenetetrazol seizures (Mazarati et al. (2001) Neuroscientist 7:506-17). Accordingly, antagonists of galanin facilitate seizures in these models. Furthermore, targeted disruption of galanin gene increases seizure susceptibility in SE, kainate and PTZ models. Similarly, galanin receptor 1 (GALR1) knock-out mice, and rats with selective knockdown of galanin receptor 2 (GALR2) by antisense oligonucleotide are more susceptible to seizures in different models of epilepsy. Mechanisms underlying the seizure-suppressant effects of galanin are not well understood. It has been demonstrated, however, that galanin exerts mostly inhibitory effect on the hippocampal formation, either by direct hyperpolarization of the principal cells (e.g. CA3 pyramidal neurons) or by inhibiting glutamate release via activation of presynaptic ATP-dependent K+channels. We demonstrated that ectopic overexpression of galanin under the PDGF-B promoter in the dentate granule cells and hippocampal and cortical pyramidal neurons delays seizure generalization during kindling, a model for human complex partial seizures, indicating that galanin could have a therapeutic value for epilepsy (Kokaia et al. (2001) PNAS 98:14006-11). Exact mechanisms of this galanin effect on kindling are not known, but inhibition of glutamate release from granule cell axon terminals appears to be involved.

There is increasing evidence that galanin like NPY has antidepressant effects. Thus intraperitoneal administration of the galanin agonist Galmic has substantial antidepressant effect in the forced swim test in rodents. Direct injection of galanin (2-11), a GALR2 agonist, into the dorsal raphe nucleus caused decreased seizure severity and increases in serotonin concentrations in the hippocampal formation. Serotonin is an important neurotransmitter in relation to depression. Many antidepressant drugs act by increasing serotonin concentrations in target brain regions.

Somatostatin.

Somatostatin is another widely distributed neuropeptide in the brain with inhibitory and endogenous antiepileptic effects (Vezzani & Hoyer (1999) Eur. J. Neurosci. 11:3767-76). In addition to its effects on seizures, somatostatin is involved in multiple biological functions, including regulation of hormone release, tumour growth, cognition and motor activity. Somatostatin in brain cells is often colocalized with NPY and other classical neurotransmitters, like the inhibitory neurotransmitter GABA. Like NPY and galanin, the expression of somatostatin is greatly increased after epileptic seizures. This appears to be a compensatory response of the brain to prevent further seizures. Somatostatin exerts its effects via binding to five known G-protein coupled receptors (SST1, SST2, SST3, SST4, SST5), leading to reductions in cyclic AMP. Antiepileptic effects of somatostatin have been shown after intracerebroventricular, intrahippocampal and intra-amygdala administration in various epilepsy models, including kindling, kainate- and picrotoxin-induced seizures. SST2 receptors appear to be importantly involved in the antiepileptic effects. However, because selective ligands for the different somatostatin receptors have only recently become available, the role of other somatostatin receptors at mediating antiepileptic effects of somatostatin is at present unclear.

Somatostatin also has anxiolytic actions when administered into the amygdala brain region, this effect appears to be mediated by SST2 receptors, since SST2 deficient mice display increased anxiety-like behaviour. However, a role of other somatostatin receptors remains to be explored. In accordance with the present invention, expression of somatostatin and one or more of its receptors in the amygdala, hippocampus and other regions via viral vectors should have therapeutic effects in human and animal patients with epilepsy, anxiety disorders and other psychiatric disorders. Expression together with combinations of NPY/galanin and/or one or more NPY/galanin receptors would be even more effective.

Gene Transfer

The brain is hard to manipulate pharmacologically mainly due to the impermeability of the blood-brain barrier to many drugs. Furthermore, the brain is composed of many areas and nuclei with different function that may respond very differently to pharmacological challenge. In addition, cells with distinct functions (e.g. glial cells or neurons) reside in close proximity complicating the matter even further. Taken together, these circumstances demonstrate the need to develop new, innovative therapeutic paradigms. One way to handle these problems would be to use gene transfer methods to influence the brain locally or to target specific cell populations.

Gene transfer is one of the major technologies used in modern neuroscience to understand functions of different proteins. It allows for manipulation and monitoring of foreign gene expression in large populations of neural cells in dissociated cultures, cultured slices and in vivo. This opens the possibility to use direct and indirect gene transfer not only for experimental purposes but also for therapeutic means. One of the most efficient methods of gene transfer to neural cells is using recombinant viral vectors. There are two main approaches to transfer genes to the CNS, the indirect (ex vivo) and direct (in vivo) approach. In ex vivo gene delivery the vector is delivered to immature cells in vitro and these cells are then transplanted to the brain into the area of choice. This method has the advantage that there is no integration of foreign DNA that may introduce dysregulation of the genome in the host cells. From a therapeutic perspective the possibility to characterize the transduced cells prior to transplantation also offers ways to add safety to the procedure.

Direct in vivo gene delivery, on the other hand relies on recombinant viral vectors that can transduce non-dividing cells such as adenoviral vectors, adeno-associated viral vectors, HSV vectors, and lentiviral vectors (Washbourne & McAllister (2002) Curr. Opin. Neurobiol. 12:566-73). The vector is directly injected in the brain parenchyma and genetically modifies the resident host cells. To date, in vivo gene transfer is the only way to genetically modify post-mitotic neurons in situ and thus represents a powerful experimental tool.

These viral vectors have been successfully used in many different applications, AAV and lentiviral vectors being most promising. For example, both AAV and lentiviral vectors have been used to transfer GDNF gene in vivo, which was shown to prevent neurotoxicity in primate and rat models of Parkinson's disease. Moreover, these vectors have been used to develop genetic models of Parkinson's and Huntington's diseases.

Gene Transfer in Epilepsy

In Vivo Gene Transfer.

The field of direct gene transfer in epilepsy is still in its embryonic state. There are a limited number of publications showing the proof-of-principle for the concept of gene therapy in epilepsy so far. The available data are mainly concerning neuropeptides and some neurotrophic factors in animal models of epilepsy.

Expression of the human prepro-NPY gene was achieved using serotype 2 or a mixture of serotypes 1 and 2 of AAV vectors (Richichi et al. (2004) J. Neurosci. 24:3051-9). The gene for NPY was targeted bilaterally into the hippocampal formation of rats and the hybrid serotype (½) showed better and uniform expression of the gene product throughout the hippocampal formation. This overexpression of NPY was associated with at least 50% decrease in kainate-induced EEG seizures and a delay in kindling epileptogenesis.

First publications on galanin gene transfer in experimental epilepsy models appeared in 2003 (Haberman et al. (2003) Nature Med. 9:1076-80; Lin et al. (2003) Eur. J. Neurosci. 18:2087-92). Haberman et al. (2003) used a fusion gene construct where the rat galanin gene sequence was coupled to the fibronectin secretory signal sequence. Since fibronectin is usually secreted by the cells, coupling of its secretory signal sequence to the galanin gene induced constitutive release of galanin from the transduced cells. Doxycycline-off regulatable AAV vector was used to deliver this construct into the rat inferior colliculus. The threshold intensity of current for induction of wild-running seizures, induced by electrical stimulation of the inferior colliculus, was significantly increased in those animals that were transduced by AAV-FIB-Galanin sequence, compared to the AAV-Galanin and AAV-FIB-GFP control sequences. Moreover, when doxycycline was added to the drinking water of the animals, the threshold decreased to the control levels and was again subsequently increased when doxycyclin was removed. Taken together, these data support the notion that constitutive release of viral vector-mediated overexpressed galanin can suppress seizure activity in animal models of epilepsy. However, this conclusion should be taken with some caution, since AAV-FIB-Galanin vector when infused into the hilar region of the hippocampal formation did not inhibit kainate-induced seizures, although it protected hilar cells from degeneration. The lack of the effect on seizures could be a limited area of the tranfection (hilus), or the fact that the vector was infused only unilaterally. The supportive evidence that bilateral overexpression of galanin gene using AAV vector could lead to an inhibitory effect on kainate-induced seizures comes from the study of Lin et al., 2003 (Lin et al. (2003) Eur. J. Neurosci. 18:2087-92). In this case, a human galanin gene-AAV vector (serotype 2) was infused into the hippocampal formation bilaterally and implanted intrahippocampal electrodes were used to monitor kainate-induced seizures. This treatment resulted in substantial reduction in the number of seizure episodes as well as ictal activity as compared to empty-Galanin vector infused animals. Subsequent histological analysis showed poor transfection of galanin gene into the hippocampal formation as assessed by clear overexpression of galanin-like immunoreactivity mostly in the hilar and dentate granule cells. These data strengthen the idea that, in the future, neuropeptide gene transfer could be a possible alternative to pharmacological and surgical treatments of epilepsy and other brain diseases.

No studies have been published using viral vectors to induce expression of somatostatin or its receptors (SST1, SST2, SST3, SST4, SST5). Considering the known antiepileptic actions of somatostatin, it is a claim of the present invention that the overexpression via viral vectors in combinations with one or more somatostatin receptors together with virally mediated NPY and/or galanin overexpression be much more effective at treating epilepsy than virally mediated NPY expression alone as described in patent PCT WO 2005/037211 A2. In rodents, increased expression of somatostatin after seizures, a potential compensatory antiepileptic response, is accompanied by decreased receptor binding sites of SST2, SST3, SST4. Thus delivery and expression of somatostatin alone via vectors described in the present application is not likely to be very efficient alone due to potential compensatory somatostatin receptor changes and delivery and expression of one or more somatostatin receptor together with somatostatin should have superior effect compared to somatostatin alone.

In conclusion, according to the present invention, delivery and expression of a combination of nucleic acid sequences encoding NPY and/or one or more of its receptors (Y1, Y2, Y4, Y5, y6), and/or galanin and/or one or more of its receptors (GALR1, GALR2, GALR3) and/or somatostatin and/or one or more of its receptors (SST1, SST2, SST3, SST4, SST5) has a much better effect than delivery and expression of NPY alone as in patent PCT WO 2005/037211 A2 and will be more efficient at treating diseases like epilepsy and psychiatric disorders. The invention is characterised by the following embodiments.

1. Use of one or more expression vectors comprising nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in the preparation of a medicament for treatment of a disorder of the nervous system.

2. Use according to embodiment 1, wherein said disorder of the nervous system is a neurological or a psychiatric disease.

3. Use according to embodiment 1 or 2, wherein said disorder is epilepsy, affective disorder, anxiety disorder or OCD.

4. Use according to embodiment 3, wherein said epilepsy is intractable epilepsy or temporal lobe epilepsy.

5. Use according to embodiment 3, wherein said affective disorder is treatment-resistant or not treatment-resistant depression or bipolar affective disorder.

6. Use according to embodiment 3, wherein said anxiety disorder is panic disorder or generalized anxiety.

7. Use according to any one of embodiments 1-6, wherein said medicament is intended for administration by stereotaxic microinjection.

8. Use according to any one of embodiments 1-7, wherein the one or more expression vectors are viral and/or non-viral expression vectors.

9. Use according to embodiment 8, wherein the one or more of the viral expression vectors are AAV vectors and/or lentivirus vectors and/or HSV vectors.

10. Use according to embodiment 9, wherein the AAV vectors and/or lentivirus vectors and/or HSV vectors are free of both wildtype and helper virus.

11. Use according to embodiment 9, wherein the one or more of the AAV vectors are serotype 2 and/or 5 AAV vectors and/or chimeric serotype AAV vectors.

12. Use according to any one of embodiments 1-11, wherein said nucleic acid sequences encode a combination of amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or derivatives or functional fragments thereof.

13. Use according to any one of embodiments 1-11, wherein said nucleic acid sequences encode amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or amino acid sequences at least 90% homologous to two or more of the following SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56.

14. Use according to any one of embodiments 1-11, wherein said are nucleic acid sequences encode amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or amino acid sequences at least 85% homologous to two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56.

15. Use according to any one of embodiments 1-11, wherein said nucleic acid sequences comprise two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or derivatives or functional fragments thereof.

16. Use according to any one of embodiments 1-11, wherein said nucleic acid sequences comprise two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or nucleic acid sequences at least 90% homologous to two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55.

17. Use according to any one of embodiments 1-11, wherein said nucleic acid sequences comprise two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or nucleic acid sequences at least 85% homologous to two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55.

18. A lentivirus vector and/or AAV vector and/or HSV vector that retain only the replication and packaging signals of lentivirus, AAV or HSV, and that comprise nucleic acid sequences encoding a combination of NPY and/or one or more of its receptors (Y2, Y5), and/or galanin, or derivatives or functional fragments thereof.

19. The lentivirus vector and/or AAV vector and/or HSV vector according to embodiment 18, wherein said nucleic acid sequences comprise nucleic acid sequences of two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or derivatives or functional fragments thereof.

20. The lentivirus vector and/or AAV vector and/or HSV vector according to embodiment 18, wherein said nucleic acid sequences encode amino acid sequences comprising two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or derivatives or functional fragments thereof.

21. A composition comprising a lentivirus vector and/or AAV vector and/or HSV vector according to any one of embodiments 18-20 and a pharmaceutically acceptable carrier.

22. A method for delivering a combination of nucleic acid sequences to mammalian nervous system target cells, wherein said nucleic acid sequences are expressible in the target cells for more than three months, said method comprising administering one or more expression vectors to the target cells, wherein said expression vectors comprise nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof.

23. The method according to embodiment 22, wherein the nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, is expressed in said target cell either constitutively or under regulatable conditions.

24. The method according to embodiment 23, wherein expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in said target cells alters neuronal excitability.

25. The method according to embodiment 23, wherein expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in said target cells reduces neuronal excitability.

26. The method according to embodiment 23, wherein expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in said target cells reduces symptoms associated with neuronal hyperexcitability.

27. The method according to embodiment 22, wherein the expression vectors are viral and/or non-viral expression vectors.

28. The method according to embodiment 27, wherein one or more of the viral expression vectors are AAV vectors and/or lentivirus vectors and/or HSV vectors.

29. The method according to embodiment 28, wherein one or more of the viral expression vectors are AAV vectors and/or lentivirus vectors and/or HSV vectors capable of transducing the target cells and said AAV vectors and/or lentivirus vectors and/or HSV vectors are free of both wildtype and helper virus.

30. The method according to embodiment 29, wherein one or more of the AAV vectors are serotype 2 and/or 5 AAV vectors and/or chimeric serotype AAV vectors.

31. The method according to embodiment 23, wherein nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, is operably linked to inducible regulatory sequences, wherein activation of said inducible regulatory sequences affect transcription of messenger RNA encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, from said nucleic acid sequences.

32. The method according embodiment 31, wherein said inducible regulatory sequences render expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, nervous system-specific or CNS-specific.

33. The method of embodiment 31, wherein expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, is specific to a medial temporal lobe or temporal cortex of the CNS.

34. The method according to embodiment 33, wherein expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, is localized to the hippocampal formation and/or amygdala and/or raphe nuclei and/or periaqueductal gray of the brain stem.

35. The method according to embodiment 33, wherein the expression is neuronal and/or glial specific.

36. The method according to embodiment 22, wherein the target cells are mammalian cells of a mammalian order selected from the group consisting of Primata, Rodenta, Lagomorpha, Carnivora, Arteriodactyla, and Perissodactyla 37. The method according to embodiment 36, wherein the target cells are human cells.

38. The method according to embodiment 22, wherein the target cells are in cell culture.

39. The method according to embodiment 22, wherein the target cells are in a living mammal.

40. The method according to embodiment 39, wherein the vectors are delivered to essentially all nervous system cells of the mammal.

41. The method according to embodiment 39, wherein the vectors are specifically delivered to particular cell types or regions of the nervous system of the mammal.

42. The method according to embodiment 22, wherein said method for delivering nucleic acids encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, to cells of the nervous system to affect expression of a combination of NPY and/or one or more of its receptors (Y1, Y2, Y4, Y5, y6), and/or galanin and/or one or more of its receptors (GALR1, GALR2, GALR3), or derivatives or functional fragments thereof, in cells of the nervous system treats a disorder of the nervous system.

43. The method according to embodiment 42, wherein said disorder of the nervous system is epilepsy, affective disorder, anxiety disorder, or OCD.

44. The method according to embodiment 43, wherein said epilepsy is intractable epilepsy, wherein said affective disorder is treatment-resistant or not treatment-resistant depression or bipolar affective disorder, and wherein said anxiety disorder is panic disorder or generalized anxiety.

45. The method according to embodiment 44, wherein said epilepsy is temporal lobe epilepsy.

46. The method according to embodiment 22, wherein said nucleic acid sequences encoding a combination of NPY and/or one or more of its receptors (Y2, Y5), and/or galanin, or derivatives or functional fragments thereof, are nucleic acid sequences encoding a combination of amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or derivatives or functional fragments thereof.

47. The method according to embodiment 22, wherein said nucleic acid sequences encoding a combination of NPY and/or one or more of its receptors (Y2, Y5), and/or galanin, or derivatives or functional fragments thereof, are nucleic acid sequences encoding amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or amino acid sequences at least 90% homologous to two or more of the following SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56.

48. The method according to embodiment 22, wherein said nucleic acid sequences encoding a combination of NPY and/or one or more of its receptors (Y2, Y5), and/or galanin, or derivatives or functional fragments thereof, are nucleic acid sequences encoding amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or amino acid sequences at least 85% homologous to two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56.

49. The method according to embodiment 22, wherein said nucleic acid sequences encoding a combination of NPY and/or one or more of its receptors (Y2, Y5), and/or galanin, or derivatives or functional fragments thereof, are nucleic acid sequences comprising two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or derivatives or functional fragments thereof.

50. The method according to embodiment 22, wherein said nucleic acid sequences encoding a combination of NPY and/or one or more of its receptors (Y2, Y5), and/or galanin, or derivatives or functional fragments thereof, are nucleic acid sequences comprising two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or nucleic acid sequences at least 90% homologous to two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55.

51. The method according to embodiment 22, wherein said nucleic acid sequences encoding a combination of NPY and/or one or more of its receptors (Y2, Y5), and/or galanin, or derivatives or functional fragments thereof, are nucleic acid sequences comprising two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or nucleic acid sequences at least 85% homologous to two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55.

52. The method according to embodiment 39, wherein said administering is by stereotaxic microinjection.

53. A method for treating a mammal with a neurological or psychiatric disease, said method comprising administering one or more expression vectors to target cells in the mammal, wherein one or more of the said expression vectors comprise nucleic acid sequences encoding a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, and wherein said administering results in expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in said target cells and said expression reduces the symptoms of the neurological or psychiatric disease, thereby treating the mammal with the neurological or psychiatric disease.

54. The method according to embodiment 53, wherein one or more of the expression vectors are viral and/or non-viral expression vectors.

55. The method according to embodiment 54, wherein one or more of the viral expression vectors are AAV vectors and/or lentivirus vectors and/or adenovirus vectors and/or HSV vectors.

56. The method according to embodiment 53, wherein said nucleic acid sequences encoding a combination of NPY and/or one or more of its receptors (Y2, Y5), or derivatives or functional fragments thereof, are nucleic acid sequences encoding amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or derivatives or functional fragments thereof.

57. The method according to embodiment 56, wherein said nucleic acid sequences encoding a combination of NPY and/or one or more of its receptors (Y2, Y5), or derivatives or functional fragments thereof, are nucleic acid sequences encoding amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or amino acid sequences at least 90% homologous to two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56.

58. The method according to embodiment 56, wherein said nucleic acid sequences encoding a combination of NPY and/or one or more of its receptors (Y2, Y5), or derivatives or functional fragments thereof, are nucleic acid sequences encoding amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56, or amino acid sequences at least 85% homologous to two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53, SEQ ID NO: 56.

59. The method according to embodiment 53, wherein said nucleic acid sequences encoding a combination of NPY and/or one or more of its receptors (Y2, Y5), or derivatives or functional fragments thereof, are nucleic acid sequences comprising two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or derivatives or functional fragments thereof.

60. The method according to embodiment 53, wherein said nucleic acid sequences encoding a combination of NPY and/or one or more of its receptors (Y2, Y5), or derivatives or functional fragments thereof, are nucleic acid sequences comprising two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or nucleic acid sequences at least 90% homologous to two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55.

61. The method according to embodiment 53, wherein said nucleic acid sequences encoding a combination of NPY and/or one or more of its receptors (Y2, Y5), or derivatives or functional fragments thereof, are nucleic acid sequences comprising two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55, or nucleic acid sequences at least 85% homologous to two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO: 25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54, SEQ ID NO: 55.

62. The method according to embodiment 53, wherein said neurological disease is epilepsy, and wherein said psychiatric disease is affective disorder, anxiety disorder, or OCD.

63. The method according to embodiment 53, wherein said neurological disease is intractable epilepsy, wherein said psychiatric disease is treatment-resistant or not treatment-resistant depression or bipolar affective disorder, wherein said psychiatric disease is panic disorder or generalized anxiety.

64. The method according to embodiment 53, wherein said neurological disease is temporal lobe epilepsy.

65. The method according to embodiment 53, wherein said administering is by stereotaxic microinjection.

66. The method according to embodiment 53, wherein said administering is by stereotaxic microinjection to a medial temporal lobe or temporal cortex and/or brain stem of the CNS.

67. The method according to embodiment 66, wherein said administering to the medial temporal lobe or temporal cortex is localized to the hippocampal formation and/or amygdala and wherein said administering to the brain stem is localized to the raphe nuclei and/or periaqueductal gray.

68. A method for delivering a combination of nucleic acid sequences to mammalian nervous system target cells, wherein said nucleic acid sequences are expressible in the target cells for more than three months, said method comprising administering one or more lentivirus vectors and/or AAV vectors, and/or HSV vectors to the target cells, wherein said vectors transduce the target cells; and wherein said vectors comprise vectors of embodiment 18, and are free of both wildtype and helper virus.

69. A method for delivering a combination of nucleic acid sequences to mammalian nervous system target cells, wherein said nucleic acid sequences are expressible in the target cells for more than three months, said method comprising administering a composition according to embodiment 21 one or more lentivirus vectors and/or AAV vectors, and/or HSV vectors to the target cells, wherein said vectors transduce the target cells; and wherein said vectors comprise vectors according to embodiment 18, and are free of both wildtype and helper virus.

70. A method for treating a mammal with a neurological or psychiatric disease, said method comprising administering one or more lentivirus vectors and/or AAV vectors, and/or HSV vectors to target cells in the mammal, wherein said lentivirus vectors and/or AAV vectors, and/or HSV vectors comprise lentivirus vectors and/or AAV vectors, and/or HSV vectors according to embodiment 18, and wherein said administering results in expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in said target cells and said expression reduces the symptoms of the neurological disease or psychiatric disease, thereby treating the mammal with the neurological or psychiatric disease.

71. A method for treating a mammal with a neurological or psychiatric disease, said method comprising administering a composition of embodiment 21 to the target cells, said composition comprising one or more lentivirus vectors and/or AAV vectors, and/or HSV vectors capable of transducing the target cells and wherein said administering results in expression of a combination of NPY and/or one or more of its receptors (Y1, Y2, Y4, Y5, y6), and/or galanin and/or one or more of its receptors (GALR1, GALR2, GALR3), and/or somatostatin and/or one or more of its receptors (SST1, SST2, SST3, SST4, SST5), or derivatives or functional fragments thereof, in said target cells and said expression reduces the symptoms of the neurological disease or psychiatric disease, thereby treating the mammal with the neurological or psychiatric disease.

EXAMPLES

The main rationale for the present patent application is the treatment of epilepsy and psychiatric disease by strengthening signalling for the neuropeptide ligands NPY, galanin, and/or somatostatin in the CNS by overexpressing the neuropeptides and their corresponding receptors in different combinations at the same time. Moreover, this approach will also minimize the risk for downregulation of the receptors due to increased neuropeptide ligand effect.

We have now produced lentiviral vectors for mouse NPY, Y2, and Y5 receptor genes. We have also acquired commercially AAV serotype vectors expressing NPY, Y2, and galanin. We will transfect mouse and rat hippocampus or other brain regions uni- or bilaterally by a combination of these genes: e.g., NPY+Y2 or NPY+Y5 or NPY+Y2+Y5 or NPY+galanin.

The experiments are or have been performed as follows:

Example I

Traditional Electrical Kindling in Mice

Adult mice are implanted with stimulation electrodes in the left hippocampus and kindling is performed according to the traditional protocol, one stimulation per day. Once mice are fully kindled (after about 3-4 weeks), we test the threshold for the induction of generalized seizures. After the last kindling stimulation, i.e., threshold detection, mice are infused by combinations of the viral vectors (see above) into the hippocampus bilaterally. Four to five weeks later, the threshold for seizure induction is tested and, subsequently, five kindling stimulations are delivered by traditional method. Seizure severity, latency to behavioural seizures, afterdischarge duration and secondary afterdischarge duration and number is analyzed and compared to pre-transfection values. A control group of mice with the infusion of viral vectors lacking corresponding genes are used as additional controls. Another control group consists of a single viral vector infusion for NPY gene only.

Expected Results I

Figure 2:
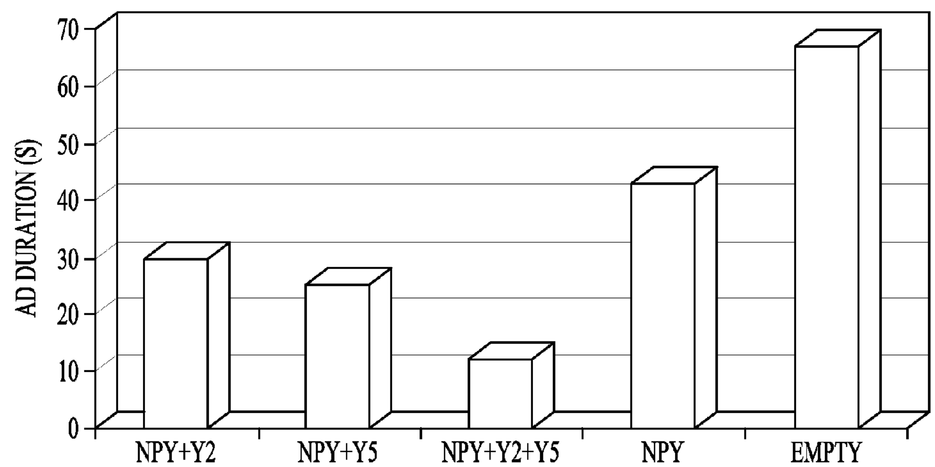
FIG. 2 depicts that mice kindled electrically by traditional one-stimulation-per-day protocol after viral vector infusion will decrease duration of the afterdischarges (AD) and seizures.
Figure 3:
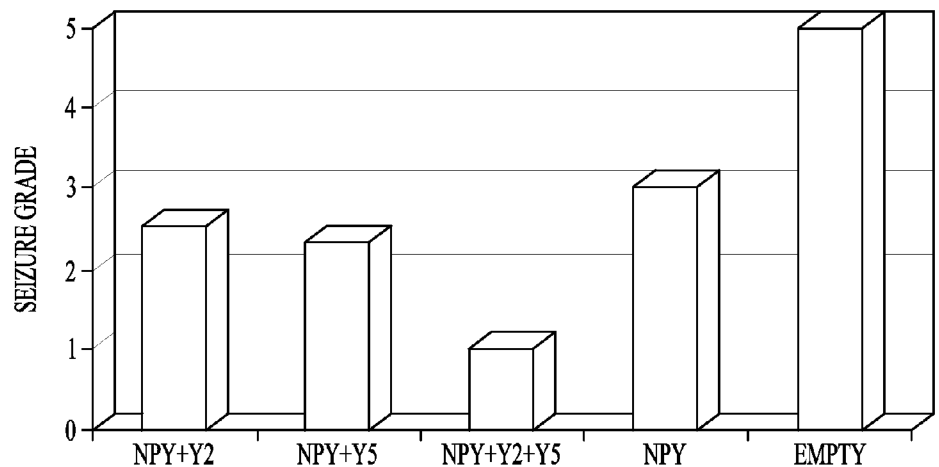
FIG. 3 depicts that mice kindled electrically by traditional one-stimulation-per-day protocol after viral vector infusion will decrease severity of the afterdischarges and seizures.
Figure 4:
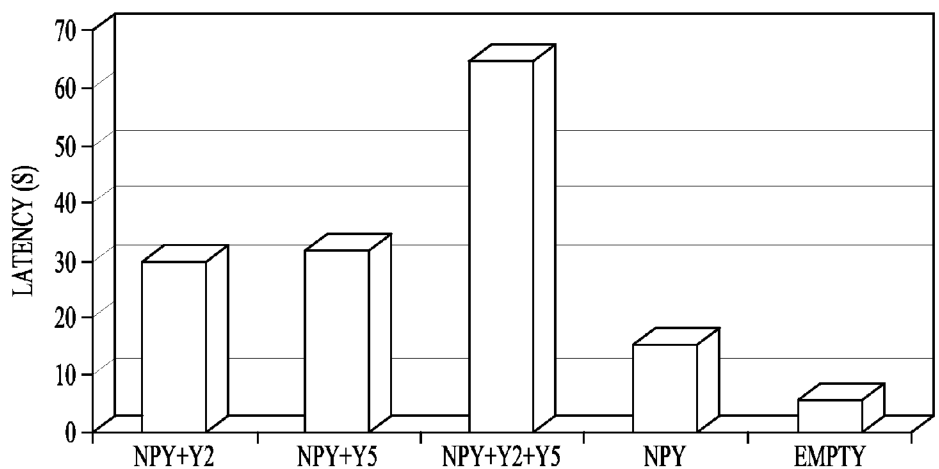
FIG. 4 depicts that mice kindled electrically by traditional one-stimulation-per-day protocol after viral vector infusion will increase latency to behavioural seizures.

We expect that mice after viral vector infusion will increase the threshold for seizure induction (FIG. 1), decrease duration (FIG. 2) and severity (FIG. 3) of the afterdischarges and seizures, respectively, as well as increase latency to behavioural seizures (FIG. 4). The effect will be more pronounced as compared to only NPY viral vectors infusions. Moreover, the control group of mice receiving viral vector lacking the corresponding genes will not exhibit these changes.

Example II

Kainate Seizures in Mice

In the next series of experiments, these combinations of the viral vectors are tested in the kainate-induced status epilepticus (SE) model. The vectors are infused into the hippocampus uni- or bilaterally, and, after 4-5 weeks, kainate (20-40 mg/kg) is injected intraperitoneally and the mice are observed for motor seizures, seizure severity and duration, latency to seizures and mortality. These parameters are compared to the control group of mice infused with NPY only or empty viral vectors.

Expected Results II

Figure 5:
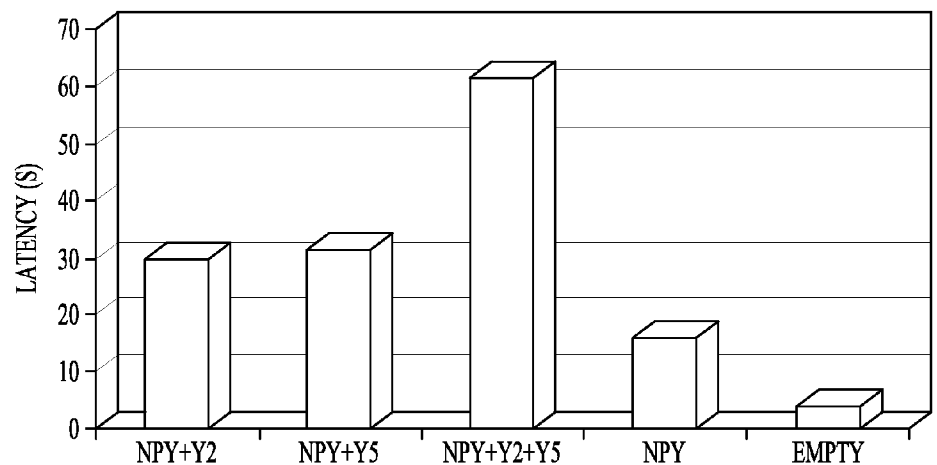
FIG. 5 depicts that mice infused with NPY+Y2, NPY+Y5 and NPY+Y2+Y5 viral vectors will display a longer latency to kainate-induced seizures.
Figure 6:
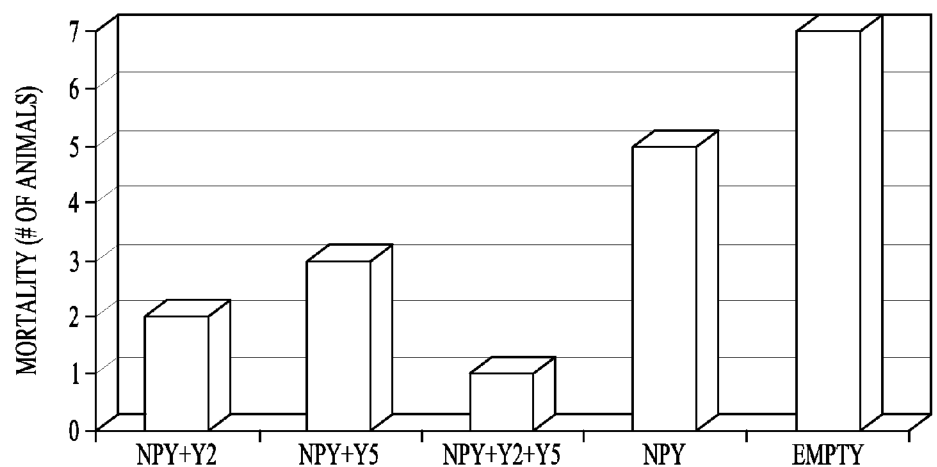
FIG. 6 depicts that mice infused with NPY+Y2, NPY+Y5 and NPY+Y2+Y5 viral vectors will display lower mortality during kainate-induced seizures.

We expect that mice infused with NPY+Y2, NPY+Y5 and NPY+Y2+Y5 viral vectors will display a lower number of motor seizures, longer latency to seizures (FIG. 5), lower mortality (FIG. 6), and decreased seizure severity as compared to NPY only or empty viral vector-infused mice.

Example III

Afterdischarge Thresholds in Seizure-Naïve and Epileptic Rats

Adult male Sprague Dawley rats (B&K, Sweden), weighing 250 g at the beginning of the experiment were anesthetized with intraperitoneal injection of Ketamine (80 mg/kg)-Xylazine (15 mg/kg), and fixed into a stereotaxic frame. Before and after surgery, the local analgesic Marcain was applied locally around the wound. The rats were housed in a 12-hour light/dark cycle with free access to food and water. All experiments were performed according to the guidelines of Sweden's Animal Welfare Agency and approved by the local Ethical Committee for Experimental Animals. The following viral vectors were bilaterally injected into the dorsal and ventral hippocampus: 1) rAAV-NPY (GeneDetect, Auckland, New Zealand), serotype (capsid): M. Prepro-NPY cDNA was subcloned into an expression cassette consisting of the rat NSE promoter, woodchuck post-translational regulatory element (WPRE), and a bovine growth hormone poly (A) signal (titer: $1.2\times10^{12}$ genomic particles/ml) (Richichi et al. (2004) J. Neurosci. 24:3051-9); 2) rAAV-galanin, serotype 2. Rat galanin cDNA was subcloned into an expression cassette also containing the fibronectin secretory signal sequence; gene expression was driven by a cytomegalovirus promotor, (titer: $1\times10^{12}$ genomic particles/ml) (Haberman et al. (2003) Nature Med. 9:1076-80); 3) combination of rAAV-NPY+rAAV-galanin as above; 4) combination of rAAV-NPY+rAAV-Y2. The Y2 receptor vector was identical to 1) except that the cDNA for the Y2 NPY receptor was subcloned into the expression cassette in place of NPY (GeneDetect, Auckland, New Zealand) 5) Control vector: vector as in 1), but without transgene ("empty"). A volume of 2 μl viral vector suspension was injected at each location in 10 min (0.1 μl/30 sec) using a thin glass pipette, and the pipette was left in place for additional 3 min after injection to allow for the spread of virus and prevent its backflow through the injection track upon retraction of the pipette. Coordinates for viral vector injection (from bregma, midline, dura) was: Dorsal hippocampus: AP −3.3, ML ±1.8, DV −2.6 mm; ventral hippocampus: AP −4.8, ML ±5.2, DV −6.4 and −3.8 mm.

Two weeks following viral vector injection the animals were anesthetised as during virus injection and a bipolar stainless-steel stimulating/recording electrode (Plastics One, Roanoke, Va., USA) was implanted stereotactically in the ventral hippocampus (AP −4.8 mm, ML ±5.2 mm, DV −6.5 mm) and fixed with dental cement as previously described (Schlifke et al. (2007) Molecular Therapy). After recovering for at least one week, the animals were stimulated electrically (1 msec duration square-wave pulses of 100 Hz delivered for 1 second) to determine the threshold for eliciting hippocampal epileptiform afterdischarges. Starting at 10 μA, the current intensity was increased in 10 μA steps every 5 min until a focal epileptiform afterdischarge of at least 5 sec duration was detected by electroencephalographic (EEG) recording. The primary and secondary afterdischarge durations were determined. The experimenter was blinded to the group identity of the individual animals when eliciting and evaluating afterdischarges.

Subsequently, the animals were subjected to a traditional rapid kindling protocol that produces a chronic epileptic condition (Kopp et al. (1999) Mol. Brain Res. 72:17-29; Schlifke et al. (2007) Molecular Therapy). Four weeks later (=seven weeks after injection of viral vectors), the afterdischarge threshold and afterdischarge durations were re-determined in the epileptic animals using the same stimulation parameters as for initial threshold determination.

Results III

Figure 7:
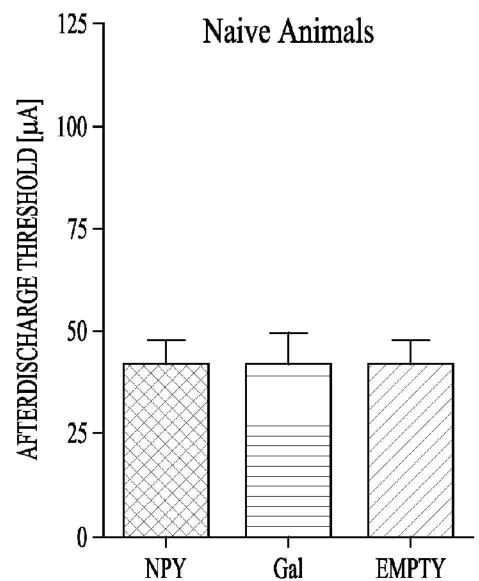
FIG. 7 depicts that infusion of single NPY AAV viral vector (n=12) or single galanin AAV viral vector (n=10) into the hippocampus of seizure-naïve rats did not significantly change the threshold for induction of epileptiform afterdischarges as compared to empty AAV vector (n=9), and, consequently, the groups were pooled into a combined control group (=NPY+galanin+empty vectors) for further analysis (see FIG. 8).
Figure 8:
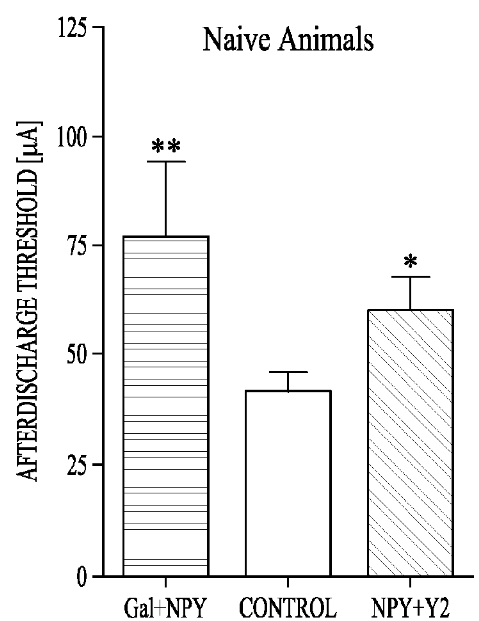
FIG. 8 depicts that seizure-naïve rats infused with a combination of NPY+galanin (n=12) or a combination of NPY+Y2 receptor (n=8) AAV viral vectors into the hippocampus three weeks later displayed increased threshold for seizure induction as compared to the control group (n=31). Thus, while single NPY vector infusion was without effect, only NPY vector in a combination with either galanin or Y2 receptor viral vector exerted significant inhibitory effect on seizure threshold. *P<0.05, **P<0.01 vs. control group; Student's t-test.

First we analysed the differences in afterdischarge induction threshold between AAV-NPY, AAV-galanin and AAV-empty vectors in seizure-naïve animals. This analysis showed that there was no difference in the afterdischarge threshold between any of these groups (FIG. 7, t-test). Therefore, these three groups were pooled together into a single control group and analysed against the vector combination groups: AAV-NPY+AAV-galanin and AAV-NPY+AAV-Y2. Both vector combination groups showed significantly higher afterdischarge thresholds as compared to the control group (FIG. 8). These data suggested that in seizure-naïve animals a combination of transgene NPY either with transgene galanin or transgene Y2 receptor has seizure preventing effect and decrease the probability of seizure occurrence by increasing the threshold for seizures. One could argue that even small effects on seizure-induction threshold will have pronounced consequences for dampening epileptic syndromes and seizure episodes.

Figure 9:
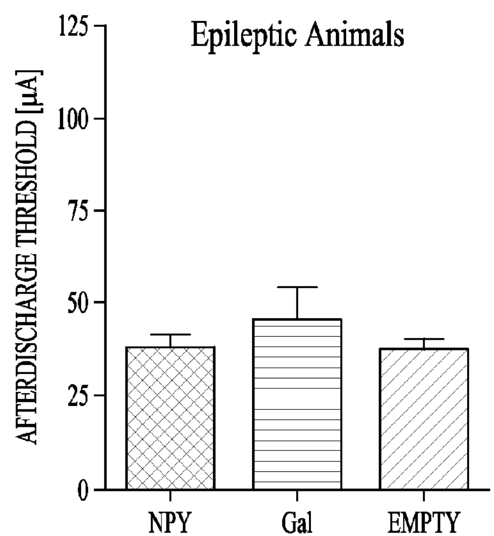
FIG. 9 depicts afterdischarge thresholds of rats kindled electrically at least four weeks earlier, a procedure that is known to result in a chronic epileptic condition (i.e., epileptic animals). Like in seizure-naïve animals, infusion of single NPY viral vector (n=12) or single galanin AAV viral vector (n=9) into the hippocampus did not significantly change the threshold for induction of epileptiform afterdischarges as compared to empty viral vector (n=7), and, consequently, the groups were pooled for further analysis (see FIG. 10).
Figure 10:
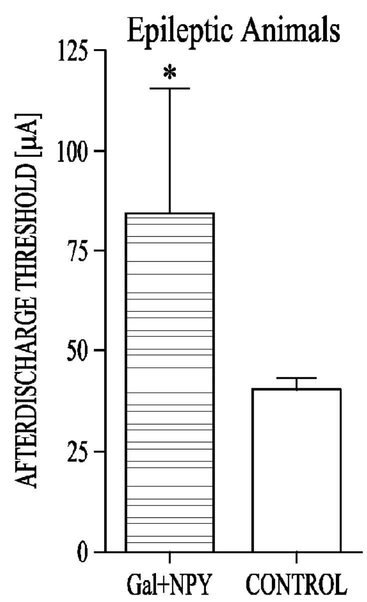
FIG. 10 depicts that epileptic rats kindled electrically at least four weeks earlier that were infused with a combination of NPY+galanin AAV viral vectors into the hippocampus displayed increased threshold for seizure induction as compared to the control group (=empty+NPY+galanin vectors; n=28). Thus, while single NPY vector infusion was without effect, only NPY vector in a combination with galanin viral vector exerted significant inhibitory effect on seizure threshold. The combination NPY+Y2 was not tested in epileptic animals, but is expected to have the same inhibitory effect as in seizure-naïve rats. *P<0.05 vs. control group; Student's t-test.

We further asked whether such an effect of combination gene therapy would have a beneficial effect even in the animals already made epileptic by kindling. Once the animals were fully kindled using rapid kindling protocol, we again tested the seizure induction threshold in these groups. Similar to what we observed in seizure-naïve animals, single AAV-NPY or single AAV-galanin did not differ significantly from empty vector controls in these epileptic animals, and the groups were consequently pooled (FIG. 9). In contrast, like in seizure-naïve rats, we found that, in epileptic rats, the combination of transgene NPY with galanin (AAV-NPY+AAV-galanin) significantly increased the afterdischarge threshold as compared to the control group (FIG. 10). The combination NPY+Y2 was not tested in epileptic animals.

Figure 11A:
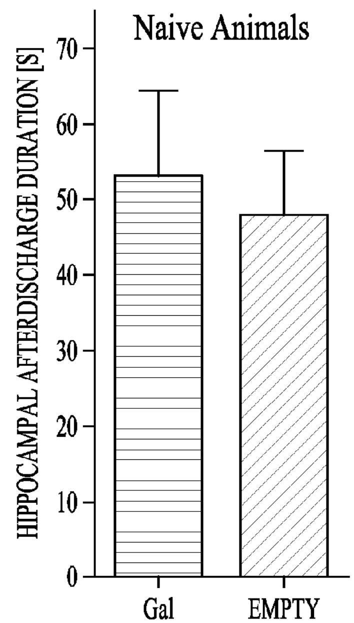
FIG. 11 depicts durations of hippocampal epileptiform afterdischarges (primary+secondary) at the threshold stimulation current in seizure-naïve rats three weeks after infusion of AAV viral vectors into the hippocampus. A. Infusion of galanin AAV viral vector (n=10) did not significantly change the afterdischarge duration as compared to empty AAV vector (n=9), and, consequently, the groups were pooled into a combined control group (=galanin+empty vectors) for further analysis. B. Both intrahipppocampal infusion of combined Galanin+NPY (n=12) and single NPY viral vector (n=12) significantly reduced epileptiform afterdischarges as compared to the control group (=empty+galanin vectors; n=19). Combined NPY+Y2 viral vector also appeared to reduce afterdischarge durations, but did not reach statistical significance. *P<0.05 vs. control group; Student's t-test.
Figure 11B:
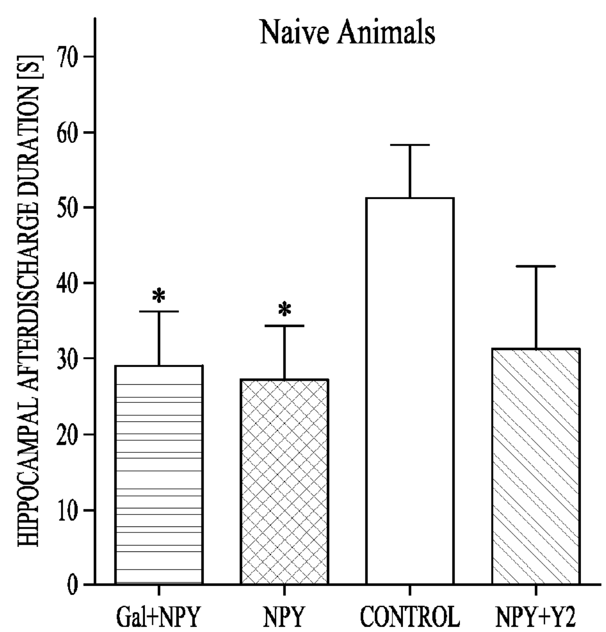
Figure 12A:
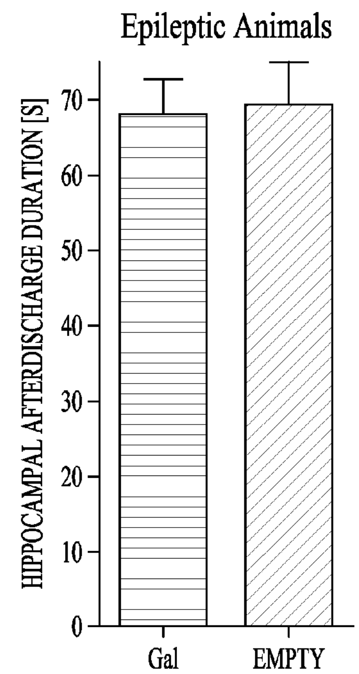
FIG. 12 depicts durations of hippocampal epileptiform afterdischarges (primary+secondary) at the threshold stimulation current of rats kindled electrically at least four weeks earlier, a procedure that is known to result in a chronic epileptic condition (i.e., epileptic animals). A. Like in seizure-naïve animals, infusion of single galanin AAV viral vector (n=9) into the hippocampus did not significantly change the afterdischarge duration as compared to empty vector (n=7). Consequently, the groups were pooled into a combined control group (=galanin+empty vectors) for further analysis. B. Both intrahipppocampal infusion of combined galanin+NPY (n=12) and single NPY viral vector (n=12) significantly reduced epileptiform afterdischarges as compared to the control group (=empty+galanin vectors; n=16). This effect was even more pronounced than in seizure-naïve rats. ***P<0.001 vs. control group; Student's t-test.
Figure 12B:
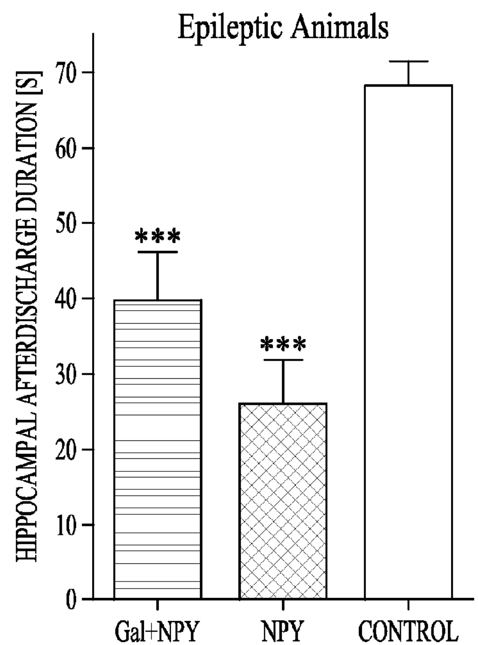
Figure 13:
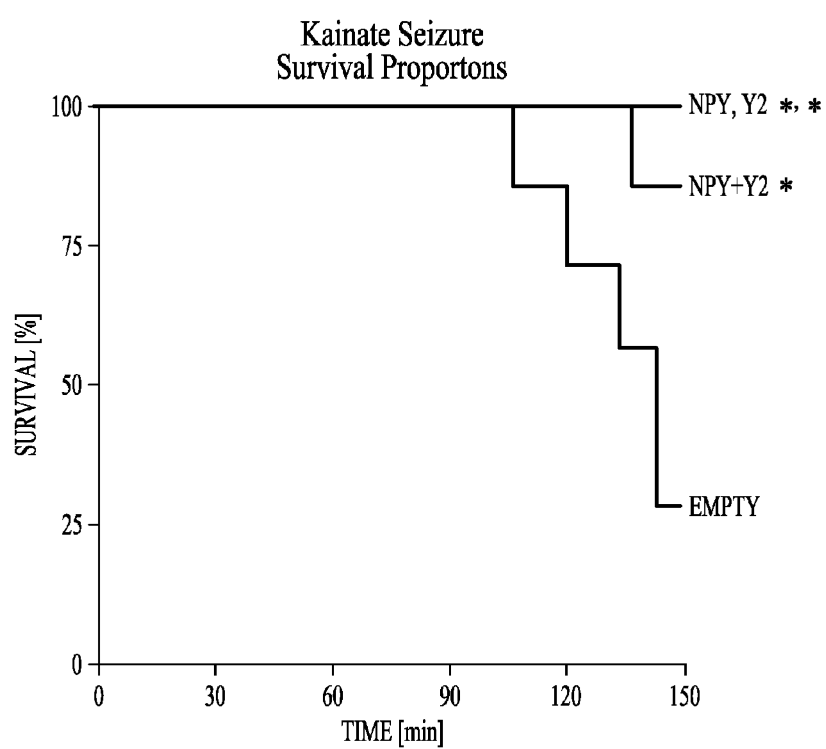
FIG. 13 depicts Kaplan-Meyer survival curves of animals treated with intraperitoneal injection of the convulsant kainate rats at three weeks after intrahippocampal infusion of NPY (n=7), Y2 (n=6), or combined NPY+Y2 (n=7) AAV viral vectors. All three types of vectors reduced seizure severity as compared to empty viral vector infusion (n=7) as revealed by significantly higher kainate seizure survival proportions during a 150 min observation period. *P<0.05 vs. empty vector; Logrank test.

Further analysis revealed that in seizure-naïve animals AAV-galanin did not differ significantly from empty vector, and, consequently, the groups were pooled for further analysis (FIG. 11A). However, AAV-NPY vector injection significantly decreased the duration of hippocampal afterdischarges as compared to the control group (FIG. 11B). The combination of transgene NPY with transgene galanin (AAV-NPY+AAV-galanin group) had a similar inhibitory effect on afterdischarge duration as the transgene NPY alone (AAV-NPY group; FIG. 11B) and the combination of transgene NPY with transgene Y2 (AAV-NPY+AAV-Y2 group) appeared to have the same effect but did not reach statistical significance (FIG. 11B). The same picture was observed in epileptic rats (FIG. 12) with the galanin+NPY viral vector combination showing similar inhibitory effect on afterdischarge duration as single NPY vector. These data indicated that the combination approach did not have any additional beneficial effect, as compared to single transgene NPY.

Taken together the results of this example indicate that the combination of transgene NPY either with transgene galanin or the Y2 receptor prevents seizure induction by increasing the threshold, but once the seizures are induced, transgene NPY alone is effectively shortening afterdischarge duration, and further addition of either transgene galanin or Y2 has no additional effect. However, since the prevention of seizure occurrence is clearly an important goal in treatment of epilepsy, the combination is clearly preferable to the single NPY transgene approach that was patented previously (PCT WO 2005/037211 A2). These results are quite unexpected based on all previous knowledge on the action of neuropeptides on seizure activity, and provide a good example of beneficial effects of combined gene therapy approach in epilepsy models.

Example IV

Kainate Seizures in Rats

Adult male Wistar rats (B&K, Sweden), weighing 250 g at the beginning of the experiment were housed in a 12-hour light/dark cycle with free access to food and water. The experiments were performed according to the guidelines of Sweden's Animal Welfare Agency and approved by the local Ethical Committee for Experimental Animals. After being anesthetized as in example III and fixed into a stereotaxic frame, the following viral vectors were bilaterally injected into the dorsal and ventral hippocampus: 1) rAAV-NPY as in example III; 2) rAAV-Y2 as in example III, 3) combination of rAAV-NPY+rAAV-Y2 as in example III, and 4) empty rAAV vector as in example III. Injection procedure and coordinates were the same as in example III.

After recovering for at least three weeks, the rats were injected subcutaneously in the neck region with the status epilepticus-inducing convulsant kainate (#K-0250, Sigma; 10 mg/kg diluted in 0.9% isotonic saline; pH 7.4)(Woldbye et al. (1997) Nature Med. 3:761-4) and the animals were observed for 150 min. The experimenter was blinded to the group identity of the individual animals when injecting and evaluating the rats.

Results IV

To further evaluate the effects of combination of transgene NPY with transgene Y2 receptor on seizures, we used subcutaneous kainate injection model. In this model, kainate-induced seizures led to high mortality of empty vector control animals due to severity of seizures (5 out of 7 rats). This was almost completely prevented in animals with intrahippocampal AAV-NPY+AAV-Y2 injections (only 1 out of 7). However, transgene NPY or Y2 alone had similar preventive effect on mortality of kainate-treated animals (0 out of 7 or 0 out 6 animals, respectively). As shown in FIG. 75, survival statistics (logrank tests) showed that the NPY+Y2 combination as well as single NPY and single Y2 vector had a significant inhibitory effect on death latency. These data support our findings in example III, and indicate that once seizures occur, the combination approach does not seem to have any additional beneficial effect as compared to a single gene therapy. On the other hand, these adata also suggest that the combination of transgene NPY and Y2 has no detrimental effect on survival of the animals after kainate treatment, and when seizures do still occur, this combination is as safe as single transgene NPY treatment.

Example V

Using the same protocols as in examples III and IV, the following AAV viral vector gene combinations are infused bilaterally into the hippocampus, piriform cortex, and/or amygdala of rodents: NPY+Y2+Y5+Y1, NPY+Y1+Y5, NPY+Y1, NPY+somatostatin, galanin+somatostatin, NPY+galanin+somatostatin, NPY+Y2+galanin, NPY+Y1+Y2+Y5+galanin, NPY+Y1+Y5+galanin, NPY+Y2+Y5+galanin, NPY+Y2+galanin+somatostatin, NPY+Y2+Y5+galanin+GALR1+GALR2+somatostatin+SST2, NPY+Y2+Y5+galanin+GALR1+GALR2+somatostatin+SST1+SST2, NPY+Y2+galanin+GALR2+somatostatin+SST2, NPY+Y2+Y1+galanin+GALR2+somatostatin+SST2, somatostatin+SSTR1+SST2, NPY+Y2+Y5+Y1+galanin+GALR2+somatostatin+SSTR2, NPY+Y2+Y5+Y1+galanin+GALR1+somatostatin+SST2, NPY+Y2+Y5+Y1+galanin+GALR1+GALR2+somatostatin+SST2, NPY+Y2+Y5+Y1+galanin+GALR1+GALR2+somatostatin+SST2+SST4, NPY+Y2+Y5+Y1+galanin+GALR1+GALR2+somatostatin+SST1+SST2+SST4. Infusion of empty vector and single gene vectors serve as control groups. In addition, combinations involving y6 receptors are also tested. Although the y6 receptor is believed to be non-functional in humans, this receptor could be functional expressed in combination with other NPY receptors. Combinations involving other neuropeptide receptor genes described in this patent above are also tested.

Expected Results V

As shown in examples III and IV with the combinations NPY+galanin and NPY+Y2, we expect that the combinations of example V will result in a long-term increase in afterdischarge threshold of higher magnitude than achieved with single vector alone, e.g., NPY AAV. A reduction in seizure severity and afterdischarge durations is also expected.

Example VI

Forced Swim Test, Open Field, and Elevated Plus Maze in Rats

Adult male Wistar rats (B&K, Sweden), weighing 250 g at the beginning of the experiment are housed in a 12-hour light/dark cycle with free access to food and water. The experiments are performed according to the guidelines of Sweden's Animal Welfare Agency and approved by the local Ethical Committee for Experimental Animals. After being anesthetized as in example III and fixed into a stereotaxic frame, the following viral vectors are bilaterally injected into the dorsal and ventral hippocampus and or amygdala: 1) rAAV-NPY as in example III; 2) rAAV-Y1 (GeneDetect, Auckland, New Zealand), serotype (capsid): f. Y1 receptor cDNA is subcloned into an expression cassette consisting of the rat NSE promoter, woodchuck post-translational regulatory element (WPRE), and a bovine growth hormone poly(A) signal (titer: $10^{12}$ genomic particles/ml); 3) combination of rAAV-NPY+rAAV-Y1; 4) rAAV-galanin (GeneDetect, Auckland, New Zealand), serotype (capsid): ½. Galanin cDNA is subcloned into an expression cassette consisting of the rat NSE promoter, woodchuck post-translational regulatory element (WPRE), and a bovine growth hormone poly(A) signal (titer: $10^{12}$ genomic particles/ml); 5) combination of rAAV-NPY+rAAV-galanin; 6) Combination of rAAV-NPY+rAAV-Y1+rAAV-galanin; 7) rAAV-somatostatin (GeneDetect, Auckland, New Zealand), serotype (capsid): ½. Somatostatin cDNA is subcloned into an expression cassette consisting of the rat NSE promoter, woodchuck post-translational regulatory element (WPRE), and a bovine growth hormone poly(A) signal (titer: $10^{12}$ genomic particles/ml); 8) combination of rAAV-NPY+rAAV-galanin+rAAV-somatostatin; 9) combination of rAAV-NPY+rAAV-Y1+rAAV-galanin+rAAV-somatostatin; 10) rAAV-Y5 (GeneDetect, Auckland, New Zealand), serotype (capsid): ½. Y5 receptor cDNA is subcloned into an expression cassette consisting of the rat NSE promoter, woodchuck post-translational regulatory element (WPRE), and a bovine growth hormone poly(A) signal (titer: $10^{12}$ genomic particles/ml); 11) combination of rAAV-NPY+rAAV-Y1+rAAV-Y5; 12) combination of rAAV-NPY+rAAV-Y1+rAAV-Y5+rAAV-galanin; 13) empty rAAV vector as in example III. Injection procedure and hippocampal coordinates are the same as in example III, coordinates of amygdala (AP −2.7 mm, ML ±5.0 mm, DV −7.5 mm) and piriform cortex (AP −2.7 mm, ML ±6.3 mm, DV −7.3 mm).

After recovering for at least three weeks, animals are subjected to open field testing (Sorensen et al. (2004) J. Neurosci. Res. 77:723-9) to determine a potential anxiolytic effect of vector treatment. Testing is conducted between 10:00 AM and 5:00 PM. After being habituated to the open field room for 1 hr, the rats are placed singly into the center of an open field (100×100×29 cm) illuminated indirectly by four 60 W white light bulbs, one in each corner of the room. The animals are allowed to explore the apparatus for 15 min. Activity is recorded and analyzed with EthoVision software. The open field is divided into a quadratic center (70×70 cm) and a rim (15 cm wide). The percentage time spent in the open field center or the rest of the open field is determined blindly as to the viral vector injected. An increased time spent in the center is believed to reflect an anxiolytic-like effect.

One week later, the same animals are subjected to elevated plus maze testing (Sorensen et al. (2004) J. Neurosci. Res. 77:723-9) also to determine a potential anxiolytic effect of vector treatment. The plus maze consists of two open (44×10 cm) and two enclosed (44×10×29 cm) arms that extend from a central open platform (10×10 cm). It is made of black-painted wood. The plus maze is mounted on a steel base that elevates it 100 cm above the floor. The animals are placed individually on the central platform of the plus maze facing an open arm, and allowed to explore the plus maze for 10 min. Before each test, the maze is cleaned with ethanol (95% w/v). Movement of the animals is recorded via a camera in the ceiling above the maze and analyzed using EthoVision Software (version 2.3; Noldus, The Netherlands). The percentage of open arm entries [open arm/(open+closed arm) entries] and percentage time in open arms [time in open arms/(open+closed arms)] are determined blindly as to the viral vector injected. Both of these parameters are indicators of anxiolytic-like activity.

One week later, the same animals are subjected to the forced swim test to determine a potential anti-depressant-like effect of vector treatment. In this animal model of depression it appears that the immobility observed in the water may reflect a state of despair in the animal. When rats are forced to swim in a restricted space they are rapidly ceasing escape and become immobile. This immobility is reduced by many anti-depressive drugs (i.e. fluoxetine, imipramine), which suggests that the immobile behaviour may reflect a state of lowered mood in the animal. The immobility should either be prevented or reduced by administration of anti-depressive drugs. The rats are individually placed into glass cylinders (diameter: 19 cm) containing 28 cm of water, maintained at 25° C. After a 15 min pre-test (which is recorded and measured) the rats are removed, dried and returned to their home cages. 24 hours later they are replaced in the water and the total duration of immobility during a 5 min. period is recorded and measured. The rats are judged to be immobile when they float in an upright position, only making small movements to keep the head above water. At the end of the experiment the rats are decapitated and the brains are quickly frozen in isopentane until further processing (gene expression, functional binding and receptor binding).

Expected Results VI

We expect that viral vector combinations tested will result in an anxiolytic-like effect in both the open field and elevated plus maze of a higher magnitude than single vector alone. Thus a recent manuscript showed that intra-amygdala administration of a Sindbis viral vector containing NPY cDNA alone has anxiolytic-like effect in the open field test (Thorsell et al. (2007) Brain 130:1330-7). This will suggest that treatment of anxiety disorders with combination of viral vectors described in this patent could be beneficial.

We also expect that the tested viral combinations will show an anti-depressant-like effect of higher magnitude than single vector alone in the forced swim test. This will indicate that the combination viral vector approach could be used to treat depression in the future.

Example VII

Using the same protocols as in example VI, the following AAV viral vector gene combinations are infused bilaterally into the hippocampus, piriform cortex, and/or amygdala of rodents: NPY+Y2+Y5+Y1, NPY+somatostatin, galanin+somatostatin, NPY+galanin+somatostatin, NPY+Y2+galanin, NPY+Y1+Y2+Y5+galanin, NPY+Y2+Y5+galanin, NPY+Y2+galanin+somatostatin, NPY+Y2+Y5+galanin+GALR1+GALR2+somatostatin+SST2, NPY+Y2+Y5+galanin+GALR1+GALR2+somatostatin+SST1+SST2, NPY+Y2+galanin+GALR2+somatostatin+SST2, NPY+Y2+Y1+galanin+GALR2+somatostatin+SST2, somatostatin+SST1+SST2, NPY+Y2+Y5+Y1+galanin+GALR2+somatostatin+SST2, NPY+Y2+Y5+Y1+galanin+GALR1+somatostatin+SST2, NPY+Y2+Y5+Y1+galanin+GALR1+GALR2+somatostatin+SST2, NPY+Y2+Y5+Y1+galanin+GALR1+GALR2+somatostatin+SST2+SST4. Infusion of empty vector and single gene vectors serve as control groups. In addition, combinations involving y6 receptors are also tested. Combinations involving other neuropeptide receptor genes described in this patent above are also tested.

Expected Results VII

We expect that the combinations of example VII will result in an anxiolytic-like effect and an anti-depressant-like effect of higher magnitude than achieved with single vector alone, e.g., NPY AAV.

In addition to these examples, overexpression of the corresponding genes in transfected animals is analyzed using immunocytochemistry, in situ hybridization for mRNA, quantitative PCR, as well as traditional NPY receptor binding and NPY-stimulated [35S] GTPgammaS functional binding for all ligands and receptors in brains from different groups of mice and rats. This analysis will provide us with the knowledge of the overexpression pattern and spread of different genes and their products in mouse and rat hippocampus, as well as other regions. Moreover, we will test for how long expression of different genes will last by taking animals at different time points after transfection. Of particular interest will be to compare downregulation of the NPY receptors in NPY only transfected animals as compared to NPY and their receptor-transfected animals.

These data will provide the proof-of-principle of our claim that using viral vectors to induce overexpression of a combination of neuropeptide ligand genes and genes for their corresponding receptors leads to more pronounced suppression of epileptic seizures as compared to one ligand only. Since epileptic seizures represent the maximum of excitatory activity a brain can experience, our results from epilepsy experiments should be transferable to other neuropsychiatric disorders where a long-term reduction in excitation in selected brain regions is desirable, i.e., anxiety disorders, depression, and OCD.

Table I below shows the correspondence between SEQ ID NO and sequence description.

TABLE I

| Sequence description | SEQ ID NO: |
|---|---|
| Nucleic acid sequence of human NPY | SEQ ID NO: 1 |
| Nucleic acid sequence of human NPY (CDS) | SEQ ID NO: 2 |
| Amino acid sequence of human NPY | SEQ ID NO: 3 |
| Nucleic acid sequence of Rhesus monkey (*Macaca mulatta*) NPY | SEQ ID NO: 4 |
| Nucleic acid sequence of Rhesus monkey (*Macaca mulatta*) NPY (CDS) | SEQ ID NO: 5 |
| Amino acid sequence of Rhesus monkey (*Macaca mulatta*) NPY | SEQ ID NO: 6 |
| Nucleic acid sequence of house mouse (*Mus musculus*) NPY | SEQ ID NO: 7 |
| Nucleic acid sequence of house mouse (*Mus musculus*) NPY (CDS) | SEQ ID NO: 8 |
| Amino acid sequence of house mouse (*Mus musculus*) NPY | SEQ ID NO: 9 |
| Nucleic acid sequence of Norway rat (*Rattus norvegicus*) NPY | SEQ ID NO: 10 |
| Nucleic acid sequence of Norway rat (*Rattus norvegicus*) NPY (CDS) | SEQ ID NO: 11 |
| Amino acid sequence of Norway rat (*Rattus norvegicus*) NPY | SEQ ID NO: 12 |
| Nucleic acid sequence of human Y1 receptor | SEQ ID NO: 13 |
| Nucleic acid sequence of human Y1 receptor (CDS) | SEQ ID NO: 14 |
| Amino acid sequence of human Y1 receptor | SEQ ID NO: 15 |
| Nucleic acid sequence of Rhesus monkey (*Macaca mulatta*) Y1 receptor | SEQ ID NO: 16 |
| Amino acid sequence of Rhesus monkey (*Macaca mulatta*) Y1 receptor | SEQ ID NO: 17 |
| Nucleic acid sequence of house mouse (*Mus musculus*) Y1 receptor | SEQ ID NO: 18 |
| Nucleic acid sequence of house mouse (*Mus musculus*) Y1 receptor | SEQ ID NO: 19 |
| Amino acid sequence of house mouse (*Mus musculus*) Y1 receptor | SEQ ID NO: 20 |
| Nucleic acid sequence of Norway rat (*Rattus norvegicus*) Y1 receptor | SEQ ID NO: 21 |
| Nucleic acid sequence of Norway rat (*Rattus norvegicus*) Y1 receptor (CDS) | SEQ ID NO: 22 |
| Amino acid sequence of Norway rat (*Rattus norvegicus*) Y1 receptor | SEQ ID NO: 23 |
| Nucleic acid sequence of human Y2 receptor | SEQ ID NO: 24 |
| Nucleic acid sequence of human Y2 receptor (CDS) | SEQ ID NO: 25 |
| Amino acid sequence of human Y2 receptor | SEQ ID NO: 26 |
| Nucleic acid sequence of Rhesus monkey (*Macaca mulatta*) Y2 receptor | SEQ ID NO: 27 |
| Amino acid sequence of Rhesus monkey (*Macaca mulatta*) Y2 receptor | SEQ ID NO: 28 |

TABLE I-continued

| Sequence description | SEQ ID NO: |
|---|---|
| Nucleic acid sequence of house mouse (*Mus musculus*) Y2 receptor | SEQ ID NO: 29 |
| Nucleic acid sequence of house mouse (*Mus musculus*) Y2 receptor (CDS) | SEQ ID NO: 30 |
| Amino acid sequence of house mouse (*Mus musculus*) Y2 receptor | SEQ ID NO: 31 |
| Nucleic acid sequence of Norway rat (*Rattus norvegicus*) Y2 receptor | SEQ ID NO: 32 |
| Nucleic acid sequence of Norway rat (*Rattus norvegicus*) Y2 receptor (CDS) | SEQ ID NO: 33 |
| Amino acid sequence of Norway rat (*Rattus norvegicus*) Y2 receptor | SEQ ID NO: 34 |
| Nucleic acid sequence of human Y4 receptor | SEQ ID NO: 35 |
| Nucleic acid sequence of human Y4 receptor (CDS) | SEQ ID NO: 36 |
| Amino acid sequence of human Y4 receptor | SEQ ID NO: 37 |
| Nucleic acid sequence of Rhesus monkey (*Macaca mulatta*) Y4 receptor | SEQ ID NO: 38 |
| Amino acid sequence of Rhesus monkey Y4 receptor | SEQ ID NO: 39 |
| Nucleic acid sequence of house mouse (*Mus musculus*) Y4 receptor | SEQ ID NO: 40 |
| Nucleic acid sequence of house mouse (*Mus musculus*) Y4 receptor (CDS) | SEQ ID NO: 41 |
| Amino acid sequence of house mouse (*Mus musculus*) Y4 receptor | SEQ ID NO: 42 |
| Nucleic acid sequence of Norway rat (*Rattus norvegicus*) Y4 receptor | SEQ ID NO: 43 |
| Nucleic acid sequence of Norway rat (*Rattus norvegicus*) Y4 receptor (CDS) | SEQ ID NO: 44 |
| Amino acid sequence of Norway rat (*Rattus norvegicus*) Y4 receptor | SEQ ID NO: 45 |
| Nucleic acid sequence of human Y5 receptor | SEQ ID NO: 46 |
| Nucleic acid sequence of human Y5 receptor (CDS) | SEQ ID NO: 47 |
| Amino acid sequence of human Y5 receptor | SEQ ID NO: 48 |
| Nucleic acid sequence of Rhesus monkey (*Macaca mulatta*) Y5 receptor | SEQ ID NO: 49 |
| Amino acid sequence of Rhesus monkey (*Macaca mulatta*) Y5 receptor | SEQ ID NO: 50 |
| Nucleic acid sequence of house mouse (*Mus musculus*) Y5 receptor | SEQ ID NO: 51 |
| Nucleic acid sequence of house mouse (*Mus musculus*) Y5 receptor (CDS) | SEQ ID NO: 52 |
| Amino acid sequence of house mouse (*Mus musculus*) Y5 receptor | SEQ ID NO: 53 |
| Nucleic acid sequence of Norway rat (*Rattus norvegicus*) Y5 receptor | SEQ ID NO: 54 |
| Nucleic acid sequence of Norway rat (*Rattus norvegicus*) Y5 receptor (CDS) | SEQ ID NO: 55 |
| Amino acid sequence of Norway rat (*Rattus norvegicus*) Y5 receptor | SEQ ID NO: 56 |
| Nucleic acid sequence of human y6 receptor | SEQ ID NO: 57 |
| Nucleic acid sequence of human y6 receptor (CDS) | SEQ ID NO: 58 |
| Amino acid sequence of human y6 receptor | SEQ ID NO: 59 |
| Nucleic acid sequence of house mouse (*Mus musculus*) y6 receptor | SEQ ID NO: 60 |
| Nucleic acid sequence of house mouse (*Mus musculus*) y6 receptor (CDS) | SEQ ID NO: 61 |
| Amino acid sequence of house mouse (*Mus musculus*) y6 receptor | SEQ ID NO: 62 |
| Nucleic acid sequence of rabbit (*Oryctolagus cuniculus*) y6 receptor | SEQ ID NO: 63 |
| Nucleic acid sequence of rabbit (*Oryctolagu scuniculus*) y6 receptor (CDS) | SEQ ID NO: 64 |
| Amino acid sequence of rabbit rat y6 receptor | SEQ ID NO: 65 |
| Nucleic acid sequence of human galanin | SEQ ID NO: 66 |
| Nucleic acid sequence of human galanin (CDS) | SEQ ID NO: 67 |

TABLE I-continued

| Sequence description | SEQ ID NO: |
|---|---|
| Amino acid sequence of human prepro-galanin | SEQ ID NO: 68 |
| Nucleic acid sequence of monkey (*Macaca nemestrina*) galanin | SEQ ID NO: 69 |
| Amino acid sequence of monkey (*Macaca nemestrina*) galanin | SEQ ID NO: 70 |
| Nucleic acid sequence of house mouse (*Mus musculus*) galanin | SEQ ID NO: 71 |
| Nucleic acid sequence of house mouse (*Mus musculus*) galanin (CDS) | SEQ ID NO: 72 |
| Amino acid sequence of house mouse (*Mus musculus*) galanin | SEQ ID NO: 73 |
| Nucleic acid sequence of Norway rat (*Rattus norvegicus*) galanin | SEQ ID NO: 74 |
| Nucleic acid sequence of Norway rat (*Rattus norvegicus*) galanin (CDS) | SEQ ID NO: 75 |
| Amino acid sequence of Norway rat (*Rattus norvegicus*) galanin | SEQ ID NO: 76 |
| Nucleic acid sequence of human GALR1 | SEQ ID NO: 77 |
| Nucleic acid sequence of human GALR1 (CDS) | SEQ ID NO: 78 |
| Amino acid sequence of human GALR1 | SEQ ID NO: 79 |
| Nucleic acid sequence of Chimpanzee (*Pan troglodytes*) GALR1 | SEQ ID NO: 80 |
| Amino acid sequence of Chimpanzee (*Pan troglodytes*) GALR1 | SEQ ID NO: 81 |
| Nucleic acid sequence of house mouse (*Mus musculus*) GALR1 | SEQ ID NO: 82 |
| Nucleic acid sequence of house mouse (*Mus musculus*) GALR1 (CDS) | SEQ ID NO: 83 |
| Amino acid sequence of house mouse (*Mus musculus*) GALR1 | SEQ ID NO: 84 |
| Nucleic acid sequence of Norway rat (*Rattus norvegicus*) GALR1 | SEQ ID NO: 85 |
| Nucleic acid sequence of Norway rat (*Rattus norvegicus*) GALR1 (CDS) | SEQ ID NO: 86 |
| Nucleic acid sequence of Norway rat (*Rattus norvegicus*) GALR1 (CDS) | SEQ ID NO: 87 |
| Amino acid sequence of Norway rat (*Rattus norvegicus*) GALR1 | SEQ ID NO: 88 |
| Amino acid sequence of Norway rat (*Rattus norvegicus*) GALR1 | SEQ ID NO: 89 |
| Nucleic acid sequence of human GALR2 | SEQ ID NO: 90 |
| Nucleic acid sequence of human GALR2 (CDS) | SEQ ID NO: 91 |
| Amino acid sequence of human GALR2 | SEQ ID NO: 92 |
| Nucleic acid sequence of Chimpanzee (*Pan troglodytes*) GALR2 | SEQ ID NO: 93 |
| Amino acid sequence of Chimpanzee (*Pan troglodytes*) GALR2 | SEQ ID NO: 94 |
| Nucleic acid sequence of house mouse (*Mus musculus*) GALR2 | SEQ ID NO: 95 |
| Amino acid sequence of house mouse (*Mus musculus*) GALR2 | SEQ ID NO: 96 |
| Nucleic acid sequence of Norway rat (*Rattus norvegicus*) GALR2 | SEQ ID NO: 97 |
| Amino acid sequence of Norway rat (*Rattus norvegicus*) GALR2 | SEQ ID NO: 98 |
| Nucleic acid sequence of human GALR3 | SEQ ID NO: 99 |
| Nucleic acid sequence of human GALR3 (CDS) | SEQ ID NO: 100 |
| Amino acid sequence of human GALR3 | SEQ ID NO: 101 |
| Nucleic acid sequence of house mouse (*Mus musculus*) GALR3 | SEQ ID NO: 102 |
| Amino acid sequence of house mouse (*Mus musculus*) GALR3 | SEQ ID NO: 103 |
| Nucleic acid sequence of Norway rat (*Rattus norvegicus*) GALR3 | SEQ ID NO: 104 |
| Amino acid sequence of Norway rat (*Rattus norvegicus*) GALR3 | SEQ ID NO: 105 |
| Nucleic acid sequence of human somatostatin | SEQ ID NO: 106 |
| Nucleic acid sequence of human somatostatin (CDS) | SEQ ID NO: 107 |
| Amino acid sequence of human somatostatin | SEQ ID NO: 108 |

TABLE I-continued

| Sequence description | SEQ ID NO: |
| --- | --- |
| Nucleic acid sequence of long-tailed macaque (*Macaca fascicularis*) somatostatin | SEQ ID NO: 109 |
| Nucleic acid sequence of long-tailed macaque (*Macaca fascicularis*) somatostatin (CDS) | SEQ ID NO: 110 |
| Amino acid sequence of long-tailed macaque (*Macaca fascicularis*) somatostatin | SEQ ID NO: 111 |
| Nucleic acid sequence of house mouse (*Mus musculus*) somatostatin | SEQ ID NO: 112 |
| Nucleic acid sequence of house mouse (*Mus musculus*) somatostatin (CDS) | SEQ ID NO: 113 |
| Amino acid sequence of house mouse (*Mus musculus*) somatostatin | SEQ ID NO: 114 |
| Nucleic acid sequence of Norway rat (*Rattus norvegicus*) somatostatin | SEQ ID NO: 115 |
| Nucleic acid sequence of Norway rat (*Rattus norvegicus*) somatostatin (CDS) | SEQ ID NO: 116 |
| Amino acid sequence of Norway rat (*Rattus norvegicus*) somatostatin | SEQ ID NO: 117 |
| Nucleic acid sequence of human somatostatin SST1 receptor | SEQ ID NO: 118 |
| Nucleic acid sequence of human somatostatin SST1 receptor (CDS) | SEQ ID NO: 119 |
| Amino acid sequence of human somatostatin SST1 receptor | SEQ ID NO: 120 |
| Nucleic acid sequence of Chimpanzee (*Pan troglodytes*) somatostatin SST1 receptor | SEQ ID NO: 121 |
| Amino acid sequence of Chimpanzee (*Pan troglodytes*) somatostatin SST1 receptor | SEQ ID NO: 122 |
| Nucleic acid sequence of house mouse (*Mus musculus*) somatostatin SST1 receptor | SEQ ID NO: 123 |
| Nucleic acid sequence of house mouse (*Mus musculus*) somatostatin SST1 receptor (CDS) | SEQ ID NO: 124 |
| Amino acid sequence of house mouse (*Mus musculus*) somatostatin SST1 receptor | SEQ ID NO: 125 |
| Nucleic acid sequence of Norway rat (*Rattus norvegicus*) somatostatin SST1 receptor | SEQ ID NO: 126 |
| Nucleic acid sequence of Norway rat (*Rattus norvegicus*) somatostatin SST1 receptor (CDS) | SEQ ID NO: 127 |
| Amino acid sequence of Norway rat (*Rattus norvegicus*) somatostatin SST1 receptor | SEQ ID NO: 128 |
| Nucleic acid sequence of human somatostatin SST2 receptor | SEQ ID NO: 129 |
| Nucleic acid sequence of human somatostatin SST2 receptor (CDS) | SEQ ID NO: 130 |
| Amino acid sequence of human somatostatin SST2 receptor | SEQ ID NO: 131 |
| Nucleic acid sequence of Chimpanzee (*Pan troglodytes*) somatostatin SST2 receptor | SEQ ID NO: 132 |
| Nucleic acid sequence of Chimpanzee (*Pan troglodytes*) somatostatin SST2 receptor (CDS) | SEQ ID NO: 133 |
| Amino acid sequence of Chimpanzee (*Pan troglodytes*) somatostatin SST2 receptor | SEQ ID NO: 134 |
| Nucleic acid sequence of house mouse (*Mus musculus*) somatostatin SST2 receptor | SEQ ID NO: 135 |
| Nucleic acid sequence of house mouse (*Mus musculus*) somatostatin SST2 receptor (CDS) | SEQ ID NO: 136 |
| Amino acid sequence of house mouse (*Mus musculus*) somatostatin SST2 receptor | SEQ ID NO: 137 |
| Nucleic acid sequence of Norway rat (*Rattus norvegicus*) somatostatin SST2 receptor | SEQ ID NO: 138 |

TABLE I-continued

| Sequence description | SEQ ID NO: |
| --- | --- |
| Nucleic acid sequence of Norway rat (*Rattus norvegicus*) somatostatin SST2 receptor (CDS) | SEQ ID NO: 139 |
| Amino acid sequence of Norway rat (*Rattus norvegicus*) somatostatin SST2 receptor | SEQ ID NO: 140 |
| Nucleic acid sequence of human somatostatin SST3 receptor | SEQ ID NO: 141 |
| Nucleic acid sequence of human somatostatin SST3 receptor (CDS) | SEQ ID NO: 142 |
| Amino acid sequence of human somatostatin SST3 receptor | SEQ ID NO: 143 |
| Nucleic acid sequence of dog (*Canis familiaris*) somatostatin SST3 receptor | SEQ ID NO: 144 |
| Amino acid sequence of dog (*Canis familiaris*) somatostatin SST3 receptor | SEQ ID NO: 145 |
| Nucleic acid sequence of house mouse (*Mus musculus*) somatostatin SST3 receptor | SEQ ID NO: 146 |
| Nucleic acid sequence of house mouse (*Mus musculus*) somatostatin SST3 receptor (CDS) | SEQ ID NO: 147 |
| Amino acid sequence of house mouse (*Mus musculus*) somatostatin SST3 receptor | SEQ ID NO: 148 |
| Nucleic acid sequence of Norway rat (*Rattus norvegicus*) somatostatin SST3 receptor | SEQ ID NO: 149 |
| Nucleic acid sequence of Norway rat (*Rattus norvegicus*) somatostatin SST3 receptor (CDS) | SEQ ID NO: 150 |
| Amino acid sequence of Norway rat (*Rattus norvegicus*) somatostatin SST3 receptor | SEQ ID NO: 151 |
| Nucleic acid sequence of human somatostatin SST4 receptor | SEQ ID NO: 152 |
| Amino acid sequence of human somatostatin SST4 receptor | SEQ ID NO: 153 |
| Nucleic acid sequence of Chimpanzee (*Pan troglodytes*) somatostatin SST4 receptor | SEQ ID NO: 154 |
| Amino acid sequence of Chimpanzee (*Pan troglodytes*) somatostatin SST4 receptor | SEQ ID NO: 155 |
| Nucleic acid sequence of house mouse (*Mus musculus*) somatostatin SST4 receptor | SEQ ID NO: 156 |
| Nucleic acid sequence of house mouse (*Mus musculus*) somatostatin SST4 receptor (CDS) | SEQ ID NO: 157 |
| Amino acid sequence of house mouse *Mus musculus*) somatostatin SST4 receptor | SEQ ID NO: 158 |
| Nucleic acid sequence of Norway rat (*Rattus norvegicus*) somatostatin SST4 receptor | SEQ ID NO: 159 |
| Nucleic acid sequence of Norway rat (*Rattus norvegicus*) somatostatin SST4 receptor (CDS) | SEQ ID NO: 160 |
| Amino acid sequence of Norway rat (*Rattus norvegicus*) somatostatin SST4 receptor | SEQ ID NO: 161 |
| Nucleic acid sequence of human somatostatin SST5 receptor | SEQ ID NO: 162 |
| Nucleic acid sequence of human somatostatin SST5 receptor (CDS) | SEQ ID NO: 163 |
| Amino acid sequence of human somatostatin SST5 receptor | SEQ ID NO: 164 |
| Nucleic acid sequence of Chimpanzee (*Pan troglodytes*) somatostatin SST5 receptor | SEQ ID NO: 165 |
| Amino acid sequence of Chimpanzee (*Pan troglodytes*) somatostatin SST5 receptor | SEQ ID NO: 166 |
| Nucleic acid sequence of house mouse (*Mus musculus*) somatostatin SST5 receptor | SEQ ID NO: 167 |

TABLE I-continued

| Sequence description | SEQ ID NO: |
|---|---|
| Nucleic acid sequence of house mouse (*Mus musculus*) somatostatin SST5 receptor (CDS) | SEQ ID NO: 168 |
| Amino acid sequence of house mouse (*Mus musculus*) somatostatin SST5 receptor | SEQ ID NO: 169 |
| Nucleic acid sequence of Norway rat (*Rattus norvegicus*) somatostatin SST5 receptor | SEQ ID NO: 170 |
| Nucleic acid sequence of Norway rat (*Rattus norvegicus*) somatostatin SST5 receptor (CDS) | SEQ ID NO: 171 |
| Amino acid sequence of Norway rat (*Rattus norvegicus*) somatostatin SST5 receptor | SEQ ID NO: 172 |

The invention claimed is:

1. A method to treat epilepsy comprising administering to a mammal in need thereof an effective amount of one or more viral expression vectors comprising nucleic acid sequences encoding a combination of Neuropeptide Y (NPY) and one or more of its NPY-Y2 and NPY-Y5 receptors so as to treat epilepsy.

2. The method of claim 1, wherein said epilepsy is intractable epilepsy or temporal lobe epilepsy.

3. The method of claim 1, wherein one or more of the viral expression vectors are AAV vectors and/or lentivirus vectors and/or HSV vectors.

4. The method of claim 1, wherein said nucleic acid sequences encode a combination of amino acid sequences comprising two or more of the following: SEQ ID NO: 3, SEQ ID NO: 6, SEQ ID NO: 9, SEQ ID NO: 12, SEQ ID NO: 26, SEQ ID NO: 28, SEQ ID NO: 31, SEQ ID NO: 34, SEQ ID NO: 48, SEQ ID NO: 50, SEQ ID NO: 53 or SEQ ID NO: 56.

5. The method of claim 1, wherein said nucleic acid sequences comprise two or more of the following: SEQ ID NO: 1, SEQ ID NO: 2, SEQ ID NO: 4, SEQ ID NO: 5, SEQ ID NO: 7, SEQ ID NO: 8, SEQ ID NO: 10, SEQ ID NO: 11, SEQ ID NO: 24, SEQ ID NO:25, SEQ ID NO: 27, SEQ ID NO: 29, SEQ ID NO: 30, SEQ ID NO: 32, SEQ ID NO: 33, SEQ ID NO: 46, SEQ ID NO: 47, SEQ ID NO: 49, SEQ ID NO: 51, SEQ ID NO: 52, SEQ ID NO: 54 or SEQ ID NO:55.

6. A lentivirus vector and/or AAV vector and/or HSV vector that retain only the replication and packaging signals of lentivirus, AAV or HSV, and that comprise nucleic acid sequences encoding a combination of Neuropeptide Y (NPY) and one or more of its NPY-Y2 and NPY-Y5 receptors.

7. A composition comprising a lentivirus vector and/or AAV vector and/or HSV vector according to claim 6 and a pharmaceutically acceptable carrier.

8. A method for delivering a combination of nucleic acid sequences to mammalian nervous system target cells, wherein said nucleic acid sequences are expressible in the target cells for more than three months, said method comprising administering one or more viral expression vectors to the target cells, wherein said expression vectors comprise nucleic acid sequences encoding a combination of Neuropeptide Y (NPY) and one or more of its NPY-Y2 and NPY-Y5 receptors.

9. A method for treating a mammal with epilepsy, said method comprising administering one or more viral expression vectors to target cells in the mammal, wherein one or more of said expression vectors comprise nucleic acid sequences encoding a combination of Neuropeptide Y (NPY) and one or more of its NPY-Y2 and NPY-Y5 receptors and wherein said administering results in expression of a combination of NPY and one or more of its NPY-Y2 and NPY-Y5 receptors, in said target cells and said expression reduces symptoms of epilepsy.

10. A method for delivering a combination of nucleic acid sequences to mammalian nervous system target cells, wherein said nucleic acid sequences are expressible in the target cells for more than three months, said method comprising administering one or more lentivirus vectors and/or AAV vectors, and/or HSV vectors to the target cells, wherein said vectors transduce the target cells; and wherein said vectors comprise vectors of claim 6, and are free of both wildtype and helper virus.

11. A method for delivering a combination of nucleic acid sequences to mammalian nervous system target cells, wherein said nucleic acid sequences are expressible in the target cells for more than three months, said method comprising administering a composition according to claim 7, wherein said vectors transduce the target cells and are free of both wildtype and helper virus.

12. A method for treating a mammal with epilepsy, said method comprising administering one or more lentivirus vectors and/or AAV vectors, and/or HSV vectors to target cells in the mammal, wherein said lentivirus vectors and/or AAV vectors, and/or HSV vectors comprise lentivirus vectors and/or AAV vectors, and/or HSV vectors according to claim 6, and wherein said administering results in expression of a combination of NPY and one or more of its NPY-Y2 and NPY-Y5 receptors, in said target cells and said expression reduces the symptoms of epilepsy, thereby treating the mammal with epilepsy.

* * * * *

UNITED STATES PATENT AND TRADEMARK OFFICE

CERTIFICATE OF CORRECTION

PATENT NO. : 8,901,094 B2
APPLICATION NO. : 12/308959
DATED : December 2, 2014
INVENTOR(S) : Kokaia et al.

It is certified that error appears in the above-identified patent and that said Letters Patent is hereby corrected as shown below:

Title Page

In item (73), in "Assignee", in column 1, line 1, after "AB", insert --, Lund--, therefor In item (30), in "Foreign Application Priority Data", in column 1, line 1, delete "0601456" and insert --0601456-7--, therefor Signed and Sealed this
Twenty-eighth Day of July, 2015

Michelle K. Lee
*Director of the United States Patent and Trademark Office*